(12) United States Patent
Kim

(10) Patent No.: US 11,866,708 B2
(45) Date of Patent: Jan. 9, 2024

(54) TAILORED MODULATION OF GENE REGULATION PROGRAMS VIA FUNCTIONAL ENHANCER RNA

(71) Applicant: Board of Regents, The University of Texas System, Austin, TX (US)

(72) Inventor: Tae Hoon Kim, Plano, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 288 days.

(21) Appl. No.: 17/076,696

(22) Filed: Oct. 21, 2020

(65) Prior Publication Data

US 2021/0115450 A1    Apr. 22, 2021

Related U.S. Application Data

(60) Provisional application No. 62/924,569, filed on Oct. 22, 2019.

(51) Int. Cl.
*C12N 15/113* (2010.01)

(52) U.S. Cl.
CPC ...... *C12N 15/1136* (2013.01); *C12N 2310/11* (2013.01)

(58) Field of Classification Search
CPC .......... C12N 15/1136; C12N 2310/11
See application file for complete search history.

(56) References Cited

FOREIGN PATENT DOCUMENTS

| WO | WO-2014187856 A1 * | 11/2014 | ............ C12N 15/113 |
| WO | WO-2014197826 A1 * | 12/2014 | ............ C12N 15/113 |

OTHER PUBLICATIONS

Hogner et al., "Macrophage-expressed IFN-beta contributes to apoptotic alveolar epithelial cell injury in severe influenza virus pneumonia", *PLoS Pathogens*, 9: e1003188 ,2013.

Jacob et al., Pharmacophore reassignment for induction of the immunosurveillance cytokine TRAIL, *Angewandte Chemie*, 53, 6628-6631, 2014.

* cited by examiner

*Primary Examiner* — J. E. Angell
(74) *Attorney, Agent, or Firm* — Parker Highlander PLLC

(57) ABSTRACT

The disclosure provides for eRNA-targeted transcriptional reprogramming through targeted reduction of eRNAs for a clinically relevant gene, TNFSF10, resulting in a selective control of interferon-induced apoptosis. A method of inhibiting a TNFSF10 gene expression in a human cell is disclosed. The methods described herein comprise contacting the human cell with a single-stranded antisense compound consisting of the sequence selected from a set of SEQ ID NOs: disclosed herein, wherein the antisense compound targets an enhancer RNA (eRNA) transcribed from a genomic enhancer sequence or region. The eRNA is an TNFSF10 eRNA sequence comprising the nucleic acid sequence selected from the SEQ ID NOs disclosed herein which inhibits expression of the TNFSF10 gene in the human cell.

8 Claims, 16 Drawing Sheets

Specification includes a Sequence Listing.

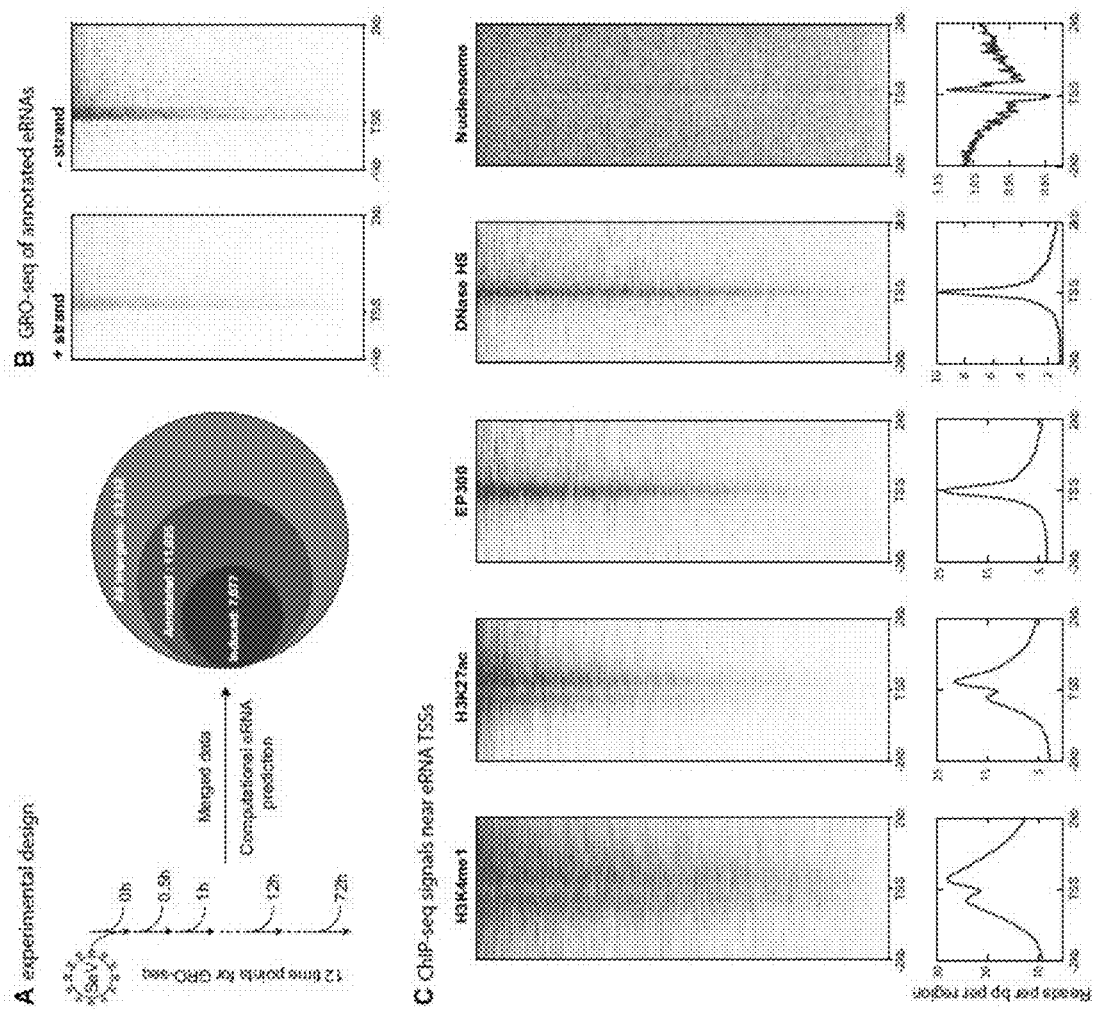
FIGS. 1A-C

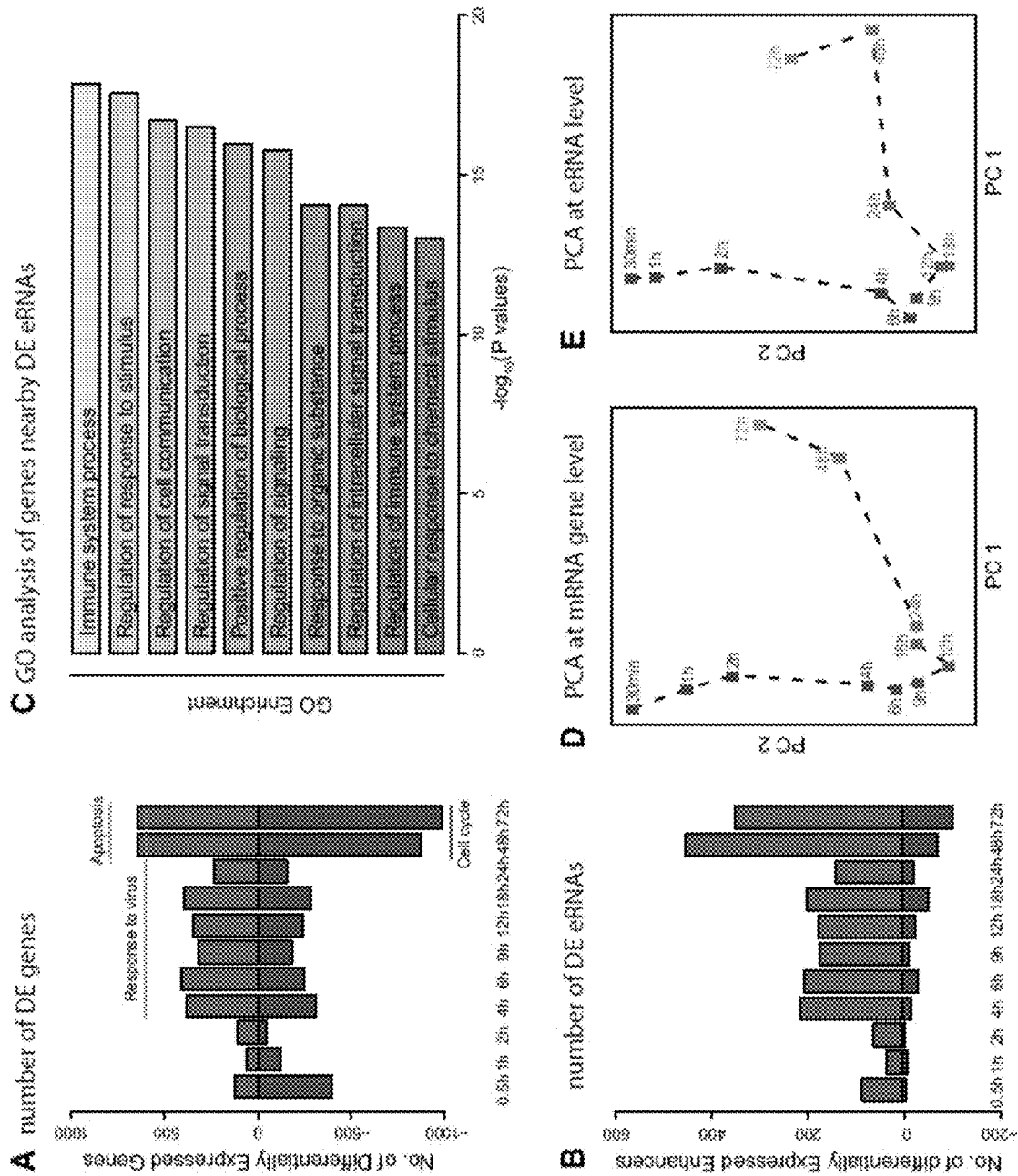
FIGS. 2A-E

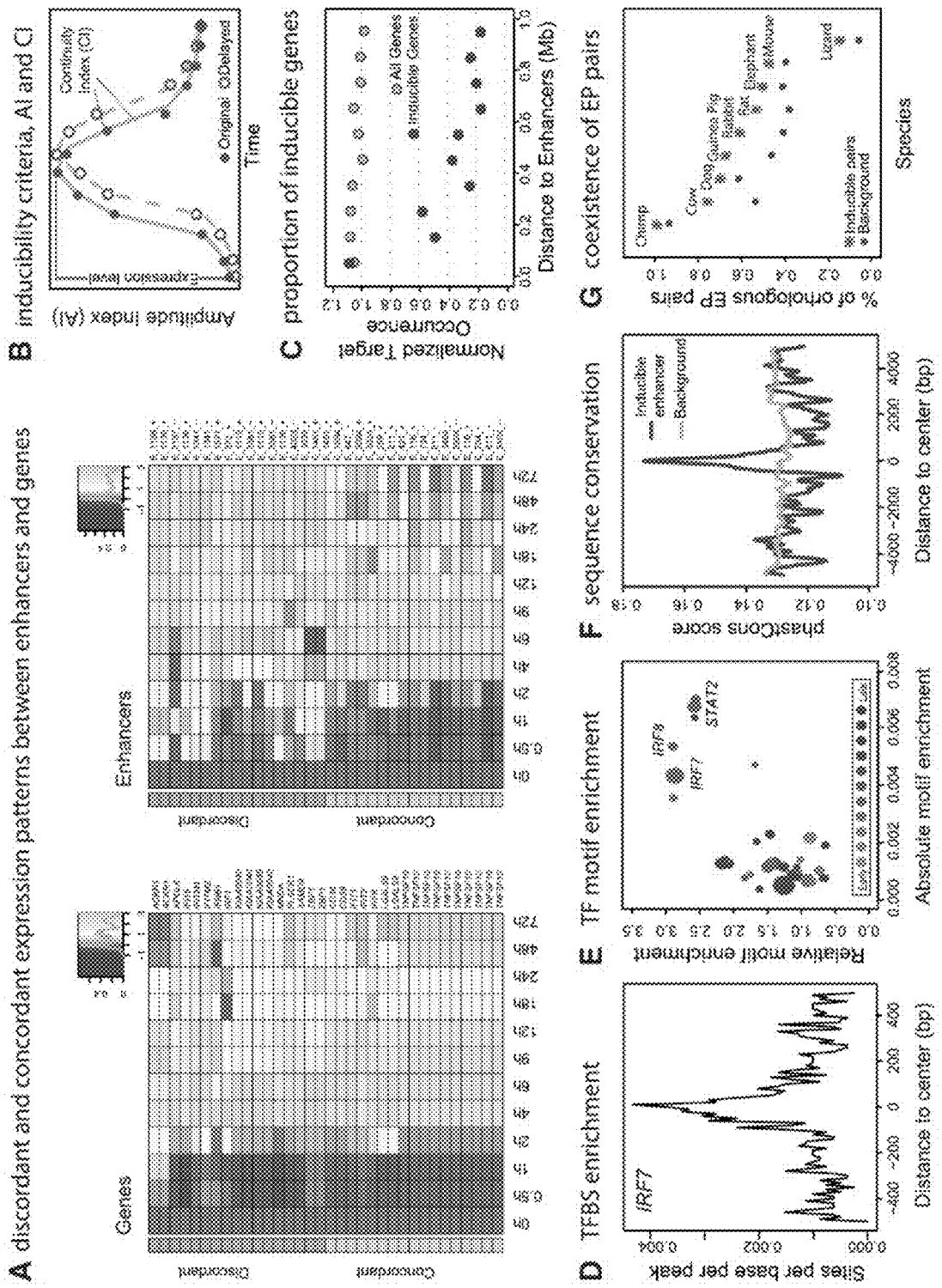
FIGS. 3A-G

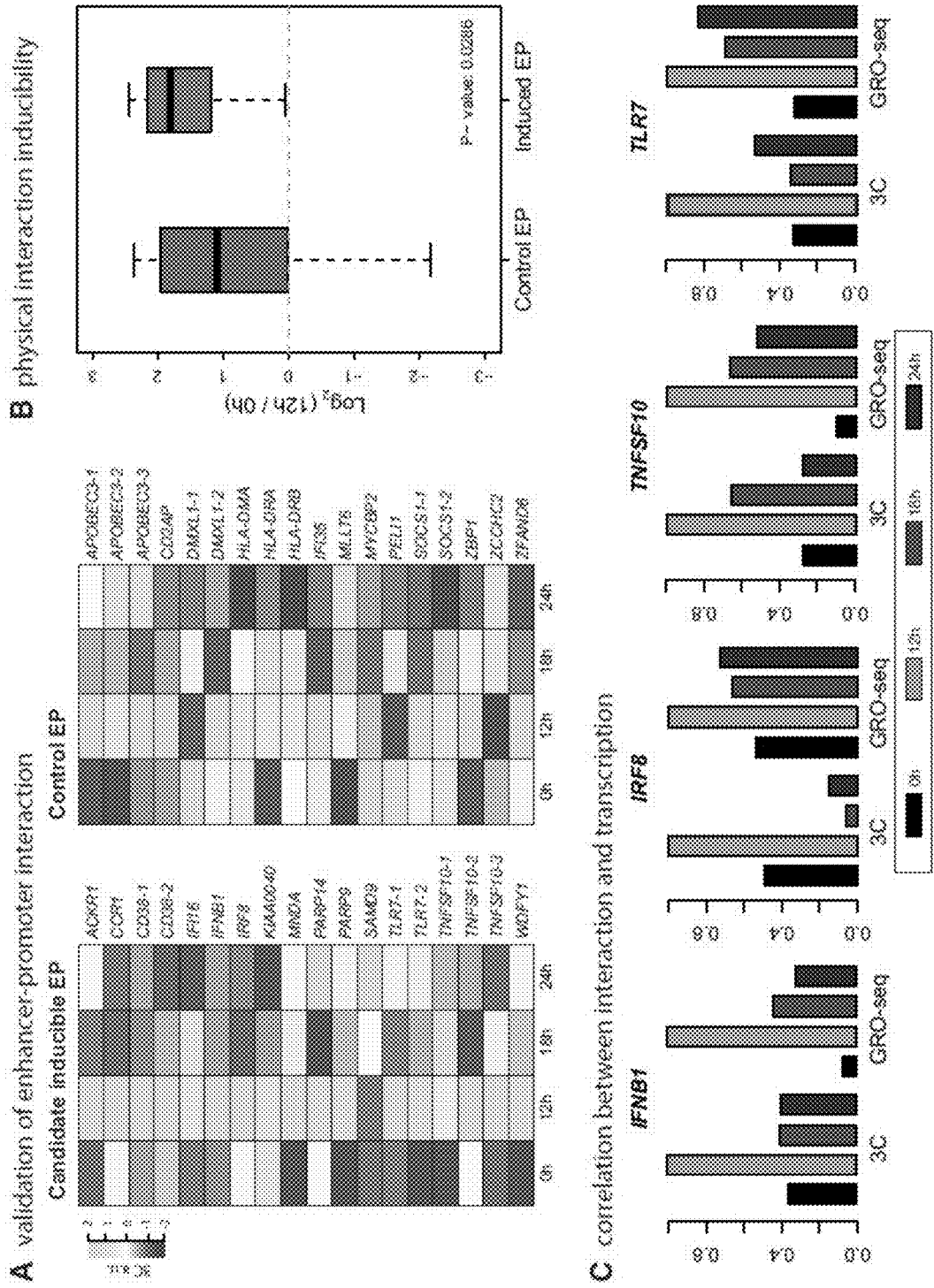
FIGS. 4A-C

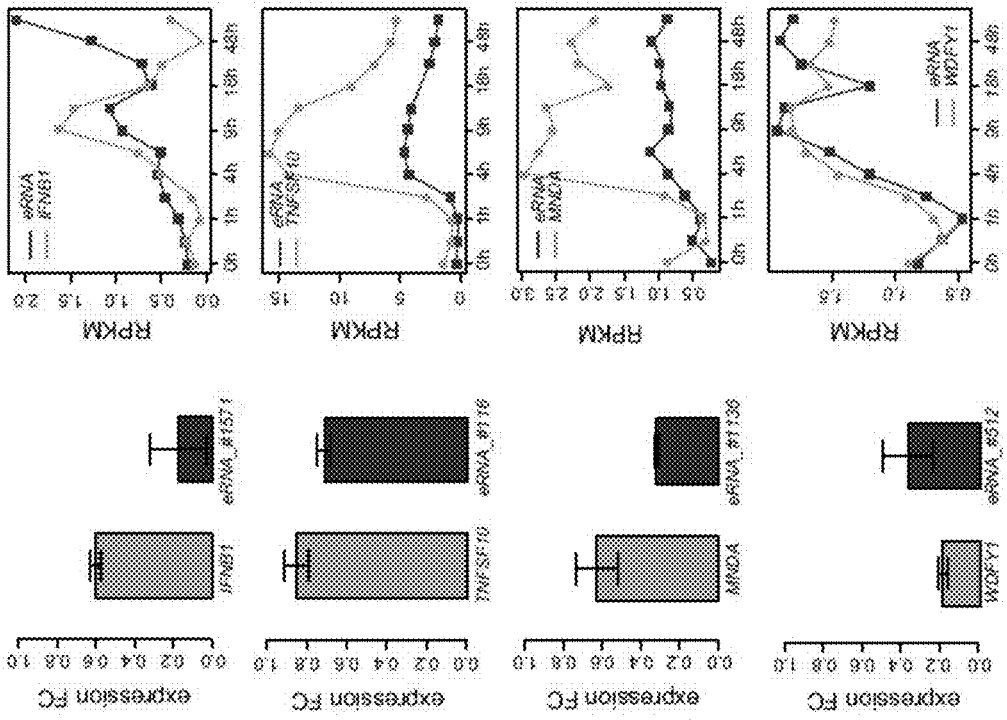
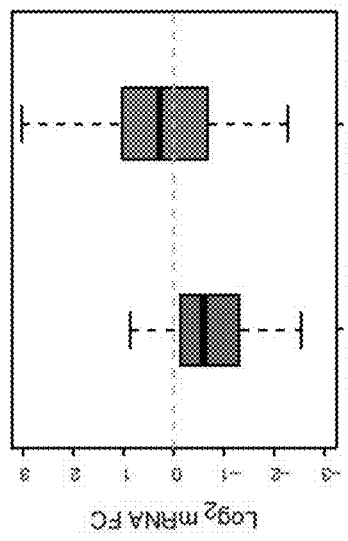
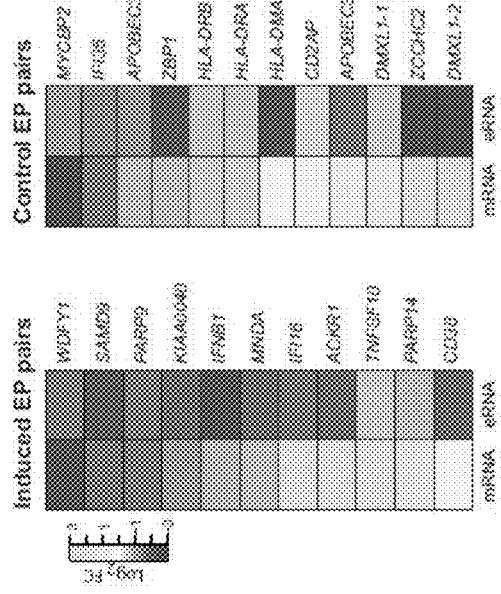
FIGS. 4D-F

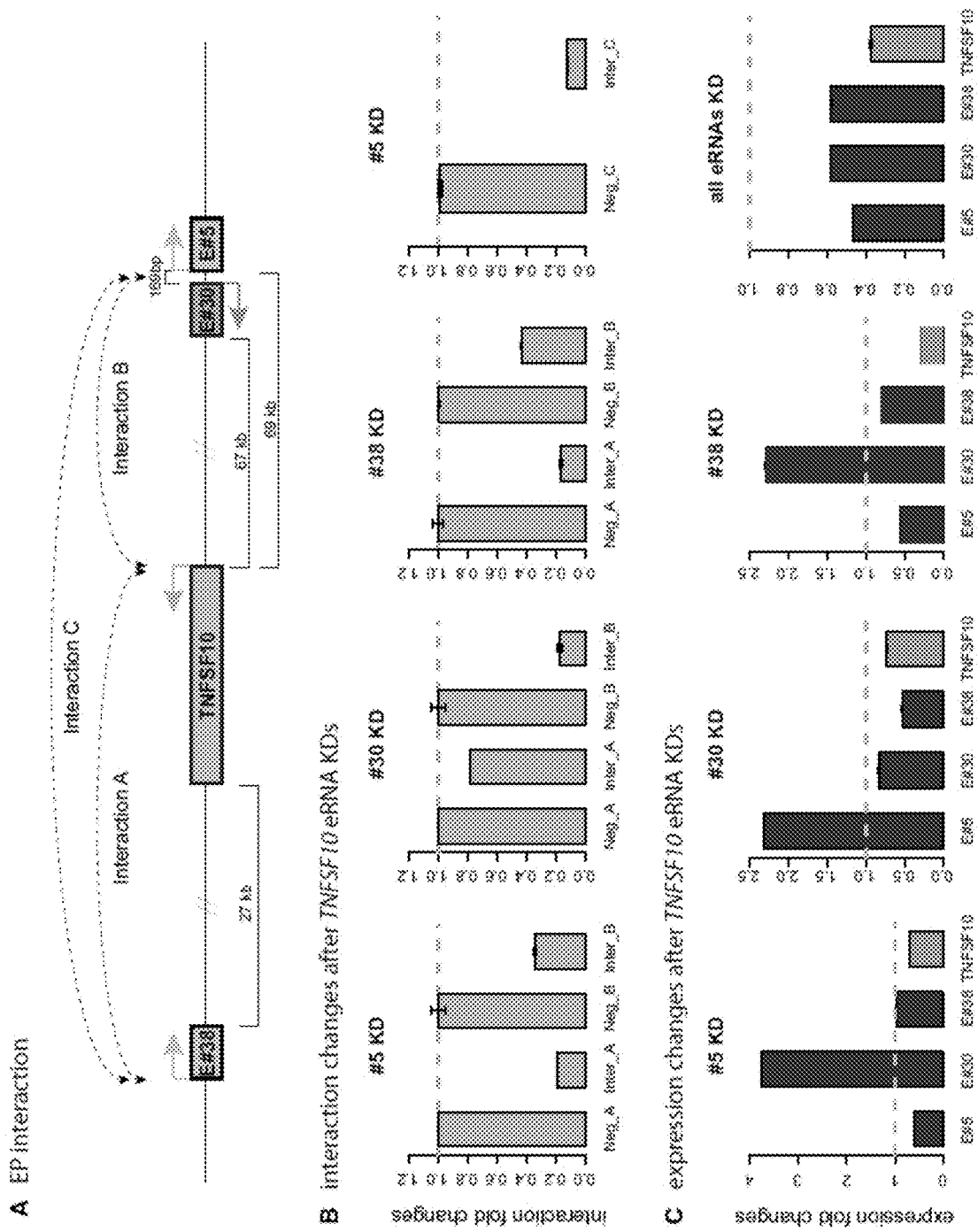
FIGS. 5A-C

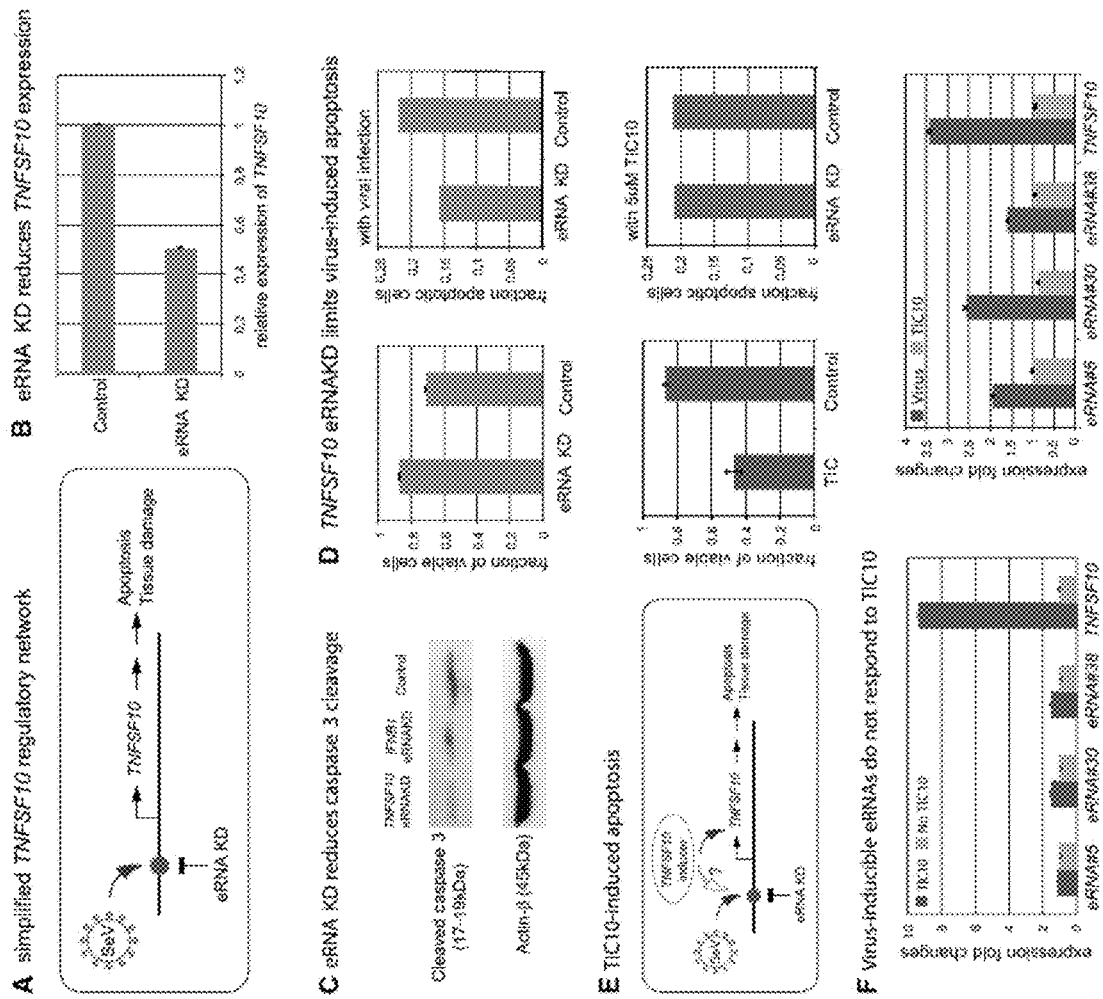
FIGS. 6A-F

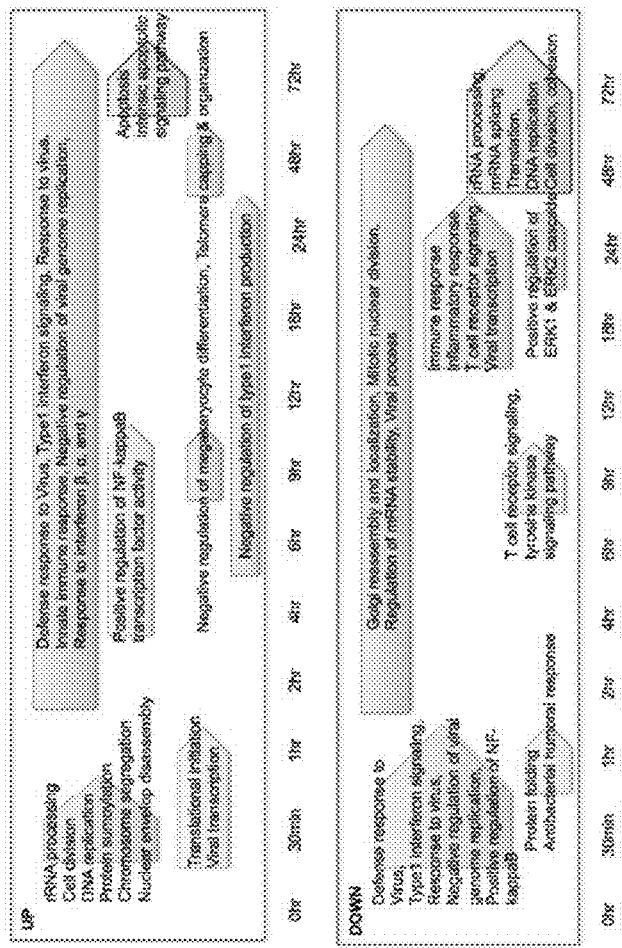
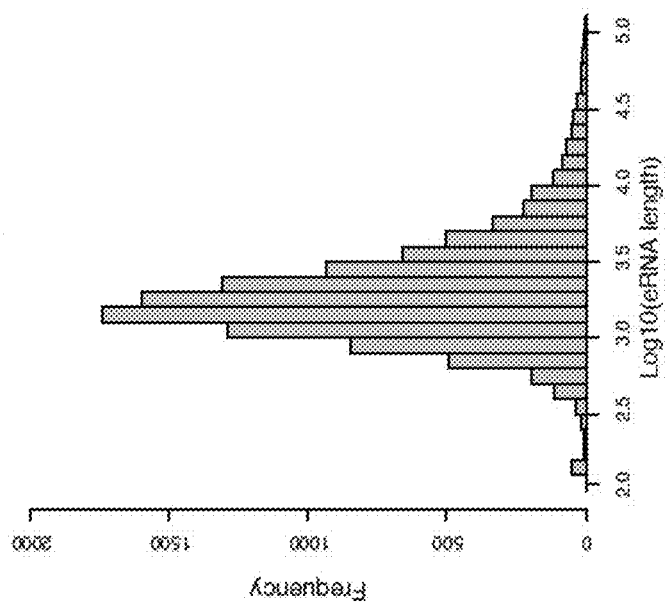
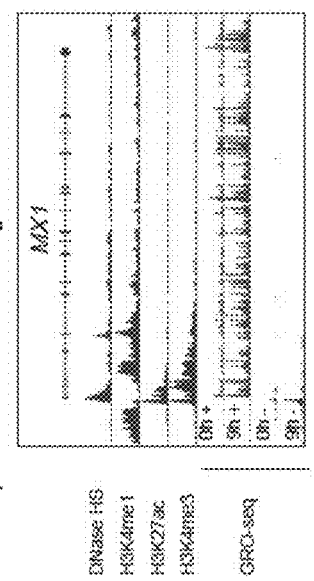
FIGS. 7A-C

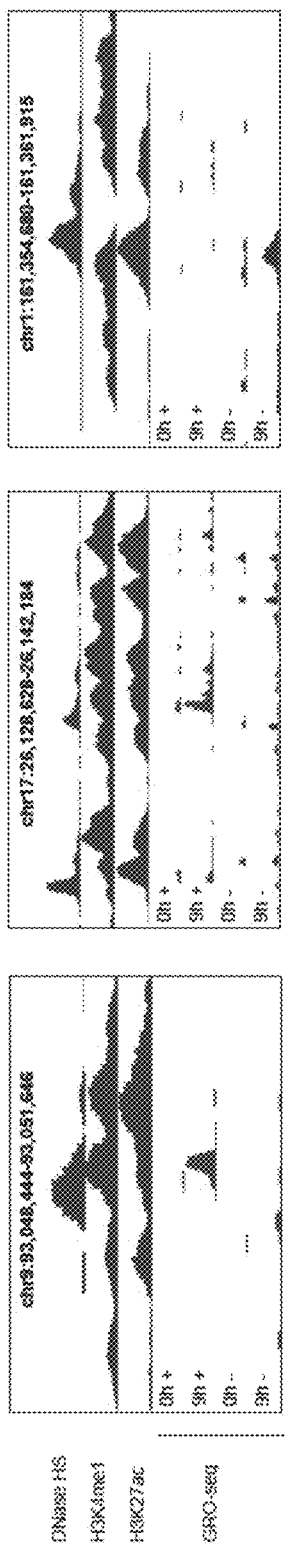
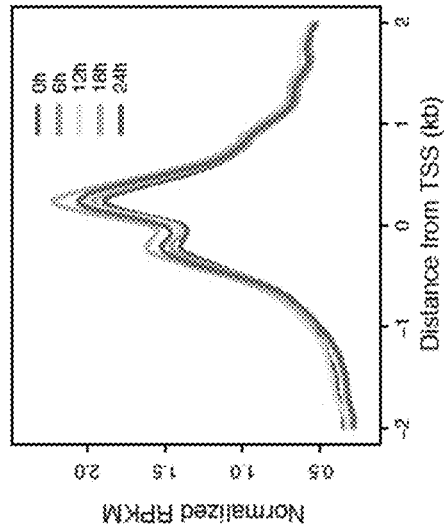
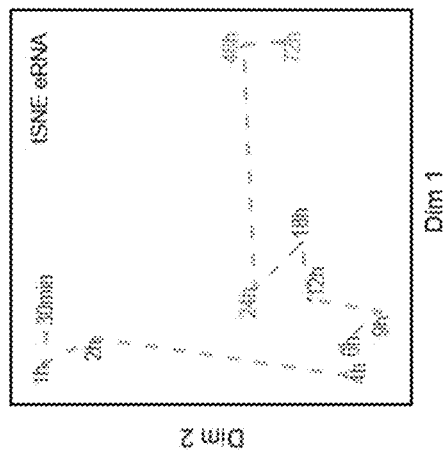
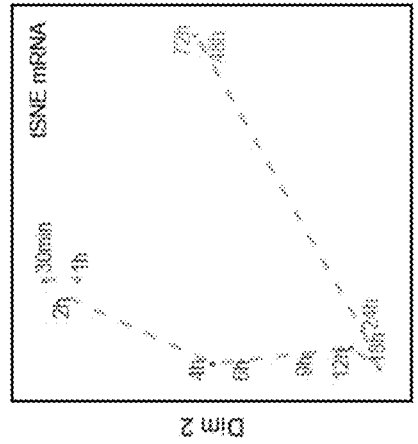
FIGS. 7D-G

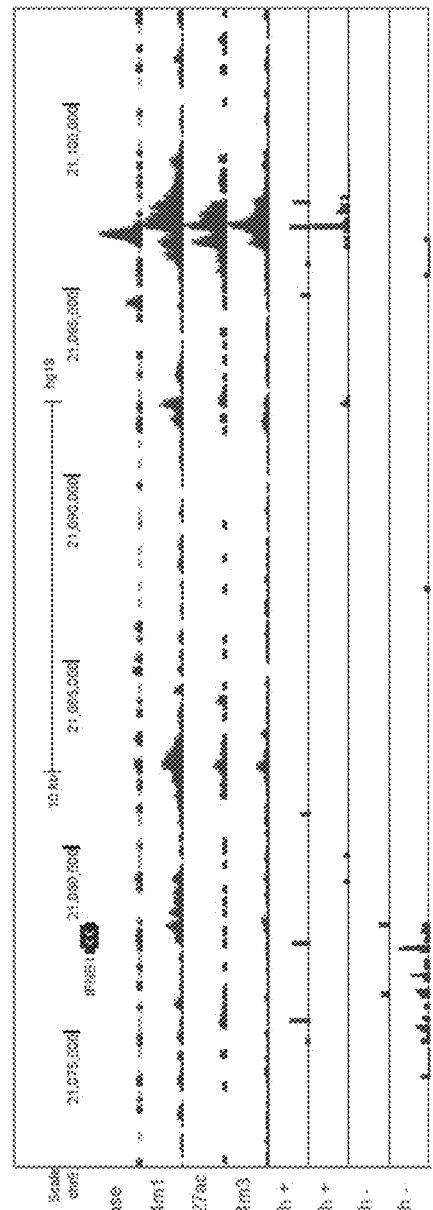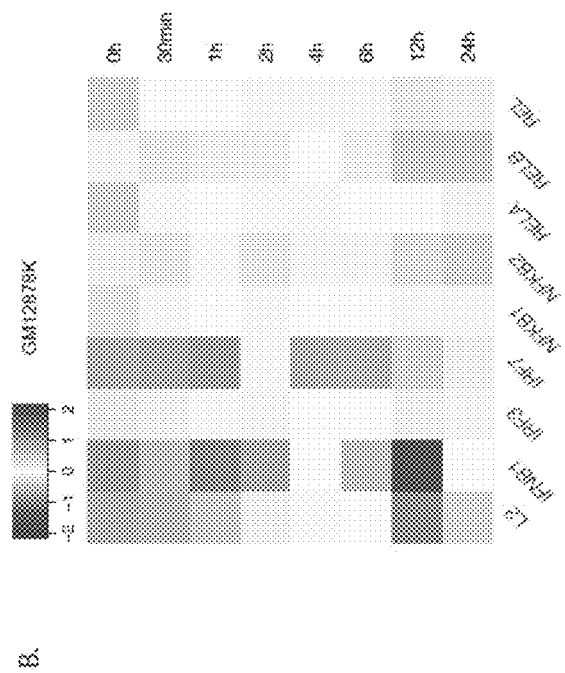
FIGS. 8A-B

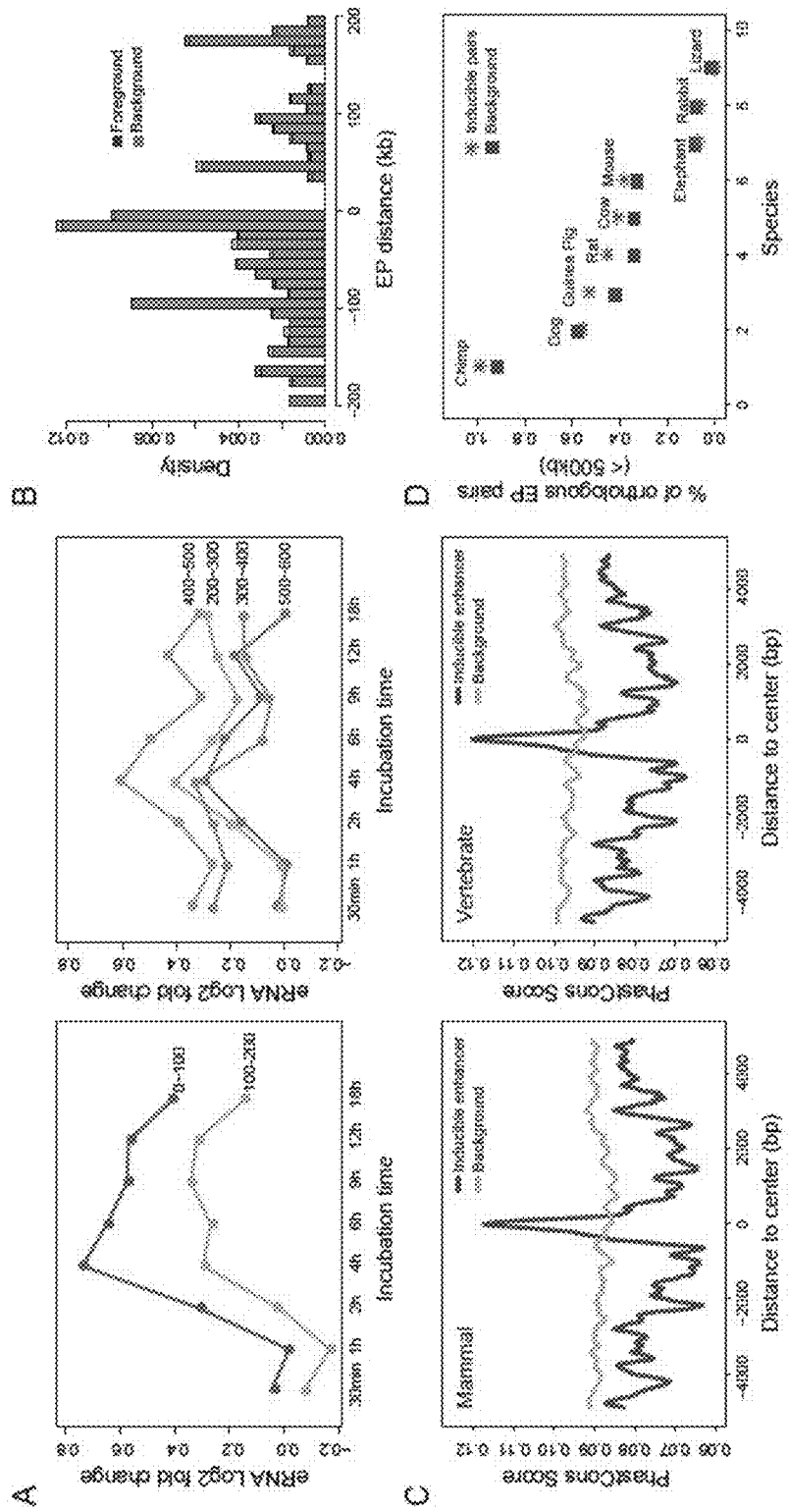
FIGS. 9A-D

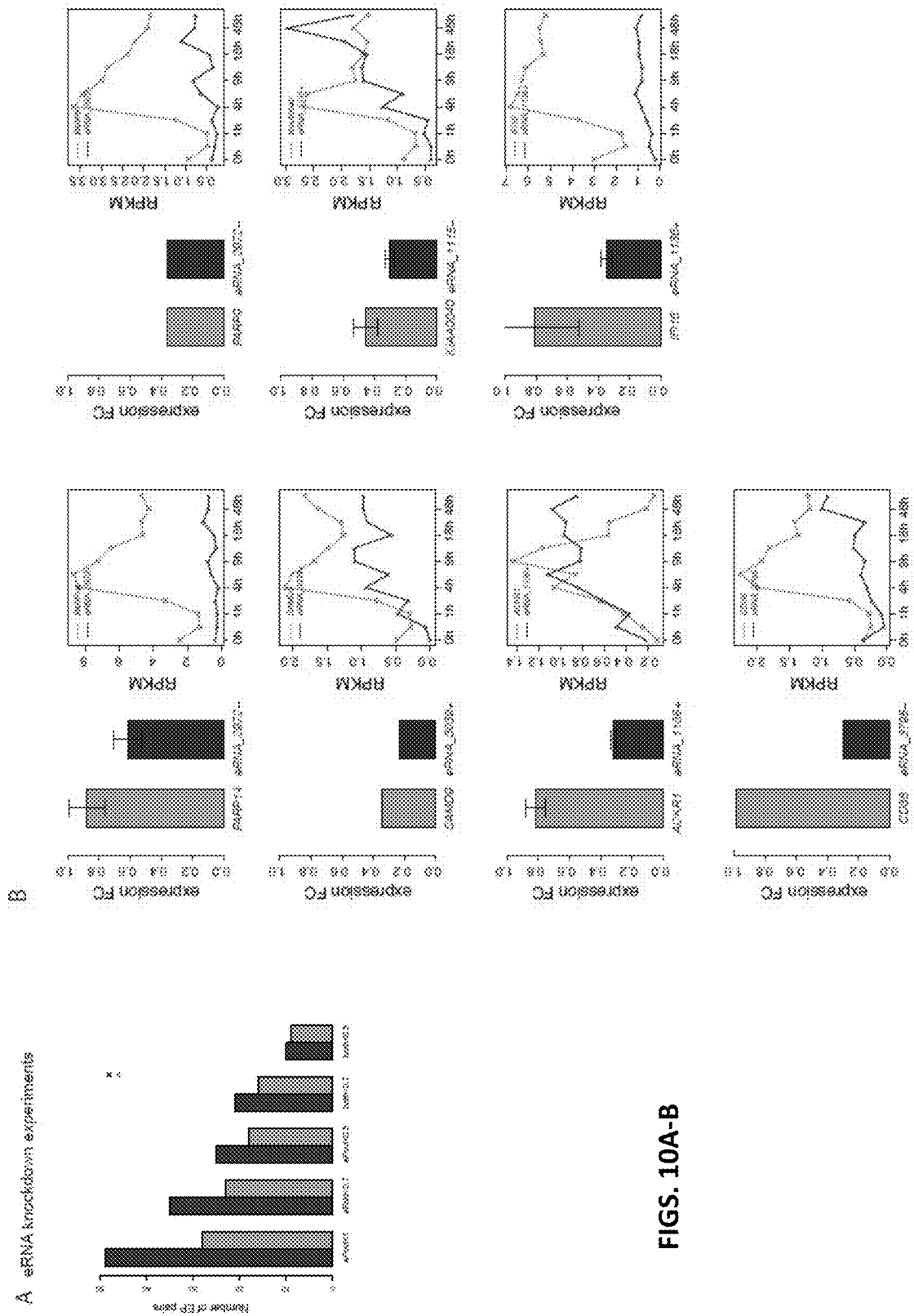
FIGS. 10A-B

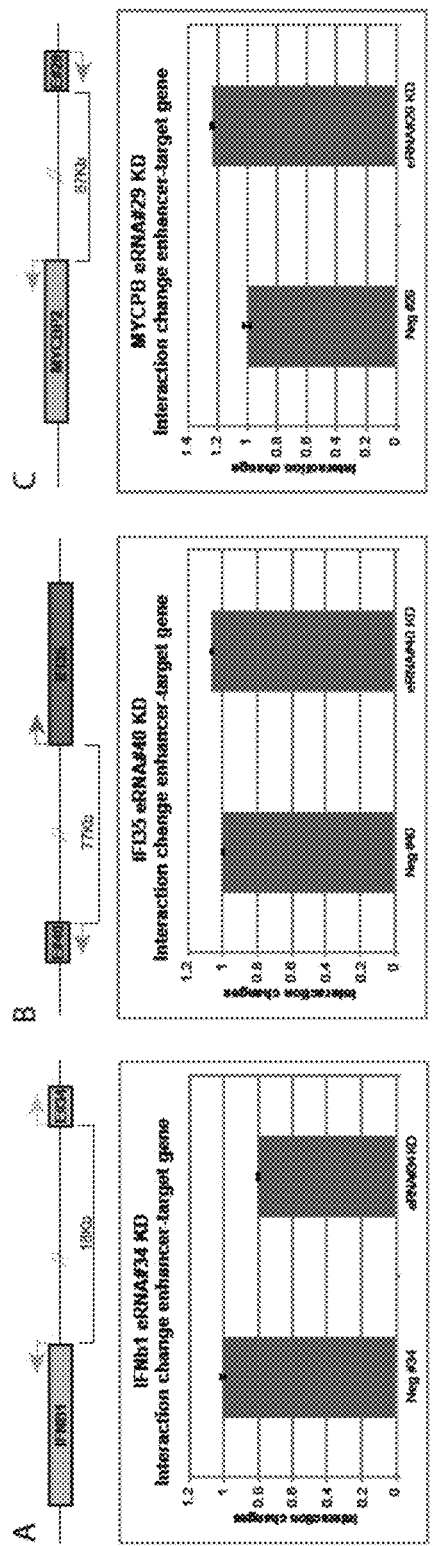
FIGS. 11A-C

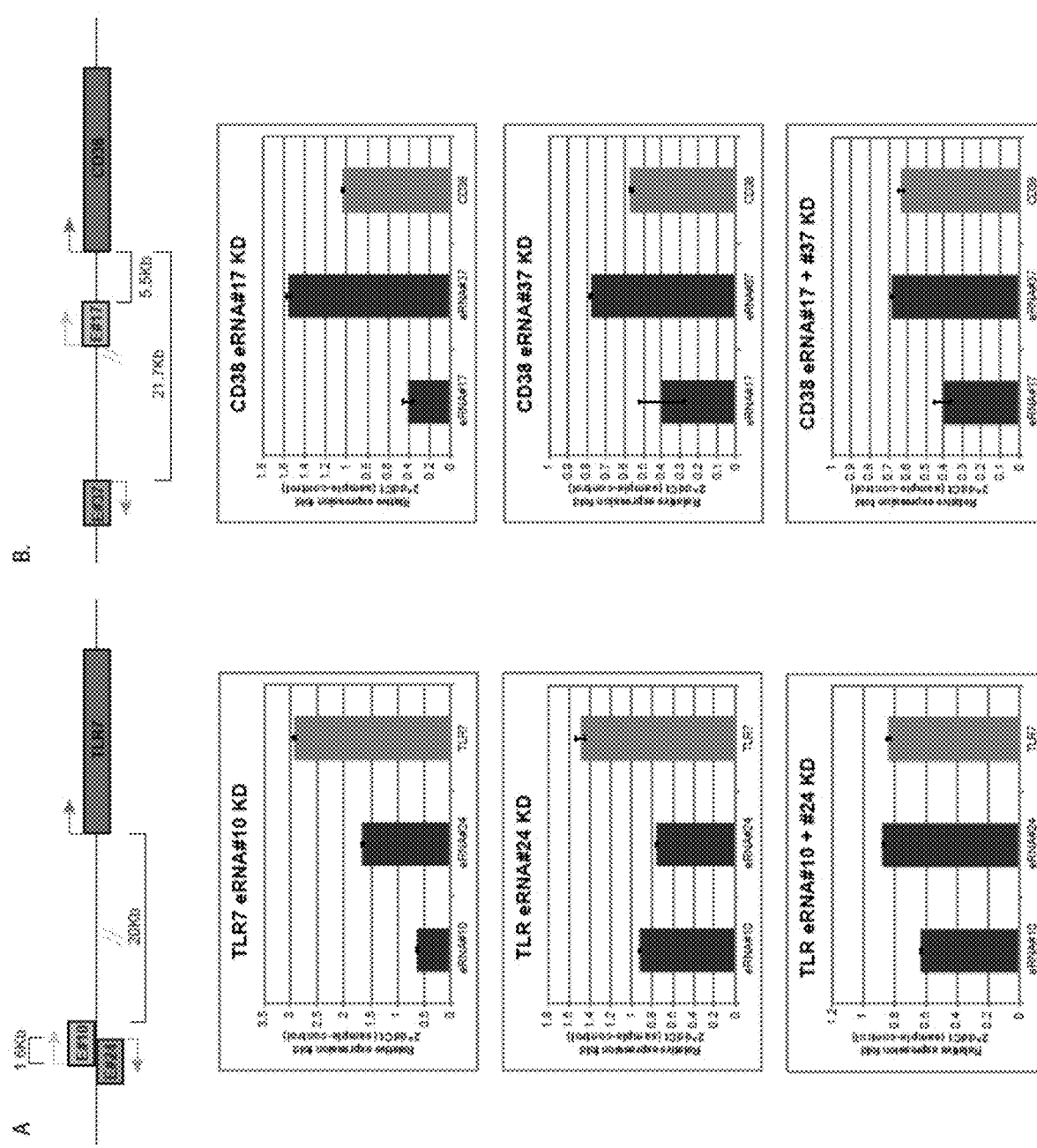
FIGS. 12A-B

SEQUENCE LISTING

<160> NUMBER OF SEQ ID NOS: 648

<210> SEQ ID NO 1
<211> LENGTH: 5090
<212> TYPE: DNA
<213> ORGANISM: Homo sapiens

<400> SEQUENCE: 1

```
ataccagtgt agtgactggg acctttgttc cttccccagc ctgaggtctg ttagggcagt      60
accactgcaa ctgcagaggc gaaggtttgt gggttcactc tggtatttat ttcctcttcg     120
aagaaatgcg ggggtgcctc tgattgaagt ggtcaggcgg aaacaggatg gtggtgctgg     180
agtctcaggt cgggcagccc tatgcagtga ggactgggac ttgtggggaa cagtctgacc     240
gcttttctaa ggtgggcgct ctgtgctggg ggtctggacc agccctggt actcacagag      300 gacttttcag agcctggaga cagtaagggc aagggctgca agacagcaaa catcacaccc     360
cccaccctct caccccccaa cccccaaaca ctgggagcgc tgtcccagag agttatggag     420
ctgctactgg ctcaatatcc ctggcagggg gtgggtggag acccaggcca ggaggactca     480
tccagtgagg agaaacaggt ttggagactt gtgtaaaaaa gcagtctggc cacttttcca     540
caggacagcc atgttgtgct ggggggtcca ctccagtcac tgatggatca ccttgcactc     600
tctaaagcct gaaggcaaca aggactgagg ctgtgaaaca gcaaagatgg ccgcctaccc     660
cttcctctga gagctccctc tcaggatgt gtaatgctgc taccagcagc tggctagagt      720
tccaagccag tgggtcttat cctgtgacct ctgaagtgct atggaagtga ggcctgcaga     780
tcatcgctgc tcagccccct ggattcagcc cctttcatag gagtaggtat gggggtctaa     840
cctcccactt ggctggagta gcagttactt ttgccaggaa gccaggatat ctaaggctcc     900
tggggctccg tgtgtacctg agcggctgct ctgccaagac tccccatagc tctgtgtatc     960
tgactgaagg ccctagtgga gtgggttcat gagggatct cctgacccaa gagtagcaac     1020
gatccatggg agaagcattg gtccgcaggg tcgctcattc actcacggct tccctggatg    1080
gggaggttcc cctggctcca tgtttctccc gtgtgggcgg ttgtcctgcc ctgcttttct    1140
ccattctcca tgggtcaggt tgttttcttg atgaattcca acatgtgtat ctgtatgttt    1200
cggttgaaag tgcagtattt actcgcccca tctatttctc tctgtgagag cagtacacac    1260
tagctgcttc tggttgagcg taagaaaaat aaatgccctt ttaatgtgtt tgctagaaga    1320
tagaaaacat tgcaaagaac agagtagaat tcatattctt aaaaacaaat atgaaaactt    1380
attctacttt ccttctttac caatgaaaat aaacatattt attgtcctca atgcactttt    1440 ttcttgaaa taataactcc tcagaaagac cgttgcagtt aagaatatca gctgtcacac      1500
agagctaaat ccttttaatt gtgaatttt tccccacaaa gcatgatgaa ctacgtcttg     1560
```

```
acagggcagg caaagtatta aagtaaaata ttttccccca cattttattt ttcttttctt    1620
tctttctttc cttttttttt tttttttttt ttttgagatg gagtttcact cttgttgtcc    1680
aggctggagt gcaatggcgt gatctcagct cactgcaacc tccacctcct gggttcaagc    1740
aattctcctg cctcagcctc tggtgtagct gggattacag gcacacgcca ccacgcctgg    1800 ctaattttg  tattttagc  agagatggga tttcaccaca ttggccaagc tggtctcaaa    1860
ctcctgacct cagtgatcca tctgcctcag cctcccaaag tgctgggatt acaggtgtga    1920
gccactgcgc ccagccccca ttttctgagg tgaaatgaag gaagagttaa tcattcatgc    1980
tccttttctt gggttcagct gccatcctta cttacctctg atggaggact agggatttct    2040
gggacttgaa ctcctgttat agaaggtcag attagcctta agctgaacag cagcagctac    2100
ctgggccttt ctcccctgaa taaaagttct gaagatctaa aatgaaaata tgaaaggaaa    2160
gaaattatca agttctgtct actaaatatc tcagtggatt tcctacctca actggtagat    2220
ttgtcttaag gcctttgttt ggagtgtttt cctacaagtc tcaaagtcta acaaaagcag    2280
gcgttcccgg tcaagctctg ccaaattcac cacgtgacct aggacctgaa gtgaactttc    2340
gtttctcctg ttctctctct ttccgacctt ccctccccgc caaggcaatg cagacaggga    2400
ctcaatatat tattttgagt tctccatagg aaaagaatta ttattaaaac aataagctct    2460
caagataaat acctttatat aatgtatata cattcatata tacatgagta tatactagct    2520
ttcatatctg tattctttt  tttctttctc acccagaact caagaagaca tgcctgtatc    2580 ccttttttt  ttctcttttg agatgaagtt tcactcttgt tgcccaggct ggagcgcaat    2640
ggcgcaatct cagcttactg taacctccac ctcctgcatt caagcaattc tcctgcctca    2700
gcctcctgag tagctgggat tacaggcgcc caccaccacg tctggctaat ttgtgtatat    2760
ttagtagaaa tggggtttca ccatgttgac caggctggtc ttgaacttct gacctcaggt    2820
gatccacccg cctcggcctc ccagtgtgct gggattacag gcatgagcca ccgcacccgg    2880
cccaacatgt ccgtattctc aaagctatag aggtgtcttt gctatttgt  tctcttaggt    2940 aagaaccggg tcctcaccct acactttatt cctcaggtga agagactctg tgtgtgtcca    3000
ttcagggaag catgagagca tttgatttca gctgagcagg tttagtcatc taggagctgc    3060
tctcttaagt gtttaacaca atcgttaact aactaaaact tgcaggaaat taatctggaa    3120
tttcccagta attacatgtt ttagataagt ttttgaattg agtccaagat gatgtgatag    3180
tgcatgttca taattaacta agaaactgag aaaagctttc ttaatctaaa aacaaagcca    3240
aaaatctttc catgcaagga aagaaaatct taattgatta actcattaat agagcaggga    3300
aaagaaaaca aaagcaaaag caaaaaaact aacttgagat atagctgaac tcataatgtg    3360
tatttgtttt tatttccagt tgctgcttac cattagctgt gcaagaccaa aggattttgt    3420
gctttctctt gcctagtaat tgttcagtcc aaaatttaac catgttgttt ttgtgttatt    3480
accaggagca agaggacatg tgtattggtg agagaagagg ggtgaggagt cagggataag    3540
atgaatctga ttaacttcag gggttattag aataaatctt gtaggcttgg agaatcttgt    3600
aggcttggag aatctagagt tctatgagaa atggtaagca gacttcataa atcctgtctg    3660
cgttgctgct atgatcttgg ccttcccctg acatactccc aagaaataga aacgaataga    3720
aatagaaatc taatagaact agaaatagaa atatttccca agaaatagaa agtaaaactg    3780
acaaagccaa tgcaaagaaa tcagttcgga agctgttaat tttcacacga tctgtgttca    3840
gtaaccgccc tctatcggct ctcctgaata gcacactata tgggacgag aatctgaaag    3900 gccttttgc  tggttttctt actaacagag agttcataaa ccaggatctt cttcagcctc    3960
```

```
caaggtaagg aaatgtgtga tctccaagct ccctcttgta tgtattgtga acgccactgt    4020
cagaagagaa acaccaaagt tattcacctg gaaatgttgc agtatgaaga ccatgtattt    4080
gatggagagg ttatttaaat ggtaactttg ttaatgaatt tctttgctaa ctttccctgc    4140
tttattttca tgccaaaaac cagagaggta cagagaacag aactcggcac acagtctaa     4200 aagtgttaag tttcaggcac aacactgctg tttttgagct gtgggtcctc agacaagcca    4260
ttttagcttt ccgagcctca gtttcccact tgcctgcttc ttcaccactt cctggggtga    4320
taagagaaga ccaaatgata tgtttgtgaa ggtgctttgc cactcatgta ccctatgcag    4380
accctattat tagtagtact ttataaaagt aagacatcat tttctcattt acaggactga    4440
ggattagaaa gaataatgct gggtttctgg ctgcctccgc ttttgagggc ctaggaggca    4500
ttctgaccta aagagagtag gcagtggagt cagacataaa tgtaaacact gttagtgtga    4560
cctttgcaga tcatctgtct gccctgtgct tctattatgc tatctatctg caaagtaaag    4620
aacttcttta caaatgcct  catacaagtg tgaatacaac aaacaagctc catctctaaa    4680
gttcttcata gaaaacagaa ttataagacg cactcagtat ccaaggataa atgataccag    4740
gaaagggcca aagttaatta atcctcttac aataaagagc atatttcaag gtaaataata    4800
aaaataatta tcttaaaatt aacaaaatgt atatggttat ttgcaactat gcattaattc    4860
ttagcccaaa gaatgttgag gagttgattt ggcatgaaga ggacacattt tcttggacaa    4920
aattatagga tggcacagtg cgactttgtt tagctcatac tacctttcgg taacaccatc    4980 aaagggatc ttttttacca aaaacatttt ttaaatcaag ggttttcatc aattttccaa    5040
agggattaaa aaaattccct gacatttaag ctggtacatt ttggaagcat              5090

<210> SEQ ID NO 2
<211> LENGTH: 700
<212> TYPE: DNA
<213> ORGANISM: Homo sapiens

<400> SEQUENCE: 2
catattgaat gcttagaact tgccaggccg tatctcagca cgtcactcat attaatcatt      60
tcctaataac cgctacaagt tgggttttgt tattatcccc atttgaataa ataaggcacg     120
gagacacaga gaggatatga cataactacc agaagccatt ggtggcaaga tctcaatcag     180
gacatgtcgg tacaatgctc tgattatctc gtctgcatcc ctgattactt atggtccaga     240
tataaactac tcctcttcac tttcattta  accagaattt gaagtcattt tattctctct     300
caagtacttt gggctttgag gaaaataagg gaaactcgcc acctggtggc agctcatagt     360
gtgtggtaac aaggtggctg cccctgtct  ggtttcaagg agagaggaga gaatgtccct    420
gccttgctat tcacgcctct caaacagctg agctgacctc tcctcaaggg ccattgtctt     480
tagaaatccc tcgccctgtc taggtccatt ctgataaaaa ttggagtagc agttttttct     540
ctatgcttca agtgaggagg ttggatggga cagagtccag cgatgagagg ccaagactct     600
cttgacctta tttcattgtc aaaaagatca gtattcatgt tctacaagaa ggaatccaca     660
gttgtccaga aaactgtcct tcaaaaatag ccagtccaca                           700

<210> SEQ ID NO 3
<211> LENGTH: 1720
<212> TYPE: DNA
<213> ORGANISM: Homo sapiens

<400> SEQUENCE: 3
```

-continued

| | |
|---|---|
| aagctctcag aggtatatga cagtctctcc accacagtga ccacatggag aggagaccat | 60 |
| tatctcctct cagtgagccc ttgaacccct gctccccaac aagtggagcc tccaactcac | 120 |
| accagcagtg cagccaccca cctcactggc tgaacattcc cagtaacagt gactctgcat | 180 |
| ttcttggggt tggagccctc aggggcaacc aaaagcctct ctgccactgc ctctgtagta | 240 |
| gtactacccc tactaccttt agactaatta acagcaaag accctaagtg cctcatccac | 300 |
| accccaaca agctgcagtt aacccaagga gaggagacca gtccatctcc cacaggtccc | 360 |
| atccacccct gctgcttgtc caccgggaac ccccagctt ggacccacag tacagatcac | 420 |
| ccatcttggg cctatcacac tgagcaattg ctgacctgca tctctgtgga gtggagcccc | 480 |
| caggagacaa gtaaaagacc cccagccaca accactgcta aggtccttct ctctgctgcc | 540 |
| tccaagctgg ggaggaaaca taaacccctga gatctcccca gagctgtggt gggcagccta | 600 |
| ggagtgccaa gtctcaatct gtagccagca ctcaaatggg agaggagtcc acacttttcag | 660 |
| agcattgaga ggtagcccag ctgcaaccat gaggaaatat agaggagtca catgactggg | 720 |
| aaagagtcta cctactgacc actacttcac aaaaccctc atttccttct gtcctcccta | 780 |
| aagcctctca gtttttgaatc tcatgtcttc aaattgtatc acccactggc ctccatgaag | 840 |
| cgcctaagca ccacctactg gatcacaccc cgcagcttca acaccaaaaa gttagaaaga | 900 |
| cttcaaatta acaacctaac atcacaacta aagaactac agaaccaaga gcaaaccaat | 960 |
| cccaaagcta gcagaagaca aaaaaacaca tgcttatctc aacagatgta tctcactaac | 1020 |
| atacccgccc tgtaaaacca agataagaa gtcagctgca ataaagacc tcgcacaaag | 1080 |
| cctcagccct gtgaaaatat tcaggaaaaa agtcttctga ctgtactcaa tctatgctgc | 1140 |
| agttaaagga acaccatac acagagatga gaaagaacca atgtaagaac tctggcaact | 1200 |
| caaatgacca gtgtcttatg tactccaaac aatagcacca gttctccaat gagggttctt | 1260 |
| aaacaggctg agttggctga atgacagaa atagaattca gagtatagat aggaatgaag | 1320 |
| atcattgaga tttaggagaa gaggaaaaca caatccaagg aaactaagaa tcacaataaa | 1380 |
| atgataaagg agctgacagg caaaatcgcc agtattaaaa agaaacctaa ctgatctgat | 1440 |
| agagctgaaa agcacactgc aagaatttca caatgcaatc gcaagtatta acagcagaat | 1500 |
| agaccaagct ggggaaagaa tctcagaact tgaagactgg ctctctgaaa caagacagcc | 1560 |
| agacaaaaat aaagaaaaaa agaatgaaaa tgaatgaaca gaaactccag aaaatatagg | 1620 |
| attatgtaag gaggccaaat ctataaatca ctggcatcac tgaaagagat ggggagaaag | 1680 |
| caaaccactt ggaaaacaca ttttaggata tcactcatga | 1720 |

<210> SEQ ID NO 4
<211> LENGTH: 3660
<212> TYPE: DNA
<213> ORGANISM: Homo sapiens

<400> SEQUENCE: 4

| | |
|---|---|
| tctatttcta ttcgtttcta tttcttggga gtatgtcagg ggaaggccaa gatcatagca | 60 |
| gcaacgcaga caggatttat gaagtctgct taccatttct catagaactc tagattctcc | 120 |
| aagcctacaa gattctccaa gcctacaaga tttattctaa taccccctga agttaatcag | 180 |
| attcatctta tccctgactc ctcaccccctc ttctctcacc aatacacatg tcctcttgct | 240 |
| cctggtaata acacaaaaac aacatggtta aattttggac tgaacaatta ctaggcaaga | 300 |
| gaaagcacaa aatccttttgg tcttgcacag ctaatggtaa gcagcaactg gaaataaaaa | 360 |
| caaatacaca ttatgagttc agctatatct caagttagtt ttttttgcttt tgcttttgtt | 420 |

| | |
|---|---|
| ttcttttccc tgctctatta atgagttaat caattaagat tttctttcct tgcatggaaa | 480 |
| gattttggc tttgttttta gattaagaaa gcttttctca gtttcttagt taattatgaa | 540 |
| catgcactat cacatcatct tggactcaat tcaaaaactt atctaaaaca tgtaattact | 600 |
| gggaaattcc agattaattt cctgcaagtt ttagttagtt aacgattgtg ttaaacactt | 660 |
| aagagagcag ctcctagatg actaaacctg ctcagctgaa atcaaatgct ctcatgcttc | 720 |
| cctgaatgga cacacacaga gtctcttcac ctgaggaata agtgtaagg tgaggacccg | 780 |
| gttcttacct aagagaacaa aatagcaaag acacctctat agctttgaga atacggacat | 840 |
| gttgggccgg gtgcggtggc tcatgcctgt aatcccagca cactgggagg ccgaggcggg | 900 |
| tggatcacct gaggtcagaa gttcaagacc agcctggtca acatggtgaa accccatttc | 960 |
| tactaaatat acacaaatta gccagacgtg gtggtgggcg cctgtaatcc cagctactca | 1020 |
| ggaggctgag gcaggagaat tgcttgaatg caggaggtgg aggttacagt aagctgagat | 1080 |
| tgcgccattg cgctccagcc tgggcaacaa gagtgaaact tcatctcaaa agagaaaaaa | 1140 |
| aaaagggata caggcatgtc ttcttgagtt ctgggtgaga agaaaaaaa agaatacaga | 1200 |
| tatgaaagct agtatatact catgtatata tgaatgtata tacattatat aaaggtattt | 1260 |
| atcttgagag cttattgttt taataataat tcttttccta tggagaactc aaaataatat | 1320 |
| attgagtccc tgtctgcatt gccttggcgg ggagggaagg tcggaaagag agaacagg | 1380 |
| agaaacgaaa gttcacttca ggtcctaggt cacgtggtga atttggcaga gcttgaccgg | 1440 |
| gaacgcctgc ttttgttaga ctttgagact tgtaggaaaa cactccaaac aaaggcctta | 1500 |
| agacaaatct accagttgag gtaggaaatc cactgagata tttagtagac agaacttgat | 1560 |
| aatttctttc ctttcatatt ttcattttag atcttcagaa cttttattca ggggagaaag | 1620 |
| gcccaggtag ctgctgctgt tcagcttaag gctaatctga ccttctataa caggagttca | 1680 |
| agtcccagaa atccctagtc ctccatcaga ggtaagtaag gatggcagct gaacccaaga | 1740 |
| aaaggagcat gaatgattaa ctcttccttc atttcacctc agaaaatggg ggctgggcgc | 1800 |
| agtggctcac acctgtaatc ccagcacttt gggaggctga ggcagatgga tcactgaggt | 1860 |
| caggagtttg agaccagctt ggccaatgtg gtgaaatccc atctctgcta aaaatacaaa | 1920 |
| aattagccag gcgtggtggc gtgtgcctgt aatcccagct acaccagagg ctgaggcagg | 1980 |
| agaattgctt gaacccagga ggtggaggtt gcagtgagct gagatcacgc cattgcactc | 2040 |
| cagcctggac aacaagagtg aaactccatc tcaaaaaaaa aaaaaaaaa aaaaggaaa | 2100 |
| gaaagaaaga aagaaaaat aaaatgtggg gaaaatatt ttactttaat actttgcctg | 2160 |
| ccctgtcaag acgtagttca tcatgctttg tggggaaaaa attcacaatt aaaaggattt | 2220 |
| agctctgtgt gacagctgat attcttaact gcaacggtct ttctgaggag ttattatttc | 2280 |
| aaagaaaaaa gtgcattgag gacaataaat atgtttattt tcattggtaa agaaggaaag | 2340 |
| tagaataagt tttcatattt gttttttaaga atatgaattc tactctgttc tttgcaatgt | 2400 |
| tttctatctt ctagcaaaca cattaaaagg gcatttattt ttcttacgct caaccagaag | 2460 |
| cagctagtgt gtactgctct cacagagaga aatagatggg gcgagtaaat actgcacttt | 2520 |
| caaccgaaac atacagatac acatgttgga attcatcaag aaaacaacct gacccatgga | 2580 |
| gaatggagaa aagcagggca ggacaaccgc ccacacggga gaaacatgga gccaggggaa | 2640 |
| cctccccatc cagggaagcc gtgagtgaat gagcgaccct gcggaccaat gcttctccca | 2700 |
| tggatcgttg ctactcttgg gtcaggagat cccctcatga acccactcca ctagggcctt | 2760 |

```
cagtcagata cacacagagcta tgggagtct tggcagagca gccgctcagg tacacacgga    2820
gccccaggag ccttagatat cctggcttcc tggcaaaagt aactgctact ccagccaagt    2880
gggaggttag accccatac ctactcctat gaaagggct gaatccaggg ggctgagcag      2940
cgatgatctg caggcctcac ttccatagca cttcagaggt cacaggataa acccactgg     3000 cttggaactc tagccagctg ctggtagcag cattacacat ccctgagagg gagctctcag    3060 aggaagggggt aggcggccat cttttgctgtt tcacagcctc agtccttgtt gccttcaggc  3120
tttagagagt gcaaggtgat ccatcagtga ctggagtgga ccccccagca aacatggct     3180 gtcctgtgga aaagtggcca gactgctttt ttacacaagt ctccaaacct gtttctcctc    3240
actggatgag tcctcctggc ctgggtctcc acccaccccc tgccagggat attgagccag    3300
tagcagctcc ataactctct gggacagcgc tcccagtgtt tggggttgg ggggtgagag     3360 ggtgggggt gtgatgtttg ctgtcttgca gcccttgccc ttactgtctc caggctctga    3420
aaagtcctct gtgagtacca ggggctggtc cagaccccca gcacagagcg cccaccttag    3480
aaaagcggtc agactgttcc ccacaagtcc cagtcctcac tgcatagggc tgcccgacct   3540
gagactccag caccaccatc ctgttttccgc ctgaccactt caatcagagg cacccccgca  3600
tttcttcgaa gaggaaataa ataccagagt gaacccacaa accttcgcct ctgcagttgc   3660
```

<210> SEQ ID NO 5
<211> LENGTH: 4245
<212> TYPE: DNA
<213> ORGANISM: Homo sapiens

<400> SEQUENCE: 5

```
ataaggctgc attcaggcat aattaaatcc aagtacttaa aagatgcagt cagaaatcaa     60
tctcctctct ctctctgtct ctcagtcttc cactccatct cccacctcca tgttgacctc    120
attcttatga gacctctctc catgtggtaa catatgggta tcagcatctc tagactcaca    180
ttctgccact taagctatac ttagaaacaa taatcttctt tctcagaaaa attcaagctg    240
ctacctcgat tgataaactg cagccacttg tgcatggctt aaacaacttt agtccattgt    300
ttccaaaatt atatttgcat gtcactggtg ctccctgaga tgatctggta gtaagcaaac    360
atttattata atacatgcca ggggctagag ggagggacg gataaatagg cagaacatgg     420
aggatattta gggaagtgaa attattccga tattatattg gtgaatgcat gctgttttac    480
atttgtcaca tgtataatta tgtgtaaatt tttatgcata ataaaaaata agtagtgcct    540
caaaattttt tttctttttgc ttgggatgag gctgaaatag gaaggaaagt agtattcatt    600
ttacaggatt agggtgagtt tcagatatgg tgatcaggca tgttcatgat cattttgtac    660
ctttacgaat cgaattatca aacaagactt aacctgttcc atgtagttga agtgctgtac    720
aggcagaaaa aatctagtca ctgttgtata ctgagggaa aatcttaggt taagtccctc     780
aaagattctg gaaaaatttc atatggtaat tcataaggca atttttgaaa ggaagtcaat    840
atgtcacaaa ttgaatgtaa cttttgaaaat ctttacccta ctttggaaaa aagtatcatt   900
ttagtataac ataaaatgaa ctacatgact gtcctctcca tggttaaatt ccttgtctgc    960
caacattata taactgactt tgtttcttc tgatttgttt tcatgcagtt aattttcaag    1020
aggaagagct tccttcctaa atttgattca aatctattcc aggaacaaac agaagcttaa    1080
agtttctttt cacagtttct tttaaggcgc cacttttgtt tctctgtggt ttcattatga    1140
gaagtaactc aaagtggaag aagattgttg taatgtattg catttctata cttgagagag    1200
tttttaagtt cttcagataa gtatggtatg tggttgcaag gtaattttca cttatttgca    1260
```

```
ataatacaaa tttgtgaatt tctgttattt gttagctaca cagtttatag tattttgtta    1320
cagcaggccc aacagaataa gagagacaat aagcagattc tgggaaaatg cagagtagg     1380 aagaaccagg aatctctctc ctgacctacc caactaatgc agtggcagaa tatgacttaa    1440
ctatcttgga actctggagt aatctaaggt tcacaatttc cagaggaagg cttaggttgt    1500
gtattagttt gttcttacgc tgttatgaag aaatacctga gactggatga tttatgaagg    1560
aaagaggttt aattgacaca caattccaca tgggtgggga ggcctcagga aacttataat    1620
catggtagaa gacaaagggg aagcgaggac cttcttcaca tggtggcaag agagagaaga    1680
gtgaaggaaa aacttccaaa cacttataaa accatcagat cttgcgagaa ctcactatca    1740
tgagaacagc atgggagaaa ctgcccccat gatccaatca cctccctccc ttgacatgtg    1800
atgattacag gtgcttccct cgaggtgtgg ggattacagt ttgagatgag atttggtggg    1860
gacacagagc caaaccatat cattccacct ctggcccctc ccaaatctca tgtcttttca    1920
catttcaaaa ccgatcatgc cttcccaaca gtccctcaaa gtcttaactc atttcagcat    1980
taactcaaaa gtccacagtc caaagtctca tctgagacaa ggcaagtctc ttccacctat    2040
aagcctgtaa aattgaaagc aagttagtta cttcctaaat acaatgggag gacaggcctt    2100
gggtaaatgc tcccattcca aatgggagaa attaaccaaa acaaaggggc gacaggcccc    2160
atgcaagtct gaaatccagc aaggcagtcc ttaaatctta aagctccaaa atgatctttt    2220
ttgactccat gtctcacacc caggacacac tgatgcaaag agtgggctcc catggccttg    2280
agtagcttct tcacaggctg gcattgagtg cctatggctt ttttaggtgc acggtgcaag    2340
aaggaggtga atctaccatt cttgggtctg gagaacagtg accctcttct cacagctccc    2400
ctaggcagtg ccccagtggg gactctgtgt gggggctcct accccatatt tcccttccac    2460
actgccctag cagaggtttt ccatgagggc tctgcccctg tagcagacct ctgcctggcc    2520
atccaggcat ttttatacct cctttgaaat ctaggcagac attcccaaac ctcaattctt    2580
gactaccatg tacccacagg cctaacacta cagggaagct gccaaggtct ggggcttgta    2640
ccctctgaag ccacagcctg agctgtacat tggctccttt tagctatggc tggagctaaa    2700
gtggctggga tgcatcatac caagtcccaa agctgcacac agcagtgggg gcctgggcct    2760
ggcccaataa atcatttta acctcctagg cctccaggcc tgtgatggga ggagctgccg    2820
ccaagatctc tgacaggctc tggagatatt tccccattg tctttgtgat taacattggg    2880
atcctcatta cttatgctaa ttttttgcagc cagtttgaat ttctccccag aaaatgggtt    2940
tttcttttct actgcatggt caggctgcaa ttttttccaaa cttttatgct ctgcttccct    3000
tttaaacgta agttccaatt tcaggtcatc tctctcaagt tcaaagttcc acagaaatct    3060
agggcagggg caaaatgtca ccagtctctt tgctaaagca tagcaagagt gactttttctc   3120 catttctcaa taagttatta atctccatct gagaccacct cagcctggac ttcattgtcc    3180
atccatatca ttatcagcat tttggtcaaa accattcaac aagtctctag gaagttccaa    3240
actttcccac atcttcctgt cttcttctga gccctccaaa ttgttccaat tctaaccat    3300 tacccagttc caaagttgct tccacatttt tttgtatttt tgtagcagta ccccactacc    3360
ttggtaccaa ttaactgtat tagtctgttt tcacactgct ataaagaagt acctgagact    3420
gggtaatgta taaaggaaag gggtttaatt gaatcactgt tccacatggc tggggaggcc    3480
tcaggaagct tacaattatg gcagaagggg aaacagccac cttcttcaca aggaagcagg    3540
agagagagca cacaggaaaa aactgccact tttaaaacca gcagatgtca taagaactca    3600
```

| | |
|---|---|
| ctcattatca tgagaacagc atgggggaaa ccaccccat gatccattca cctccctccc | 3660 |
| ttgacatgtg ggaattacat gttcctccct caacacaaat agggattata attcaagatt | 3720 |
| cgatttgtct ggggacacag agccaaacaa tatcaggttg taaattgcag ttagtttcag | 3780 |
| tcattgtcag ctgtagccat cccttaccct cagcggcttg gcaggcagct gtgcagatga | 3840 |
| tcctggagta gcttacacat agctttgccc agtgtggaca aaggaatgct gtactctaat | 3900 |
| tattggggat ctgtgctcta aattgttgct tctaaacata gaagtacaga aaaaggaaac | 3960 |
| cactgttgca tgttctctta ttgttgcccc cctcccccac cgaccccact tcccccaccc | 4020 |
| tctagtgact tccaggaaat ttgaaaggca agtgcttttt ccccactttc atttttctcc | 4080 |
| tttcttttct ggagggtcag acattaagga ctaggacatt tgaaattaag tcaccacata | 4140 |
| aacccgggga aagggtaca gactcagaaa acacttgaga agaccttacg tttgcacctc | 4200 |
| aggctaatgc tcagcacaca gatagcctac aaccacccca caaaa | 4245 |

<210> SEQ ID NO 6
<211> LENGTH: 962
<212> TYPE: DNA
<213> ORGANISM: Homo sapiens

<400> SEQUENCE: 6

| | |
|---|---|
| aacttatatt tcctctttgc agctatgttt tgggacttcc tctttcaccc atcaaaatat | 60 |
| ttctttaaaa aaaaaaatct ttccttccaa gttttttctt cctttgttac tatgacatga | 120 |
| ataaatcacc ttgtagattc tctgtgtttt gactgccttc tcatggtcag ggactagaaa | 180 |
| gacctgttgt gtggccattt gctatggtct gccctaccct gaccctcag ttcctacatt | 240 |
| gaagtcccaa cctcccagct gatggtagta agaggtggga tcttttggag ggtgactgga | 300 |
| tcatgatggc caagctcctg tgaatgggat tagtgccctt ctaaaatagg cccaagggag | 360 |
| ctcattcacc tcttgtcacc tcttttcacc tcttccacca tgcaaagaca cagcaagaag | 420 |
| atgctgtctt tgaaccagga aagctagccc tcacagacac caagtctgcc ttgatcttaa | 480 |
| actttccagg ccctggaact gtgagaagta aatttctgtg gtttataaac cacccagttt | 540 |
| aagatatttt gttgtagaaa ccccaacaga ctaagtcagc aatgcaaaaa atattagaac | 600 |
| taaagggacc ttgcactaat ctcatataag cccttcattt ttaaatatga aaacaaaaca | 660 |
| aaaccgaagt cctggcaatt agcctactaa atccacaggt agccagaggt agaactgact | 720 |
| cattgttatg tctccccagc tcaaacgtgt tcttccagat cataaacatt ggcttatgct | 780 |
| tctttccatc tcctttaaac cccagacaac tgctgggcac atgtaatact ttaaaaatat | 840 |
| ttctatatcg gccaggcatg atggctcatg cctgtaatcc cagcactttg ggaggccgag | 900 |
| gtgggtgcat tacctgaggt caggagtttg agaccagcct gagtaatatg gtgaaacacc | 960 |
| gt | 962 |

<210> SEQ ID NO 7
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 7

| | |
|---|---|
| tcacgaacac ccagagatgt | 20 |

<210> SEQ ID NO 8
<211> LENGTH: 20

```
<212> TYPE: DNA
<213> ORGANISM: Artificial sequence
<220> FEATURE:
<223> OTHER INFORMATION: Synthetic nucleic acid

<400> SEQUENCE: 8
accaccagac attagcccag                                               20

<210> SEQ ID NO 9
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 9
tgctgccaca agaacatttg                                               20

<210> SEQ ID NO 10
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 10
gtgtgtgtgt gtgtgtgtgt                                               20

<210> SEQ ID NO 11
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 11
tcacgaacac ccagagatgt                                               20

<210> SEQ ID NO 12
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 12
tccccagtca ttagcacagt                                               20

<210> SEQ ID NO 13
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 13
atagcctgcc ccaaatcact                                               20

<210> SEQ ID NO 14
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 14
```
tcttgggacc gtgaaagtgt                                          20

<210> SEQ ID NO 15
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 15
tcacgaacac ccagagatgt                                          20

<210> SEQ ID NO 16
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 16
tggttggaca gtaggggaag                                          20

<210> SEQ ID NO 17
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 17
tggttggaca gtaggggaag                                          20

<210> SEQ ID NO 18
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 18
agcatttagg agtgcacgtt                                          20

<210> SEQ ID NO 19
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 19
ctgtcccaca caccccatat                                          20

<210> SEQ ID NO 20
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 20
ctgtcccaca caccccatat                                          20

<210> SEQ ID NO 21
<211> LENGTH: 20
<212> TYPE: DNA
<213> ORGANISM: Artificial sequence

```
<220> FEATURE:
<223> OTHER INFORMATION: Synthetic nucleic acid

<400> SEQUENCE: 21
tctccatggg tcaggttgtt                                                 20

<210> SEQ ID NO 22
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 22
ctccatgttt ctcccgtgtg                                                 20

<210> SEQ ID NO 23
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 23
gcaataaacg tgggaatgcc                                                 20

<210> SEQ ID NO 24
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 24
cacagaaagc attgcccctt                                                 20

<210> SEQ ID NO 25
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 25
ctggtcttct cttccccact                                                 20

<210> SEQ ID NO 26
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 26
ctggtcttct cttccccact                                                 20

<210> SEQ ID NO 27
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 27
ctgctggtct tctcttcccc                                                 20
```

```
<210> SEQ ID NO 28
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 28
acaatcagtc actaggagga gg                                           22

<210> SEQ ID NO 29
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 29
ccatgtttgc taggctggtc                                              20

<210> SEQ ID NO 30
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 30
ccatgtttgc taggctggtc                                              20

<210> SEQ ID NO 31
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 31
cacttctcat ttctccaacc aca                                          23

<210> SEQ ID NO 32
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 32
tccaaacatg cagcagtcac                                              20

<210> SEQ ID NO 33
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 33
tcaccacctt ccggactttt                                              20

<210> SEQ ID NO 34
<211> LENGTH: 20
<212> TYPE: DNA
<213> ORGANISM: Artificial sequence
<220> FEATURE:
<223> OTHER INFORMATION: Synthetic nucleic acid
```

<400> SEQUENCE: 34
ccaaaagcac aagacagcct                                               20

<210> SEQ ID NO 35
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 35
ctgtgggtca aatgggagga                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 36
agggacaagc aagcatctct                                               20

<210> SEQ ID NO 37
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 37
aacttgagcc cagacaacct                                               20

<210> SEQ ID NO 38
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 38
gcttgcctct ctttgcctta                                               20

<210> SEQ ID NO 39
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 39
ccttggtttc ctggcctcta                                               20

<210> SEQ ID NO 40
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 40
tgcatgaggc agacttgttc                                               20

<210> SEQ ID NO 41

```
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 41
tgtggtccat atcccgtaga                                              20

<210> SEQ ID NO 42
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 42
cacgcccagc taatgtttgt                                              20

<210> SEQ ID NO 43
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 43
aactctgatg gcctcctctg                                              20

<210> SEQ ID NO 44
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 44
ggagggcagt gttgttcaaa                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 45
tcctgttgtg tacctggctt                                              20

<210> SEQ ID NO 46
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 46
ggagacccag ggaagagttg                                              20

<210> SEQ ID NO 47
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 47
```

```
gcagtgatca aaattatgtc cca                                               23

<210> SEQ ID NO 48
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 48
gcaaaggaaa gcaaacgacc                                                   20

<210> SEQ ID NO 49
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 49
gaagtgctct gctttccgag                                                   20

<210> SEQ ID NO 50
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 50
atccaagtgt ttccaaccgc                                                   20

<210> SEQ ID NO 51
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 51
caaatcaacg ggagcaagct                                                   20

<210> SEQ ID NO 52
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 52
tcatatctct ctggctgctc c                                                 21

<210> SEQ ID NO 53
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 53
atctcttggc catggagctt                                                   20

<210> SEQ ID NO 54
<211> LENGTH: 20
<212> TYPE: DNA
```

```
<213> ORGANISM: Artificial sequence
<220> FEATURE:
<223> OTHER INFORMATION: Synthetic nucleic acid

<400> SEQUENCE: 54
gatgttaggg gctctgcaga                                                   20

<210> SEQ ID NO 55
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 55
caggaagagg gagagcagag                                                   20

<210> SEQ ID NO 56
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 56
caggaagagg gagagcagag                                                   20

<210> SEQ ID NO 57
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 57
tacaggttct ttggtgccca                                                   20

<210> SEQ ID NO 58
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 58
tacaggttct ttggtgccca                                                   20

<210> SEQ ID NO 59
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 59
gagcaggaca cgtagactca                                                   20

<210> SEQ ID NO 60
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 60
aggctggtct tgaactccaa                                                   20
```

<210> SEQ ID NO 61
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 61
gcctcagcct ctagagtagc                                          20

<210> SEQ ID NO 62
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 62
actcccaacc tcatgatccg                                          20

<210> SEQ ID NO 63
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 63
tcgaactccc aacctcatga                                          20

<210> SEQ ID NO 64
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 64
aaggattggg gagtctctcg                                          20

<210> SEQ ID NO 65
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 65
atccctgcgg ccgaaatat                                           19

<210> SEQ ID NO 66
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 66
tccacacact tcctctggac                                          20

<210> SEQ ID NO 67
<211> LENGTH: 20
<212> TYPE: DNA
<213> ORGANISM: Artificial sequence
<220> FEATURE:

<223> OTHER INFORMATION: Synthetic nucleic acid

<400> SEQUENCE: 67
ggccgaagta cctagcatgt                                                   20

<210> SEQ ID NO 68
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 68
tccaaaggca cctgaatgag                                                   20

<210> SEQ ID NO 69
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 69
attccccata cagcacttcc                                                   20

<210> SEQ ID NO 70
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 70
gagagagacc acagcccttt                                                   20

<210> SEQ ID NO 71
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 71
tattccaggg cctagaacgg                                                   20

<210> SEQ ID NO 72
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 72 gaagggtgg aggtgagtac                                                    20

<210> SEQ ID NO 73
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 73
cgatgcgttt tctttatagc ca                                                22

-continued

```
<210> SEQ ID NO 74
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 74
gcggtcttat gtggtatgcc                                                   20

<210> SEQ ID NO 75
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 75
agtcaagatc ctggtggctt                                                   20

<210> SEQ ID NO 76
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 76
cccaagtctc ccttctacca                                                   20

<210> SEQ ID NO 77
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 77
ccaggctggc aaattgagtt                                                   20

<210> SEQ ID NO 78
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 78
gcggagactt taagggcttg                                                   20

<210> SEQ ID NO 79
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 79
ttggtcaccc tttctccagg                                                   20

<210> SEQ ID NO 80
<211> LENGTH: 20
<212> TYPE: DNA
<213> ORGANISM: Artificial sequence
<220> FEATURE:
<223> OTHER INFORMATION: Synthetic nucleic acid
```

<400> SEQUENCE: 80
cttcctcacg gcattgctac                                                  20

<210> SEQ ID NO 81
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 81
ggagtccaaa ggcagtctct                                                  20

<210> SEQ ID NO 82
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 82
tcctgttgtg tacctggctt                                                  20

<210> SEQ ID NO 83
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 83
tccaaggcca tctacagagc                                                  20

<210> SEQ ID NO 84
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 84
tccccactgc cttgttcata                                                  20

<210> SEQ ID NO 85
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 85
tgggcatttg gtggaattcg                                                  20

<210> SEQ ID NO 86
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 86
ctttctccga acgctcaagg                                                  20

<210> SEQ ID NO 87
<211> LENGTH: 20

```
<212> TYPE: DNA
<213> ORGANISM: Artificial sequence
<220> FEATURE:
<223> OTHER INFORMATION: Synthetic nucleic acid

<400> SEQUENCE: 87
atcatgagaa cagcacggga                                                  20

<210> SEQ ID NO 88
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 88
tcttggtcca atgcagtcct                                                  20

<210> SEQ ID NO 89
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 89
tgaggaccct actgttgctg                                                  20

<210> SEQ ID NO 90
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 90
tgagcacttt ggaaggcaag                                                  20

<210> SEQ ID NO 91
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 91
gagggtttca tttgctgggg                                                  20

<210> SEQ ID NO 92
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 92
gagggtttca tttgctgggg                                                  20

<210> SEQ ID NO 93
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 93
```
gagctgagat catgcactgc                                              20

<210> SEQ ID NO 94
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 94
gagctgagat catgcactgc                                              20

<210> SEQ ID NO 95
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 95
tgcccatttt cagcatacaa aa                                           22

<210> SEQ ID NO 96
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 96
tgtaggagga gcaggtttgg                                              20

<210> SEQ ID NO 97
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 97
cctagggtag cctcacgtg                                               19

<210> SEQ ID NO 98
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 98
cacctctctg tgcctctgac                                              20

<210> SEQ ID NO 99
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 99
cacctctctg tgcctctgac                                              20

<210> SEQ ID NO 100
<211> LENGTH: 20
<212> TYPE: DNA
<213> ORGANISM: Artificial sequence

```
<220> FEATURE:
<223> OTHER INFORMATION: Synthetic nucleic acid

<400> SEQUENCE: 100
gtatgtgtgg gcatttgtgc                                               20

<210> SEQ ID NO 101
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 101
ctgcatgcca aacttaaaac ct                                            22

<210> SEQ ID NO 102
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 102
agaaaggtgt ttgtggtgca                                               20

<210> SEQ ID NO 103
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 103
caagctactc aggaggctga                                               20

<210> SEQ ID NO 104
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 104
tctgctcagg atcactaggt                                               20

<210> SEQ ID NO 105
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 105
ttgcttctct gttttctttc cc                                            22

<210> SEQ ID NO 106
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 106
aaactctccc acgttcaccc                                               20
```

<210> SEQ ID NO 107
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 107
catctccctc ttggcttcca                                            20

<210> SEQ ID NO 108
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 108
ctccttcagc cacttcagga                                            20

<210> SEQ ID NO 109
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 109
gcccggccaa atatcagtag                                            20

<210> SEQ ID NO 110
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 110
agtcaagatc ctggtggctt                                            20

<210> SEQ ID NO 111
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 111
gcggtcttat gtggtatgcc                                            20

<210> SEQ ID NO 112
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 112
gtgtgaagtc aggtgcatgg                                            20

<210> SEQ ID NO 113
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 113
ccactcttca gcctactcgt                                          20

<210> SEQ ID NO 114
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 114
ttaaacattt tagcatcccc agg                                      23

<210> SEQ ID NO 115
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 115
tccgtagtga aagttttggg a                                        21

<210> SEQ ID NO 116
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 116
ctgctcttgt tctccactgc                                          20

<210> SEQ ID NO 117
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 117
tgatcctttc cttggcctca                                          20

<210> SEQ ID NO 118
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 118
attacagcac tttgggaggc                                          20

<210> SEQ ID NO 119
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 119
gtgctgtctc ccttctgtct                                          20

<210> SEQ ID NO 120

```
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 120
tcaggtaatg tgatgcctcc a                                              21

<210> SEQ ID NO 121
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 121
tgttaattac ctgaagcgcg t                                              21

<210> SEQ ID NO 122
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 122
aaagaaaatg ccaggcccag                                                20

<210> SEQ ID NO 123
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 123
tgagttggct gtaaatgtgt gt                                             22

<210> SEQ ID NO 124
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 124
gggtcaaaga gatggcagga                                                20

<210> SEQ ID NO 125
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 125
ttacaggcac gtaccaccat                                                20

<210> SEQ ID NO 126
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 126
```
tttgctgtaa ctgccctcct                                              20

<210> SEQ ID NO 127
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 127
gtaaaccact gcagactggc                                              20

<210> SEQ ID NO 128
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 128
catgccaaga tctgtagaca tct                                          23

<210> SEQ ID NO 129
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 129
gccatgcgcg ggatataatc                                              20

<210> SEQ ID NO 130
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 130
gaggactaca gtaacgaccc t                                            21

<210> SEQ ID NO 131
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 131
acattgtgcc cagatgttcc                                              20

<210> SEQ ID NO 132
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 132
ctggcagaca cctccactta                                              20

<210> SEQ ID NO 133
<211> LENGTH: 20
<212> TYPE: DNA

```
<213> ORGANISM: Artificial sequence
<220> FEATURE:
<223> OTHER INFORMATION: Synthetic nucleic acid

<400> SEQUENCE: 133
gggattacag gtgcccagaa                                                    20

<210> SEQ ID NO 134
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 134
gggattacag gtgcccagaa                                                    20

<210> SEQ ID NO 135
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 135
acagagttca ggacagtggt                                                    20

<210> SEQ ID NO 136
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 136
tggtaggagc ccagattctg                                                    20

<210> SEQ ID NO 137
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 137
ccctgctgct tccctttgaa                                                    20

<210> SEQ ID NO 138
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 138
atccacagaa ccatgctcca                                                    20

<210> SEQ ID NO 139
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 139
gacccaggaa gagctgatgt                                                    20
```

<210> SEQ ID NO 140
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 140
ctgaagagtg acacctcctc a                                              21

<210> SEQ ID NO 141
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 141
ctgaagagtg acacctcctc a                                              21

<210> SEQ ID NO 142
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 142
ccagcccctt atgcctctta                                                20

<210> SEQ ID NO 143
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 143
cagcttgaag tgccttgtgg                                                20

<210> SEQ ID NO 144
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 144
tttcatggct ccaacaacct                                                20

<210> SEQ ID NO 145
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 145
cacttctggt ttctcattct cga                                            23

<210> SEQ ID NO 146
<211> LENGTH: 19
<212> TYPE: DNA
<213> ORGANISM: Artificial sequence
<220> FEATURE:

```
<223> OTHER INFORMATION: Synthetic nucleic acid

<400> SEQUENCE: 146
ctctgcccag cctaggaac                                                      19

<210> SEQ ID NO 147
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 147
caggaggctc tgggaagaat                                                     20

<210> SEQ ID NO 148
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 148
aacgggagct tcgactgtaa                                                     20

<210> SEQ ID NO 149
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 149
caagtcctgc cctggtttac                                                     20

<210> SEQ ID NO 150
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 150
gaacaaaagc tcctgaggcc                                                     20

<210> SEQ ID NO 151
<211> LENGTH: 154
<212> TYPE: DNA
<213> ORGANISM: Artificial sequence
<220> FEATURE:
<223> OTHER INFORMATION: Synthetic nucleic acid

<400> SEQUENCE: 151
taaaccagga tcttcttcag cctccaaggt aaggaaatgt gtgatctcca agctccctct         60
tgtatgtatt gtgaacgcca ctgtcagaag agaaacacca aagttattca cctggaaatg       120
ttgcagtatg aagaccatgt atttgatgga gagg                                    154

<210> SEQ ID NO 152
<211> LENGTH: 152
<212> TYPE: DNA
<213> ORGANISM: Artificial sequence
<220> FEATURE:
<223> OTHER INFORMATION: Synthetic nucleic acid

<400> SEQUENCE: 152
```

```
ggctcaggct gagaggatat tctgccgttg tagttttgct cggggccatt cgtttttaaga    60 agactggaga gtcagttcca gtttgtcttg ggggactaag ttcttatcat gtggtttcta   120
ctggtggctt attagaacac atgcaggtac ag                                  152
```

<210> SEQ ID NO 153
<211> LENGTH: 304
<212> TYPE: DNA
<213> ORGANISM: Artificial sequence
<220> FEATURE:
<223> OTHER INFORMATION: Synthetic nucleic acid

<400> SEQUENCE: 153

```
cccagccctc agtggcccca cagcagcttg gctgttcttg gttttgtttc tctctgcttc    60
tgcatgatat ctttgaacaa aaagtcccaa gtgtacaaaa agtcccgaaa ggcgttcgca   120
aaccactgac ctagatggag ggaattgtga ggagcagagg gcaccctctt ataaaatgcc   180
tgtacttcgg tgcagggttt ggtggtgtcg gcggtttgga ggcccttaa gcttcctaac    240 tccttgtcac tggtggatgg tggggtgccg gcaggagggc atccctttac ataggggctc   300
attg                                                                304
```

<210> SEQ ID NO 154
<211> LENGTH: 171
<212> TYPE: DNA
<213> ORGANISM: Artificial sequence
<220> FEATURE:
<223> OTHER INFORMATION: Synthetic nucleic acid

<400> SEQUENCE: 154

```
ggggaatgag aaacaaaaga caaggttaat tatgacaccg gggctttaca atgctaaaaa    60
tatcctatat acaaagggat atgtaggctg tgttcttttt ccatgtcatt acaaagaaca   120
ggctcaaggt atctgcaaat ttctaataaa aatattatta cttgaaaaat g            171
```

<210> SEQ ID NO 155
<211> LENGTH: 118
<212> TYPE: DNA
<213> ORGANISM: Artificial sequence
<220> FEATURE:
<223> OTHER INFORMATION: Synthetic nucleic acid

<400> SEQUENCE: 155

```
gtccactttt aggagtgtat gtacttggac acctaaaaaa tatgctgcca caagaacatt    60
tgttgtagca ttctgtgctc atttatacag gtctagttaa gtaaactcta gcatacta     118
```

<210> SEQ ID NO 156
<211> LENGTH: 166
<212> TYPE: DNA
<213> ORGANISM: Artificial sequence
<220> FEATURE:
<223> OTHER INFORMATION: Synthetic nucleic acid

<400> SEQUENCE: 156

```
gcctttgaaa gtctcgcatc tgctgttttt caggtctcca agtccattct ttgtgtttgg    60
actggtgagt gtttctcaca ctctataatc gcaaagtagg gaggtatctc ttcaagaaga   120
caagtgtcat tcaaatattt ctgcataaca aaccagacaa aactta                  166
```

<210> SEQ ID NO 157
<211> LENGTH: 277
<212> TYPE: DNA

<213> ORGANISM: Artificial sequence
<220> FEATURE:
<223> OTHER INFORMATION: Synthetic nucleic acid

<400> SEQUENCE: 157

```
agactattta tgcatgcatt ggtctttgag ctgttccgcc tgctgtcttg taaactcaga      60
agcagttttc ctgaggtggg tattactgac catctagctc accatctgag actcataagt     120
agatttgtga gtggtgaggt gtagtgaaga ccacttgttt gggattcaac atacatgcca     180
gccaatgaaa atgttaactc acatctgcat atgccttcat cttgttatgg aactggaggc     240
accatcattc ataatgctta aaaataaaac acctgca                              277
```

<210> SEQ ID NO 158
<211> LENGTH: 147
<212> TYPE: DNA
<213> ORGANISM: Artificial sequence
<220> FEATURE:
<223> OTHER INFORMATION: Synthetic nucleic acid

<400> SEQUENCE: 158

```
gttaggttac atatcaagtt aggttcactg tgtactgaaa aacctttagg ccaaaattaa      60
aatatgtaca acggaggctt tagtccaaac ttaatttaac agtactacaa ttaagtatca     120
gtattgccat aatgtatcag tcagggt                                         147
```

<210> SEQ ID NO 159
<211> LENGTH: 116
<212> TYPE: DNA
<213> ORGANISM: Artificial sequence
<220> FEATURE:
<223> OTHER INFORMATION: Synthetic nucleic acid

<400> SEQUENCE: 159

```
gcttggaccc acagtacaga tcacccatct tgggcctatc acactgagca attgctgacc      60
tgcatctctg tggagtggag cccccaggag acaagtaaaa gaccccagc cacaac          116
```

<210> SEQ ID NO 160
<211> LENGTH: 151
<212> TYPE: DNA
<213> ORGANISM: Artificial sequence
<220> FEATURE:
<223> OTHER INFORMATION: Synthetic nucleic acid

<400> SEQUENCE: 160

```
ttcttctggc tgcctggaag atgcctctgt tattttagtg aaaacattta gctcctcgaa      60
aggtagagag aaccaagagg taaagtgtgc cattgtagac agctggtgtg tgtgccaggt     120
agcagtgctt ctgtctacat cctgggatat t                                    151
```

<210> SEQ ID NO 161
<211> LENGTH: 101
<212> TYPE: DNA
<213> ORGANISM: Artificial sequence
<220> FEATURE:
<223> OTHER INFORMATION: Synthetic nucleic acid

<400> SEQUENCE: 161

```
tttctgctat ctagatcttt gactaccaac cagccaggag tggtctgcct cttctttggt      60
ctgagcttgc cttgtgctta tattgttgta cccaagcgag t                         101
```

<210> SEQ ID NO 162
<211> LENGTH: 158

<212> TYPE: DNA
<213> ORGANISM: Artificial sequence
<220> FEATURE:
<223> OTHER INFORMATION: Synthetic nucleic acid

<400> SEQUENCE: 162
cgcgaccgtt ccattcttga gtttcttcac tttgccagct tgggtgtctc tcccgaggcc    60
gtcgttctag ttatggctca tccagctgac gctgcaactt ctcttgttct gtagcatttc   120
ttctacttct ctttctctac cagctgtgtc aaccggct                            158

<210> SEQ ID NO 163
<211> LENGTH: 189
<212> TYPE: DNA
<213> ORGANISM: Artificial sequence
<220> FEATURE:
<223> OTHER INFORMATION: Synthetic nucleic acid

<400> SEQUENCE: 163
cacatctcac ccccagacct gccattggca tgcacatctt taaccacaaa ccacgattga    60
aaatgagaaa gaaaactctc ctctagctgg gcgcttcata ggactagcca ggtacgacca   120
tctctgaggg tctttgacag ctcagtttta ctgcataatc tgttttcaag acccttaaa    180 agaccagat                                                           189

<210> SEQ ID NO 164
<211> LENGTH: 111
<212> TYPE: DNA
<213> ORGANISM: Artificial sequence
<220> FEATURE:
<223> OTHER INFORMATION: Synthetic nucleic acid

<400> SEQUENCE: 164
cataactacc agaagccatt ggtggcaaga tctcaatcag acatgtcgg tacaatgctc      60 tgattatctc gtctgcatcc ctgattactt atggtccaga tataaactac t             111

<210> SEQ ID NO 165
<211> LENGTH: 84
<212> TYPE: DNA
<213> ORGANISM: Artificial sequence
<220> FEATURE:
<223> OTHER INFORMATION: Synthetic nucleic acid

<400> SEQUENCE: 165
gtccttaagg ctgatgtgaa tctctgccct ttccaatgtg tcatgtgatt gctccaaatt    60
aaaacaccta ttattattat tttg                                          84

<210> SEQ ID NO 166
<211> LENGTH: 146
<212> TYPE: DNA
<213> ORGANISM: Artificial sequence
<220> FEATURE:
<223> OTHER INFORMATION: Synthetic nucleic acid

<400> SEQUENCE: 166
cacctcactt ctgttttctg tccattaatg cttcctgccc acgttgtggg gaggagctct    60
ctgaacctct gctgcttctg agggattcaa gaatatattt tttgctcaat taaactccta   120
aatctaattt gtctaaagct tttctt                                        146

<210> SEQ ID NO 167
<211> LENGTH: 171
<212> TYPE: DNA

<213> ORGANISM: Artificial sequence
<220> FEATURE:
<223> OTHER INFORMATION: Synthetic nucleic acid

<400> SEQUENCE: 167

```
acttcctgtc cgcgaccgtt ccattcttga gtttcttcac tttgccagct tgggtgtctc      60
tcccgaggcc gtcgttctag ttatggctca tccagctgac gctgcaactt ctcttgttct    120
gtagcatttc ttctacttct ctttctctac cagctgtgtc aaccggcttt g             171
```

<210> SEQ ID NO 168
<211> LENGTH: 265
<212> TYPE: DNA
<213> ORGANISM: Artificial sequence
<220> FEATURE:
<223> OTHER INFORMATION: Synthetic nucleic acid

<400> SEQUENCE: 168

```
tgattacctc actctcatgc agggctgaat attactgttt cccctgttaa acaagggtgt      60
attacttccg aaatctgaca accccaagca ccaaaaggtt taaaaatatc tcgagattgt    120
aaagcctccg acagaatgct gaaacaggat tgcacagttg accaggagct tctgaggttg    180
tggcggaccc tccatgtttc tgactgccgg acagtcacag ccccctcttc cctaatgcca    240
ccagatgttc cctgggacac ctgcc                                          265
```

<210> SEQ ID NO 169
<211> LENGTH: 101
<212> TYPE: DNA
<213> ORGANISM: Artificial sequence
<220> FEATURE:
<223> OTHER INFORMATION: Synthetic nucleic acid

<400> SEQUENCE: 169

```
tttctgctat ctagatcttt gactaccaac cagccaggag tggtctgcct cttctttggt      60
ctgagcttgc cttgtgctta tattgttgta cccaagcgag t                        101
```

<210> SEQ ID NO 170
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 170

```
gccactgtca gaagagaaa                                                   19
```

<210> SEQ ID NO 171
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 171

```
tcttcagcct ccaaggtaa                                                   19
```

<210> SEQ ID NO 172
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 172

```
ggaaatgtgt gatctccaa                                                19
```

<210> SEQ ID NO 173
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 173

```
gagaggatat tctgccgtt                                                19
```

<210> SEQ ID NO 174
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 174

```
ggtttctact ggtggctta                                                19
```

<210> SEQ ID NO 175
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 175

```
ctctgcttct gcatgatat                                                19
```

<210> SEQ ID NO 176
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 176

```
gagggcatcc ctttacata                                                19
```

<210> SEQ ID NO 177
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 177

```
ggctcaaggt atctgcaaa                                                19
```

<210> SEQ ID NO 178
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 178

```
agcattctgt gctcattta                                                19
```

<210> SEQ ID NO 179
<211> LENGTH: 19
<212> TYPE: DNA

```
<213> ORGANISM: Artificial sequence
<220> FEATURE:
<223> OTHER INFORMATION: Synthetic nucleic acid

<400> SEQUENCE: 179
gagtgtatgt acttggaca                                                 19

<210> SEQ ID NO 180
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 180
gagtgtttct cacactcta                                                 19

<210> SEQ ID NO 181
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 181
ggaggtatct cttcaagaa                                                 19

<210> SEQ ID NO 182
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 182
gaggcaccat cattcataa                                                 19

<210> SEQ ID NO 183
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 183
ctcaccatct gagactcat                                                 19

<210> SEQ ID NO 184
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 184
ggctttagtc caaacttaa                                                 19

<210> SEQ ID NO 185
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 185
gccataattg tatcagtca                                                 19
```

<210> SEQ ID NO 186
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 186
taggttcact gtgtactga                                                19

<210> SEQ ID NO 187
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 187
cacactgagc aattgctga                                                19

<210> SEQ ID NO 188
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 188
ctgtctacat cctgggata                                                19

<210> SEQ ID NO 189
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 189
taaagtgtgc cattgtaga                                                19

<210> SEQ ID NO 190
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 190
cttatattgt tgtacccaa                                                19

<210> SEQ ID NO 191
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 191
ctatctagat ctttgacta                                                19

<210> SEQ ID NO 192
<211> LENGTH: 19
<212> TYPE: DNA
<213> ORGANISM: Artificial sequence
<220> FEATURE:

<223> OTHER INFORMATION: Synthetic nucleic acid

<400> SEQUENCE: 192
caacttctct tgttctgta                                                19

<210> SEQ ID NO 193
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 193
ctcttgttct gtagcattt                                                19

<210> SEQ ID NO 194
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 194
ccgttccatt cttgagttt                                                19

<210> SEQ ID NO 195
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 195
gagggtcttt gacagctca                                                19

<210> SEQ ID NO 196
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 196
ctgccattgg catgcacat                                                19

<210> SEQ ID NO 197
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 197
gcatgcacat ctttaacca                                                19

<210> SEQ ID NO 198
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 198
ctgattatct cgtctgcat                                                19

<210> SEQ ID NO 199
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 199
ctgcatccct gattactta                                                19

<210> SEQ ID NO 200
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 200
tacttatggt ccagatata                                                19

<210> SEQ ID NO 201
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 201
gaatctctgc cctttccaa                                                19

<210> SEQ ID NO 202
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 202
tccaatgtgt catgtgatt                                                19

<210> SEQ ID NO 203
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 203
caattaaact cctaaatct                                                19

<210> SEQ ID NO 204
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 204
ctgagggatt caagaatat                                                19

<210> SEQ ID NO 205
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 205
ctgaacctct gctgcttct                                            19

<210> SEQ ID NO 206
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 206
caacttctct tgttctgta                                            19

<210> SEQ ID NO 207
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 207
ccgttccatt cttgagttt                                            19

<210> SEQ ID NO 208
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 208
ccgacagaat gctgaaaca                                            19

<210> SEQ ID NO 209
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 209
gggtgtatta cttccgaaa                                            19

<210> SEQ ID NO 210
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 210
ctcatgcagg gctgaatat                                            19

<210> SEQ ID NO 211
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 211
cttatattgt tgtacccaa                                            19

<210> SEQ ID NO 212
<211> LENGTH: 19

```
<212> TYPE: DNA
<213> ORGANISM: Artificial sequence
<220> FEATURE:
<223> OTHER INFORMATION: Synthetic nucleic acid

<400> SEQUENCE: 212
ctatctagat ctttgacta                                              19

<210> SEQ ID NO 213
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 213
gccacuguca gaagagaaa                                              19

<210> SEQ ID NO 214
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 214
ucuucagccu ccaagguaa                                              19

<210> SEQ ID NO 215
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 215
ggaaaugugu gaucuccaa                                              19

<210> SEQ ID NO 216
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 216
gagaggauau ucugccguu                                              19

<210> SEQ ID NO 217
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 217
gguuucuacu gguggcuua                                              19

<210> SEQ ID NO 218
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 218
```

-continued cucugcuucu gcaugauau                                                19

<210> SEQ ID NO 219
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 219
gagggcaucc cuuuacaua                                                19

<210> SEQ ID NO 220
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 220
ggcucaaggu aucugcaaa                                                19

<210> SEQ ID NO 221
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 221
agcauucugu gcucauua                                                 19

<210> SEQ ID NO 222
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 222
gaguguaugu acuuggaca                                                19

<210> SEQ ID NO 223
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 223
gaguguuucu cacacucua                                                19

<210> SEQ ID NO 224
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 224
ggagguaucu cuucaagaa                                                19

<210> SEQ ID NO 225
<211> LENGTH: 19
<212> TYPE: RNA
<213> ORGANISM: Artificial sequence

```
<220> FEATURE:
<223> OTHER INFORMATION: Synthetic nucleic acid

<400> SEQUENCE: 225
gaggcaccau cauucauaa                                                    19

<210> SEQ ID NO 226
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 226
cucaccaucu gagacucau                                                    19

<210> SEQ ID NO 227
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 227
ggcuuuaguc caaacuuaa                                                    19

<210> SEQ ID NO 228
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 228
gccauaauug uaucaguca                                                    19

<210> SEQ ID NO 229
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 229
uagguucacu guguacuga                                                    19

<210> SEQ ID NO 230
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 230
cacacugagc aauugcuga                                                    19

<210> SEQ ID NO 231
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 231
cugucuacau ccugggaua                                                    19
```

```
<210> SEQ ID NO 232
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 232
uaaagugugc cauuguaga                                                     19

<210> SEQ ID NO 233
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 233
cuuauauugu uguacccaa                                                     19

<210> SEQ ID NO 234
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 234
cuaucuagau cuuugacua                                                     19

<210> SEQ ID NO 235
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 235
caacuucucu uguucugua                                                     19

<210> SEQ ID NO 236
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 236
cucuuguucu guagcauuu                                                     19

<210> SEQ ID NO 237
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 237
ccguuccauu cuugaguuu                                                     19

<210> SEQ ID NO 238
<211> LENGTH: 19
<212> TYPE: RNA
<213> ORGANISM: Artificial sequence
<220> FEATURE:
<223> OTHER INFORMATION: Synthetic nucleic acid
```

```
<400> SEQUENCE: 238
gagggucuuu gacagcuca                                                19

<210> SEQ ID NO 239
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 239
cugccauugg caugcacau                                                19

<210> SEQ ID NO 240
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 240
gcaugcacau cuuuaacca                                                19

<210> SEQ ID NO 241
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 241
cugauuaucu cgucugcau                                                19

<210> SEQ ID NO 242
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 242
cugcaucccu gauuacuua                                                19

<210> SEQ ID NO 243
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 243
uacuuauggu ccagauaua                                                19

<210> SEQ ID NO 244
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 244
gaaucucugc ccuuuccaa                                                19

<210> SEQ ID NO 245
```

```
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 245 uccaugugu caugugauu                                                    19

<210> SEQ ID NO 246
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 246
caauuaaacu ccuaaaucu                                                   19

<210> SEQ ID NO 247
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 247
cugagggauu caagaauau                                                   19

<210> SEQ ID NO 248
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 248
cugaaccucu gcugcuucu                                                   19

<210> SEQ ID NO 249
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 249
caacuucucu uguucugua                                                   19

<210> SEQ ID NO 250
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 250
ccguuccauu cuugaguuu                                                   19

<210> SEQ ID NO 251
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 251
```

```
ccgacagaau gcugaaaca                                                19

<210> SEQ ID NO 252
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 252
ggguguauua cuuccgaaa                                                19

<210> SEQ ID NO 253
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 253
cucaugcagg gcugaauau                                                19

<210> SEQ ID NO 254
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 254
cuuauauugu uguacccaa                                                19

<210> SEQ ID NO 255
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 255
cuaucuagau cuuugacua                                                19

<210> SEQ ID NO 256
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 256
uuucucuucu gacauggc                                                 19

<210> SEQ ID NO 257
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 257
uuaccuugga ggcugaaga                                                19

<210> SEQ ID NO 258
<211> LENGTH: 19
<212> TYPE: RNA
```

<213> ORGANISM: Artificial sequence
<220> FEATURE:
<223> OTHER INFORMATION: Synthetic nucleic acid

<400> SEQUENCE: 258
uuggagauca cacauuucc                                                      19

<210> SEQ ID NO 259
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 259
aacggcagaa uauccucuc                                                      19

<210> SEQ ID NO 260
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 260
aacggcagaa uauccucuc                                                      19

<210> SEQ ID NO 261
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 261
auaucaugca gaagcagag                                                      19

<210> SEQ ID NO 262
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 262
uauguaaagg gaugcccuc                                                      19

<210> SEQ ID NO 263
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 263
uuugcagaua ccuugagcc                                                      19

<210> SEQ ID NO 264
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 264
uaaaugagca cagaaugcu                                                      19

<210> SEQ ID NO 265
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 265
uguccaagua cauacacuc                                                  19

<210> SEQ ID NO 266
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 266
uagaguguga gaaacacuc                                                  19

<210> SEQ ID NO 267
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 267
uucuugaaga gauaccucc                                                  19

<210> SEQ ID NO 268
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 268
uuaugaauga uggugccuc                                                  19

<210> SEQ ID NO 269
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 269
augagucuca gauggugag                                                  19

<210> SEQ ID NO 270
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 270
uuaaguuugg acuaaagcc                                                  19

<210> SEQ ID NO 271
<211> LENGTH: 19
<212> TYPE: RNA
<213> ORGANISM: Artificial sequence
<220> FEATURE:

<223> OTHER INFORMATION: Synthetic nucleic acid

<400> SEQUENCE: 271
ugacugauac aauuauggc                                           19

<210> SEQ ID NO 272
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 272
ucaguacaca gugaaccua                                           19

<210> SEQ ID NO 273
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 273
ucagcaauug cucagugug                                           19

<210> SEQ ID NO 274
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 274
uaucccagga uguagacag                                           19

<210> SEQ ID NO 275
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 275
ucuacaaugg cacacuuua                                           19

<210> SEQ ID NO 276
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 276
uuggguacaa caauauaag                                           19

<210> SEQ ID NO 277
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 277
uagucaaaga ucuagauag                                           19

```
<210> SEQ ID NO 278
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 278
uacagaacaa gagaaguug                                                    19

<210> SEQ ID NO 279
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 279
aaaugcuaca gaacaagag                                                    19

<210> SEQ ID NO 280
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 280
aaacucaaga auggaacgg                                                    19

<210> SEQ ID NO 281
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 281
ugagcuguca aagacccuc                                                    19

<210> SEQ ID NO 282
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 282
augugcaugc caauggcag                                                    19

<210> SEQ ID NO 283
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 283
ugguuaaaga ugugcaugc                                                    19

<210> SEQ ID NO 284
<211> LENGTH: 19
<212> TYPE: RNA
<213> ORGANISM: Artificial sequence
<220> FEATURE:
<223> OTHER INFORMATION: Synthetic nucleic acid
```

```
<400> SEQUENCE: 284
augcagacga gauaaucag                                              19

<210> SEQ ID NO 285
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 285
uaaguaauca gggaugcag                                              19

<210> SEQ ID NO 286
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 286
uauaucugga ccauaagua                                              19

<210> SEQ ID NO 287
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 287
uuggaaaggg cagagauuc                                              19

<210> SEQ ID NO 288
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 288
aaucacauga cacauugga                                              19

<210> SEQ ID NO 289
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 289
agauuuagga guuuaauug                                              19

<210> SEQ ID NO 290
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 290
auauucuuga aucccucag                                              19

<210> SEQ ID NO 291
<211> LENGTH: 19
```

```
<212> TYPE: RNA
<213> ORGANISM: Artificial sequence
<220> FEATURE:
<223> OTHER INFORMATION: Synthetic nucleic acid

<400> SEQUENCE: 291
agaagcagca gagguucag                                                    19

<210> SEQ ID NO 292
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 292
uacagaacaa gagaaguug                                                    19

<210> SEQ ID NO 293
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 293
aaacucaaga auggaacgg                                                    19

<210> SEQ ID NO 294
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 294
uguuucagca uucugucgg                                                    19

<210> SEQ ID NO 295
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 295
uuucggaagu aauacaccc                                                    19

<210> SEQ ID NO 296
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 296
auauucagcc cugcaugag                                                    19

<210> SEQ ID NO 297
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 297
```

-continued uugggu acaa caauauaag                                                    19

<210> SEQ ID NO 298
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 298
uagucaaaga ucuagauag                                                     19

<210> SEQ ID NO 299
<211> LENGTH: 312
<212> TYPE: DNA
<213> ORGANISM: Artificial sequence
<220> FEATURE:
<223> OTHER INFORMATION: Synthetic nucleic acid

<400> SEQUENCE: 299
acagtctaca aagaggccgt ggaagctgtc ggggaaggag aatgttcaag tagcacaggc         60
aatcaaacac ttcctattgc tccaggtgcc aaagcaggaa tgaaaacctg tcccctctgt        120
tgaatactct tcttcttcac tcctaaaact acacacctga tgttagtcgt cagccctctt        180
cttatcactc tacacctgct gctctggaga actcatccag gcctgtggct ccctgcacgt        240
ctacactagt aacctctgaa tccacggtct ccagcactcc ctcctgctcc catccccagg        300
tggcagtcag gt                                                           312

<210> SEQ ID NO 300
<211> LENGTH: 273
<212> TYPE: DNA
<213> ORGANISM: Artificial sequence
<220> FEATURE:
<223> OTHER INFORMATION: Synthetic nucleic acid

<400> SEQUENCE: 300
gaattcaaag ggtctcttct agaggatcct gggttatgtc ctccacagga actttggtgt         60
tggcccctct tcctcaaatg tgaggatgta ccaatggcct ccccattatc tcctttcttt        120
ttctttctaa ctccaatgtt tataaagcct atatccctgt agtgtatgta ggttctctga        180
cagaagttat acttagtgct ctgtctttct tatggggaaa aatccctgga actgaagcta        240
agatctttag tacttggagt caccctacag ata                                    273

<210> SEQ ID NO 301
<211> LENGTH: 216
<212> TYPE: DNA
<213> ORGANISM: Artificial sequence
<220> FEATURE:
<223> OTHER INFORMATION: Synthetic nucleic acid

<400> SEQUENCE: 301
atggtttgtt ttcccctctc cctgctagaa gcacaagggg attttctctc gataatcatt         60
gtgagaacct gttagaactc ctggaggtaa aactcaaaag tatggcggcc cccctgaatg        120
agtcttcctg gaattaactg tcaaacttgc cactctgagt ctccagcaat tcttgaatta        180
caattcagat tttcctatcc tggtacaggt tcctgt                                 216

<210> SEQ ID NO 302
<211> LENGTH: 179
<212> TYPE: DNA
<213> ORGANISM: Artificial sequence

```
<220> FEATURE:
<223> OTHER INFORMATION: Synthetic nucleic acid

<400> SEQUENCE: 302
taccaatgtc tctgggcctt gctctactag tacaacagag gagagagaaa ttctagaaga    60
ttttcaactc ccctcctgct ctgtaactct ggttcgctat gtgctaaatg cacccttgaaa  120 taaacacttc ctttgtgtgt gtgtgttgcg cggtggaatc ctcactttac agaagagga    179

<210> SEQ ID NO 303
<211> LENGTH: 131
<212> TYPE: DNA
<213> ORGANISM: Artificial sequence
<220> FEATURE:
<223> OTHER INFORMATION: Synthetic nucleic acid

<400> SEQUENCE: 303
cacttgcttc taggctgagg agggcggggc tgttgtcaga gcccagaatc aaagccagag    60
gagcaggtgg acgctgagac tgtcccctca ccctgctcca cgggcaatgt tgaagtgggc  120
atctgggtgt t                                                       131

<210> SEQ ID NO 304
<211> LENGTH: 303
<212> TYPE: DNA
<213> ORGANISM: Artificial sequence
<220> FEATURE:
<223> OTHER INFORMATION: Synthetic nucleic acid

<400> SEQUENCE: 304
accatgactc accctctttc ctcgtcacct gctagtcctc ccattcactc cccttcagtc    60
atattggcct tgcttctctt cagacgggcc agccacactc agggcctttg cactgactat  120
tccttctgcc tggaatgttc ctcctccaag tatccatatg gctaactccc tcaattcttt  180
gagatcttta accacaaggc gctttcccaa ataagtcttc tctggctacc cttttttaaaa 240 ttttaacccc caccctttcac attttatata ctcccctttcc ttgccttttt tcagcttctt 300
gtc                                                                303

<210> SEQ ID NO 305
<211> LENGTH: 184
<212> TYPE: DNA
<213> ORGANISM: Artificial sequence
<220> FEATURE:
<223> OTHER INFORMATION: Synthetic nucleic acid

<400> SEQUENCE: 305
caatcgctgc ctgagtacct atgtgttcgt ggcttgattt accttatctg taattcctgg    60
atgttaaaag gacaccaaaa atctctgaca ccctgattag cctaccttga agaacccaag  120
cccaggattt ctgcctttgc ctagaaaaag gactgattca gaacttcctg agctacctag  180
tatt                                                               184

<210> SEQ ID NO 306
<211> LENGTH: 188
<212> TYPE: DNA
<213> ORGANISM: Artificial sequence
<220> FEATURE:
<223> OTHER INFORMATION: Synthetic nucleic acid

<400> SEQUENCE: 306
cacaatgaga gttgtcccta gatttcactg gaatgtaaat aaaagccttg atcattctca    60
```

```
ctgctcgaca gccacagttt cactttgttc ttcatggctc tgccaaccct ctgaaactct    120
cagtcacggg gactgtgctc tcagctttcc tccaagaatt tctccactgc cattgcctcc    180
tgtttttt                                                             188
```

<210> SEQ ID NO 307
<211> LENGTH: 206
<212> TYPE: DNA
<213> ORGANISM: Artificial sequence
<220> FEATURE:
<223> OTHER INFORMATION: Synthetic nucleic acid

<400> SEQUENCE: 307

```
atcctctgac ttggggcaga gctgaggtag acatctgggt gtgtctggga aacccggggg    60
aaggttcctt tctgtcctgt cactgtctgt gtgtgcttat gtgtctgtgt gtgtctgtgt   120
ctttgccacc agaaggagtt gggcctgttt gctcatgagc agctgtcgag gaggcccact   180
gtgtaccaca tatgcggctc ctgagg                                         206
```

<210> SEQ ID NO 308
<211> LENGTH: 166
<212> TYPE: DNA
<213> ORGANISM: Artificial sequence
<220> FEATURE:
<223> OTHER INFORMATION: Synthetic nucleic acid

<400> SEQUENCE: 308

```
gcctttgaaa gtctcgcatc tgctgttttt caggtctcca agtccattct tgtgtttgg     60 actggtgagt gttctctcaca ctctataatc gcaaagtagg gaggtatctc ttcaagaaga   120
caagtgtcat tcaaatattt ctgcataaca aaccagacaa aactta                   166
```

<210> SEQ ID NO 309
<211> LENGTH: 271
<212> TYPE: DNA
<213> ORGANISM: Artificial sequence
<220> FEATURE:
<223> OTHER INFORMATION: Synthetic nucleic acid

<400> SEQUENCE: 309

```
ctatctctct ctttcatggg tcagtttcta tttccctctg tgtttctgtt cattgtcttc    60
ctggtggcta acttctgctt atagtttctg ctcccttta acttctgtgt gcacatgact    120
tggacttgtt atggtactat gctctgtgct ggaaacgtag cggtgagtaa ggcagccctg   180
acttctcagc tctgcatagg acccacagta gggtagggaa taaacacaca cacacacaca   240
cacacacaca cacagttgtg atgtgctatg a                                   271
```

<210> SEQ ID NO 310
<211> LENGTH: 200
<212> TYPE: DNA
<213> ORGANISM: Artificial sequence
<220> FEATURE:
<223> OTHER INFORMATION: Synthetic nucleic acid

<400> SEQUENCE: 310

```
aggaactagc taacataggt tttgttatct gcttcgagtg tgctctgtgt gcatccacac    60
ccaagtccca ggccccaaga gtctgtgtgg agctgtgtga tgggctgatg gtacctctta   120
catgaggcct tttgggagat actgagaaag cactgactag gagttgaggc tccaccccag   180
attagtcatc atctgtgtgt                                                200
```

-continued

```
<210> SEQ ID NO 311
<211> LENGTH: 93
<212> TYPE: DNA
<213> ORGANISM: Artificial sequence
<220> FEATURE:
<223> OTHER INFORMATION: Synthetic nucleic acid

<400> SEQUENCE: 311
tgtaattatt tgtttactgt aggcctcccc tttgatgagg agcccctgg gagtgtcagg      60 ctctctgctg tccccccagc accagcacaa ggc                                 93

<210> SEQ ID NO 312
<211> LENGTH: 135
<212> TYPE: DNA
<213> ORGANISM: Artificial sequence
<220> FEATURE:
<223> OTHER INFORMATION: Synthetic nucleic acid

<400> SEQUENCE: 312
ttagtttcag ttctttgata cttttttgag aggcctgaag gtcctttcct gatatagaac    60
tcacgtaaac aaataaaagc ttcaagtttt aagacaagaa gggtcaattt ctttgtttat   120
ccaaaaaact atcta                                                    135

<210> SEQ ID NO 313
<211> LENGTH: 241
<212> TYPE: DNA
<213> ORGANISM: Artificial sequence
<220> FEATURE:
<223> OTHER INFORMATION: Synthetic nucleic acid

<400> SEQUENCE: 313
cctacactga agcccatgg ggttgaagca ggatttggtt cacgctagaa cttctgagag      60
tcagtgtgta tcttgataaa cagcaacaga gcttagtcat gagttccctg taactggctg   120
ctcagagagt ttgctcccca cctcctgggg agaacttacc tgggaagagg ccaatgtttc   180
tatctaagcc tgtcccgtcc tctgagtttc caaccttcta atttcacgtt gggagtgcct   240
c                                                                   241

<210> SEQ ID NO 314
<211> LENGTH: 265
<212> TYPE: DNA
<213> ORGANISM: Artificial sequence
<220> FEATURE:
<223> OTHER INFORMATION: Synthetic nucleic acid

<400> SEQUENCE: 314
tgattacctc actctcatgc agggctgaat attactgttt ccctgttaa acaagggtgt     60 attacttccg aaatctgaca accccaagca ccaaaaggtt taaaaatatc tcgagattgt   120
aaagcctccg acagaatgct gaaacaggat tgcacagttg accaggagct tctgaggttg   180
tggcggaccc tccatgtttc tgactgccgg acagtcacag ccccctcttc cctaatgcca   240
ccagatgttc cctgggacac ctgcc                                         265

<210> SEQ ID NO 315
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 315
```

-continued cacctgatgt tagtcgtca                                               19

<210> SEQ ID NO 316
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 316
ctcttcttct tcactccta                                               19

<210> SEQ ID NO 317
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 317
ctttctaact ccaatgttt                                               19

<210> SEQ ID NO 318
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 318
gtatgtaggt tctctgaca                                               19

<210> SEQ ID NO 319
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 319
cctcaaatgt gaggatgta                                               19

<210> SEQ ID NO 320
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 320
ctctgagtct ccagcaatt                                               19

<210> SEQ ID NO 321
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 321
gtgagaacct gttagaact                                               19

<210> SEQ ID NO 322
<211> LENGTH: 19
<212> TYPE: DNA
<213> ORGANISM: Artificial sequence

```
<220> FEATURE:
<223> OTHER INFORMATION: Synthetic nucleic acid

<400> SEQUENCE: 322
ctgtaactct ggttcgcta                                                  19

<210> SEQ ID NO 323
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 323
gagagaaatt ctagaagat                                                  19

<210> SEQ ID NO 324
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 324
ttgtcagagc ccagaatca                                                  19

<210> SEQ ID NO 325
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 325
gctccacggg caatgttga                                                  19

<210> SEQ ID NO 326
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 326
ctaactccct caattcttt                                                  19

<210> SEQ ID NO 327
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 327
ctcgtcacct gctagtcct                                                  19

<210> SEQ ID NO 328
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 328
gtgttcgtgg cttgattta                                                  19
```

<210> SEQ ID NO 329
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 329
ttcagaactt cctgagcta					19

<210> SEQ ID NO 330
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 330
ctgacaccct gattagcct					19

<210> SEQ ID NO 331
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 331
cagctttcct ccaagagat					19

<210> SEQ ID NO 332
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 332
gccacagttt cactttgtt					19

<210> SEQ ID NO 333
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 333
ctctgccaac cctctgaaa					19

<210> SEQ ID NO 334
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 334
cactgtctgt gtgtgctta					19

<210> SEQ ID NO 335
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 335
ctgtgtcttt gccaccaga                                              19

<210> SEQ ID NO 336
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 336
gagtgtttct cacactcta                                              19

<210> SEQ ID NO 337
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 337
ggaggtatct cttcaagaa                                              19

<210> SEQ ID NO 338
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 338
ctctctcttt catgggtca                                              19

<210> SEQ ID NO 339
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 339
ctgtgtttct gttcattgt                                              19

<210> SEQ ID NO 340
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 340
cccacagtag ggtagggaa                                              19

<210> SEQ ID NO 341
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 341
gatggtacct cttacatga                                              19

<210> SEQ ID NO 342

```
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 342
tgctctgtgt gcatccaca                                                    19

<210> SEQ ID NO 343
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 343
gggagatact gagaaagca                                                    19

<210> SEQ ID NO 344
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 344
gtgtcaggct ctctgctgt                                                    19

<210> SEQ ID NO 345
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 345
gggtcaattt ctttgttta                                                    19

<210> SEQ ID NO 346
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 346
gtcctttcct gatatagaa                                                    19

<210> SEQ ID NO 347
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 347
caatttcttt gtttatcca                                                    19

<210> SEQ ID NO 348
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 348
```
cagtgtgtat cttgataaa                                              19

<210> SEQ ID NO 349
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 349
gagtcagtgt gtatcttga                                              19

<210> SEQ ID NO 350
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 350
ccgacagaat gctgaaaca                                              19

<210> SEQ ID NO 351
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 351
gggtgtatta cttccgaaa                                              19

<210> SEQ ID NO 352
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 352
ctcatgcagg gctgaatat                                              19

<210> SEQ ID NO 353
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 353
caccugaugu uagucguca                                              19

<210> SEQ ID NO 354
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 354
cucuucuucu ucacuccua                                              19

<210> SEQ ID NO 355
<211> LENGTH: 19
<212> TYPE: RNA

```
<213> ORGANISM: Artificial sequence
<220> FEATURE:
<223> OTHER INFORMATION: Synthetic nucleic acid

<400> SEQUENCE: 355
cuuucuaacu ccaauguuu                                                  19

<210> SEQ ID NO 356
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 356
guauguaggu ucucugaca                                                  19

<210> SEQ ID NO 357
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 357
ccucaaaugu gaggaugua                                                  19

<210> SEQ ID NO 358
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 358
cucugagucu ccagcaauu                                                  19

<210> SEQ ID NO 359
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 359
gugagaaccu guuagaacu                                                  19

<210> SEQ ID NO 360
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 360
cuguaacucu gguucgcua                                                  19

<210> SEQ ID NO 361
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 361
gagagaaauu cuagaagau                                                  19
```

```
<210> SEQ ID NO 362
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 362
uugucagagc ccagaauca                                                    19

<210> SEQ ID NO 363
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 363
gcuccacggg caauguuga                                                    19

<210> SEQ ID NO 364
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 364
cuaacucccu caauucuuu                                                    19

<210> SEQ ID NO 365
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 365
cucgucaccu gcuaguccu                                                    19

<210> SEQ ID NO 366
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 366
guguucgugg cuugauuua                                                    19

<210> SEQ ID NO 367
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 367
uucagaacuu ccugagcua                                                    19

<210> SEQ ID NO 368
<211> LENGTH: 19
<212> TYPE: RNA
<213> ORGANISM: Artificial sequence
<220> FEATURE:
```

<223> OTHER INFORMATION: Synthetic nucleic acid

<400> SEQUENCE: 368
cugacacccu gauuagccu                                                    19

<210> SEQ ID NO 369
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 369
cagcuuuccu ccaagagau                                                    19

<210> SEQ ID NO 370
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 370
gccacaguuu cacuuuguu                                                    19

<210> SEQ ID NO 371
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 371
cucugccaac ccucugaaa                                                    19

<210> SEQ ID NO 372
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 372
cacugucugu gugugcuua                                                    19

<210> SEQ ID NO 373
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 373
cugugucuuu gccaccaga                                                    19

<210> SEQ ID NO 374
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 374
gaguguuucu cacacucua                                                    19

```
<210> SEQ ID NO 375
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 375
ggagguaucu cuucaagaa                                                  19

<210> SEQ ID NO 376
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 376
cucucucuuu caugguca                                                   19

<210> SEQ ID NO 377
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 377
cuguguuucu guucauugu                                                  19

<210> SEQ ID NO 378
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 378
cccacaguag gguagggaa                                                  19

<210> SEQ ID NO 379
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 379
gaugguaccu cuuacauga                                                  19

<210> SEQ ID NO 380
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 380
ugcucugugu gcauccaca                                                  19

<210> SEQ ID NO 381
<211> LENGTH: 19
<212> TYPE: RNA
<213> ORGANISM: Artificial sequence
<220> FEATURE:
<223> OTHER INFORMATION: Synthetic nucleic acid
```

```
<400> SEQUENCE: 381
gggagauacu gagaaagca                                                    19

<210> SEQ ID NO 382
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 382
gugucaggcu cucugcugu                                                    19

<210> SEQ ID NO 383
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 383
gggucaauuu cuuuguuua                                                    19

<210> SEQ ID NO 384
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 384
guccuuuccu gauauagaa                                                    19

<210> SEQ ID NO 385
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 385
caauuucuuu guuuaucca                                                    19

<210> SEQ ID NO 386
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 386
caguguguau cuugauaaa                                                    19

<210> SEQ ID NO 387
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 387
gagucagugu guaucuuga                                                    19

<210> SEQ ID NO 388
<211> LENGTH: 19
```

```
<212> TYPE: RNA
<213> ORGANISM: Artificial sequence
<220> FEATURE:
<223> OTHER INFORMATION: Synthetic nucleic acid

<400> SEQUENCE: 388
ccgacagaau gcugaaaca                                              19

<210> SEQ ID NO 389
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 389
ggguguauua cuuccgaaa                                              19

<210> SEQ ID NO 390
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 390
cucaugcagg gcugaauau                                              19

<210> SEQ ID NO 391
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 391
ugacgacuaa caucaggug                                              19

<210> SEQ ID NO 392
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 392
uaggagugaa gaagaagag                                              19

<210> SEQ ID NO 393
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 393
aaacauugga guuagaaag                                              19

<210> SEQ ID NO 394
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 394
```
ugucagagaa ccuacauac                                              19

<210> SEQ ID NO 395
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 395
uacauccuca cauuugagg                                              19

<210> SEQ ID NO 396
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 396
aauugcugga gacucagag                                              19

<210> SEQ ID NO 397
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 397
aguucuaaca gguucucac                                              19

<210> SEQ ID NO 398
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 398
uagcgaacca gaguuacag                                              19

<210> SEQ ID NO 399
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 399
aucuucuaga auuucucuc                                              19

<210> SEQ ID NO 400
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 400
ugauucuggg cucugacaa                                              19

<210> SEQ ID NO 401
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 401
ucaacauugc ccguggagc                                          19

<210> SEQ ID NO 402
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 402
aaagaauuga gggaguuag                                          19

<210> SEQ ID NO 403
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 403
aggacuagca ggugacgag                                          19

<210> SEQ ID NO 404
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 404
uaaaucaagc cacgaacac                                          19

<210> SEQ ID NO 405
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 405
uagcucagga aguucugaa                                          19

<210> SEQ ID NO 406
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 406
aggcuaauca gggugucag                                          19

<210> SEQ ID NO 407
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 407
aucucuugga ggaaagcug                                          19

```
<210> SEQ ID NO 408
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 408
aacaaaguga aacuguggc                                                19

<210> SEQ ID NO 409
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 409
uuucagaggg uuggcagag                                                19

<210> SEQ ID NO 410
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 410
uaagcacaca cagacagug                                                19

<210> SEQ ID NO 411
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 411
ucugguggca aagacacag                                                19

<210> SEQ ID NO 412
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 412
uagaguguga gaaacacuc                                                19

<210> SEQ ID NO 413
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 413
uucuugaaga gauaccucc                                                19

<210> SEQ ID NO 414
<211> LENGTH: 19
<212> TYPE: RNA
<213> ORGANISM: Artificial sequence
<220> FEATURE:
<223> OTHER INFORMATION: Synthetic nucleic acid
```

-continued

<400> SEQUENCE: 414
ugacccauga aagagagag                                                    19

<210> SEQ ID NO 415
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 415
acaaugaaca gaaacacag                                                    19

<210> SEQ ID NO 416
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 416
uucccuaccc uacuguggg                                                    19

<210> SEQ ID NO 417
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 417
ucauguaaga gguaccauc                                                    19

<210> SEQ ID NO 418
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 418
uguggaugca cacagagca                                                    19

<210> SEQ ID NO 419
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 419
ugcuuucuca guaucuccc                                                    19

<210> SEQ ID NO 420
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 420
acagcagaga gccugacac                                                    19

<210> SEQ ID NO 421

```
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 421
uaaacaaaga aauugaccc                                              19

<210> SEQ ID NO 422
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 422
uucuauauca ggaaaggac                                              19

<210> SEQ ID NO 423
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 423
uggauaaaca aagaaauug                                              19

<210> SEQ ID NO 424
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 424
uuuaucaaga uacacacug                                              19

<210> SEQ ID NO 425
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 425
ucaagauaca cacugacuc                                              19

<210> SEQ ID NO 426
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 426
uguuucagca uucugucgg                                              19

<210> SEQ ID NO 427
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 427
```
uuucggaagu aauacaccc                                           19

<210> SEQ ID NO 428
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 428
auauucagcc cugcaugag                                           19

<210> SEQ ID NO 429
<211> LENGTH: 312
<212> TYPE: DNA
<213> ORGANISM: Artificial sequence
<220> FEATURE:
<223> OTHER INFORMATION: Synthetic nucleic acid

<400> SEQUENCE: 429
acagtctaca aagaggccgt ggaagctgtc ggggaaggag aatgttcaag tagcacaggc    60
aatcaaacac ttcctattgc tccaggtgcc aaagcaggaa tgaaaacctg tcccctctgt   120
tgaatactct tcttcttcac tcctaaaact acacacctga tgttagtcgt cagccctctt   180
cttatcactc tacacctgct gctctggaga actcatccag gctgtggct ccctgcacgt    240 ctacactagt aacctctgaa tccacggtct ccagcactcc ctcctgctcc catcccagg   300 tggcagtcag gt                                                      312

<210> SEQ ID NO 430
<211> LENGTH: 273
<212> TYPE: DNA
<213> ORGANISM: Artificial sequence
<220> FEATURE:
<223> OTHER INFORMATION: Synthetic nucleic acid

<400> SEQUENCE: 430
gaattcaaag ggtctcttct agaggatcct gggttatgtc ctccacagga actttggtgt    60
tggcccctct tcctcaaatg tgaggatgta ccaatggcct ccccattatc tcctttcttt   120
ttctttctaa ctccaatgtt tataaagcct atatccctgt agtgtatgta ggttctctga   180
cagaagttat acttagtgct ctgtctttct tatgggaaa aatccctgga actgaagcta    240
agatctttag tacttggagt caccctacag ata                                273

<210> SEQ ID NO 431
<211> LENGTH: 154
<212> TYPE: DNA
<213> ORGANISM: Artificial sequence
<220> FEATURE:
<223> OTHER INFORMATION: Synthetic nucleic acid

<400> SEQUENCE: 431
taaaccagga tcttcttcag cctccaaggt aaggaaatgt gtgatctcca agctccctct    60
tgtatgtatt gtgaacgcca ctgtcagaag agaaacacca aagttattca cctggaaatg   120
ttgcagtatg aagaccatgt atttgatgga gagg                               154

<210> SEQ ID NO 432
<211> LENGTH: 216
<212> TYPE: DNA
<213> ORGANISM: Artificial sequence
<220> FEATURE:

<223> OTHER INFORMATION: Synthetic nucleic acid

<400> SEQUENCE: 432

```
atggtttgtt tccccctctc cctgctagaa gcacaagggg attttctct gataatcatt    60
gtgagaacct gttagaactc ctggaggtaa aactcaaaag tatggcggcc cccctgaatg   120
agtcttcctg gaattaactg tcaaacttgc cactctgagt ctccagcaat tcttgaatta   180
caattcagat tttcctatcc tggtacaggt tcctgt                              216
```

<210> SEQ ID NO 433
<211> LENGTH: 153
<212> TYPE: DNA
<213> ORGANISM: Artificial sequence
<220> FEATURE:
<223> OTHER INFORMATION: Synthetic nucleic acid

<400> SEQUENCE: 433

```
ggctcaggct gagaggatat tctgccgttg tagttttgct cggggccatt cgttttaaga    60
agactggaga gtcagttcca gtttgtcttg ggggactaag ttcttatcat gtggtttcta   120
ctggtggctt attgagaaca catgcaggta cag                                 153
```

<210> SEQ ID NO 434
<211> LENGTH: 304
<212> TYPE: DNA
<213> ORGANISM: Artificial sequence
<220> FEATURE:
<223> OTHER INFORMATION: Synthetic nucleic acid

<400> SEQUENCE: 434

```
cccagccctc agtggcccca cagcagcttg gctgttcttg gttttgtttc tctctgcttc    60
tgcatgatat ctttgaacaa aaagtcccaa gtgtacaaaa agtcccgaaa ggcgttcgca   120
aaccactgac ctagatggag ggaattgtga ggagcagagg cacctctt ataaaatgcc    180
tgtacttcgg tgcagggttt ggtggtgtcg gcggtttgga ggccctttaa gcttcctaac   240
tccttgtcac tggtggatgg tggggtgccg gcaggagggc atccctttac ataggggctc   300
attg                                                                 304
```

<210> SEQ ID NO 435
<211> LENGTH: 179
<212> TYPE: DNA
<213> ORGANISM: Artificial sequence
<220> FEATURE:
<223> OTHER INFORMATION: Synthetic nucleic acid

<400> SEQUENCE: 435

```
taccaatgtc tctgggcctt gctctactag tacaacagag gagagagaaa ttctagaaga    60
ttttcaactc ccctcctgct ctgtaactct ggttcgctat gtgctaaatg caccttgaaa   120
taaacacttc ctttgtgtgt gtgtgttgcg cggtggaatc ctcactttac agaagagga    179
```

<210> SEQ ID NO 436
<211> LENGTH: 171
<212> TYPE: DNA
<213> ORGANISM: Artificial sequence
<220> FEATURE:
<223> OTHER INFORMATION: Synthetic nucleic acid

<400> SEQUENCE: 436

```
ggggaatgag aaacaaaaga caaggttaat tatgacaccg ggctttaca atgctaaaaa    60
tatcctatat acaaagggat atgtaggctg tgttcttttt ccatgtcatt acaaagaaca   120
```

```
ggctcaaggt atctgcaaat ttctaataaa aatattatta cttgaaaaat g        171
```

<210> SEQ ID NO 437
<211> LENGTH: 132
<212> TYPE: DNA
<213> ORGANISM: Artificial sequence
<220> FEATURE:
<223> OTHER INFORMATION: Synthetic nucleic acid

<400> SEQUENCE: 437

```
cacttgcttc taggctgagg agggcggggc tgttgtcaga gcccagaatc aaagccagag    60
gagcaggtgg acgctgagac tgtcccctca ccctgctcca cgggcaatgt tgaagtgggc   120
atctgggtgt gt                                                       132
```

<210> SEQ ID NO 438
<211> LENGTH: 303
<212> TYPE: DNA
<213> ORGANISM: Artificial sequence
<220> FEATURE:
<223> OTHER INFORMATION: Synthetic nucleic acid

<400> SEQUENCE: 438

```
accatgactc accctctttc ctcgtcacct gctagtcctc ccattcactc cccttcagtc    60
atattggcct tgcttctctt cagacgggcc agccacactc agggcctttg cactgactat   120
tccttctgcc tggaatgttc ctcctccaag tatccatatg gctaactccc tcaattcttt   180
gagatcttta accacaaggc gctttcccaa ataagtcttc tctggctacc cttttaaaa   240 ttttaacccc cacccttcac attttatata ctccccttcc ttgccttttt tcagcttctt   300
gtc                                                                 303
```

<210> SEQ ID NO 439
<211> LENGTH: 184
<212> TYPE: DNA
<213> ORGANISM: Artificial sequence
<220> FEATURE:
<223> OTHER INFORMATION: Synthetic nucleic acid

<400> SEQUENCE: 439

```
caatcgctgc ctgagtacct atgtgttcgt ggcttgattt accttatctg taattcctgg    60
atgttaaaag gacaccaaaa atctctgaca ccctgattag cctaccttga agaacccaag   120
cccaggattt ctgcctttgc ctagaaaaag gactgattca gaacttcctg agctacctag   180
tatt                                                                184
```

<210> SEQ ID NO 440
<211> LENGTH: 118
<212> TYPE: DNA
<213> ORGANISM: Artificial sequence
<220> FEATURE:
<223> OTHER INFORMATION: Synthetic nucleic acid

<400> SEQUENCE: 440

```
gtccactttt aggagtgtat gtacttggac acctaaaaaa tatgctgcca caagaacatt    60
tgttgtagca ttctgtgctc atttatacag gtctagttaa gtaaactcta gcatacta    118
```

<210> SEQ ID NO 441
<211> LENGTH: 204
<212> TYPE: DNA
<213> ORGANISM: Artificial sequence
<220> FEATURE:

<223> OTHER INFORMATION: Synthetic nucleic acid

<400> SEQUENCE: 441

```
atcctctgac ttggggcaga gctgaggtag acatctgggt gtgtctggga accccgggg      60
aaggttcctt tctgtcctgt cactgtctgt gtgtgcttat gtgtctgtgt gtgtctgtgt    120
ctttgccacc agaaggagtt gggcctgttt gctcatgagc actgtcgagg aggcccactg    180
tgtccacata tgcggctcct gagg                                           204
```

<210> SEQ ID NO 442
<211> LENGTH: 167
<212> TYPE: DNA
<213> ORGANISM: Artificial sequence
<220> FEATURE:
<223> OTHER INFORMATION: Synthetic nucleic acid

<400> SEQUENCE: 442

```
gcctttgaaa gtctcgcatc tgctgttttt caggtctcca agtccattct ttgtgtttgg     60
actggtgagt gtttctcaca ctctataatc gcaaagtagg gaggtatctc ttcaagaaga   120
caagtgtcat tcaaatattt ctgcataaca aaccagtaca aaactta                 167
```

<210> SEQ ID NO 443
<211> LENGTH: 278
<212> TYPE: DNA
<213> ORGANISM: Artificial sequence
<220> FEATURE:
<223> OTHER INFORMATION: Synthetic nucleic acid

<400> SEQUENCE: 443

```
agactattta tgcatgcatt ggtctttgag ctgttccgcc tgctgtcttg taaactcaga     60
agcagttttc ctgaggtggg tattactgac catctagctc accatctgag actcataagt   120
agatttgtga gtggtgaggt gtagtgaaga ccacttgttt gggattcaac atacatggcc   180
agccaatgaa aatgttaact cacatctgca tatgccttca tcttgttatg gaactggagg   240
caccatcatt cataatgctt aaaaataaaa cacctgca                           278
```

<210> SEQ ID NO 444
<211> LENGTH: 271
<212> TYPE: DNA
<213> ORGANISM: Artificial sequence
<220> FEATURE:
<223> OTHER INFORMATION: Synthetic nucleic acid

<400> SEQUENCE: 444

```
ctatctctct ctttcatggg tcagtttcta tttccctctg tgtttctgtt cattgtcttc     60
ctggtggcta acttctgctt atagtttctg ctcccttta acttctgtgt gcacatgact    120
tggacttgtt atggtactat gctctgtgct ggaaacgtag cggtgagtaa ggcagccctg   180
acttctcagc tctgcatagg acccacagta gggtagggaa taaacacaca cacacacaca   240
cacacacaca cacagttgtg atgtgctatg a                                  271
```

<210> SEQ ID NO 445
<211> LENGTH: 148
<212> TYPE: DNA
<213> ORGANISM: Artificial sequence
<220> FEATURE:
<223> OTHER INFORMATION: Synthetic nucleic acid

<400> SEQUENCE: 445

```
gttaggttac atatcaagtt aggttcactg tgtactgaaa aacctttagg ccaaaattaa     60
```

```
aatatgtaca acggaggctt tagtccaaac ttaatttaac agtactacaa ttaagtatca    120
gtattgccat aattgtatca gtcagggt                                      148

<210> SEQ ID NO 446
<211> LENGTH: 202
<212> TYPE: DNA
<213> ORGANISM: Artificial sequence
<220> FEATURE:
<223> OTHER INFORMATION: Synthetic nucleic acid

<400> SEQUENCE: 446
aggaactagc taacataggt tttgttatct gcttcgagtg tgctctgtgt gcatccacac    60
ccaagtccca ggccccaaga gtctgtgtgg agctgtgtga tgggctgatg gtacctctta   120
catgaggcct tttgggagat actgagaaag cactggacta ggagttgagg ctccaacccc   180
agattagtca tcatctgtgt gt                                            202

<210> SEQ ID NO 447
<211> LENGTH: 116
<212> TYPE: DNA
<213> ORGANISM: Artificial sequence
<220> FEATURE:
<223> OTHER INFORMATION: Synthetic nucleic acid

<400> SEQUENCE: 447
gcttggaccc acagtacaga tcacccatct tgggcctatc acactgagca attgctgacc    60
tgcatctctg tggagtggag cccccaggag acaagtaaaa gaccccccagc cacaac       116

<210> SEQ ID NO 448
<211> LENGTH: 151
<212> TYPE: DNA
<213> ORGANISM: Artificial sequence
<220> FEATURE:
<223> OTHER INFORMATION: Synthetic nucleic acid

<400> SEQUENCE: 448
ttcttctggc tgcctggaag atgcctctgt tattttagtg aaaacattta gctcctcgaa    60
aggtagagag aaccaagagg taaagtgtgc cattgtagac agctggtgtg tgtgccaggt   120
agcagtgctt ctgtctacat cctgggatat t                                  151

<210> SEQ ID NO 449
<211> LENGTH: 101
<212> TYPE: DNA
<213> ORGANISM: Artificial sequence
<220> FEATURE:
<223> OTHER INFORMATION: Synthetic nucleic acid

<400> SEQUENCE: 449
tttctgctat ctagatcttt gactaccaac cagccaggag tggtctgcct cttctttggt    60
ctgagcttgc cttgtgctta tattgttgta cccaagcgag t                       101

<210> SEQ ID NO 450
<211> LENGTH: 158
<212> TYPE: DNA
<213> ORGANISM: Artificial sequence
<220> FEATURE:
<223> OTHER INFORMATION: Synthetic nucleic acid

<400> SEQUENCE: 450
cgcgaccgtt ccattcttga gtttcttcac tttgccagct tgggtgtctc tcccgaggcc    60
```

```
gtcgttctag ttatggctca tccagctgac gctgcaactt ctcttgttct gtagcatttc    120
ttctacttct ctttctctac cagctgtgtc aaccggct                           158
```

<210> SEQ ID NO 451
<211> LENGTH: 189
<212> TYPE: DNA
<213> ORGANISM: Artificial sequence
<220> FEATURE:
<223> OTHER INFORMATION: Synthetic nucleic acid

<400> SEQUENCE: 451

```
cacatctcac ccccagacct gccattggca tgcacatctt taaccacaaa ccacgattga    60
aaatgagaaa gaaaactctc ctctagctgg gcgcttcata ggactagcca ggtacgacca   120
tctctgaggg tctttgacag ctcagttta ctgcataatc tgttttcaag acccttaaa    180 agaccagat                                                          189
```

<210> SEQ ID NO 452
<211> LENGTH: 111
<212> TYPE: DNA
<213> ORGANISM: Artificial sequence
<220> FEATURE:
<223> OTHER INFORMATION: Synthetic nucleic acid

<400> SEQUENCE: 452

```
cataactacc agaagccatt ggtggcaaga tctcaatcag gacatgtcgg tacaatgctc    60
tgattatctc gtctgcatcc ctgattactt atggtccaga tataaactac t            111
```

<210> SEQ ID NO 453
<211> LENGTH: 135
<212> TYPE: DNA
<213> ORGANISM: Artificial sequence
<220> FEATURE:
<223> OTHER INFORMATION: Synthetic nucleic acid

<400> SEQUENCE: 453

```
ttagtttcag ttctttgata cttttttgag aggcctgaag gtcctttcct gatatagaac    60
tcacgtaaac aaataaaagc ttcaagtttt aagacaagaa gggtcaattt ctttgtttat   120
ccaaaaaact atcta                                                   135
```

<210> SEQ ID NO 454
<211> LENGTH: 241
<212> TYPE: DNA
<213> ORGANISM: Artificial sequence
<220> FEATURE:
<223> OTHER INFORMATION: Synthetic nucleic acid

<400> SEQUENCE: 454

```
cctacactga aagcccatgg ggttgaagca ggatttggtt cacgctagaa cttctgagag    60
tcagtgtgta tcttgataaa cagcaacaga gcttagtcat gagttccctg taactggctg   120
ctcagagagt ttgctcccca cctcctgggg agaacttacc tgggaagagg ccaatgtttc   180
tatctaagcc tgtcccgtcc tctgagtttc aaccttcta atttcacgtt gggagtgcct   240
c                                                                  241
```

<210> SEQ ID NO 455
<211> LENGTH: 84
<212> TYPE: DNA
<213> ORGANISM: Artificial sequence
<220> FEATURE:
<223> OTHER INFORMATION: Synthetic nucleic acid

<400> SEQUENCE: 455

| gtccttaagg ctgatgtgaa tctctgccct ttccaatgtg tcatgtgatt gctccaaatt | 60 |
| aaaacaccta ttattattat tttg | 84 |

<210> SEQ ID NO 456
<211> LENGTH: 100
<212> TYPE: DNA
<213> ORGANISM: Artificial sequence
<220> FEATURE:
<223> OTHER INFORMATION: Synthetic nucleic acid

<400> SEQUENCE: 456

| cacctcactt ctgttttctg tccattaatg cttcctgccc acgttgtggg gaggagctct | 60 |
| ctgaacctct gctgcttctg agggattcaa gaatatattt | 100 |

<210> SEQ ID NO 457
<211> LENGTH: 171
<212> TYPE: DNA
<213> ORGANISM: Artificial sequence
<220> FEATURE:
<223> OTHER INFORMATION: Synthetic nucleic acid

<400> SEQUENCE: 457

| acttcctgtc cgcgaccgtt ccattcttga gtttcttcac tttgccagct tgggtgtctc | 60 |
| tcccgaggcc gtcgttctag ttatggctca tccagctgac gctgcaactt ctcttgttct | 120 |
| gtagcatttc ttctacttct ctttctctac cagctgtgtc aaccggcttt g | 171 |

<210> SEQ ID NO 458
<211> LENGTH: 265
<212> TYPE: DNA
<213> ORGANISM: Artificial sequence
<220> FEATURE:
<223> OTHER INFORMATION: Synthetic nucleic acid

<400> SEQUENCE: 458

| tgattacctc actctcatgc agggctgaat attactgttt ccctgttaa acaagggtgt | 60 |
| attacttccg aaatctgaca accccaagca ccaaaaggtt taaaaatatc tcgagattgt | 120 |
| aaagcctccg acagaatgct gaaacaggat tgcacagttg accaggagct tctgaggttg | 180 |
| tggcggaccc tccatgtttc tgactgccgg acagtcacag ccccctcttc cctaatgcca | 240 |
| ccagatgttc cctgggacac ctgcc | 265 |

<210> SEQ ID NO 459
<211> LENGTH: 101
<212> TYPE: DNA
<213> ORGANISM: Artificial sequence
<220> FEATURE:
<223> OTHER INFORMATION: Synthetic nucleic acid

<400> SEQUENCE: 459

| tttctgctat ctagatcttt gactaccaac cagccaggag tggtctgcct cttctttggt | 60 |
| ctgagcttgc cttgtgctta tattgttgta cccaagcgag t | 101 |

<210> SEQ ID NO 460
<211> LENGTH: 26
<212> TYPE: DNA
<213> ORGANISM: Artificial sequence
<220> FEATURE:
<223> OTHER INFORMATION: Synthetic nucleic acid

```
<400> SEQUENCE: 460
cttcttcact cctaaaacta cacacc                                      26

<210> SEQ ID NO 461
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 461
aatgaaaacc tgtccctct g                                            21

<210> SEQ ID NO 462
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 462
ctccccatta tctcctttct ttt                                         23

<210> SEQ ID NO 463
<211> LENGTH: 26
<212> TYPE: DNA
<213> ORGANISM: Artificial sequence
<220> FEATURE:
<223> OTHER INFORMATION: Synthetic nucleic acid

<400> SEQUENCE: 463
gtgtatgtag gttctctgac agaagt                                      26

<210> SEQ ID NO 464
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 464
tcctccacag gaactttggt                                             20

<210> SEQ ID NO 465
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 465
ttgtatgtat tgtgaacgcc act                                         23

<210> SEQ ID NO 466
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 466
aggatcttct tcagcctcca                                             20

<210> SEQ ID NO 467
<211> LENGTH: 23
```

```
<212> TYPE: DNA
<213> ORGANISM: Artificial sequence
<220> FEATURE:
<223> OTHER INFORMATION: Synthetic nucleic acid

<400> SEQUENCE: 467
tcttcctgga attaactgtc aaa                                          23

<210> SEQ ID NO 468
<211> LENGTH: 26
<212> TYPE: DNA
<213> ORGANISM: Artificial sequence
<220> FEATURE:
<223> OTHER INFORMATION: Synthetic nucleic acid

<400> SEQUENCE: 468 gggattttc tctgataatc attgtg                                        26

<210> SEQ ID NO 469
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 469
tgagaggata ttctgccgtt g                                            21

<210> SEQ ID NO 470
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 470
tgggggacta agttcttatc atgt                                         24

<210> SEQ ID NO 471
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 471
tggctgttct tggttttgtt t                                            21

<210> SEQ ID NO 472
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 472
actccttgtc actggtggat g                                            21

<210> SEQ ID NO 473
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 473
```

```
ttttcaactc ccctcctgct                                               20

<210> SEQ ID NO 474
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 474
tctctgggcc ttgctctact                                               20

<210> SEQ ID NO 475
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 475
aggctgtgtt cttttccat gt                                             22

<210> SEQ ID NO 476
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 476
cacttgcttc taggctgagg a                                             21

<210> SEQ ID NO 477
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 477
aggtggacgc tgagactgt                                                19

<210> SEQ ID NO 478
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 478
ctggaatgtt cctcctccaa                                               20

<210> SEQ ID NO 479
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 479
accctctttc ctcgtcacct                                               20

<210> SEQ ID NO 480
<211> LENGTH: 20
<212> TYPE: DNA
<213> ORGANISM: Artificial sequence
```

```
<220> FEATURE:
<223> OTHER INFORMATION: Synthetic nucleic acid

<400> SEQUENCE: 480
cctatgtgtt cgtggcttga                                                  20

<210> SEQ ID NO 481
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 481
aagaacccaa gcccaggat                                                   19

<210> SEQ ID NO 482
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 482
aaggacacca aaatctctg aca                                               23

<210> SEQ ID NO 483
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 483
gtagcattct gtgctcattt atac                                             24

<210> SEQ ID NO 484
<211> LENGTH: 26
<212> TYPE: DNA
<213> ORGANISM: Artificial sequence
<220> FEATURE:
<223> OTHER INFORMATION: Synthetic nucleic acid

<400> SEQUENCE: 484
ccacttttag gagtgtatgt acttgg                                           26

<210> SEQ ID NO 485
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 485
atctgggtgt gtctgggaaa                                                  20

<210> SEQ ID NO 486
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 486
atgagcagct gtcgaggag                                                   19
```

```
<210> SEQ ID NO 487
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 487
tccattcttt gtgtttggac tg                                              22

<210> SEQ ID NO 488
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 488
cgcaaagtag ggaggtatct ctt                                             23

<210> SEQ ID NO 489
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 489
tatggaactg gaggcaccat                                                 20

<210> SEQ ID NO 490
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 490
tgaccatcta gctcaccatc tg                                              22

<210> SEQ ID NO 491
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 491
tctctctttc atgggtcagt ttc                                             23

<210> SEQ ID NO 492
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 492
cagccctgac ttctcagctc                                                 20

<210> SEQ ID NO 493
<211> LENGTH: 25
<212> TYPE: DNA
<213> ORGANISM: Artificial sequence
<220> FEATURE:
<223> OTHER INFORMATION: Synthetic nucleic acid
```

```
<400> SEQUENCE: 493
ggccaaaatt aaaatatgta caacg                                          25

<210> SEQ ID NO 494
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 494
caacggaggc tttagtccaa                                                20

<210> SEQ ID NO 495
<211> LENGTH: 26
<212> TYPE: DNA
<213> ORGANISM: Artificial sequence
<220> FEATURE:
<223> OTHER INFORMATION: Synthetic nucleic acid

<400> SEQUENCE: 495
ggttacatat caagttaggt tcactg                                         26

<210> SEQ ID NO 496
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 496
ctgtgtggag ctgtgtgatg                                                20

<210> SEQ ID NO 497
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 497
ctgcttcgag tgtgctctgt                                                20

<210> SEQ ID NO 498
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 498
ggcctttggg gagatactga                                                20

<210> SEQ ID NO 499
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 499
ccatcttggg cctatcacac                                                20

<210> SEQ ID NO 500
```

```
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 500
tttagctcct cgaaaggtag aga                                              23

<210> SEQ ID NO 501
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 501
gcctggaaga tgcctctgtt                                                  20

<210> SEQ ID NO 502
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 502
ctgctatcta gatctttg                                                    18

<210> SEQ ID NO 503
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 503
cgaccgttcc attcttgagt                                                  20

<210> SEQ ID NO 504
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 504
cgaccgttcc attcttgagt                                                  20

<210> SEQ ID NO 505
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 505
tgggcgcttc ataggact                                                    18

<210> SEQ ID NO 506
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 506
```

-continued acatctcacc cccagacct                                              19

<210> SEQ ID NO 507
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 507
tggtggcaag atctcaatca                                             20

<210> SEQ ID NO 508
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 508
cggtacaatg ctctgattat ctcg                                        24

<210> SEQ ID NO 509
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 509
tcacgtaaac aaataaaagc ttca                                        24

<210> SEQ ID NO 510
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 510
tttttgagag gcctgaaggt                                             20

<210> SEQ ID NO 511
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 511
atggggttga agcaggattt                                             20

<210> SEQ ID NO 512
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 512
aaggctgatg tgaatctctg c                                           21

<210> SEQ ID NO 513
<211> LENGTH: 20
<212> TYPE: DNA

```
<213> ORGANISM: Artificial sequence
<220> FEATURE:
<223> OTHER INFORMATION: Synthetic nucleic acid

<400> SEQUENCE: 513
tctgctgctt ctgagggatt                                               20

<210> SEQ ID NO 514
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 514
ccacgttgtg gggaggag                                                 18

<210> SEQ ID NO 515
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 515
ggccgtcgtt ctagttatgg                                               20

<210> SEQ ID NO 516
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 516
cgaccgttcc attcttgagt                                               20

<210> SEQ ID NO 517
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 517
accaaaaggt ttaaaaatat ctcg                                          24

<210> SEQ ID NO 518
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 518
cactctcatg cagggctga                                                19

<210> SEQ ID NO 519
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 519
caggagtggt ctgcctcttc                                               20
```

```
<210> SEQ ID NO 520
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 520
tgctatctag atctttgact accaacc                                        27

<210> SEQ ID NO 521
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 521
agagtgataa gaagagggct ga                                             22

<210> SEQ ID NO 522
<211> LENGTH: 26
<212> TYPE: DNA
<213> ORGANISM: Artificial sequence
<220> FEATURE:
<223> OTHER INFORMATION: Synthetic nucleic acid

<400> SEQUENCE: 522
aggtgtgtag ttttaggagt gaagaa                                         26

<210> SEQ ID NO 523
<211> LENGTH: 26
<212> TYPE: DNA
<213> ORGANISM: Artificial sequence
<220> FEATURE:
<223> OTHER INFORMATION: Synthetic nucleic acid

<400> SEQUENCE: 523
agggatatag gctttataaa cattgg                                         26

<210> SEQ ID NO 524
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 524
tttttcccca taagaaagac aga                                            23

<210> SEQ ID NO 525
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 525
ggccattggt acatcctcac                                                20

<210> SEQ ID NO 526
<211> LENGTH: 23
<212> TYPE: DNA
<213> ORGANISM: Artificial sequence
<220> FEATURE:
```

<223> OTHER INFORMATION: Synthetic nucleic acid

<400> SEQUENCE: 526
catttccagg tgaataactt tgg                                      23

<210> SEQ ID NO 527
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 527
aatacataca agagggagct tgg                                      23

<210> SEQ ID NO 528
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 528
tgtaattcaa gaattgctgg agac                                     24

<210> SEQ ID NO 529
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 529
ttgagtttta cctccaggag ttct                                     24

<210> SEQ ID NO 530
<211> LENGTH: 25
<212> TYPE: DNA
<213> ORGANISM: Artificial sequence
<220> FEATURE:
<223> OTHER INFORMATION: Synthetic nucleic acid

<400> SEQUENCE: 530
gaactgactc tccagtcttc ttaaa                                    25

<210> SEQ ID NO 531
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 531
cctgcatgtg ttctcaataa gc                                       22

<210> SEQ ID NO 532
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 532
cgggactttt tgtacacttg g                                        21

-continued

<210> SEQ ID NO 533
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 533
gcccctatgt aaagggatgc                                         20

<210> SEQ ID NO 534
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 534
tttcaaggtg catttagcac a                                       21

<210> SEQ ID NO 535
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 535
gcaggagggg agttgaaaat                                         20

<210> SEQ ID NO 536
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 536
agaaatttgc agataccttg agc                                     23

<210> SEQ ID NO 537
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 537
tcctctggct ttgattctgg                                         20

<210> SEQ ID NO 538
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 538
ccagatgccc acttcaacat                                         20

<210> SEQ ID NO 539
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 539
aagcgccttg tggttaaaga                                               20

<210> SEQ ID NO 540
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 540
gcaaggccaa tatgactgaa                                               20

<210> SEQ ID NO 541
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 541
tttggtgtcc ttttaacatc ca                                            22

<210> SEQ ID NO 542
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 542
gctcaggaag ttctgaatca gtc                                           23

<210> SEQ ID NO 543
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 543
atcctgggct tgggttctt                                                19

<210> SEQ ID NO 544
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 544
taaatgagca cagaatgc                                                 18

<210> SEQ ID NO 545
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 545
caaatgttct tgtggcagca                                               20

<210> SEQ ID NO 546
<211> LENGTH: 21

```
<212> TYPE: DNA
<213> ORGANISM: Artificial sequence
<220> FEATURE:
<223> OTHER INFORMATION: Synthetic nucleic acid

<400> SEQUENCE: 546
gcacacacag acagtgacag g                                              21

<210> SEQ ID NO 547
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 547
acacagacag tgcctcagga                                                20

<210> SEQ ID NO 548
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 548
tgcgattata gagtgtgaga aaca                                           24

<210> SEQ ID NO 549
<211> LENGTH: 25
<212> TYPE: DNA
<213> ORGANISM: Artificial sequence
<220> FEATURE:
<223> OTHER INFORMATION: Synthetic nucleic acid

<400> SEQUENCE: 549
tgcagaaata tttgaatgac acttg                                          25

<210> SEQ ID NO 550
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 550
tgcaggtgtt ttatttttaa gca                                            23

<210> SEQ ID NO 551
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 551
tcccaaacaa gtggtcttca                                                20

<210> SEQ ID NO 552
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 552
```
gcagaagtta gccaccagga                                              20

<210> SEQ ID NO 553
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 553
caactgtgtg tgtgtgtgtg tg                                           22

<210> SEQ ID NO 554
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 554
actgttaaat taagtttgga ctaaagc                                      27

<210> SEQ ID NO 555
<211> LENGTH: 26
<212> TYPE: DNA
<213> ORGANISM: Artificial sequence
<220> FEATURE:
<223> OTHER INFORMATION: Synthetic nucleic acid

<400> SEQUENCE: 555
gactgataca attatggcaa tactga                                       26

<210> SEQ ID NO 556
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 556
ttttggccta aaggtttttc a                                            21

<210> SEQ ID NO 557
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 557
ctcccaaaag gcctcatgta                                              20

<210> SEQ ID NO 558
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 558
tcacacagct ccacacagac t                                            21

<210> SEQ ID NO 559
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 559
ggttggagcc tcaactccta                                                    20

<210> SEQ ID NO 560
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 560
ctccacagag atgcaggtca                                                    20

<210> SEQ ID NO 561
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 561
tttagctcct cgaaaggtag aga                                                23

<210> SEQ ID NO 562
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 562
ctacctggca cacacaccag                                                    20

<210> SEQ ID NO 563
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 563
ctcgcttggg tacaacaat                                                     19

<210> SEQ ID NO 564
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 564
agagaagttg cagcgtcagc                                                    20

<210> SEQ ID NO 565
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 565
agagaagttg cagcgtcagc                                                    20

```
<210> SEQ ID NO 566
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 566 tctggtctttt taaagggtct tga                                              23

<210> SEQ ID NO 567
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 567
ctatgaagcg cccagctaga                                                   20

<210> SEQ ID NO 568
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 568
tcagggatgc agacgagata                                                   20

<210> SEQ ID NO 569
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 569
ggaccataag taatcaggga tgc                                               23

<210> SEQ ID NO 570
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 570
caaagaaatt gacccttctt gtc                                               23

<210> SEQ ID NO 571
<211> LENGTH: 25
<212> TYPE: DNA
<213> ORGANISM: Artificial sequence
<220> FEATURE:
<223> OTHER INFORMATION: Synthetic nucleic acid

<400> SEQUENCE: 571
tgaagctttt atttgtttac gtgag                                             25

<210> SEQ ID NO 572
<211> LENGTH: 21
<212> TYPE: DNA
<213> ORGANISM: Artificial sequence
<220> FEATURE:
<223> OTHER INFORMATION: Synthetic nucleic acid
```

-continued

```
<400> SEQUENCE: 572
cagccagtta cagggaactc a                                              21

<210> SEQ ID NO 573
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 573
tggagcaatc acatgacaca                                                20

<210> SEQ ID NO 574
<211> LENGTH: 26
<212> TYPE: DNA
<213> ORGANISM: Artificial sequence
<220> FEATURE:
<223> OTHER INFORMATION: Synthetic nucleic acid

<400> SEQUENCE: 574
gatttaggag tttaattgag caaaaa                                         26

<210> SEQ ID NO 575
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 575
gaatccctca gaagcagcag                                                20

<210> SEQ ID NO 576
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 576
ccggttgaca cagctggtag                                                20

<210> SEQ ID NO 577
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 577
tcagctggat gagccataac t                                              21

<210> SEQ ID NO 578
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 578
acctcagaag ctcctggtca                                                20

<210> SEQ ID NO 579
```

```
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 579
gtgcttgggg ttgtcagatt                                                  20

<210> SEQ ID NO 580
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 580
actcgcttgg gtacaacaat                                                  20

<210> SEQ ID NO 581
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 581
gaagaggcag accactcctg                                                  20

<210> SEQ ID NO 582
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 582
gatctaaggc caccctctcg                                                  20

<210> SEQ ID NO 583
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 583
tcccgagctc tactgactcc                                                  20

<210> SEQ ID NO 584
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 584
ccagcatggt gtgtctgaag                                                  20

<210> SEQ ID NO 585
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 585
```
aaggaagggc ttcagtgacc                                            20

<210> SEQ ID NO 586
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 586
ccaatccagt ggctctcct                                             19

<210> SEQ ID NO 587
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 587
tcgacaccag ccagttcttc                                            20

<210> SEQ ID NO 588
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 588
agctcatggg agtatgaagg a                                          21

<210> SEQ ID NO 589
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 589
ccctccttgc gagtgtatgt                                            20

<210> SEQ ID NO 590
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 590
tcccatcaga ggctcatgga                                            20

<210> SEQ ID NO 591
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 591
aacttggctc actgcaacct                                            20

<210> SEQ ID NO 592
<211> LENGTH: 20
<212> TYPE: DNA

<213> ORGANISM: Artificial sequence
<220> FEATURE:
<223> OTHER INFORMATION: Synthetic nucleic acid

<400> SEQUENCE: 592
tgctgggaca cctttgtgta                                                    20

<210> SEQ ID NO 593
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 593
gtgtccgttg caggactagg                                                    20

<210> SEQ ID NO 594
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 594
cctgagggaa cacttggaga                                                    20

<210> SEQ ID NO 595
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 595
gcgctgaaga gactggtagg                                                    20

<210> SEQ ID NO 596
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 596
gggaggtgca gtttcagaac                                                    20

<210> SEQ ID NO 597
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 597
catctccaac caaggacccc                                                    20

<210> SEQ ID NO 598
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 598
aacactcacc gtgaaggtct g                                                  21

<210> SEQ ID NO 599
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 599
ggccgaaatc cactccag                                                 18

<210> SEQ ID NO 600
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 600
gaaggaggtc gctgtctttg                                               20

<210> SEQ ID NO 601
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 601
ctggagcact acgtggcg                                                 18

<210> SEQ ID NO 602
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 602
tctcctagcc tgtgcctctg                                               20

<210> SEQ ID NO 603
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 603
gaataggagc aagccagcac                                               20

<210> SEQ ID NO 604
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 604
tacttccaga gcccgaagag                                               20

<210> SEQ ID NO 605
<211> LENGTH: 20
<212> TYPE: DNA
<213> ORGANISM: Artificial sequence
<220> FEATURE:

<223> OTHER INFORMATION: Synthetic nucleic acid

<400> SEQUENCE: 605
gggaggtgca gtttcagaac                                              20

<210> SEQ ID NO 606
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 606
agggatttca cggaaatgaa                                              20

<210> SEQ ID NO 607
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 607
ccgttaaaac cagaatgagg a                                            21

<210> SEQ ID NO 608
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 608
ttcaggaagt tgtgcctgtg                                              20

<210> SEQ ID NO 609
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 609
ctgccctttc actgaactcc                                              20

<210> SEQ ID NO 610
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 610
gcatctattt ccgggctgta                                              20

<210> SEQ ID NO 611
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 611
tggctctaac aagtgccatt                                              20

```
<210> SEQ ID NO 612
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 612
ctgtcccatt gtcccctaga                                           20

<210> SEQ ID NO 613
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 613
gcagctcctt ggttctgttc                                           20

<210> SEQ ID NO 614
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 614
tgatagccca tgattcctga                                           20

<210> SEQ ID NO 615
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 615
agccagtggg gagctcag                                             18

<210> SEQ ID NO 616
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 616
gactgcagga gcactgtgaa                                           20

<210> SEQ ID NO 617
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 617
cctccgtccg ctgtttatta                                           20

<210> SEQ ID NO 618
<211> LENGTH: 20
<212> TYPE: DNA
<213> ORGANISM: Artificial sequence
<220> FEATURE:
<223> OTHER INFORMATION: Synthetic nucleic acid
```

```
<400> SEQUENCE: 618
ctcttcccag cctcttctgc                                                   20

<210> SEQ ID NO 619
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 619
agtagaccag cgggttctcg                                                   20

<210> SEQ ID NO 620
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 620
ccgctgctgc tagtggag                                                     18

<210> SEQ ID NO 621
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 621
atgattgtct gtggccaggg                                                   20

<210> SEQ ID NO 622
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 622
gagttcgaga ccagcctgac                                                   20

<210> SEQ ID NO 623
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 623
ccatccttca gtttccctga                                                   20

<210> SEQ ID NO 624
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 624
ccacggagaa gcagtggt                                                     18

<210> SEQ ID NO 625
<211> LENGTH: 20
```

```
<212> TYPE: DNA
<213> ORGANISM: Artificial sequence
<220> FEATURE:
<223> OTHER INFORMATION: Synthetic nucleic acid

<400> SEQUENCE: 625
aacttgcacg gctctacctc                                         20

<210> SEQ ID NO 626
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 626
gctcctcctc ctcctcctc                                          19

<210> SEQ ID NO 627
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 627
cgaggatcag gaccaggata                                         20

<210> SEQ ID NO 628
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 628
cacacagtgg gcacattttg t                                       21

<210> SEQ ID NO 629
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 629
cgtctggagt ctgtcccttc                                         20

<210> SEQ ID NO 630
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 630
ctccttgggg atgagcag                                           18

<210> SEQ ID NO 631
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 631
```
acacacagcc cttttccaac                                              20

<210> SEQ ID NO 632
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 632
aggggaagga gctcaggtag                                              20

<210> SEQ ID NO 633
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 633
gccatcagtc acttaaacag ca                                           22

<210> SEQ ID NO 634
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 634
aagttcccag aaacggaacc                                              20

<210> SEQ ID NO 635
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 635
cgggtagaag aacaccagga                                              20

<210> SEQ ID NO 636
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 636
cgaggatcag gaccaggata                                              20

<210> SEQ ID NO 637
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 637
aagggctgtg gtctctctca                                              20

<210> SEQ ID NO 638
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 638
tgtggggaaa accatctctt                                               20

<210> SEQ ID NO 639
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 639
tgtgttccct gccttcctac                                               20

<210> SEQ ID NO 640
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 640
cgaaggaagc tggagagcta                                               20

<210> SEQ ID NO 641
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 641
ctgcaaggag tcggagagac                                               20

<210> SEQ ID NO 642
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 642
cactgtccgt aaagctttgg a                                             21

<210> SEQ ID NO 643
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 643
ctgtcgaggc tgcataatga                                               20

<210> SEQ ID NO 644
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 644
caagcagaag acggcatacg a                                             21

```
<210> SEQ ID NO 645
<211> LENGTH: 26
<212> TYPE: DNA
<213> ORGANISM: Artificial sequence
<220> FEATURE:
<223> OTHER INFORMATION: Synthetic nucleic acid

<400> SEQUENCE: 645
aatgatacgg cgaccaccga caggtt                                        26

<210> SEQ ID NO 646
<211> LENGTH: 32
<212> TYPE: DNA
<213> ORGANISM: Artificial sequence
<220> FEATURE:
<223> OTHER INFORMATION: Synthetic nucleic acid

<400> SEQUENCE: 646
cgacaggttc agagttctac agtccgacga tc                                 32

<210> SEQ ID NO 647
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 647
tgcaccacca actgcttagc                                               20

<210> SEQ ID NO 648
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 648
ggcatggact gtggtcatga g                                             21
```

TAILORED MODULATION OF GENE REGULATION PROGRAMS VIA FUNCTIONAL ENHANCER RNA

PRIORITY CLAIM

This application claims benefit of priority to U.S. Provisional Application Ser. No. 62/924,569, filed Oct. 22, 2019, the entire contents of which are hereby incorporated by reference.

STATEMENT OF GOVERNMENT INTEREST

This invention was made with government support under Grant No. R21 AI107067 and Grant No. R01 CA140485 awarded by the National Institutes of Health. The government has certain rights in the invention.

SEQUENCE LISTING

The present application is being filed along with a Sequence Listing in electronic format. The Sequence Listing is provided as a file entitled UTSFP0152US_ST25.txt created Oct. 21, 2020, which is approximately 158 KB in size. The information in the electronic format of the sequence listing is incorporated herein by reference in its entirety.

BACKGROUND

Enhancers are key cis-regulatory elements that play an essential role in genome expression to determine cell fates and functions. There are millions of enhancers in the human genome and these enhancers function to shape cell identity by directing distinct genome expression programs. In practice, these enhancers can be systematically identified by the presence of histone modification of H3K4me1 (Heintzman et al., 2009; Heintzman et al., 2007) and H3K27Ac (Rada-Iglesias et al., 2011), the association of transcription factors and coactivators (Heinz et al., 2015), and/or DNase I hypersensitivity (Consortium et al., 2007; Thurman et al., 2012). Functional hierarchies among these enhancers have been described (Ernst and Kellis, 2010). Recently, enhancers were found to be transcriptionally active and generate noncoding RNAs known as enhancer RNAs (eRNAs) as relatively unstable transcripts (Kim et al., 2010; Wang et al., 2011). Several studies have demonstrated eRNA producing enhancers are more potent and associated with higher expression of nearby genes than enhancers without eRNAs. Thus, eRNA producing enhancers are likely active and functional enhancers that define the identity and function of a given cell (Heinz et al., 2015; Romanoski et al., 2015; Wang et al., 2011). Moreover, targeting enhancer activity for therapeutic development has been recently proposed and pursued by several groups and companies (Bradner et al., 2017). By targeting particular enhancers, disease specific modulation of gene expression would be possible without affecting the normal expression in other tissues and organs. However, for the over two million enhancers that have been annotated (Roadmap Epigenomics et al., 2015), currently only tens of thousands of eRNAs have been detected in the human genome through isolated studies (Li et al., 2016). A systematic detection and annotation of eRNAs is necessary to enable functional characterization of eRNA gene regulation, which is a fundamental step toward therapeutic development.

In-depth studies of eRNAs in regulation of key biological processes requires accurate prediction of target genes. Existing methods are mostly based on eRNA and mRNA levels in steady state cells, which may not provide enough information for functional associations. Active enhancers may have multiple nearby genes and vice versa, but functionally associated pairs will be triggered to be transcriptionally active in a synchronized fashion. Thus, eRNA/pre-mRNA dynamics, induced by a stimulus, may represent a highly informative feature for more reliable enhancer target predictions. For example, in the inventor's previous study (Banerjee et al., 2014), the inventor took advantage of the dynamic physical chromatin interactions to identify a functional enhancer responsible for the IFNB1 gene, a critical component of innate and adaptive immunity.

SUMMARY

Active enhancers of the human genome generate long noncoding transcripts known as eRNAs. How dynamic transcriptional changes of eRNAs are physically and functionally linked with target gene transcription remains unclear. To investigate the dynamic functional relationships among eRNAs and target promoters, the inventor obtained a dense time series of GRO-seq and ChIP-seq data to generate a time-resolved enhancer activity map of a cell undergoing an innate antiviral immune response. Dynamic changes in eRNA and pre-mRNA transcription activities suggest distinct regulatory roles of enhancers. Using a criterion based on proximity and transcriptional inducibility, the inventor identified 123 highly confident pairs of virus inducible enhancers and their target genes. These enhancers interact with their target promoters transiently and concurrently at the peak of gene activation. Accordingly, their physical disassociation from the promoters is likely involved in post-induction repression. Functional assessments further establish that these eRNAs are necessary for full induction of the target genes and that a complement of inducible eRNAs functions together to achieve full activation. Lastly, the inventor demonstrates the potential for eRNA-targeted transcriptional reprogramming through targeted reduction of eRNAs for a clinically relevant gene, TNFSF10, resulting in a selective control of interferon-induced apoptosis.

In accordance with the present disclosure, a method of inhibiting a TNFSF10 gene expression in a mammalian cell is disclosed. The method comprises contacting the mammalian cell with a single-stranded antisense compound comprising a sequence selected from a set of SEQ ID NOs: 1, 2, 3, 4, 5, or 6 (shown in the sequence listings in Table 1), wherein the antisense compound targets an enhancer RNA (eRNA) transcribed from a genomic enhancer sequence or region. The eRNA is an TNFSF10 eRNA sequence comprising the nucleic acid sequence selected from SEQ ID NOs: 1, 2, 3, 4, 5, or 6 which inhibits expression of the TNFSF10 gene in the mammalian cell.

In some embodiments, the eRNA transcription is initiated from a RNA polymerase II (PolII) binding site and is capable of elongating bidirectionally. In other embodiments, the eRNA transcription is initiated from a RNA polymerase II (PolII) binding site and is capable of elongating unidirectionally.

It is further conceived, that in some embodiments, the eRNA is capable of enhancing transcription of the TNFSF10 gene. In another aspect of the disclosure, the transcriptional start site of the TNFSF10 gene is located on a chromosome at least about 1 kilobase (kb) from the genomic enhancer sequence or region.

The method may be applied to mammalian cells which may include epithelium cells, a hematopoietic cells, monocytes, macrophages, neurons, breast cells, or cancer cells. In another aspect, the mammalian cell contacted with the antisense compound is in a subject.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-C. Genome-wide eRNA identification. (FIG. 1A) Venn diagram shows the number of all the intergenic transcribed regions (outer circle, light blue), high confident enhancer regions (middle circle, blue), and inducible enhancer regions (inner circle, dark blue). (FIG. 1B) Heatmap summarizes GRO-seq data in eRNA-TSS flanking regions (from 1 Kb upstream to 2 Kb downstream). eRNAs from + (yellow) and − (purple) strands are shown separately. Predicted eRNA-expressing enhancer regions are centered at the TSS. (FIG. 1C) Heatmap (upper panel) and metagene profiles (lower panel) are plotted for epigenetic signals including H3K4me1, H3K27ac and P300 ChIP-seq, DNase-seq, and MNase-seq data.

FIGS. 2A-E. Analysis of differentially expressed genes. (FIG. 2A) Number of up—(red) and down—(blue) regulated genes in time course after virus infection. (FIG. 2B) Number of up—(red) and down—(blue) regulated enhancers through time course. (FIG. 2C) Bar-plot of GO terms enriched for the nearest genes linked to the inducible enhancers. (FIGS. 2D-E) First two principal components of PCA analysis based on mRNA (FIG. 2D) and eRNA (FIG. 2E) expression level. The plots are color-coded with blue representing early and orange late time points.

FIGS. 3A-G. Prediction of virus inducible enhancer-promoter (EP) pairs and validation of their interactions. (FIG. 3A) Heat-map of discordant and concordant expression pairs of target genes (left panel) and their enhancers (right panel). Rows are matched. Expression levels were normalized as log 2 fold-changes relative to 0 h. (FIG. 3B) Diagram describes the identification of inducible enhancers and genes with two indices: the continuity index (CI) and the amplitude index (AI). (FIG. 3C) Number of inducible genes as a function of EP distance is analyzed. Inducible genes were counted within each 100 Kb bin to inducible enhancers (blue points). As a control, the number of all genes in each bin was calculated (grey points). Each group was normalized by the maximum count for the sake of comparison. (FIG. 3D) Enrichment of TF IRF7 motif in the 1 Kb TSS-flanking region of inducible enhancers is shown. (FIG. 3E) Motif enrichment of inducible enhancers. X-axis (absolute enrichment) is the maximum sites per base per peak (SBP). Y-axis (relative enrichment) is the SBP ratio between center (−100 to 100 bp) and rest (−500 to −100 bp and 100 to 500 bp) flanking regions. Point sizes indicate the GRO-seq RPKM fold-changes of TFs. Colors indicate the first time point when the TF reaches half induction. (FIG. 3F) Average PhastCon conservation scores of primates across inducible enhancer regions is shown, relative to randomly selected background. (FIG. 3G) Percentage of inducible human EP pairs that co-exist in other species is shown.

FIGS. 4A-F. Effects of eRNA KD on target genes. (FIG. 4A) Heatmaps of 3C signals for 18 inducible EP pairs and 18 control EP pairs within 200 Kb are shown. Signals are normalized by BAC 3C interaction frequency. (FIG. 4B) Boxplot of 3C log fold-changes is shown (12 h vs. 0 h) for control and induced EP pairs with p-values from Kolmogorov-Smirnov (KS) test. (FIG. 4C) Representative examples of 3C results are shown and compared with GRO-seq signal (RPKM) of the corresponding immune-related genes. (FIG. 4D) Boxplot shows mRNA fold-changes for successful eRNA KD (eRNA <70%) and unsuccessful eRNA KD (eRNA >70%). (FIG. 4E) Heatmap shows mRNA/eRNA log fold-changes. 11 inducible EP pairs and 12 control pairs are included. (FIG. 4F) Representative examples of EP pairs where eRNA KD led to mRNA repression. mRNA/eRNA expression levels were measured by RT-qPCR. Y-axis of expression curves represent GRO-seq signal (RPKM).

FIGS. 5A-C. Effects of multiple enhancers regulation on target gene expression and chromosomal conformation. (FIG. 5A) Schematic diagram of TNFSF10 gene with its multiple enhancers. TNFSF10 has #38 enhancer 27 Kb upstream, and #30 and #5 enhancers 67 Kb and 69 Kb downstream. Colored arrows from the gene and enhancer indicate transcriptional direction. Dashed lines show physical interaction between promoter and enhancer (Interaction A and B) or between different enhancers (Interaction C). (FIG. 5B) Interaction changes between enhancer and promoter regions (Interaction A and B) after individual eRNA KD and all three combined eRNA KD. (FIG. 5C) Three eRNAs (dark blue) and target gene (orange) expression fold changes after each individual eRNA KD and after all three eRNA KD by combining three corresponding siRNAs.

FIGS. 6A-F. Effect of selective inhibition of TNFSF10 by eRNA knockdown on viral induced apoptosis. (FIG. 6A) Simplified representation of the TNFSF10 regulatory network. (FIG. 6B) Relative expression of TNFSF10 in eRNAs knockdown (#5, #30 and #38, triple eRNA KD) and control cells. Triple KD of eRNAs regulating the TNFSF10 results in loss of TNFSF10 expression. (FIG. 6C) Western blot using cleaved caspase-3 antibody to assess apoptosis. Stronger signal of cleaved caspase-3 indicates higher fraction apoptotic cells. As an internal standard, β-actin was used. (FIG. 6D) Cell viability by live cell counts (left panel) and apoptotic cells counts (right panel) for TNFSF10 eRNA and control KD cells are shown. (FIG. 6E) Regulation of apoptosis by TIC10 or virus induced TNFSF10 expression. Possible mechanism through eRNA or direct gene activation is shown in left figure panel. Cell viability by live cell counts (middle panel) for TIC10 treated cell and control cell, and apoptotic cell counts (right panel) for eRNAs KD (triple KD) and control KD in TIC10 treatment for 48 hours. (FIG. 6F) TNFSF10 and its three eRNAs expression fold changes with or without TIC 10 treatment for 48 hours (left panel), and with SeV or TIC10 treatment for 9 hours (right panel).

FIGS. 7A-G. Differentially expressed genes and enhancer by SeV virus infection (FIG. 7A) Histogram of eRNA lengths is shown. X-axis represents the log 10 of eRNA lengths and Y-axis represents the frequency. (FIG. 7B) Gene ontology terms enriched by up-regulated genes (UP) and down-regulated gene (DOWN) are shown with spans of arrows showing duration of gene activation. (FIG. 7C) and (FIG. 7D) Representative genome browser track views of activated immune-related genes, MX1, ISG15 and CCL5, and activated enhancers. Epigenetic (DNase HS, H3K4me1 or H3K4me3 and H3K27ac) signals were normalized to the maximum levels in the regions. The y-axis of GRO-seq data represents normalized read density in reads per 10 million. (FIG. 7E) and (FIG. 7F) The results from t-distributed stochastic neighbor embedding (t-SNE) dimension-reduction analysis for mRNA and eRNA are shown. The plots are color-coded with blue and orange representing early and late time points, respectively. (FIG. 7G) K27Ac enrichment level at the inducible enhancer with time course after virus infection is shown.

FIGS. 8A-B. L2, IFNB1 enhancer and IFNB1 transcriptional changes before (0 h) and after virus infection (9 h). (FIG. 8A) Genome browser track of L2 and IFNB1 is shown. Epigenetic (Sg1, H3K4me1/3 and H3K27ac) signals were normalized by the maximum levels in the regions. The Y-axis represents GRO-seq signal in reads per 10 million. (FIG. 8B) Heat map summarizes GRO-seq RPKM level of L2 and IFNB1 as well as its signal related genes, IRFs, NFκBs, and RELs through the incubation times from 0 hour to 24 hours after infection.

FIGS. 9A-E. Prediction of virus inducible enhancer-promoter (EP) pairs. (FIG. 9A) Average logarithm fold-changes of expressed enhancers near inducible genes, divided into two groups according to EP distance are shown: 0-100 Kb, 100-200 Kb, 200-300 Kb, 300-400 Kb, 400-500 Kb, and 500-600 Kb. (FIG. 9B) Distribution of EP distance between inducible (red) and background (grey) pairs is shown. (FIG. 9C) Average PhastCon conservation scores of each mammal and vertebrate across inducible enhancer regions, relative to randomly selected background are shown. (FIG. 9D) Percentage of inducible human EP pairs (EP distance <500 Kb) that co-exist in other species is shown. (FIG. 9E) Violin plots showing the logarithmic fold change values of enhancers at each time point after infection. Enhancers were divided into groups based on distances from inducible genes.

FIGS. 10A-B. Effects of eRNA KD on target gene transcription. Individual KD experiments of inducible EP pairs are shown. Barplots (FIG. 10A) show the ratio of eRNA (blue)/mRNA (orange) expression level before and after siRNA treatment. Expression profiles (FIG. 10B) show GRO-seq signal (RPKM) of eRNA (blue)/mRNA (orange) during virus incubation time.

FIGS. 11A-C. eRNA KD effect on physical EP interaction. (FIGS. 11A-C) (Top) Schematic diagrams of IFNB1/IF135/MYCBP2 and corresponding enhancer are shown. (Lower left) Fold-change of 3C interaction between EPs after eRNA KD is shown, compared with negative controls.

FIGS. 12A-B Cases of genes with multiple enhancers. (FIGS. 12A-B) Schematic diagram of TLR7 and CD38 and their nearby inducible enhancers is shown (top). Fold changes of eRNA (blue)/mRNA (orange) after individual and combined eRNA KD is plotted.

DETAILED DESCRIPTION OF THE EMBODIMENTS

Figure 9E:
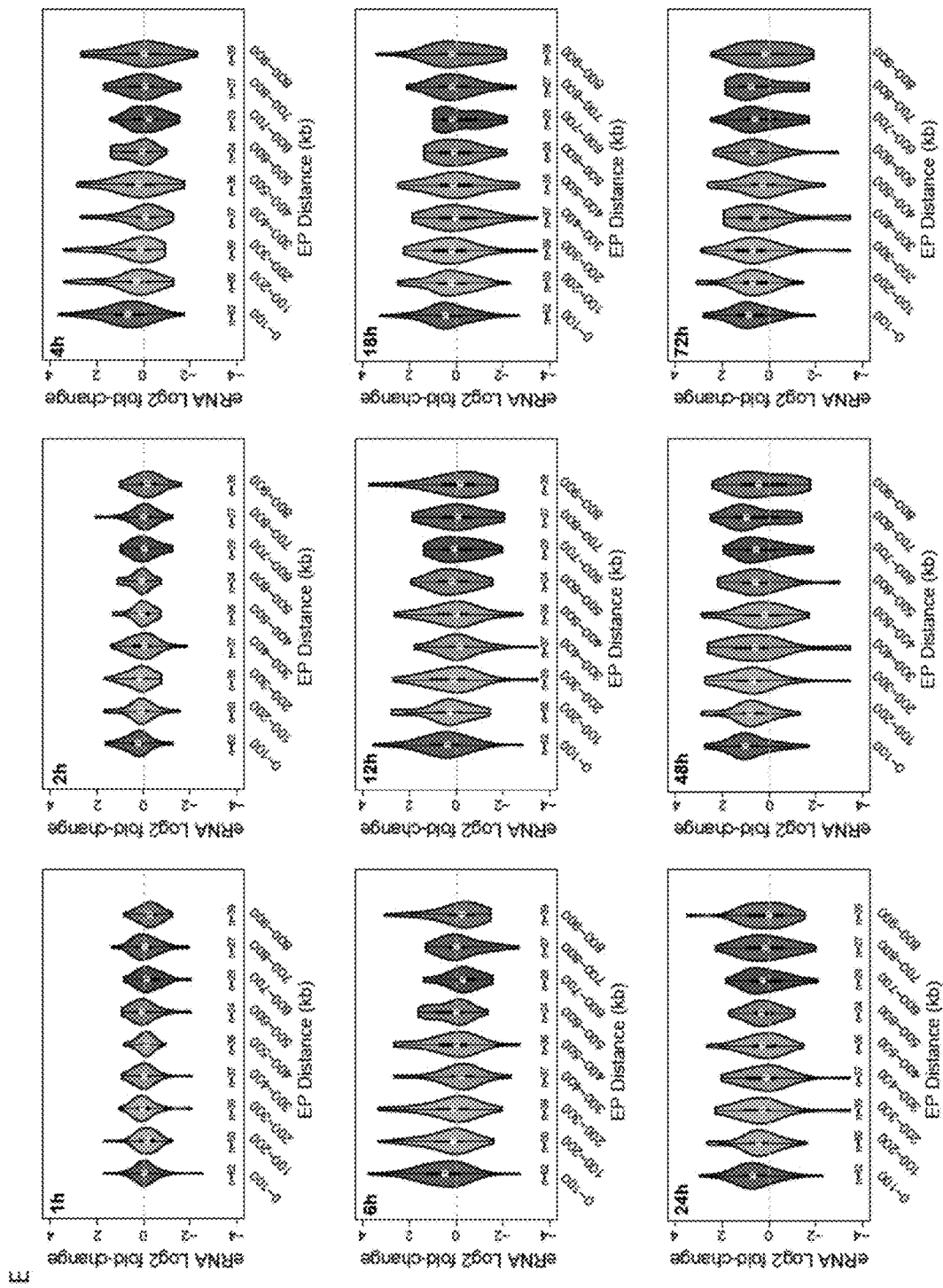
Figure 13:
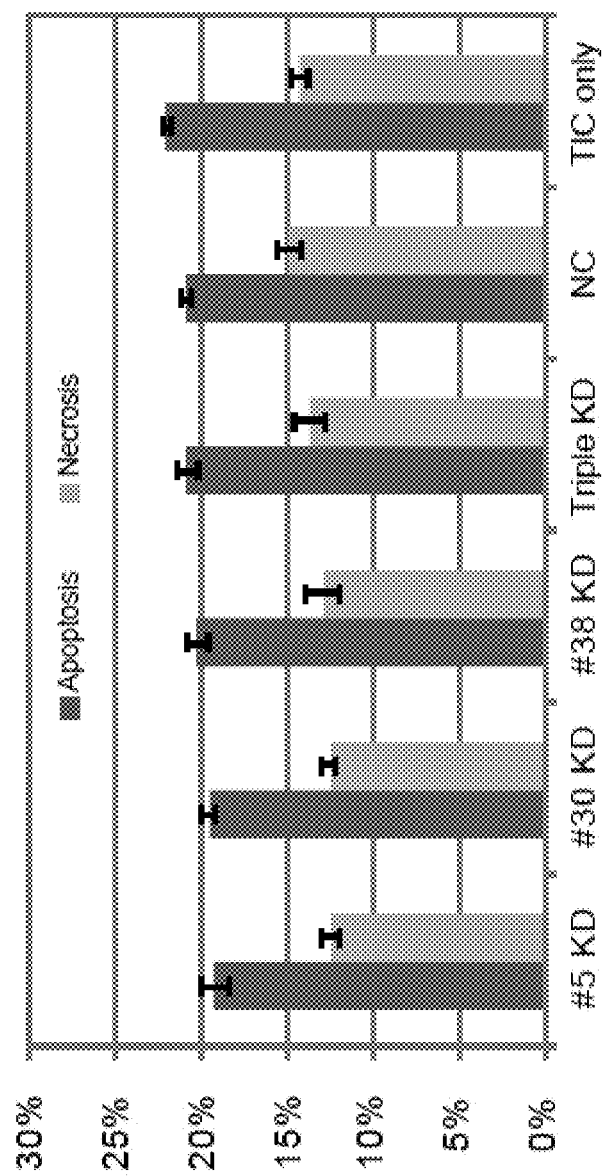
FIG. 13. eRNA KD and TIC10 treatment. Y-axis shows the fraction of apoptotic and necrotic cells after 48 h TIC10 incubation, with single, triple or control eRNA KD.

In order to systematically investigate the functionality of eRNAs in the human genome, the inventor employed a battery of comprehensive, unbiased functional genomic experiments across large time points to annotate and investigate huge dynamics of enhancer and target gene activation. He also designed a novel computational strategy for determining functional eRNAs that are virus inducible and mediate innate anti-viral response. Combined with functional assessment using RNAi and time course chromosome conformation capture (3C), the inventor examined functional relevance of these virus inducible eRNAs and their regulatory trajectories and modes of action.

A. eRNAs

Enhancer RNAs (eRNAs) represent a class of relatively short non-coding RNA molecules (50-2000 nucleotides) transcribed from the DNA sequence of enhancer regions. They were first detected in 2010 through the use of genome-wide techniques such as RNA-seq and ChIP-seq. eRNAs can be subdivided into two main classes: 1D eRNAs and 2D eRNAs, which differ primarily in terms of their size, polyadenylation state, and transcriptional directionality. The expression of a given eRNA seems to correlate with the activity of its corresponding enhancer in a context-dependent fashion. Increasing evidence suggests that eRNAs actively play a role in transcriptional regulation in cis and in trans, and while their mechanisms of action remain unclear, a few models have been proposed.

Enhancers as sites of extragenic transcription were initially discovered in genome-wide studies that identified enhancers as common regions of RNA polymerase II (RNA pol II) binding and non-coding RNA transcription. The level of RNA pol II-enhancer interaction and RNA transcript formation were found to be highly variable among these initial studies. Using explicit chromatin signature peaks, a significant proportion (~70%) of extragenic RNA Pol II transcription start sites were found to overlap enhancer sites in murine macrophages. Out of 12,000 neuronal enhancers in the mouse genome, almost 25% of the sites were found to bind RNA Pol II and generate transcripts. These eRNAs, unlike messenger RNAs (mRNAs), lacked modification by polyadenylation, were generally short and non-coding, and were bidirectionally transcribed. Later studies revealed the transcription of another type of eRNAs, generated through unidirectional transcription, that were longer and contained a poly A tail. Furthermore, eRNA levels were correlated with mRNA levels of nearby genes, suggesting the potential regulatory and functional role of these non-coding enhancer RNA molecules.

eRNAs are transcribed from DNA sequences upstream and downstream of extragenic enhancer regions. Previously, several model enhancers have demonstrated the capability to directly recruit RNA Pol II and general transcription factors and form the pre-initiation complex (PIC) prior to the transcription start site at the promoter of genes. In certain cell types, activated enhancers have demonstrated the ability to both recruit RNA Pol II and also provide a template for active transcription of their local sequences.

Depending on the directionality of transcription, enhancer regions generate two different types of non-coding transcripts, 1D-eRNAs and 2D-eRNAs. The nature of the pre-initiation complex and specific transcription factors recruited to the enhancer may control the type of eRNAs generated. After transcription, the majority of eRNAs remain in the nucleus. In general, eRNAs are very unstable and actively degraded by the nuclear exosome. Not all enhancers are transcribed, with non-transcribed enhancers greatly outnumbering the transcribed ones in the order of magnitude of dozens of thousands in every given cell type.

Evidence that eRNAs cause downstream effects on the efficiency of enhancer activation and gene transcription suggests its functional capabilities and potential importance. The transcription factor p53 has been demonstrated to bind enhancer regions and generate eRNAs in a p53-dependent manner. In cancer, p53 plays a central role in tumor suppression as mutations of the gene are shown to appear in 50% of tumors. These p53-bound enhancer regions (p53BERs) are shown to interact with multiple local and distal gene targets involved in cell proliferation and survival. Furthermore, eRNAs generated by the activation of p53BERs are shown to be required for efficient transcription of the p53 target genes, indicating the likely important regulatory role of eRNAs in tumor suppression and cancer.

Variations in enhancers have been implicated in human disease but a therapeutic approach to manipulate enhancer activity is currently not possible. With the emergence of eRNAs as important components in enhancer activity, powerful therapeutic tools such as RNAi may provide promising routes to target disruption of gene expression.

B. TNFSF10

In the field of cell biology, TNF-related apoptosis-inducing ligand (TRAIL), is a protein functioning as a ligand that induces the process of cell death called apoptosis. TRAIL has also been designated CD253 (cluster of differentiation 253) and TNFSF10 (tumor necrosis factor (ligand) superfamily, member 10).

TRAIL is a cytokine that is produced and secreted by most normal tissue cells. It causes apoptosis primarily in tumor cells, by binding to certain death receptors. TRAIL and its receptors have been used as the targets of several anti-cancer therapeutics since the mid-1990s, such as Mapatumumab. However, as of 2013, these have not shown significant survival benefit. TRAIL has also been implicated as a pathogenic or protective factor in various pulmonary diseases, particularly pulmonary arterial hypertension.

TRAIL shows homology to other members of the tumor necrosis factor superfamily. It is composed of 281 amino acids and has characteristics of a type II transmembrane protein. The N-terminal cytoplasmic domain is not conserved across family members, however, the C-terminal extracellular domain is conserved and can be proteolytically cleaved from the cell surface. TRAIL forms a homotrimer that binds three receptor molecules.

In humans, the gene that encodes TRAIL is located at chromosome 3q26, which is not close to other TNF family members. The genomic structure of the TRAIL gene spans approximately 20 kb and is composed of five exonic segments 222, 138, 42, 106, and 1245 nucleotides and four introns of approximately 8.2, 3.2, 2.3 and 2.3 kb. The TRAIL gene lacks TATA and CAAT boxes and the promoter region contains putative response elements for transcription factors GATA, AP-1, C/EBP, SP-1, OCT-1, AP3, PEA3, CF-1, and ISRE.

TRAIL has been shown to interact with TNFRSF10B. It also binds to the death receptors DR4 (TRAIL-RI) and DR5 (TRAIL-RII). The process of apoptosis is caspase-8-dependent. Caspase-8 activates downstream effector caspases including procaspase-3, –6, and –7, leading to activation of specific kinases. TRAIL also binds the receptors DcR1 and DcR2, which do not contain a cytoplasmic domain (DcR1) or contain a truncated death domain (DcR2). DcR1 functions as a TRAIL-neutralizing decoy-receptor. The cytoplasmic domain of DcR2 is functional and activates NFκB. In cells expressing DcR2, TRAIL binding therefore activates NFκB, leading to transcription of genes known to antagonize the death signaling pathway and/or to promote inflammation. Application of engineered ligands that have variable affinity for different death (DR4 and DR5) and decoy receptors (DCR1 and DCR2) may allow selective targeting of cancer cells by controlling activation of Type 1/Type 2 pathways of cell death and single cell fluctuations.

Luminescent iridium complex-peptide hybrids, which mimic TRAIL, have recently been synthesized in vitro. These artificial TRAIL mimics bind to DR4/DR5 on cancer cells and induce cell death via both apoptosis and necrosis, which makes them a potential candidate for anticancer drug development.

TIC10 (which causes expression of TRAIL) was investigated in mice with various tumor types. The small molecule ONC201 causes expression of TRAIL which kills some cancer cells. In clinical trials only a small proportion of cancer patients responded to various drugs that targeted TRAIL death receptors. Many cancer cell lines develop resistance to TRAIL and limits the efficacy of TRAIL-based therapies.

C. Modified Nucleobases

In certain embodiments, compounds of the disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, T-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, $CF_3$, $OCF_3$, O, S, or $N(R_m)$-alkyl; O, S, or $N(R_m)$-alkenyl; O, S or $N(R_m)$-alkynyl; O-alkylenyl-O-alkyl, alkynyl, alkaryl, aralkyl, O-alkaryl, O-aralkyl, $O(CH_2)_2SCH_3$, $O(CH_2)_2$—O—$N(R_m)(R_n)$ or O—$CH_2$—C(=O)—$N(R_m)$ $(R_n)$, where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH=$CH_2$, O—$CH_2$—CH=$CH_2$, $OCH_2CH_2OCH_3$, $O(CH_2)_2SCH_3$, O—$(CH_2)_2$—O—$N(R_m)(R_n)$, $O(CH_2)_2O(CH_2)_2N(CH_3)_2$, and N-substituted acetamide (O—$CH_2$—C(=O)—$N(R_m)$ $(R_n)$ where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)_2SCH_3$, $O(CH_2)_2$—O—$N(CH_3)_2$, —$O(CH_2)_2O$ $(CH_2)_2N(CH_3)_2$, and O—$CH_2$—C(=O)—$N(H)CH_3$.

In certain embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —$[C(R_a)(R_b)]_n$—, —$[C(R_a)(R_b)]_n$—O—, —$C(R_aR_b)$—N (R)—O— or, —$C(R_aR_b)$—O—N(R)—; 4'-$CH_2$-2', 4'-$(CH_2)_2$-2', 4'-$(CH_2)$—O-2' (LNA); 4'-$(CH_2)$—S-2'; 4'-$(CH_2)_2$-O-2' (ENA); 4'-CH($CH_3$)—O-2' (cEt) and 4'-CH ($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya et al., J. Org. Chem., 2009, 74, 118-134); and 4'-$CH_2$—C(=$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —$[C(R_a)(R_b)]_n$—, —$C(R_a)$=$C(R_b)$—, —$C(R_a)$=N—, —C(=$NR_a$)—, —C(=O)—, —C(=S)—, —O—, —$Si(R_a)_2$—, —S(=O)$_x$—, and —$N(R_a)$—; wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_1$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_2$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-CH2-N(R)-2') BNA, (I) methyl carbocyclic (4'-$CH_2$—CH($CH_3$)-2') BNA, (J) propylene carbocyclic (4'-$(CH_2)_3$-2') BNA, and (K) Methoxy(ethyleneoxy) (4'-CH ($CH_2OMe$)-O-2') BNA (also referred to as constrained MOE or cMOE).

Additional bicyclic sugar moieties are known in the art, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000,97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-8379 (Jul. 4, 2007); Elayadi et al., Curr. Opinion Invens. Drugs, 2001, 2, 5561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794, 499, 7,034,133, 6,525,191, 6,670,461, and 7,399,845; WO 2004/106356, WO 1994/14226, WO 2005/021570, and WO 2007/134181; U.S. Patent Publication Nos. US2004/ 0171570, US2007/0287831, and US2008/0039618; U.S. Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., Nucleic Acids Research, 2003, 21, 6365-6372).

In certain embodiments, substituted sugar moieties comprise one or more non-bridging sugar substituent and one or more bridging sugar substituent (e.g., 5'-substituted and 4'-2' bridged sugars; PCT International Application WO 2007/ 134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US20050130923, published on Jun. 16, 2005) and/or the 5' position. By way of additional example, carbocyclic bicyclic nucleosides having a 4'-2' bridge have been described (see, e.g., Freier et al., Nucleic Acids Research, 1997, 25(22), 4429-4443 and Albaek et al., J. Org. Chem., 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. Bioorg. & Med. Chem. (2002) 10:841-854), and fluoro HNA (F-HNA).

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, Bioorganic & Medicinal Chemistry, 2002, 10, 841-854).

Combinations of modifications are also provided without limitation, such as 2'-F-5'-methyl substituted nucleosides (see PCT International Application WO2008/101157 Published on Aug. 21, 2008 for other disclosed 5',2'-bis substituted nucleosides) and replacement of the ribosyl ring oxygen atom with S and further substitution at the 2'-position (see U.S. Patent Publication US20050130923, published on Jun. 16, 2005) or alternatively 5'-substitution of a bicyclic nucleic acid (see PCT International Application WO2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., J. Am. Chem. Soc. 2007, 129(26), 8362-8379).

In certain embodiments, the present disclosure provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

In certain embodiments, nucleosides of the present disclosure comprise one or more unmodified nucleobases. In certain embodiments, nucleosides of the present disclosure comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2 (3H)-one), carbazole cytidine ($^2$H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; those disclosed by Englisch et al., Angewandte Chemie, International Edition, 1991, 30, 613; and those disclosed by Sanghvi, Y. S., Chapter 15, Antisense Research and Applications, Crooke, S. T. and Lebleu, B., Eds., CRC Press, 1993, 273-288.

Representative United States Patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, each of which is herein incorporated by reference in its entirety.

In certain embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetyl (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present disclosure involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553), cholic acid (Manoharan et al., Bioorg. Med. Chem. Lett., 1994, 4, 1053), a thioether, e.g., hexyl-5-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylaminocarbonyl-oxycholesterol moiety (Crooke et al., J. Pharmacol. Exp. Ther., 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned, and each of which is herein incorporated by reference.

D. Pharmaceutical Composition and Methods of Delivery

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals. One will generally desire to employ appropriate salts, buffers, and lipids to render delivery of the oligonucleotides to allow for uptake by target cells. Such methods an compositions are well known in the art, for example, as disclosed in U.S. Pat. Nos. 6,747,014 and 6,753,423. Compositions of the present disclosure comprise an effective amount of the oligonucleotide to cells, dissolved or dispersed in a pharmaceutically acceptable carrier or medium.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents, liposomes, cationic lipid formulations, microbubble nanoparticles, and the like. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. This includes oral, nasal, buccal, or topical. Alternatively, administration may be by intradermal, subcutaneous, intramuscular, intraperitoneal or intravenous injection, or introduction into the CNS, such as into spinal fluid. Such compositions would normally be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, lipids, nanoparticles, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the oligonucleotides of the present disclosure may be incorporated with excipients. The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Of particular interest to the present disclosure is the use of lipid delivery vehicles. Lipid vehicles encompass micelles, microemulsions, macroemulsions, liposomes, and similar carriers. The term micelles refers to colloidal aggregates of amphipathic (surfactant) molecules that are formed at a well-defined concentration known as the critical micelle concentration. Micelles are oriented with the nonpolar portions at the interior and the polar portions at the exterior surface, exposed to water. The typical number of aggregated molecules in a micelle (aggregation number) is 50 to 100. Microemulsions are essentially swollen micelles, although not all micellar solutions can be swollen to form microemulsions. Microemulsions are thermodynamically stable, are formed spontaneously, and contain particles that are extremely small. Droplet diameters in microemulsions typically range from 10 100 nm. In contrast, the term macroemulsions refers to droplets with diameters greater than 100 nm. Liposomes are closed lipid vesicles comprising lipid bilayers that encircle aqueous interiors. Liposomes typically have diameters of 25 nm to 1 μm.

In one embodiment of a liposome formulation, the principal lipid of the vehicle may be phosphatidylcholine. Other useful lipids include various natural (e.g., tissue derived L-α-phosphatidyl: egg yolk, heart, brain, liver, soybean) and/or synthetic (e.g., saturated and unsaturated 1,2-diacyl-SN-glycero-3-phosphocholines, 1-acyl-2-acyl-SN-glycero-3-phosphocholines, 1,2-diheptanoyl-SN-glycero-3-phosphocholine) derivatives of the same. Such lipids can be used alone, or in combination with a secondary lipid. Such secondary helper lipids may be non-ionic or uncharged at physiological pH, including non-ionic lipids such as cholesterol and DOPE (1,2-dioleolylglyceryl phosphatidylethanolamine). The molar ratio of a phospholipid to helper lipid can range from about 3:1 to about 1:1, from about 1.5:1 to about 1:1, and about 1:1.

Another specific lipid formulation comprises the SNALP formulation, containing the lipids 3-N—[(ω methoxypoly (ethylene glycol)$_{2000}$) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar % ratio.

Exemplary amounts of lipid constituents used for the production of the liposome include, for instance, 0.3 to 1 mol, 0.4 to 0.6 mol of cholesterol; 0.01 to 0.2 mol, 0.02 to 0.1 mol of phosphatidylethanolamine; 0.0 to 0.4 mol, or 0-0.15 mol of phosphatidic acid per 1 mol of phosphatidylcholine.

Liposomes can be constructed by well-known techniques. Lipids are typically dissolved in chloroform and spread in a thin film over the surface of a tube or flask by rotary evaporation. If liposomes comprised of a mixture of lipids are desired, the individual components are mixed in the original chloroform solution. After the organic solvent has been eliminated, a phase consisting of water optionally containing buffer and/or electrolyte is added and the vessel agitated to suspend the lipid. Optionally, the suspension is then subjected to ultrasound, either in an ultrasonic bath or with a probe sonicator, until the particles are reduced in size and the suspension is of the desired clarity. For transfection, the aqueous phase is typically distilled water and the suspension is sonicated until nearly clear, which requires several minutes depending upon conditions, kind, and quality of the sonicator. Commonly, lipid concentrations are 1 mg/ml of aqueous phase, but could be higher or lower by about a factor of ten.

Lipids, from which the solvents have been removed, can be emulsified by the use of a homogenizer, lyophilized, and melted to obtain multilamellar liposomes. Alternatively, unilamellar liposomes can be produced by the reverse phase evaporation method (Szoka and Papahadjopoulos, 1978).

Unilamellar vesicles can also be prepared by sonication or extrusion. Sonication is generally performed with a bath-type sonifier, such as a Branson tip sonifier (G. Heinemann Ultrashall and Labortechnik, Schwabisch Gmund, Germany) at a controlled temperature as determined by the melting point of the lipid. Extrusion may be carried out by biomembrane extruders, such as the Lipex Biomembrane Extruder (Northern Lipids Inc, Vancouver, British Columbia, Canada). Defined pore size in the extrusion filters may generate unilamellar liposomal vesicles of specific sizes. The liposomes can also be formed by extrusion through an asymmetric ceramic filter, such as a Ceraflow Microfilter (commercially available from the Norton Company, Worcester, Mass.).

Liposomes can be extruded through a small-pore polycarbonate membrane or an asymmetric ceramic membrane to yield a well-defined size distribution. Typically, a suspension is cycled through the membrane one or more times until the desired liposome size distribution is achieved. The liposomes may be extruded through successively smaller-pore membranes, to achieve a gradual reduction in liposome size. For use in the present disclosure, liposomes have a size of about 0.05 microns to about 0.5 microns, or having a size of about 0.05 to about 0.2 microns.

In certain embodiments, the oligonucleotide compounds and compositions as described herein are administered parenterally. In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, oligonucleotide compounds and compositions are delivered to the CNS. In certain embodiments, oligonucleotide compounds and compositions are delivered to the cerebrospinal fluid. In certain embodiments, oligonucleotide compounds and compositions are administered to the brain parenchyma. In certain embodiments, oligonucleotide compounds and compositions are delivered to an animal by intrathecal administration, or intracerebroventricular administration. Broad distribution of oligonucleotide compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

In certain embodiments, delivery of an oligonucleotide compound or composition described herein can affect the pharmacokinetic profile of the oligonucleotide compound or composition. In certain embodiments, injection of a oligonucleotide compound or composition described herein, to a targeted tissue improves the pharmacokinetic profile of the oligonucleotide compound or composition as compared to infusion of the oligonucleotide compound or composition. In a certain embodiment, the injection of an oligonucleotide compound or composition improves potency compared to broad diffusion, requiring less of the compound or composition to achieve similar pharmacology. In certain embodiments, similar pharmacology refers to the amount of time that a target mRNA and/or target protein is down-regulated (e.g., duration of action). In certain embodiments, methods of specifically localizing a pharmaceutical agent, such as by bolus injection, decreases median effective concentration ($EC_{50}$) by a factor of about 50 (e.g., 50-fold less concentration in tissue is required to achieve the same or similar pharmacodynamic effect). In certain embodiments, methods of specifically localizing a pharmaceutical agent, such as by bolus injection, decreases median effective concentration ($EC_{50}$) by a factor of 20, 25, 30, 35, 40, 45 or 50.

In certain embodiments, delivery of an oligonucleotide compound or composition, as described herein, to the CNS results in 47% down-regulation of a target mRNA and/or target protein for at least 91 days. In certain embodiments, delivery of a compound or composition results in at least 25%, at least 30%, at least 35%, at least 40%, at least 45%, at least 50%, at least 55%, at least 60%, at least 65%, at least 70%, or at least 75% down-regulation of a target mRNA and/or target protein for at least 20 days, at least 30 days, at least 40 days, at least 50 days, at least 60 days, at least 70 days, at least 80 days, at least 85 days, at least 90 days, at least 95 days, at least 100 days, at least 110 days, at least 120 days. In certain embodiments, delivery to the CNS is by intraparenchymal administration, intrathecal administration, or intracerebroventricular administration.

In certain embodiments, an oligonucleotide is delivered by injection or infusion once every week, every two weeks, every month, every two months, every 90 days, every 3 months, every 6 months, twice a year or once a year.

E. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Results

A time-resolved enhancer activity map. In order to obtain the informative features of eRNA/mRNA dynamics, the inventor performed a large time series GRO-seq analysis of B-lymphoblasts (GM12878) during innate anti-viral immune response. The inventor used Sendai Virus (SeV) to activate the immune response signal-cascade gene induction system as a model to study the anti-viral program. The inventor first combined all GRO-seq data obtained from 12 time points from 0 to 72 hours post-infection to determine a compendium of eRNA-producing enhancers responding to virus, then used HOMER (Heinz et al., 2010) to identify the eRNA transcripts (see Methods). Of 32,832 total intergenic transcripts, 11,025 transcripts overlapped with H3K4me1 or H3K27Ac histone modification peaks, representative enhancer marks (FIG. 1A). The inventor annotated transcription start/termination sites (TSS/TTS) for the 11,025 eRNAs (FIG. 1B). The average predicted length of eRNAs from the inventor's annotation efforts was 1,746 bp (FIG. 7A). Other enhancer marks including p300 and DNase hypersensitivity signals were highly enriched at the TSS of eRNAs (FIG. 1C) (Lai and Pugh, 2017). Additionally, the patterns of H3K4me1 and H3K27Ac ChIP-seq, DNase hypersensitivity and MNase-seq indicated an open chromatin region at the eRNA TSS. Notably, a majority (64%) of the eRNAs were below detection levels prior to virus infection, thereby indicating a dramatic induction of eRNA synthesis upon virus infection (FIG. 1A). This is further supported by the fact that only ~28% of the inventor's eRNA annotations overlapped with that of the FANTOM5 human enhancer atlas (Andersson et al., 2014), underscoring condition specific differences and. In addition, the inventor found 18,999 intergenic transcripts, lacking initial eRNA production and enhancer marks, being transcribed after infection. These transcripts showed similar lengths as eRNAs defined above (P-value 0.14, t-test). A previous study showed that enhancers initially lacking known enhancer marks, like the 18,999 enhancers that the inventor found here, could acquire enhancer-associated epigenetic modifications upon stimuli (Kaikkonen et al., 2013).

Rapid and dynamic transcriptional response of genes and enhancers. The inventor quantified expression levels of the RefSeq genes and performed differential expression (DE) analysis. Based on the expression dynamics of DE genes (FIG. 2A), the time course can be divided into three stages: 0 h-2 h, limited changes; 4 h-24 h, significant changes with more induced genes (early-up) than repressed; 48 h-72 h, large changes comprised of both up—(late-up) and down—(late-down) regulated genes. To understand these expression dynamics more meaningfully, the inventor performed gene ontology (GO) analysis at each time point (FIG. 7B). DE gene-enriched functions were highly consistent between time points within each of the three stages. For example, the most frequently enriched GO terms of early-up, late-up and late-down groups were "responses to virus," "apoptosis" and "cell cycle," respectively. The inventor also performed DE analysis with the annotated eRNAs. Their expression dynamics could also be divided into three stages, exactly matching those of DE genes (FIG. 2B). Representative examples of inducible genes and eRNAs are shown in FIGS. 7C and 7D. Furthermore, nearest genes of the inducible eRNAs (described in the section describing enhancer-promoter pairs) were functionally enriched in immune system processes (FIG. 2C).

To visualize and verify the dynamics of eRNA and gene expression patterns, the inventor performed principal component analysis (PCA), which showed a trajectory of cellular states (FIGS. 2D-E). The first two principal components (PC) clearly separated samples from each time points. Principal component 2 (PC2) values showed an interesting trajectory, which moved away from the baseline in early time and returned after 18 h, matching the expression dynamics of immune related genes (GO term "defense response to virus," P-value 2.5E-12). Similar analysis was performed for genes correlated with PC1, showing enrichment of GO terms "translation," "apoptosis," and "RNA decay." Likewise, the first two PCs of eRNAs showed similar dynamics as those of gene expression, indicating connected regulatory processes between eRNA and gene expression. In addition, t-distributed stochastic neighbor embedding (t-SNE) (Jamieson et al., 2010) result showed almost identical patterns. (FIGS. 7E-F).

Cytokine IFNB1 as a representative transient transcript. As a representative virus-inducible case, the inventor investigated the IFNB1 gene and its enhancer L2, which the inventor previously identified as a novel virus inducible long-range enhancer regulating IFNB1 transcription in IMR90 lung fibroblasts (Banerjee et al., 2014). An independent study (Decque et al., 2016) has also demonstrated that the L2 is a major enhancer regulating IFNB1 expression in bone marrow derived dendritic cells and macrophages. The inventor's GRO-seq data in GM12878 cells indicate strong transcription at IFNB1 and the L2 element in early time points just after SeV infection (FIGS. 8A-B). L2 eRNA was transcribed first at 1 hour and then IFNB1 transcript emerged around 1 hour after L2, implying that eRNA generation precedes target gene transcription. Interestingly, L2 transcription continues to be detected even at 72 hours post infection when IFNB1 has become repressed by post-induction repression mechanisms (Ren et al., 1999), implicating a potentially novel enhancer inactivation and decommissioning mechanism. The inventor also investigated other well-known transcription factors of IRF and NFκB families which are also up-regulated at these earliest time points (FIG. 8B).

Construction of an enhancer-target gene map for viral response. Accurate cell-specific and genome-wide enhancer target identification is a challenging task. Despite several improvements in the past few years (Cao et al., 2017; Jin et al., 2013; Whalen et al., 2016), the accuracy is still far from satisfactory for in-depth case studies of individual genes or enhancers. Using metagene analysis, these results, as well as several other studies (Hah et al., 2013 and Kaikkonen et al., 2013), have shown the coordinated transcriptional dynamics of enhancers and neighbor genes should be highly enriched with functional targets. Can one take advantage of the paired expression profiles to further refine target prediction for individual enhancers? To this end, the inventor carefully examined the expression profiles of eRNA/gene pairs that were significantly activated by SeV infection. In addition to the expected, correlated pattern of concordant on/off behaviors between enhancers and genes, the inventor also observed a discordant expression pattern showing persistent eRNA transcription after target gene repression (FIG. 3A). Interestingly, this discordant pattern was exhibited by the previously validated L2-IFNB1 EP (enhancer-promoter) pair. Thus, the co-inducibility of eRNAs and target genes is a potentially important feature for inferring functional enhancer targets, regardless of regulatory divergence of the concordant and discordant sets of eRNA/gene pairs. To identify inducible enhancers and genes, the inventor constructed two indices: the continuity index (CI) and the amplitude index (AI) (FIG. 3B; see Example 3). The CI index is used to filter out random fluctuations in the expression levels, especially for eRNAs which are lowly expressed and more subject to technical variability. The AI index is designed to represent the maximum induced levels, which is stable with respect to the specific expression patterns but can be highly variable for each EP pair. 299 genes and 787 enhancers were identified as inducible. Consistent with the induced transcriptional activity, the H3K27Ac levels of these 787 enhancers were also induced by SeV infection (FIG. 7G). Genomic proximity is also an important factor for identifying enhancer targets (Sanyal et al., 2012). The inventor found that inducible genes were highly enriched within 200 Kb from the inducible enhancers (FIG. 3C) and vice versa (FIG. 9A). The inventor assigned the inducible enhancers with the nearest inducible genes within 200 Kb and obtained 123 highly confident enhancer-promoter (EP) pairs (Supplemental Table S1). Extending the proximity window farther enabled us to define more enhancer-promoter pairs, but this increased sensitivity of identifying more EP pairs also resulted in significant increases in the false positive rate for the inventor's inducible EP prediction. For example, the percentage of inducible genes decreased from ~50% to ~30% if the distance threshold was increased by another 100 Kb. In addition, the current analysis focused only on the mRNA encoding target genes and excluded possible target genes encoding noncoding RNAs due to the limited functional information regarding these genes. This highly prioritized inducible eRNA and target gene set included not only the previously validated L2-IFNB1 pair, but also other critical genes involved in immune function such as the CD38, IRF8, TNFSF10 and TLR7 genes, whose distal regulatory elements were largely unknown.

TABLE S1

All predicted induced eRNAs and their target genes.

| Target_gene(Refseq) | Enhancer_id | Target_gene (symbol) | enh_hg19 |
|---|---|---|---|
| NM_002036 | MetaEnhancer_1136_+ | ACKR1 | chr1 158975648 158977353 |
| NM_001122951 | MetaEnhancer_1136_+ | ACKR1 | chr1 158975648 158977353 |
| NM_004833 | MetaEnhancer_1136_+ | AIM2 | chr1 158975648 158977353 |
| NM_001136540 | MetaEnhancer_1799_− | APOL1 | chr22 36805195 36806192 |
| NM_001136540 | MetaEnhancer_862_− | APOL1 | chr22 36846877 36848115 |
| NM_030882 | MetaEnhancer_1799_− | APOL2 | chr22 36805195 36806192 |
| NM_145637 | MetaEnhancer_1799_− | APOL2 | chr22 36805195 36806192 |
| NM_030641 | MetaEnhancer_3137_− | APOL6 | chr22 36030413 36031205 |
| NM_174919 | MetaEnhancer_2379_− | ARHGAP27 | chr17 43433743 43435137 |
| NM_001128616 | MetaEnhancer_2422_+ | ARHGEF3 | chr3 56726327 56729181 |
| NM_019555 | MetaEnhancer_2422_+ | ARHGEF3 | chr3 56726327 56729181 |
| NM_001731 | MetaEnhancer_3101_+ | BTG1 | chr12 92586863 92587704 |
| NM_001295 | MetaEnhancer_258_− | CCR1 | chr3 46149958 46152633 |
| NM_001295 | MetaEnhancer_1961_+ | CCR1 | chr3 46150916 46156022 |
| NM_001775 | MetaEnhancer_3795_− | CD38 | chr4 15757373 15758209 |
| NM_001775 | MetaEnhancer_847_− | CD38 | chr4 15767579 15773083 |
| NM_001775 | MetaEnhancer_1694_+ | CD38 | chr4 15773236 15774381 |
| NM_001243794 | MetaEnhancer_2191_+ | CHST12 | chr7 2439830 2441170 |
| NM_172210 | MetaEnhancer_3084_+ | CSF1 | chr1 110435830 110436993 |
| NM_172212 | MetaEnhancer_3084_+ | CSF1 | chr1 110435830 110436993 |
| NM_000757 | MetaEnhancer_3084_+ | CSF1 | chr1 110435830 110436993 |
| NM_138287 | MetaEnhancer_2972_− | DTX3L | chr3 122380136 122380883 |
| NM_001034194 | MetaEnhancer_2326_− | EXOSC9 | chr4 122708957 122710268 |
| NM_001034194 | MetaEnhancer_1507_− | EXOSC9 | chr4 122714858 122717023 |
| NM_001034194 | MetaEnhancer_1473_+ | EXOSC9 | chr4 122716718 122718546 |
| NM_153230 | MetaEnhancer_2571_− | FBXO39 | chr17 6842901 6843791 |
| NM_014824 | MetaEnhancer_94_+ | FCHSD2 | chr11 72864171 72888511 |
| NM_002053 | MetaEnhancer_1625_+ | GBP1 | chr1 89546827 89547678 |
| NM_052941 | MetaEnhancer_1625_+ | GBP4 | chr1 89546827 89547678 |
| NM_052941 | MetaEnhancer_2172_+ | GBP4 | chr1 89739974 89742358 |
| NM_001206567 | MetaEnhancer_1136_+ | IFI16 | chr1 158975648 158977353 |
| NM_002038 | MetaEnhancer_1613_− | IFI6 | chr1 28014868 28016573 |
| NM_001270927 | MetaEnhancer_2029_− | IFIT1 | chr10 91052142 91055958 |
| NM_001270927 | MetaEnhancer_3024_+ | IFIT1 | chr10 91055858 91057638 |
| NM_001547 | MetaEnhancer_4002_− | IFIT2 | chr10 90922933 90923624 |
| NM_001547 | MetaEnhancer_1253_+ | IFIT2 | chr10 90923524 90925010 |
| NM_001547 | MetaEnhancer_2029_− | IFIT2 | chr10 91052142 91055958 |
| NM_001547 | MetaEnhancer_3024_+ | IFIT2 | chr10 91055858 91057638 |
| NM_001289758 | MetaEnhancer_4002_− | IFIT3 | chr10 90922933 90923624 |
| NM_001031683 | MetaEnhancer_4002_− | IFIT3 | chr10 90922933 90923624 |
| NM_001289758 | MetaEnhancer_1253_+ | IFIT3 | chr10 90923524 90925010 |
| NM_001031683 | MetaEnhancer_1253_+ | IFIT3 | chr10 90923524 90925010 |
| NM_001289758 | MetaEnhancer_2029_− | IFIT3 | chr10 91052142 91055958 |
| NM_001031683 | MetaEnhancer_2029_− | IFIT3 | chr10 91052142 91055958 |
| NM_001289758 | MetaEnhancer_3024_+ | IFIT3 | chr10 91055858 91057638 |
| NM_001031683 | MetaEnhancer_3024_+ | IFIT3 | chr10 91055858 91057638 |
| NM_012420 | MetaEnhancer_2029_− | IFIT5 | chr10 91052142 91055958 |
| NM_012420 | MetaEnhancer_3024_+ | IFIT5 | chr10 91055858 91057638 |
| NM_003641 | MetaEnhancer_1268_+ | IFITM1 | chr11 188083 189410 |
| NM_003641 | MetaEnhancer_1341_− | IFITM1 | chr11 347562 351028 |
| NM_003641 | MetaEnhancer_230_− | IFITM1 | chr11 353806 356185 |
| NM_006435 | MetaEnhancer_1268_+ | IFITM2 | chr11 188083 189410 |
| NM_006435 | MetaEnhancer_1341_− | IFITM2 | chr11 347562 351028 |
| NM_006435 | MetaEnhancer_230_− | IFITM2 | chr11 353806 356185 |
| NM_002176 | MetaEnhancer_1571_+ | IFNB1 | chr9 21096515 21098279 |
| NM_002198 | MetaEnhancer_250_− | IRF1 | chr5 131828856 131832505 |
| NM_002198 | MetaEnhancer_372_+ | IRF1 | chr5 131831379 131847154 |
| NM_002163 | MetaEnhancer_2143_+ | IRF8 | chr16 85922550 85923645 |
| NM_002163 | MetaEnhancer_259_+ | IRF8 | chr16 86028925 86034443 |
| NM_005547 | MetaEnhancer_3423_+ | IVL | chr1 152844459 152845369 |
| NM_005547 | MetaEnhancer_2511_+ | IVL | chr1 152940836 152941593 |
| NM_001162895 | MetaEnhancer_633_− | KIAA0040 | chr1 175173105 175173615 |
| NM_001162893 | MetaEnhancer_633_− | KIAA0040 | chr1 175173105 175173615 |
| NM_001162895 | MetaEnhancer_1625_− | KIAA0040 | chr1 175201951 175206691 |
| NM_001162893 | MetaEnhancer_1625_− | KIAA0040 | chr1 175201951 175206691 |
| NM_001162895 | MetaEnhancer_3581_− | KIAA0040 | chr1 175255261 175256747 |
| NM_001162893 | MetaEnhancer_3581_− | KIAA0040 | chr1 175255261 175256747 |
| NM_001162895 | MetaEnhancer_1115_+ | KIAA0040 | chr1 175256708 175258040 |
| NM_001162893 | MetaEnhancer_1115_+ | KIAA0040 | chr1 175256708 175258040 |
| NM_002308 | MetaEnhancer_606_− | LGALS9 | chr17 26131567 26137792 |

TABLE S1-continued

All predicted induced eRNAs and their target genes.

| Target_gene(Refseq) | Enhancer_id | Target_gene (symbol) | enh_hg19 |
|---|---|---|---|
| NM_002308 | MetaEnhancer_211_+ | LGALS9 | chr17 26135260 26137784 |
| NM_002308 | MetaEnhancer_421_+ | LGALS9 | chr17 26137777 26140602 |
| NM_002432 | MetaEnhancer_1136_+ | MNDA | chr1 158975648 158977353 |
| NM_013262 | MetaEnhancer_3166_+ | MYLIP | chr6 15989743 15990881 |
| NM_022750 | MetaEnhancer_1844_+ | PARP12 | chr7 139910100 139913318 |
| NM_017554 | MetaEnhancer_2972_− | PARP14 | chr3 122380136 122380883 |
| NM_001146102 | MetaEnhancer_2972_− | PARP9 | chr3 122380136 122380883 |
| NM_001146104 | MetaEnhancer_2972_− | PARP9 | chr3 122380136 122380883 |
| NM_001146103 | MetaEnhancer_2972_− | PARP9 | chr3 122380136 122380883 |
| NM_001146106 | MetaEnhancer_2972_− | PARP9 | chr3 122380136 122380883 |
| NM_021105 | MetaEnhancer_4023_− | PLSCR1 | chr3 146268426 146269080 |
| NM_002787 | MetaEnhancer_1544_− | PSMA2 | chr7 43110543 43112396 |
| NM_006871 | MetaEnhancer_844_− | RIPK3 | chr14 24741839 24743689 |
| NM_001193307 | MetaEnhancer_3039_+ | SAMD9 | chr7 92666321 92666833 |
| NM_001303496 | MetaEnhancer_3039_+ | SAMD9L | chr7 92666321 92666833 |
| NM_015474 | MetaEnhancer_1375_− | SAMHD1 | chr20 35493353 35495639 |
| NM_015295 | MetaEnhancer_510_− | SMCHD1 | chr18 2634970 2637532 |
| NM_015295 | MetaEnhancer_730_− | SMCHD1 | chr18 2637665 2641759 |
| NM_013306 | MetaEnhancer_2509_+ | SNX15 | chr11 64918212 64918934 |
| NM_001308205 | MetaEnhancer_2826_+ | SSR3 | chr3 156323933 156325284 |
| NM_001308204 | MetaEnhancer_2826_+ | SSR3 | chr3 156323933 156325284 |
| NM_001308197 | MetaEnhancer_2826_+ | SSR3 | chr3 156323933 156325284 |
| NM_001308205 | MetaEnhancer_2114_+ | SSR3 | chr3 156361733 156363160 |
| NM_001308204 | MetaEnhancer_2114_+ | SSR3 | chr3 156361733 156363160 |
| NM_001308197 | MetaEnhancer_2114_+ | SSR3 | chr3 156361733 156363160 |
| NM_001308205 | MetaEnhancer_3846_+ | SSR3 | chr3 156374076 156375609 |
| NM_001308204 | MetaEnhancer_3846_+ | SSR3 | chr3 156374076 156375609 |
| NM_001308197 | MetaEnhancer_3846_+ | SSR3 | chr3 156374076 156375609 |
| NM_016562 | MetaEnhancer_341_− | TLR7 | chrX 12859229 12863555 |
| NM_016562 | MetaEnhancer_502_+ | TLR7 | chrX 12862239 12865018 |
| NM_001190942 | MetaEnhancer_2005_+ | TNFSF10 | chr3 172194931 172195631 |
| NM_001190943 | MetaEnhancer_2005_+ | TNFSF10 | chr3 172194931 172195631 |
| NM_001190942 | MetaEnhancer_3924_− | TNFSF10 | chr3 172263822 172264784 |
| NM_001190943 | MetaEnhancer_3924_− | TNFSF10 | chr3 172263822 172264784 |
| NM_001190942 | MetaEnhancer_3404_− | TNFSF10 | chr3 172295508 172299753 |
| NM_001190943 | MetaEnhancer_3404_− | TNFSF10 | chr3 172295508 172299753 |
| NM_001190942 | MetaEnhancer_734_− | TNFSF10 | chr3 172308346 172310066 |
| NM_001190943 | MetaEnhancer_734_− | TNFSF10 | chr3 172308346 172310066 |
| NM_001190942 | MetaEnhancer_116_+ | TNFSF10 | chr3 172310235 172315325 |
| NM_001190943 | MetaEnhancer_116_+ | TNFSF10 | chr3 172310235 172315325 |
| NM_001190942 | MetaEnhancer_811_− | TNFSF10 | chr3 172310301 172313961 |
| NM_001190943 | MetaEnhancer_811_− | TNFSF10 | chr3 172310301 172313961 |
| NM_025195 | MetaEnhancer_733_− | TRIB1 | chr8 126614669 126617093 |
| NM_001282985 | MetaEnhancer_733_− | TRIB1 | chr8 126614669 126617093 |
| NM_025195 | MetaEnhancer_1012_+ | TRIB1 | chr8 126617345 126619945 |
| NM_001282985 | MetaEnhancer_1012_+ | TRIB1 | chr8 126617345 126619945 |
| NM_030961 | MetaEnhancer_931_+ | TRIM56 | chr7 100893754 100895706 |
| NM_001301144 | MetaEnhancer_501_− | TRIM69 | chr15 45073139 45076695 |
| NM_001301144 | MetaEnhancer_1609_+ | TRIM69 | chr15 45076646 45078317 |
| NM_020830 | MetaEnhancer_512_− | WDFY1 | chr2 224812655 224817461 |
| NM_017523 | MetaEnhancer_2571_− | XAF1 | chr17 6842901 6843791 |
| NM_001160417 | MetaEnhancer_1451_+ | ZBP1 | chr20 56008141 56009316 |
| NM_001160419 | MetaEnhancer_1451_+ | ZBP1 | chr20 56008141 56009316 |

TABLE S2

Genomic information for eRNAs and target genes of induced EP pairs tested

| eRNA | | Whole region | | | High enrichment region | | | | Target Genes | |
|---|---|---|---|---|---|---|---|---|---|---|
| enhancer ID | strand | chr | start | end | chr | start | end | eRNA length | Gene name | strand |
| MetaEnhancer_1136_+ | + | chr 1 | 157242272 | 157243977 | chr 1 | 157242460 | 157242561 | 1705 | ACKR1 | + |
| MetaEnhancer_258_− | − | chr 3 | 46124962 | 46127637 | chr 3 | 46127469 | 46127636 | 2675 | CCR1 | − |
| MetaEnhancer_1694_+ | + | chr 4 | 15382334 | 15383479 | chr 4 | 15382463 | 15382581 | 1145 | CD38-1 | + |
| MetaEnhancer_3795_− | − | chr 4 | 15366471 | 15367307 | chr 4 | 15366966 | 15367155 | 836 | CD38-2 | + |
| MetaEnhancer_1136_+ | + | chr 1 | 157242272 | 157243977 | chr 1 | 157242460 | 157242561 | 1705 | IFI16 | + |
| MetaEnhancer_1571_+ | + | chr 9 | 21086515 | 21088279 | chr 9 | 21086643 | 21086794 | 1764 | IFNB1 | − |
| MetaEnhancer_259_+ | + | chr 16 | 84586426 | 84591944 | chr 16 | 84586456 | 84586609 | 5518 | IRF8 | + |
| MetaEnhancer_1115_+ | + | chr 1 | 173523331 | 173524663 | chr 1 | 173523395 | 173523541 | 1332 | KIAA0040 | − |
| MetaEnhancer_1136_+ | + | chr 1 | 157242272 | 157243977 | chr 1 | 157242460 | 157242561 | 1705 | MNDA | + |

TABLE S2-continued

Genomic information for eRNAs and target genes of induced EP pairs tested

| | | | | | | | | | | |
|---|---|---|---|---|---|---|---|---|---|---|
| MetaEnhancer_2972_− | − | chr 3 | 123862826 | 123863573 | chr 3 | 123863236 | 123863394 | 747 | PARP14 | + |
| MetaEnhancer_2972_− | − | chr 3 | 123862826 | 123863573 | chr 3 | 123863233 | 123863404 | 747 | PARP9 | − |
| MetaEnhancer_3039_+ | + | chr 7 | 92504257 | 92504769 | chr 7 | 92504452 | 92504536 | 512 | SAMD9 | − |
| MetaEnhancer_502_+ | + | chr X | 12772160 | 12774939 | chr X | 12772218 | 12772389 | 2779 | TLR7-1 | + |
| MetaEnhancer_341_− | − | chr X | 12769150 | 12773476 | chr X | 12771691 | 12771969 | 4326 | TLR7-2 | + |
| MetaEnhancer_116_+ | + | chr 3 | 173798019 | 173792929 | chr 3 | 173796365 | 173797019 | 5090 | TNFSF 10-1 | − |
| MetaEnhancer_734_− | − | chr 3 | 173791040 | 173792760 | chr 3 | 173792248 | 173792364 | 1720 | TNFSF 10-2 | − |
| MetaEnhancer_2005_+ | + | chr 3 | 173677625 | 173678325 | chr 3 | 173677765 | 173677876 | 700 | TNFSF 10-3 | − |
| MetaEnhancer_512_− | − | chr 2 | 224520899 | 224525705 | chr 2 | 224525490 | 224525639 | 4806 | WDFY1 | − |

| eRNA enhancer ID | Whole region | | | First exon region | | | gene length |
|---|---|---|---|---|---|---|---|
| | chr | start | end | chr | start | end | |
| MetaEnhancer_1136_+ | chr 1 | 157440426 | 157442914 | chr 1 | 1.6E+08 | 1.6E+08 | 2488 |
| MetaEnhancer_258_− | chr 3 | 46218203 | 46224836 | chr 3 | 4.6E+07 | 4.6E+07 | 6633 |
| MetaEnhancer_1694_+ | chr 4 | 15389028 | 15459804 | chr 4 | 1.5E+07 | 1.5E+07 | 70776 |
| MetaEnhancer_3795_− | chr 4 | 15389028 | 15459804 | chr 4 | 1.5E+07 | 1.5E+07 | 70776 |
| MetaEnhancer_1136_+ | chr 1 | 157246305 | 157291569 | chr 1 | 1.6E+08 | 1.6E+08 | 45264 |
| MetaEnhancer_1571_+ | chr 9 | 21067103 | 21067943 | chr 9 | 2.1E+07 | 2.1E+07 | 840 |
| MetaEnhancer_259_+ | chr 16 | 84490274 | 84513712 | chr 16 | 8.4E+07 | 8.4E+07 | 23438 |
| MetaEnhancer_1115_+ | chr 1 | 173392745 | 173428852 | chr 1 | 1.7E+08 | 1.7E+08 | 36107 |
| MetaEnhancer_1136_+ | chr 1 | 157067791 | 157085894 | chr 1 | 1.6E+08 | 1.6E+08 | 18103 |
| MetaEnhancer_2972_− | chr 3 | 123882361 | 123932377 | chr 3 | 1.2E+08 | 1.2E+08 | 50016 |
| MetaEnhancer_2972_− | chr 3 | 123729449 | 123766213 | chr 3 | 1.2E+08 | 1.2E+08 | 36764 |
| MetaEnhancer_3039_+ | chr 7 | 92566761 | 92585272 | chr 7 | 9.3E+07 | 9.3E+07 | 18511 |
| MetaEnhancer_502_+ | chr X | 12795122 | 12818401 | chr X | 1.3E+07 | 1.3E+07 | 23279 |
| MetaEnhancer_341_− | chr X | 12795122 | 12818401 | chr X | 1.3E+07 | 1.3E+07 | 23279 |
| MetaEnhancer_116_+ | chr 3 | 173705991 | 173723991 | chr 3 | 1.7E+08 | 1.7E+08 | 18000 |
| MetaEnhancer_734_− | chr 3 | 173705991 | 173723991 | chr 3 | 1.7E+08 | 1.7E+08 | 18000 |
| MetaEnhancer_2005_+ | chr 3 | 173705991 | 173723991 | chr 3 | 1.7E+08 | 1.7E+08 | 18000 |
| MetaEnhancer_512_− | chr 2 | 224448308 | 224518296 | chr 2 | 2.2E+08 | 2.2E+08 | 69988 |

TABLE S3

Genomic information for eRNAs and target genes of control EP pairs tested.

| eRNA enhancer ID | strand | Whole region | | | High enrichment region | | | eRNA length | Target Genes | |
|---|---|---|---|---|---|---|---|---|---|---|
| | | chr | start | end | chr | start | end | | Gene name | strand |
| MetaEnhancer_600_+ | + | chr 22 | 37680218 | 37682221 | chr 22 | 37680446 | 37680578 | 2003 | APOBE C3B | + |
| MetaEnhancer_600_+ | + | chr 22 | 37680218 | 37682221 | chr 22 | 37680446 | 37680578 | 2003 | APOBE C3D-1 | + |
| MetaEnhancer_94_− | − | chr 22 | 37680141 | 37679971 | chr 22 | 37679971 | 37680116 | 2143 | APOBE C3D-2 | + |
| MetaEnhancer_1529_+ | + | chr 6 | 47490687 | 47491589 | chr 6 | 47490697 | 47490886 | 902 | CD2AP | + |
| MetaEnhancer_699_+ | + | chr 5 | 118395014 | 118397954 | chr 5 | 118395699 | 118396002 | 2940 | DMXL1-1 | + |
| MetaEnhancer_454_− | − | chr 5 | 118393146 | 118393146 | chr 5 | 118396304 | 118396575 | 3465 | DMXL1-2 | + |
| MetaEnhancer_475_+ | + | chr 6 | 33105577 | 33105577 | chr 6 | 33105577 | 33105889 | 3627 | HLA-DMA | − |
| MetaEnhancer_157_− | − | chr 6 | 32546422 | 32549330 | chr 6 | 32548510 | 32548783 | 2908 | HLA-DRA | + |
| MetaEnhancer_157_− | − | chr 6 | 32546422 | 32549330 | chr 6 | 32548510 | 32548783 | 2908 | HLA-DRB5 | − |
| MetaEnhancer_820_− | − | chr 17 | 38333528 | 38334970 | chr 17 | 38334705 | 38334946 | 1442 | IFI35 | + |
| MetaEnhancer_311_+ | + | chr 17 | 34064382 | 34065788 | chr 17 | 34064375 | 34064679 | 1406 | MLLT6 | + |
| MetaEnhancer_544_− | − | chr 13 | 76886469 | 76887807 | chr 13 | 76887554 | 76887756 | 1338 | MYCBP2 | − |
| MetaEnhancer_327_+ | + | chr 2 | 64303953 | 64307226 | chr 2 | 64303970 | 64304149 | 3273 | PELI1 | + |
| MetaEnhancer_1477_− | − | chr 16 | 11297248 | 11299746 | chr 16 | 11297809 | 11297902 | 2498 | SOCS1-1 | − |
| MetaEnhancer_810 − | − | chr 16 | 11308132 | 11312802 | chr 16 | 11312513 | 11312648 | 4670 | SOCS1-2 | − |
| MetaEnhancer_1228_+ | + | chr 20 | 55489469 | 55491648 | chr 20 | 55489512 | 55489777 | 2179 | ZBP1 | + |
| MetaEnhancer_804_+ | + | chr 18 | 58324203 | 58326493 | chr 18 | 58324896 | 58325080 | 2290 | ZCCHC2 | + |
| MetaEnhancer_246_+ | + | chr 15 | 78096744 | 78104705 | chr 15 | 78100853 | 78101069 | 7961 | ZFAND6 | + |

| eRNA enhancer ID | Whole region | | | First exon region | | | gene length |
|---|---|---|---|---|---|---|---|
| | chr | start | end | chr | start | end | |
| MetaEnhancer_600_+ | chr 22 | 37708349 | 37718730 | chr 22 | 3.8E+07 | 3.8E+07 | 10381 |
| MetaEnhancer_600_+ | chr 22 | 37747063 | 37759202 | chr 22 | 3.8E+07 | 3.8E+07 | 12139 |
| MetaEnhancer_94_− | chr 22 | 37747063 | 37759202 | chr 22 | 3.8E+07 | 3.8E+07 | 12139 |
| MetaEnhancer_1529_+ | chr 6 | 47553483 | 47702955 | chr 6 | 4.8E+07 | 4.8E+07 | 149472 |
| MetaEnhancer_699_+ | chr 5 | 118434982 | 118612721 | chr 5 | 1.2E+08 | 1.2E+08 | 177739 |
| MetaEnhancer_454_− | chr 5 | 118434982 | 118612721 | chr 5 | 1.2E+08 | 1.2E+08 | 177739 |
| MetaEnhancer_475_+ | chr 6 | 33024368 | 33028877 | chr 6 | 3.3E+07 | 3.3E+07 | 4509 |
| MetaEnhancer_157_− | chr 6 | 32515596 | 32520802 | chr 6 | 3.3E+07 | 3.3E+07 | 5206 |
| MetaEnhancer_157_− | chr 6 | 32593131 | 32605984 | chr 6 | 3.3E+07 | 3.3E+07 | 12853 |
| MetaEnhancer_820_− | chr 17 | 38412267 | 38420002 | chr 17 | 3.8E+07 | 3.8E+07 | 7735 |

TABLE S3-continued

Genomic information for eRNAs and target genes of control EP pairs tested.

| | | | | | | | | |
|---|---|---|---|---|---|---|---|---|
| MetaEnhancer_311_+ | chr 17 | 34115398 | 34139582 | chr 17 | 3.4E+07 | 3.4E+07 | 24184 |
| MetaEnhancer_544_− | chr 13 | 76516792 | 76799178 | chr 13 | 7.7E+07 | 7.7E+07 | 282386 |
| MetaEnhancer_327_+ | chr 2 | 64173289 | 64225109 | chr 2 | 6.4E+07 | 6.4E+07 | 51820 |
| MetaEnhancer_1477_− | chr 16 | 11255774 | 11257540 | chr 16 | 1.1E+07 | 1.1E+07 | 1766 |
| MetaEnhancer_810 − | chr 16 | 11255774 | 11257540 | chr 16 | 1.1E+07 | 1.1E+07 | 1766 |
| MetaEnhancer_1228_+ | chr 20 | 55612307 | 55629038 | chr 20 | 5.6E+07 | 5.6E+07 | 16731 |
| MetaEnhancer_804_+ | chr 18 | 58341637 | 58396798 | chr 18 | 5.8E+07 | 5.8E+07 | 55161 |
| MetaEnhancer_246 _+ | chr 15 | 78138964 | 78217790 | chr 15 | 7.8E+07 | 7.8E+07 | 78826 |

Inducible enhancers have conserved sequences. Since enhancers activate their target genes by recruiting transcriptional factors (TF), the inventor hypothesized that these inducible enhancers might have distinct TF binding motifs supporting virus inducible gene regulation. The inventor analyzed human TF motif occurrences within the inducible enhancers and found a strong enrichment of binding sites for IRF- and STAT-family proteins, which are known interferon responsive factors (FIGS. 3D-E). In addition, IRF7 and STAT2 were up-regulated by more than 2-fold post SeV treatment (FIG. 3E). Most TF with high motif enrichment reached 50% of their maximum expression levels no later than 6 hours after virus infection (FIG. 3E), thus supporting the inventor's hypothesis of enhancer induction through TF activation.

These inducible enhancers, interestingly, showed a significantly higher evolutionary sequence conservation level than carefully selected background regions (FIG. 3F; FIGS. 9B-C), especially near the TSS of eRNAs. Synteny of enhancer and promoters across 11 species spanning the vertebrate phylogenetic tree was also examined (see Example 3). The inventor found that the induced EP pairs had ~10% higher chance than the random background to be immobilized on the same chromosome across the 11 vertebrate genomes (FIG. 3G). Moreover, the induced pairs showed a higher probability to remain in close proximity to each other (<500 Kb; FIG. 9D).

Dynamic physical EP association correlated with target gene expression patterns. Physical interaction between an enhancer and its target promoter has been accepted as a general mechanism of gene activation. It is thought that many inducible genes are regulated through pre-existing interactions with enhancers (Jin et al., 2013); however, the fate of these interactions after induction when the gene is turned off has not been adequately addressed. The inventor examined the dynamic physical interaction of 18 inducible EP pairs using a time course chromosome conformation capture (3C) assays. The inventor also sampled 18 active enhancers and genes within 200 Kb that did not pass the inducibility criterion as a control set (Supplemental Tables S2 and S3). Most inducible EP pairs showed the highest interaction between enhancer and promoter at 12 hours (FIG. 4A). This transient physical interaction correlated with the corresponding target gene expression profiles (FIG. 4C). In contrast, the control pairs showed highly variable interaction patterns during the time course and a lower inducibility of physical interaction (FIGS. 4A-B). The inducible EP pairs showed a significantly higher inducible interaction frequency (Kolmogorov-Smirnov test, P-value=0.0286; FIG. 4B). A notable observation from this analysis is that, in most cases, a decrease in physical interaction after 12 hours post infection coincided with a concomitant decrease in target gene transcription. Thus, this transient physical EP interaction may determine the maximal promoter activity. In addition, some eRNAs can continue to be transcribed beyond 12 hours post infection (FIGS. 11A-C), as in the case for the IFNB1 and L2 and many other EP pairs. Therefore, physical dissociation of an enhancer from its target promoter might be a critical mechanism of post-induction repression of these target genes, irrespective of the status of eRNA synthesis at the enhancers.

Functional relevance of eRNA expression on target gene activation. Although many eRNAs have been shown to be important for target promoter regulation by a number of studies (Li et al., 2013; Melo et al., 2013; Mousavi et al., 2013), there is an emerging debate concerning the general functionality of eRNAs from several studies that suggest eRNAs are dispensable for enhancer function (Engreitz et al., 2016; Hah et al., 2013; Kaikkonen et al., 2013; Rahman et al., 2017). To examine the functional relevance of the inducible eRNAs that the inventor has identified, he employed systematic siRNA-mediated eRNA knockdown (KD) assays and determined their target gene expression before and after siRNA transfection. In total, the inventor used 85 siRNAs for depleting eRNAs of both induced and control EP pairs (Supplemental Tables S5, S6). 49 siRNAs were able to reduce eRNA expression levels from 28 enhancers (FIG. 10A; eRNA fold-change (eFold)<1). The inventor performed statistical analysis and determined eFold<0.7 as a reasonable threshold for assessing the effectiveness of eRNA KD experiments (FIG. 4D). 11 inducible and 12 control EP pairs that passed this threshold were further examined. Interestingly, all target genes in the inducible EP pairs were repressed by eRNA KD (FIG. 4E, left). In contrast, half of target genes from the control EP pairs were not repressed, and some were even activated upon eRNA reduction (FIG. 4E, right). Representative cases from the inducible EP pairs are shown in FIG. 4F. Similar to the inventor's 3C results, this knockdown analysis of eRNAs demonstrates that the inducible eRNAs are biochemically functional in mediating target gene activation.

Inducible eRNAs promote physical interaction with the target promoter. According to the inventor's current 3C results and the results of previous reported studies (Banerjee et al., 2014; Schaukowitch et al., 2014), the transient physical association pattern was highly correlated with the transient transcription pattern of the target genes (FIG. 4A). Also, the eRNA KD results indicated functional relevance of these inducible eRNAs in the target gene transcription (FIG. 4E). Based on these results, the inventor investigated if eRNAs play a general role in mediating physical interactions. The inventor first analyzed the physical higher order chromatin interactions by 3C assay upon eRNA KD of the IFNB1 gene. This led to decreased physical interaction of the enhancer with the promoter by about 20% (FIG. 11A). The inventor also examined the TNFSF10 locus containing three distinct inducible enhancers, enabling us to examine the effect of single eRNA KD on multiple EP interactions.

Single eRNA KD led to dissociation of the corresponding enhancer from the promoter, as well as reduced interaction between the other enhancers and the TNFSF10 promoter (Interaction A-B in FIGS. 11A-B) and among the three enhancers (Interaction C in FIGS. 5A-B). The IFI35 and MYCBP2 EP pairs were analyzed as control pairs (FIGS. 11B-C). Their eRNA KD did not affect the interaction between the enhancer and the promoter. Surprisingly, MYCBP2 eRNA KD resulted in an increase of EP interaction and the elevated target gene expression levels. This observation was not a unique case, as the inventor has identified a number of eRNAs with similar functional profiles (FIG. 4E), suggesting there may be diverse classes of eRNAs (i.e., activator- and repressor-eRNAs). From these targeted studies, inducible eRNAs exhibit a strong physical and functional association with the target genes. In contrast, non-inducible eRNAs exhibit much weaker functional and physical association with the target genes.

Multiple eRNAs collaborate for regulating target gene transcription. Since genes can be regulated by a combination of multiple enhancers (Joo et al., 2016), the inventor asked how might multiple inducible eRNAs coordinate their action on their target gene. He performed combinatorial eRNA KD by applying combined siRNAs to determine how eRNAs may function together. He examined the TNFSF10 gene, which has three inducible enhancers based on the inventor's analysis (#5, #30, and #38; FIG. 5A; Table 1 and Sequence Listing). Single eRNA KD decreased EP interaction and TNFSF10 transcription (FIGS. 5B-C). However, the effects on the levels of other eRNAs showed a complex pattern (FIG. 5C): #5KD reduced #38 but increased #30; #30KD decreased #38 but increased #5; #38KD reduced #5 but increased #30. One clear pattern from this analysis is that there is a reciprocal and compensatory relationship between #5 and #30 eRNAs, which are bidirectional divergent transcripts originating from a single enhancer. This reciprocal effect was also observed in the inventor's previous work on the L2 enhancer (Banerjee et al., 2014). When all three siRNAs were combined, all three eRNAs decreased, as well as the target TNFSF10 mRNA (FIG. 5C). The inventor also analyzed the TLR7 and CD38 genes, each with two inducible eRNAs (FIGS. 12A-B). Overlapping bidirectional eRNAs from TLR7 also showed the reciprocal effect under single eRNA KD. In the case of CD38, one eRNA (#37) seems to be more dominant than the other in its contribution to the target gene activation. For both TLR7 and CD38, double KD of eRNAs reduced the corresponding mRNA expression incrementally. Taken together, these targeted analyses demonstrate how inducible eRNAs collaborate to support their target gene transcription. Overlapping, bidirectional eRNAs represent an interesting class of eRNAs displaying a compensating expression pattern upon knockdown and likely serve redundant roles to maintain the target gene expression. In addition, the transcriptional direction of eRNAs does not seem to be an important factor in determining their functional contribution to target gene expression.

TABLE 1

TNFSF10 SEQUENCE LISTING

SEQ ID NO: 1; LENGTH: 5090; TYPE: DNA; ORGANISM: Homo sapiens

```
ataccagtgtagtgactgggacctttgttccttccccagcctgaggtctgttagggcagtaccactgcaactgcagaggcgaagg
tttgtgggttcactctggtatttatttcctcttcgaagaaatgcgggggtgcctctgattgaagtggtcaggcggaaacaggatg
gtggtgctggagtctcaggtcgggcagccctatgcagtgaggactgggacttgtggggaacagtctgaccgcttttctaaggtgg
gcgctctgtgctgggggtctggaccagccctggtactcacagaggacttttcagagcctggagacagtaagggcaagggctgc
aagacagcaaacatcacaccccccacccctctcaccccccaaccaccaaacactgggagcgctgtcccagagagttatggagct
gctactggctcaatatccctggcaggggggtgggtggagacccaggccaggaggactcatccagtgaggagaaacaggtttggag
acttgtgtaaaaaagcagtctggccacttttccacaggacagccatgttgtgctgggggggtccactccagtcactgatggatca
ccttgcactctctaaagcctgaaggcaacaaggactgaggctgtgaaacagcaaagatggccgcctaccccttcctctgagagc
tccctctcagggatgtgtaatgctgctaccagcagctggctaggttccaagccagtgggtcttatcctgtgacctctgaagtgc
tatggaagtgaggcctgcagatcatcgctgctcagcccctggattcagcccctttcataggagtaggtatggggtgctaacctc
ccacttggctggagtagcagttacttttgccaggaagccaggatatctaaggctcctggggctccgtgtgtacctgagcggctgc
tctgccaagactccccatagctctgtgtatctgactgaaggccctagtggagtgggtcatgagggggatctcctgacccaagagt
agcaacgatccatgggagaagcattggtccgcagggtcgctcattcactcacggcttccctggatgggggagggttccccctggctcc
atgtttctcccgtgtgggcggttgtcctgccctgcttttctccattctccatgggtcaggttgttttcttgatgaattccaacat
gtgtatctgtatgtttcggttgaaagtgcagtatttactcgcccatctatttctctctgtgagagcagtacacactagctgctt
ctggttgagcgtaagaaaaataaatgcccttttaatgtgtttgctagaagatagaaaacattgcaaagaacagagtagaattcat
attcttaaaaacaaatatgaaaacttattctactttccttcttttaccaatgaaaataaacatatttattgtcctcaatgcactt
tttctttgaaataataactcctcagaaagaccgttgcagttaagaatatcagctgtcacacagagctaaatcctttttaattgtga
attttttccccacaaagcatgatgaactacgtcttgacagggcaggcaaagtattaaagtaaaatattttcccacattttatt
tttcttttctttctttctttccttttttttttttttttttttgagatggagtttcactcttgttgtccaggctggagtgcaa
tggcgtgatctcagctcactgcaacctccacctcctgggttcaagcaattctcctgcctcagcctctggtgtagctgggattaca
ggcacacgccaccacgcctggctaattttgtatttttagcagagatgggatttcaccacattggcaagctggtctcaaactcc
tgacctcagtgatccatctgcctcagcctcccaaagtgctgggattacaggtgtgagccactgcgcccagccccatttctgag
gtgaaatgaaggaagagttaatcattcatgctccttttcttgggttcagctgccatccttacttacctctgatggaggactaggg
atttctgggacttgaactcctgttatagaaggtcagattagccttaagctgaacagcagcagctcacctgggcctttctccctga
ataaaagttctgaagatctaaaatgaaaatatgaaaggaaagaaattatcaagttctgtctactaaatatctcagtggatttcct
acctcaactggtagatttgtcttaaggcctttgtttggagtgttttcctacaagtctcaaagtctaacaaaagcaggcgttcccg
gtcaagctctgccaaattcaccacgtgacctaggacctgaagtgaactttcgtttctcctgttctctctcttccgaccttccct
ccccgccaaggcaatgcagacagggactcaatatattattttgagttctccataggaaaagaattattattaaaacaataagctc
tcaagataaatacctttatataatgtatataacattcatatatacatgagtatatactagcttcatatctgtattctattttct
ttctcacccagaactcaagaagacatgcctgtatccctttttttttttctcttttgagatgaagtttcactcttgttgcccaggct
ggagcgcaatggcgcaatctcagcttactgtaacctccacctcctgcattcaagcaattctcctgcctcagcctcctgagtagct
gggattacaggcgcccaccaccacgtctggctaatttgtgtatatttagtagaaatgggggtttcaccatgttgaccaggctggtc
ttgaacttctgacctcaggtgatccaccccgcctcggcctcccagtgtgctgggattacaggcatgagccaccgcacccggcccaa
catgtccgtattctcaaagctatagaggtgtcttttgctatttttgttctcttaggtaagaaccgggtcctcaccttacacttatt
cctcaggtgaagagactctgtgtgtgtccatcagggaagcatgagagcatttgatttcagctgagcaggtttagtcatctagga
gctgctctcttaagtgtttaacacaatcgttaactaactaaaacttgcaggaaattaatctggaatttcccagtaattacatgtt
ttagataagttttttgaattgagtccaagatgatgtgatagtgcatgttcataattaactaagaaactgagaaaagcttcttaat
ctaaaaacaaagccaaaaatctttccatgcaaggaaagaaaatcttaattgattaactcattaatagagcagggaaaagaaaaca
aaagcaaaagcaaaaaaactaacttgagatatagctgaactcataatgtgtatttgtttttatttccagttgctgcttaccatta
```

TABLE 1-continued

TNFSF10 SEQUENCE LISTING

```
gctgtgcaagaccaaaggattttgtgctttctcttgcctagtaattgttcagtccaaaatttaaccatgttgttttgtgttatt
accaggagcaagaggacatgtgtattggtgagagaagaggggtgaggagtcagggataagatgaatctgattaacttcaggggtt
attagaataaatcttgtaggcttggagaatcttgtaggcttggagaatctagagttctatgagaaatggtaagcagacttcataa
atcctgtctgcgttgctgctatgatcttggccttccccctgacatactcccaagaaatagaaacgaatagaaatagaaatctaata
gaactagaaatagaaatatttcccaagaaatagaaagtaaaactgacaaagccaatgcaaagaaatcagttcggaagctgttaat
tttcacacgatctgtgttcagtaaccgccctctatcggctctcctgaatagcacactatatgggacggagaatctgaaaggcctt
tttgctggttttcttactaacagagagttcataaaccaggatcttcttcagcctccaaggtaaggaaatgtgtgatctccaagct
ccctcttgtatgtattgtgaacgccactgtcagaagagaaacaccaaagttattcacctggaaatgttgcagtatgaagaccatg
tatttgatggagaggttatttaaatggtaactttgttaatgaatttctttgctaactttccctgctttattttcatgccaaaaac
cagagaggtacagagaacagaactcggcaccacagtctaaaagtgttaagtttcaggcacaacactgctgtttttgagctgtggg
tcctcagacaagccattttagctttccgagcctcagtttcccacttgcctgcttcttcaccacttcctggggtgataagagaaga
ccaaatgatatgtttgtgaaggtgctttgccactcatgtacccatgcagaccctattattagtagtactttataaaagtaagac
atcattttctcatttacaggactgaggattagaaagaataatgctgggtttctggctgcctccgcttttgagggcctaggaggca
ttctgacctaaagagagtaggcagtggagtcagacataaatgtaaacactgttagtgtgacctttgcagatcatctgtctgccct
gtgcttctattatgctatctatctgcaaagtaaagaacttctttacaaaatgcctcataaagtgtgaatacaacaaacaagctc
catctctaaagttcttcatagaaaacagaattataagacgcactcagtatccaaggataaatgataccaggaaagggccaaagtt
aattaatcctcttacaataaagagcatatttcaaggtaaataataaaatatctctaaaattaacaaaatgtatatggttat
ttgcaactatgcattaattcttagcccaaagaatgttgaggagttgatttggcatgaagaggacacattttcttggacaaaatta
taggatggcacagtgcgactttgtttagctcatactacctttcggtaacaccatcaaaggggatcttttttaccaaaaacattttt
ttaaatcaagggttttcatcaattttccaaagggattaaaaaaattccctgacatttaagctggtacattttggaagcat
```

SEQ ID NO: 2; LENGTH: 700; TYPE: DNA; ORGANISM: Homo sapiens

```
catattgaatgcttagaacttgccaggccgtatctcagcacgtcactcatattaatcatttcctaataaccgctacaagttgggt
tttgttattatcccccatttgaataaataaggcacggagacacagagaggatatgacataactaccagaagccattggtggcaaga
tctcaatcaggacatgtcgtacaatgctctgattatctcgtctgcatccctgattacttatggtccagatataaactactcctc
ttcactttcattttaaccagaatttgaagtcatttttattctctctcaagtactttgggctttgaggaaaataaggaaactcgcc
acctggtggcagctcatagtgtgtggtaacaaggtggctgcccctgtctggtttcaaggagagaggagaatgtccctgcctt
gctattcacgcctctcaaacagctgagctgacctctcctcaagggccattgtctttagaaatccctcgccctgtctaggtccatt
ctgataaaaattggagtagcagttttttctctatgcttcaagtgaggaggttggatgggacagagtccagcgatgagggccaag
actctcttgaccttatttcattgtcaaaaagatcagtattcatgttctacaagaaggaatccacagttgtccagaaaactgtcct
tcaaaaatagccagtccaca
```

SEQ ID NO: 3; LENGTH: 1720; TYPE: DNA; ORGANISM: Homo sapiens

```
aagctctcagaggtatatgacagtctctccaccacagtgaccacatggagaggagaccattatctcctctcagtgagcccttgaa
cccctgctccccaacaagtggagcctccaactcacaccagcagtgcagccacccacctcactggctgaacattcccagtaacagt
gactctgcatttcttggggttggagccctcaggggcaaccaaaagcctctctgccactgcctctgtagtagtactaccccctacta
cctttagactaattaaacagcaaagaccctaagtgcctcatccacacccccaacaagctgcagttaacccaaggagaggagacc
agtccatctcccacaggtcccatccaccccctgctgcttgtcaccagggaaccccccagcttggacccacagtacagatcaccca
tcttgggcctatcacactgagcaattgctgacctgcatctctgtggagtggagccccaggagacaagtaaaagaccccccagcca
caaccactgctaagtgccttctctctgctgcctccaagctggggagggaaactaaaccctgagatctccccagagctgtggtgg
gcagcctaggagtgccaagtctcaatctgtagccagcactcaaatgggagaggagtccacacttttcagagcattgagaggtagc
ccagctgcaaccatgaggaaatatagaggagtcacatgactgggaaagagtctacctactgaccactacttcacaaaacccctc
atttccttctgtcctccctaaagcctctcagttttgaatctcatgtcttcaaattgtatcaccactggcctccatgaagcgcct
aagcaccacctactggatcacaccccgcagcttcaacaccaaaagttagaaagacttcaaattaacaacctaacatcacaacta
aaagaactacagaaccaagagcaaaccaatcccaaagtcagcagaagacaaaaaaaacacatgcttatctcaacagatgtatctca
ctaacataccgccctgtaaaaccaaagataagaagtcagctgcaaataaagacctcgcacaaagcctcagccctgtgaaaatat
tcaggaaaaaagtcttctgactgtactcaatctatgctgcagttaaaggaacacccatacacagagatgagaaagaaccaatgta
agaactctggcaactcaaatgaccagtgtcttatgtactccaaacaatagcaccagttctccaatgaggggttcttaaacaggctg
agttggctgaaatgacagaaatagaattcagagtatagataggaatgaagatcattgagatttaggagaaggagaaaacacaatc
caaggaaactaagaatcacaataaaatgataaaggagctgacaggcaaaatcgccagtattaaaaagaaacctaactgatctgat
agagctgaaaagcacactgcaagaatttcacaatgcaatcgcaagtattaacagcagaatagaccaagctggggaaagaatctca
gaacttgaagactggctctctgaaacaagacagccagacaaaaataaagaaaaaaagaatgaaaatgaatgaacagaaactccag
aaaatataggattatgtaaggaggccaaatctataaatcactggcatcactgaaagagatggggagaaagcaaaccacttggaa
aacacattttaggatatcactcatga
```

SEQ ID NO: 4; LENGTH: 3660; TYPE: DNA; ORGANISM: Homo sapiens

```
tctatttctattcgtttctatttcttgggagtatgtcagggaggccaagatcatagcagcaacgcagacaggatttatgaagt
ctgcttaccatttctcatagaactctagattctccaagcctacaagattctccaagcctacaagatttattctaataaccctga
agttaatcagattcatcttatccctgactcctcacccctcttctctcaccaatacacatgtcctcttgctcctggtaataacaca
aaaacaacatggtttaaattttggactgaacaattactaggcaagagaaagcacaaaatccttggtcttgcacagctaatggtaa
gcagcaactggaaataaaaacaaatacacattagttcagctatatctcaagttgtattgcttttgctttttgattctttt
ccctgctctattaatgagttaatcaattaagattttctttccttgcatgaaagattttggctttgtttttagattaagaagc
ttttctcagtttcttagttaattatgaacatgcactatcacatcatcttggactcaattcaaaaacttatctaaaacatgtaatt
actgggaaattccagattaatttcctgcaagtttttagttagttaacgattgtgttaaacacttaagagagcagctcctagatgac
taaacctgctcagctgaaatcaaatgctctcatgcttccctgaatggacacacacagatctcttcacctgaggaataaagtgta
aggtgaggaccccggttcttacctaagagaacaaaatagcaaagacacctctatagctttgagaatacggacatgttgggccgggt
gcggtggctcatgcctgtaatcccagcacactgggaggccgaggcgggtggatcacctgaggtcagaagttcaagaccagcctgg
tcaacatggtgaaaccccatttctactaaatatacacaaattagccagacgtggtggtgggcgcctgtaatcccagctactcagg
aggctgaggcaggagaattgcttgaatgcaggaggtggaggttacagtaagctgaattgcgctccagcctgggcaa
caagagtgaaacttcatctcaaagagaaaaaaaagggatacaggcatgtcttcttgagttctgggtgagaaagaaaaaaaag
aatacagatatgaaagctagtatatactcatgtatatatgaatgtatatacattatataaaggtatttatcttgagagcttattg
ttttaataataattcttttcctatggagaactcaaaataatatattgagtccctgtctgcattgccttggcggggaggaaggtc
ggaaagagagaacaggagaacagaaagttcacttcaggtcctaggtcacgtggtgaattggcagagcttgaccgggaacgcc
tgcttttgttagactttgagacttgtaggaaaacactccaaacaaaggccttaagacaaatctaccagttgaggtaggagaaatcca
ctgagatatttagtagacagaacttgataatttctttcctttcatattttcattttagatcttcagaacttttattcaggggaga
aaggcccaggtagctgctgctgttcagcttaaggctaatctgaccttctataacaggagttcaagtcccagaaatccctagtcct
ccatcagaggtaagtaaggatggcagctgaacccaagaaaaggagcatgaatgattaactcttccttcatttcacctcagaaaat
gggggctgggcgcagtggctcacacctgtaatcccagcactttgggaggctgaggcagatggatcactgaggtcaggagtttgag
```

TABLE 1-continued

TNFSF10 SEQUENCE LISTING accagcttggccaatgtggtgaaatcccatctctgctaaaaatacaaaaattagccaggcgtggtggcgtgtgcctgtaatccca
gctacaccagaggctgaggcaggagaattgcttgaacccaggaggtggaggttgcagtgagctgagatcacgccattgcactcca
gcctggacaacaagagtgaaactccatctcaaaaaaaaaaaaaaaaaaaggaaagaaagaaagaaaagaaaaataaaatgt
ggggaaaaatattttacttttaatactttgcctgccctgtcaagacgtagttcatcatgctttgtggggaaaaaattcacaattaa
aaggatttagctctgtgtgacagctgatattcttaactgcaacggtcttctgaggagttattatttcaaagaaaaaagtgcatt
gaggacaataaatatgtttattttcattggtaaagaaggaaagtagaataagttttcatatttgatttaagaatatgaattctac
tctgttctttgcaatgattctatcttctagcaaacacattaaaagggcattttatttttcttacgctcaaccagaagcagctagtg
tgtactgctctcacagagagaaatagatggggcgagtaaatactgcacttttcaaccgaaacatacagatacacatgttggaattc
atcaagaaaacaacctgacccatggagaatggagaaaagcagggcaggacaaccgcccacacgggagaaacatggagccagggga
acctccccatccagggaagccgtgagtgaatgagcgaccctgcggaccaatgcttctcccatggatcgttgctactcttgggtca
ggagatcccctcatgaacccactccactagggccttcagtcagatacacagagctatggggagtcttggcagagcagccgctcag
gtacacacggagccccaggagccttagatatcctggcttcctggcaaaagtaactgctactccagccaagtggggaggttagaccc
ccatacctactcctatgaaaggggctgaatccaggggggctgagcagcgatgatctgcaggcctcacttccatagcacttcagagg
tcacaggataagacccactggcttggaactctagccagctgctggtagcagcattacacatccctgagagggagctctcagagga
aggggtaggcggccatctttgctgtttcacagcctcagtccttgttccaggcttt agagagtgcaaggtgatccatcagtg
actggagtggacccccagcacaacatggctgtcctgtggaaaagtggccagactgctttttt acacaagtctccaaacctgttt
ctcctcactggatgagtcctcctggcctgggtctccaccacccctgccagggatattgagccagtagcagctccataactctc
tgggacagcgctcccagtgtttgggggttgggggtgagagggtgggggtgtgatgtttgctgtcttgcagcccttgccct tac
tgtctccaggctctgaaaagtcctctgtgagtaccagggctggtccagaccccagcacagagccgcccaccttagaaagcggt
cagactgttccccacaagtcccagtcctcgtcataggctgcccgacctgagactccagcaccaccatcctgtttccgcctga
ccacttcaatcagaggcaccccgcatttcttcgaagaggaaataaataccagagtgaacccacaaaccttcgcctctgcagttg
c SEQ ID NO: 5; LENGTH: 4245; TYPE: DNA; ORGANISM: Homo sapiens
ataaggctgcattcaggcataattaaatccaagtactt aaaagatgcagtcagaaatcaatctcctctctctctctgtctctcag
tcttccactccatctcccacctccatgttgacctcattcttatgagacctctctccatgtggtaacatatgggtatcagcatctc
tagactcacattctgccacttaagctatacttagaaacaataatcttctttctcagaaaaattcaagctgctacctcgattgata
aactgcagccacttgtgcatggcttaaacaacttttagtccattgtttccaaaattatatttgcatgtcactggtgctccctgaga
tgatctggtagtaagcaaacatttt attataatacatgccaggggctagaggggagggacggataaataggcagaacatggaggat
atttagggaagtgaaattattccgatattatattggtgaatgcatgctgttttacatttgtcacatgtataattatgtgtaaatt
tttatgcataataaaaataagtagtgcctcaaaattattttcttttt gcttgggatgaggctgaaataggaaggaaagtagtatt
cattttacaggattagggtgagtttcagatatggtgatcaggcatgttcatgatcatttttgtaaccttttacgaatcgaattatcaa
acaagacttaacctgttccatgtagttgaagtgctgtacaggcagaaaaaatctagtcactgtttgtatactgaggggaaaatctt
aggttaagtccctcaaagattctggaaaaatttcatatggtaattcataaggcaattttt gaaaggaagtcaatatgtcacaaat
tgaatgtaactttgaaaatctttaccctactttggaaaaaaagtatcattttagtataacataaaatgaactacatgactgtcctc
tccatggttaaattccttgtctgccaacattatataactgactttgtttcttctgatttgttttcatgcagttaatttt caaga
ggaagagcttccttcctaaatttgattcaaatctattccaggaacaaacagaagcttaaagtttcttttcacagtttctttt aag
gcgccacttttgttt ctctgtggtttcattatgagaagtaactcaaagtggaagaagattgttgtaatgtattgcatttctatac
ttgagagagttttaagttcttcagataagtatggtatgtggttgcaagtaattttcacttatttgcaataatacaaatttgtg
aattctgttatttgttagctacacagtttatagtattttgttacagcaggcccaacagaataagagagacaagtaagcagattct
gggaaaatggcagagtaggaagaaccaggaatctctctcctgacctaccc aactaatgcagtggcagaatatgacttaactatct
tggaactctggagtaatctaaggttcacaatttccagaggaaggcttaggttgtgtattagtttgttcttacgctgttatgaaga
aatacctgagactggatgatttatgaaggaaagaggttt aattgacacacaattccacatgggtggggaggcctcaggaaactta
taatcatggtagaagacaaaggggaaggaccttcttcacagtagcaaagagagaagagtgaaggaaaaacttccaaac
acttataaaaccatcagatcttgcgagaactcactatcatgagaacagcatgggagaaactgccccccatgatccaatcacctccc
tcccttgacatgtgatgattacaggtgcttccctcgaggtgtggggattacagtttgagatgagatttggtggggacacagagcc
aaaccatatcattccacctctggcccctcccaaatctcatgtcttttcacatttcaaaaccgatcatgccttcccaacagtccct
caaagtcttaactcatttcagcattaactcaaaagtccacagtccaaagtctcatctgacgacaagggcaagtctcttccacctata
agcctgtaaaattgaaagcaagttagttacttcctaaatacaatgggaggacaggccttgggtaaatgctcccattccaaatggg
agaaattaaccaaaacaaaggggcgacaggccccatgcaagtctgaaatccagcaaggcagtccttaaatcttaaagctccaaaa
tgatcttttttgactccatgtctcacacccaggacacactgatgcaaagagtgggctcccatggccttgagtagcttcttcacag
gctggcattgagtgcctatggcttttttaggtgcacggtgcaagaagggaggtgaatctaccattcttgggtctggagaacagtga
ccctcttctcacagctccctaggcagtgccccagtggggactctgtgtggggggctcctaccccatatttccctt ccacactgcc
ctagcagaggttttccatgagggctctgcccctgtagcagacctctgcctggccatccaggcatttttat acctcctttgaaatc
taggcagacattcccaaacctcaattcttgactaccatgtacccacaggcctaacactacagggaagctgccaaggtctggggct
tgtaccctctgaagccacagcctgagctgtacattggctccttttagctatggctggagctaaagtggctgggatgcatcatacc
aagtcccaaagctgcacacagcaggtgggggcctggcccaataaaatcattttt aacctcctaggcctccaggcctgtgat
gggaggagctgccgccaagatctctgacaggctctggagatattttcccccattgtctttgtgattaacattgggatcctcattac
ttatgctaattt ttgcagccagtttgaatttctcccca gaaaatgggttt ttcttttctactgcatggtcaggctgcaattttc
caaacttttatgctctgcttccctttt aaacgtaagttccaatttcaggtcatctctctcaagttcaaagttccacagaaatcta
gggcagggcaaaatgtcaccagtctctttgctaaagcatagcaaggtgactttttct ccattt ctcaataagttattaatctcc
atctgagaccacctcagcctggacttcattgtccatccatatcattatcagcatttt ggtcaaaaccattcaacaagtctctagg
aagttccaaacttt cccacatcttcctgtcttctt ctgagccctccaaatt gttccaatctctaaccattaccagttccaaagt
tgcttccacatttttt gtatttttgtagcagtaccccactaccttggtaccaattaactgtattagtctgttttcacactgcta
taaagaagtacctgagactgggtaatgtataaaggaaaggggttt aattgaatcactgttccacatggctgggggaggcctcagga
agcttacaattatggcagaaggggaaacagccaccttcttcacaaggaagcaggagagagagcacacaggaaaaactgccactt
ttaaaaccagcagatgtcataagaactcactcattatcatgagaacagcatgggggaaaccacccccatgatccattcacctccc
tcccttgacatgtgggaattacatgttcctccctcaacacaaatagggattataattcaagattcgatttgtctggggacacaga
gccaaacaatatcaggttgtaaattgcagttagtttcagtcattgtcagctgtagccatcccttaccctcagcggcttggcaggc
agctgtgcagatgatcctggagtagcttacacatagcttt gcccagtgtggacaaaggaatgctgtactctaattattggggatc
tgtgctctaaattgttgcttctaaacatagaagtacagaaaaaggaaaccactgttgcatgtctcttattgttgccccctccc
ccaccgaccccacttcccccaccctctagtgacttccaggaaatttgaaaggcaagtgctttt ccccactttcattttt ctcct
ttcttttctggagggtcagacattaaggactaggacatttgaaattaagtcaccacataaacccggggaaaggggtacagactca
gaaaacacttgagaagaccttacgtttgcacctcaggctaatgctcagcacacagatagcctacaaccaccccacaaaa SEQ ID NO: 6; LENGTH: 962; TYPE: DNA; ORGANISM: Homo sapiens
Aacttatatttcctctttgcagctatgtttgggacttcctcttt cacccatcaaaatatttcttt aaaaaaaaaatcttt cct
tccaagtttttt cttcctttgttactatgacatgaataaatcaccttgtagattctctgtgttttgactgccttctcatggtcag TABLE 1-continued

| TNFSF10 SEQUENCE LISTING |
|---|
| ggactagaaagacctgttgtgtggccatttgctatggtctgccctaccctgacccctcagttcctacattgaagtcccaacctcc<br>cagctgatggtagtaagaggtgggatcttttggagggtgactggatcatgatggccaagctcctgtgaatgggattagtgccctt<br>ctaaaataggcccaagggagctcattcacctcttgtcacctcttttcacctcttccaccatgcaaagacacagcaagaagatgct<br>gtctttgaaccaggaaagctagccctcacagacaccaagtctgccttgatcttaaactttccaggccctggaactgtgagaagta<br>aatttctgtggtttataaaccacccagtttaagatattttgttgtagaaaccccaacagactaagtcagcaatgcaaaaaatatt<br>agaactaaagggaccttgcactaatctcatataagcccttcatttttaaatatgaaaacaaaacaaaaccgaagtcctggcaatt<br>agcctactaaatccacaggtagccagaggtagaactgactcattgttatgtctccccagctcaaacgtgttcttccagatcataa<br>acattggcttatgcttctttccatctcctttaaaccccagacaactgctgggcacatgtaatactttaaaaatatttctatatcg<br>gccaggcatgatggctcatgcctgtaatcccagcactttgggaggccgaggtgggtgcattacctgaggtcaggagtttgagacc<br>agcctgagtaatatggtgaaacaccgt |

Targeting TNFSF10 eRNA activity limits cell apoptosis. Thus far, the inventor has identified a highly validated set of functional eRNAs and established that modulation of these eRNAs can yield selective changes in target gene expression. These findings may be valuable for a therapeutic intervention by targeted enhancement or reduction of disease-relevant genes. In the context of the anti-viral response in human and mouse, overexpression of the TNFSF10 gene has been implicated in inducing lung damage by influenza virus (Hogner et al., 2013). The inventor reasoned that by targeted reduction of TNFSF10 eRNAs to decrease TNFSF10 expression, he may be able to limit apoptosis without affecting interferon production or response. In order to examine the possibility of eRNA modulation for reducing apoptosis, the inventor performed siRNA-mediated reduction of TNFSF10 eRNAs and checked cell viability (FIG. 6A). TNFSF10 expression level, upon triple eRNA KD, decreased about 50%, compared to control (FIG. 6B). Control cells showed a stronger signal for cleaved Caspase 3 than the TNFSF10 eRNA KD cells and a positive control, IFNB1 eRNA KD cells (FIG. 6C). Furthermore, reduction of TNFSF10 eRNA resulted in a higher proportion of live cells and a corresponding decrease in apoptotic cells (FIG. 6D). To confirm TNFSF10 eRNA KD is specific for limiting the viral induced apoptosis, the inventor induced TNFSF10 expression by a distinct mechanism using TIC10, a small molecule inducer of Foxo3a that activates the TNFSF10 promoter (Jacob et al., 2014). Thus, TIC10 treatment would result in apoptosis via a distinct mechanism, compared to viral infection induced apoptosis. As expected, TNFSF10 eRNAs KD, either individual KD or triple KD, did not affect TIC10-induced apoptosis (FIG. 6E; FIG. 13). In addition, TIC10 treatment induced TNFSF10 expression significantly, but it did not affect expression of the virus inducible eRNAs associated with the TNFSF10 gene (FIG. 6F, Left). In contrast, virus infection induced expression of those eRNAs as well as the TNFSF10 gene (FIG. 6F, Right). Taken together, these results demonstrate that targeted reduction of eRNAs can specifically inhibit interferon induced apoptosis.

Example 2—Discussion

Regulatory genomic elements outnumber genes by two orders of magnitude. More than two million enhancers have been annotated in the human genome (Romanoski et al., 2015). One fundamental question is whether all these enhancers are functionally equivalent or whether there are distinct classes of enhancers that are more relevant in different conditions. To explore the landscape of potentially functional enhancers and associated eRNAs, the inventor used the virus inducible gene expression model. He identified potentially functional eRNAs by taking advantage of the dynamic expression information from global transcriptional analysis and using associated genomic proximity and transcriptional activity as criteria. Specifically, the inventor considered inducibility of enhancers upon virus infection and applied this activity-based association strategy to identify their target gene. From this strategy, he was able to assign 123 eRNAs to their most likely target genes. Using these highly confident EP pairs, the inventor tested the functionality of eRNAs at both physical interaction level and biochemical level. More than 80% of the inducible EP pairs showed a higher physical interaction frequency at 12 hours—a time point representing the peak of transcription level. In addition, reduction of eRNA levels by RNAi decreased target gene transcription for all inducible eRNAs tested. From these results, the inventor concludes that the virus inducible eRNAs are indeed functional. The control pairs for the inventor's experiments were selected by general criteria that other groups have routinely used for determining active enhancers. The inventor's 3C results and targeted eRNA reduction results from control sets might explain why many groups have argued that eRNAs are dispensable for enhancer function. Thus, co-inducibility of eRNAs and genes would be relevant for identifying other functional eRNAs in different biological conditions.

One unexpected finding from this study is that the fate of an enhancer can be different from the promoter it regulates after their transient functional and physical association. In many independent cases, eRNA production continues while the enhancer becomes disengaged from its associated promoter and the target gene undergoes post-induction repression. In other cases that conform to the current paradigm of gene regulation, when an enhancer disengages from its promoter, both eRNA and mRNA production are shut off concordantly. Furthermore, dependence of eRNAs for physical interaction between enhancers and promoters does not seem to be a universal mechanism across different loci (Li et al., 2013; Schaukowitch et al., 2014). Rather, each locus exhibits different dependencies on eRNAs for enhancer-promoter interaction. Notably, some loci display competition among enhancers and promoters when assayed for physical interaction. In reduced-function assays using RNAi, enhancers within the same locus can also compete for production of corresponding eRNAs. Despite the complex regulatory dependencies among enhancers and promoters, a combined reduction of all eRNAs for a given target gene resulted in the largest decrease in target gene expression compared to individual eRNA knockdowns, suggesting a complete pool of functionally relevant eRNAs is necessary for proper regulation. Thus, the human genome displays dynamic and complex exchanges of physical and functional associations among enhancers and promoters to define genome expression. Intriguingly, these functional properties of eRNAs are consistent with a recently proposed model of RNA-mediated phase separation for gene regulation (Hnisz et al., 2017).

Lastly, the inventor demonstrated that he can modulate one particular enhancer of the anti-viral program to achieve a specifically modified cellular behavior that can aid in reducing excessive inflammation. With hundreds of functional eRNAs identified in this study, targeted therapies with tailored modulation of multiple enhancers may be an approach to achieve a personalized clinical response.

Example 3—Methods

Cell culture and virus infection. B-Lymphocyte, GM12878 cells, were obtained from Coriell Institute for Medical Research and cultivated according to the supplier's instructions. 15% fetal bovine serum was added to Roswell Park Memorial Institute media 1640 (RPMI-1640) with 2 mM L-glutamine for the culture. Sendai Virus (Cantrell strain) obtained from Charles River was infected for inducing immune response signaling gene expression system, of which 50 µL was added to 1 mL media. Cell samples were taken at 30 min, 1 h, 2 h, 4 h, 6 h, 12 h, 18 h, 24 h, 48 h, and 72 h after virus infection for GRO-seq experiment. For the other experiments, 3C assay and ChIP-seq experiment, the cells incubated for 6 h, 12 h, 18 h, and 24 h after infection were sampled. Untreated GM12878 cells were used as a control, which is 0 h sample.

GRO-seq analysis. Global run-on and library preparation for sequencing was performed based on the method published by John Lis et al. in 2008 (Core et al., 2008). Some parts of the protocol were modified to accommodate the inventor's experimental purposes and multiplexing (Kim et al., 2013).

Nuclei isolation. Two 15-cm plates of confluent cells (~10-20 million cells) were washed 3 times with ice cold PBS buffer and incubated for 5 min with 10 mL cold swelling buffer (10 mM Tris-Cl pH 7.5, 2 mM $MgCl_2$, 3 mM $CaCl_2$)) for each plate on ice. Cells were scraped from the plate, harvested, centrifuged at 500×g for 10 min at 4° C., and were resuspended in 1 mL of lysis buffer (swelling buffer with 0.5% IGEPAL, 10% glycerol and 4 U/mL SUPERaseIn) with gentle mixing by pipetting with a widened boar pipette tip up and down 20 times. For the isolation of nuclei, 9 mL of the same lysis buffer (up to total 10 mL) was added. After collecting the nuclei by centrifugation (at 300×g for 5 min at 4° C.), it was resuspended in 1 mL freezing buffer per 5 million nuclei, and pelleted and resuspended to the final volume of 100 µL (about 5-10 million nuclei/100 µL) of freezing buffer (50 mM Tris pH 8.3, 5 mM $MgC_2$, 0.1 mM EDTA, 40% glycerol).

Nuclear Run-On (NRO). Before the NRO reaction, NRO reaction buffer (10 mM Tris-Cl pH 8.0, 5 mM $MgCl_2$, 1 mM DTT, 300 mM KCl, 50 M ATP, GTP and Br-UTP, 2 µM CTP, 0.4 U/µL RNasin, and 2% sarkosyl) was generated and pre-heated to 30° C. for 5 min. An equal volume (100 µL) of NRO reaction buffer was mixed with 100 µL of thawed nuclei solution in freezing buffer and was incubated at 30° C. for 5 min with mixing at 800 rpm on a thermomixer. Then, RQ1 DNaseI (Promega) was added along with DNaseI reaction buffer and samples were incubated at 37° C. for 20 min with mixing 800 rpm. To stop the NRO reaction, 225 µL NRO stop solution was added to the reaction and 25 µL of Proteinase K was added. The sample was incubated for 1 hr at 55° C. Nuclear RNA was extracted with acidic phenol (Sigma) then with chloroform (Sigma) and was precipitated and washed. RNA was then resuspended in 20 µL of nuclease free water and subjected to base hydrolysis by addition of 5 µL of 1N NaOH on ice for 10 min. The reaction was neutralized with 50 µL of 0.5 M Tris-Cl pH 6.8. Then, RNA was purified through BioRad P-30 RNase-free spin column (BioRad) following to the manufacturer's instructions and was treated with 7 µL of DNaseI buffer and 3 µL RQ1 DNaseI (Promega) for 10 min at 37° C., and purified again with a BioRad P-30 column.

Anti-BrU agarose beads (Santa Cruz Biotech) were equilibrated by washing them 2 times in 500 µL BrU binding Buffer (0.25×SSPE, 1 mM EDTA, 0.05% Tween-20, 37.5 mM NaCl) and blocked in 1 mL BrU blocking buffer (1× binding buffer, 0.1% PVP, and 1 mg/mL BSA) for 1 hr with rotation at 4° C. During the blocking step, beads were washed 2 times with 500 µL binding buffer, NRO RNA sample was heated at 65° C. for 5 min then placed on ice at least for 2 min. 50 µL of the blocked bead mixture was combined with RNA sample in 450 µL binding buffer and combined with bind RNA to beads for 1 hr by rotating at 4° C. After binding, beads were washed once in low salt buffer (0.2×SSPE, 1 mM EDTA, 0.05% Tween-20), once in high salt buffer (0.25×SSPE, 1 mM EDTA, 0.05% Tween-20, 137.5 mM NaCl), and twice in TET buffer (TE with 0.05% Tween-20). BrU-incorporated RNA was eluted 4 times with 100 µL elution buffer (20 mM DTT, 300 mM NaCl, 5 mM Tris-Cl pH 7.5, 1 mM EDTA and 0.1% SDS). RNA was then extracted and precipitated as described above. The precipitated RNA was re-suspended in 20 µL of water.

TAP/PNK treatment. RNA was heated to 65° C. for 5 min and cooled on ice at least for 2 min. The RNA was treated with TAP (by adding 3 µL 10× TAP buffer, 5 µL water, 1 µL SUPERaseIn (Promega), 0.5 µL TAP) at 37 for 1.5 hr, and then preincubated with PNK reaction premix (1 µL PNK (NEB), 1 µL 300 mM $MgCl_2$, 1 µL 100 mM ATP) for 30 min. Afterward, PNK reaction main mix (20 µL PNK buffer (NEB), 2 µL 100 mM ATP (Roche), and 142 µL water, 1 µL SUPERaseIN (Promega) and another 2 µL PNK (NEB)) was added to the preincubated RNA sample and incubated at 37° C. for 30 min. The RNA was extracted and precipitated again as above and resuspended in 9 µL water.

5'-adaptor ligation. BrU-RNA, 5' adaptor (5 uM) and PEG was heated on 65° C. for 5 min then cooled on ice. Ligation mixture (1.5 µL 5' adaptor (5 uM), 2 uL 10× RNA ligation buffer, 1.5 uL T4 RNA ligase, 1 uL SUPERaseIn, 5 uL 50% PEG 8000) was added to the 9 uL BrU-RNA and incubated at 22° C. or RT for 4-6 hours. Then, 5' adaptor ligated BrU-RNA was purified with the bead binding method as described above.

3'-adaptor ligation. The same ligation reaction for the 5'-adaptor ligation described above was performed with the 3' adaptor in place of the 5' adaptor.

RT-reaction. RNA and RT oligo (5'-CAAGCAGAA-GACGGCATACGA-3'(SEQ ID NO: 644)) was heated to 65° C. for 10 min and cooled on ice. RT reagent mixture (1 µL RT oligo (100 µM), 5× first strand buffer (Invitrogen), 10 mM dNTPs (Roche), 100 mM DTT (Invitrogen), 1 µL RNase inhibitor (Promega) without Superscript III (Invitrogen) was added to RNA sample and incubated at 48° C. for 3 min, and then 1 µL superscript III was added to the RT reaction sample and incubated at 48° C. for 20 min, 50° C. for 45 min, sequentially. After RT reaction, RNA was eliminated by adding RNase cocktail and RNaseH and incubating at 37° C. for 30 min.

PCR amplification. The ssDNA template was amplified by PCR using the Phusion High-Fidelity enzyme (NEB) according to the manufacturer's instructions. The small RNA PCR primers (5'-CAAGCAGAAGACGGCATACGA- 3′(SEQ ID NO: 644)) and (5′AATGATACGGCGAC-CACCGACAGGTT-3′(SEQ ID NO: 645)) were used to generate DNA for sequencing. PCR was performed with an initial 5 min denaturation at 98° C., followed by 10~14 cycles of 10 sec denaturation at 98° C., 30 sec annealing at 54° C., and 15 sec extension at 72° C. The PCR product was purified by run on a 6% native polyacrylamide TBE gel and recovered by cutting the region of the gel between 100 bp to 300 bp. The product was purified through the gel extraction method. The prepared DNA was then sequenced on the Illumina Genome Analyzer II according to the manufacturer's instructions with small RNA sequencing primer 5′-CGACAGGTTCAGAGTTCTACAGTCCGACGATC-3′ (SEQ ID NO: 646).

eRNA annotation. The inventor first merged GRO-seq data across time points and used HOMER (Heinz et al., 2010) for de novo transcript identification with option '-style groseq'. Intergenic transcripts, which were >1 Kb from 5′ ends and >10 Kb from 3′ ends of RefSeq gene annotations, were selected as eRNA candidates. The RefSeq annotation was downloaded through an R package called "GenomicFeatures" (Lawrence et al., 2013), with "GenomicFeature" version 1.20.3 and creation time "2015-11-24 13:48:33-0600 (Tue, 24 Nov. 2015)". The inventor filtered out regions that did not overlap with either H3K4me1 or H3K27Ac peak regions.

ENCODE epigenetic data analyzed here can be downloaded from GEO under accession numbers GSE29611 (H3K4me1 and H3K27Ac), GSE29692 (DNase-seq), GSE35586 (MNase-seq), and GSE31477 (P300). Human enhancer atlas data were downloaded from (slidebase-.binf.ku.dk/human_enhancers/, the permissive enhancer set).

Expression analysis of coding and non-coding transcription. Expression levels of genes and enhancers were calculated as Reads per Kilobase per Million (RPKM). R package DEseq2 (Love et al., 2014) was used to perform differential analysis between two time points. Differential gene sets were submitted to David Bioinformatics Resources Database (Huang da et al., 2009a, b) for functional enrichment analysis. Principle Component Analysis (PCA) and t-Distributed Stochastic Neighbor Embedding (t-SNE) methods were applied with expressed genes/enhancers (mean RPKM>0.5) for data visualization.

The inventor designed one-step delayed auto-correlation to control noise levels and the absolute fold-change to identify responsive genes/enhancers. Selected genes/enhancers were subject for clustering by the 'Partitioning Around Medoids' (PAM) algorithm, resulting in three clusters: "inducible early," "inducible late," and "repressed."

Determining inducible enhancers and genes. The inventor identified inducible enhancers/genes using the amplitude index (AI) and continuity index (CI). The expression level at time t is represented as e(t). AI is defined as the maximum logarithm fold increases before 24 h:

$$AI = \log_2 \left[ \frac{\max_{t \leq 24h} e(t)}{e(0)} \right]$$

CI is defined as the one-step delayed auto-correlation, to filter out enhancers/genes with noisy expression pattern:

$$CI = \text{correlation}\{[e(t_1), \ldots, e(t_{n-1})], [e(t_2), \ldots, e(t_n)]\}$$

The inventor then selected enhancers and genes with AI>1 and CI>0.2 as inducible.

Concordant and discordant EP pairs. Inducible EP pairs were ranked by the Spearman correlation coefficients (SCC) between enhancers and genes. Pairs ranked at the top 30% and bottom 30% of the list are designated as concordant and discordant, respectively.

Pairing enhancer and target genes. Fold changes at each time point were calculated for enhancers near inducible genes. The inventor divided enhancers into groups according to their distance from genes and found enhancers <200 Kb from these genes showed significantly stronger inducibility. He named inducible genes and enhancers within 200 Kb distance as inducible EP pairs.

Motif analysis. The inventor used TF binding motif PWM matrices from HOmo sapiens COmprehensive MOdel COllection (HOCOMOCO) v10 (Kulakovskiy et al., 2016). The inventor applied HOMER module annotatePeaks.pl to identify motif occurrence in inducible enhancers and genes.

Synteny analysis. The inventor analyzed EP co-localization in 11 species covering different levels of metazoan animals, including chimp, marmoset, mouse, rat, guinea pig, rabbit, cow, dog, elephant, armadillo, and lizard. Orthologs of enhancers and promoters were identified using UCSC LiftOver tool with minimal match ratio set to 0.1. The inventor tested the percentage of inducible human EP pairs locating in the same chromosome on other species. For statistical analysis, the inventor generated a background set by paring 10,000 random promoter regions with the same number of intergenic regions, following the distance distribution of inducible pairs.

Chromatin Immunoprecipitation (ChIP) sequencing. Chromatin was prepared and immunoprecipitated as described previously (Kim et al., 2011), except that protein A/G dynabeads (Invitrogen) were used instead of organism-specific secondary antibody bound beads. 25% of the amount of chromatin was used to reduce oversaturation of bead binding. K27Ac antibody from Abcam (ab4729) was used for ChIP experiment. The ThruPLEX DNA-seq kit from Rubicon Genomics was used for multiplexed ChIP-seq and Input sample library prep of GM12878 chromatin. Indexed samples were quantitated with qPCR and mixed in equimolar amounts. The Yale Stem Cell Center Genomics and Bioinformatics Core Facility conducted the sequencing on an Illumina HiSeq 2000 platform. ChIP-seq peaks were called with MACS 2 with the default mode. The inventor analyzed the inventor's ChIP-seq data using the inventor's scripts and tools.

Chromosome Conformation Capture (3C). The 3C assay was performed as described (Banerjee et al., 2014; Kim et al., 2011), with minor modifications. Briefly, one million cells were cross-linked with 1% formaldehyde for 15 min at room temperature, and resuspended in lysis buffer (10 mM Tris, pH 8.0, 10 mM NaCl, and 0.2% NP40) and incubated on ice for 90 min. Ten million of these prepared nuclei were digested with EcoRI (New England Biolabs) overnight at 37° C., followed by ligation with T4 DNA ligase (New England Biolabs) at 16° C. for 4 hrs. The ligated DNA was incubated with Proteinase K at 65° C. for 12 hrs to reverse the cross-links. Following incubation, the DNA was treated with RNase A. The treated DNA was extracted with phenol: chloroform and precipitated with sodium acetate and ethanol. The DNA concentration of the recovered 3C library was determined using Qubit dsDNA HS assay kit (Invitrogen). Quantitative real-time PCR was performed to confirm the specific ligation between two DNA fragments in the sample and control 3C libraries. The position and sequence of primers designed for 3C qPCR assay is listed in Supplemental Table S4. Interaction frequencies were calculated by dividing the amount of PCR product obtained with the sample 3C library constructed from nuclei by the amount of PCR product obtained with the control library DNA generated from ligating EcoRI fragments from the corresponding bacterial artificial clones (BAC, Supplemental Table S4): interaction frequency=2^(dCt sample−dCt control). All 3C analyses were performed, at a minimum, in triplicate.

TABLE S4

3C assay primers and BAC clone for induced EP interaction (a) and control EP interaction (b).

| Enhancer ID | eRNA-primer | SEQ ID NO: | Target gene name | Target promoter-primer1 | SEQ ID NO: | Target promoter-Primer2 | SEQ ID NO: | Control primer | SEQ ID NO: | BAC done |
|---|---|---|---|---|---|---|---|---|---|---|
| | eRNA | | | Target genes | | | | Control | | |

A. Induced EP interaction

| MetaEnhancer_1136_+ | TCACGAACACC CAGAGATGT | 7 | ACKR1 | AACTCTGATGG CCTCCTCTG | 43 | TTGGTCACCC TTTCTCCAGG | 79 | TCCGTAGTGAA AGTTTTGGGA | 115 | RP11-621D16 + RP11-1065J8 |
| MetaEnhancer_258_- | ACCACCAGACA TTAGCCCAG | 8 | CCR1 | GGAGGGCAGT GTTGTTCAAA | 44 | CTTCCTCACG GCATTGCTAC | 80 | CTGCTCTTGT TCTCCACTGC | 116 | RP11-793E15 |
| MetaEnhancer_1694_+ | TGCTGCCACAA GAACATTTG | 9 | CD38-1 | TCCTGTTGTGT ACCTGGCTT | 45 | GGAGTCCAAA GGCAGTCTCT | 81 | TGATCCTTTC CTTGGCCTCA | 117 | RP11-640L4 |
| MetaEnhancer_3795_- | GTGTGTGTGTG TGTGTGTGT | 10 | CD38-2 | GGAGACCCAG GGAAGAGTTG | 46 | TCCTGTTGTG TACCTGGCTT | 82 | ATTACAGCAC TTTGGGAGGC | 118 | RP11-640L4 |
| MetaEnhancer_1136_+ | TCACGAACACC CAGAGATGT | 11 | IFI16 | GCAGTGATCAAA ATTATGTCCCA | 47 | TCCAAGGCCA TCTACAGAGC | 83 | GTGCTGTCTC CCTTCTGTCT | 119 | RP11-265E4 |
| MetaEnhancer_1571_+ | TCCCCAGTCAT TAGCACAGT | 12 | IFNb1 | GCAAAGGAAA GCAAACGACC | 48 | TCCCCACTGC CTTGTTCATA | 84 | TCAGGTAATGT GATGCCTCCA | 120 | RP11-372B20 |
| MetaEnhancer_259_+ | ATAGCCTGCCC CAAATCACT | 13 | IRF8 | GAAGTGCTCTG CTTTCCGAG | 49 | TGGGCATTTG GTGGAATTCg | 85 | TGTTAATTAC CTGAAGCGCGT | 121 | RP11-478M13 + RP11-152O13 |
| MetaEnhancer_1115_+ | TCTTGGGACCG TGAAAGTGT | 14 | KIAA0040 | ATCCAAGTGTT TCCAACCGC | 50 | CTTTCTCCGA ACGCTCAAGG | 86 | AAAGAAAATGC CAGGCCCAG | 122 | RP11-661N21 |
| MetaEnhancer_1136_+ | TCACGAACACC CAGAGATGT | 15 | MNDA | CAAATCAACG GGAGCAAGCT | 51 | ATCATGAGAA CAGCACGGGA | 87 | TGAGTTGGCTG TAAATGTGTGT | 123 | RP11-110D10 + RP11-1065J8 |
| MetaEnhancer_2972_- | TGGTTGGACA GTAGGGGAAG | 16 | PARP14 | TCATATCTCTC TGGCTGCTCC | 52 | TCTTGGTCCA ATGCAGTCCT | 88 | GGGTCAAAGAG ATGGCAGGA | 124 | RP11-90P23 |
| MetaEnhancer_2972_- | TGGTTGGACA GTAGGGGAAG | 17 | PARP9 | ATCTCTTGGCC ATGGAGCTT | 53 | TGAGGACCCT ACTGTTGCTG | 89 | TTACAGGCACG TACCACCAT | 125 | RP11-90P23 |
| MetaEnhancer_3039_+ | AGCATTTAGGA GTGCACGTT | 18 | SAMD9 | GATGTTAGGG GCTCTGCAGA | 54 | TGAGCACTTT GGAAGGCAAG | 90 | TTTGCTGTAAC TGCCCTCCT | 126 | RP11-962H11 |
| MetaEnhancer_502_+ | CTGTCCCACAC ACCCCATAT | 19 | TLR7-1 | CAGGAAGAGG GAGAGCAGAG | 55 | GAGGGTTTCAT TTGCTGGGG | 91 | GTAAACCACTG CAGACTGGC | 127 | RP11-166I19 |
| MetaEnhancer_341_- | CTGTCCCACAC ACCCCATAT | 20 | TLR7-2 | CAGGAAGAGG GAGAGCAGAG | 56 | GAGGGTTTCAT TTGCTGGGG | 92 | CATGCCAAGAT CTGTAGACATCT | 128 | RP11-166I19 |
| MetaEnhancer_116_+ | TCTCCATGGGT CAGGTTGTT | 21 | TNFSF10-1 | TACAGGTTCT TTGGTGCCCA | 57 | GAGCTGAGAT CATGCACTGC | 93 | GCCATGCGCGG GATATAATC | 129 | RP11-240B20 |
| MetaEnhancer_734_- | CTCCATGTTTC TCCCGTGTG | 22 | TNFSF10-2 | TACAGGTTCT TTGGTGCCCA | 58 | GAGCTGAGAT CATGCACTGC | 94 | GAGGACTACAG TAACGACCCT | 130 | RP11-183A2 |
| MetaEnhancer_2005_+ | GCAATAAACGT GGGAATGCC | 23 | TNFSF10-3 | GAGCAGGACA CGTAGACTCA | 59 | TGCCCATTTC AGCATACAAAA | 95 | ACATTGTGCCC AGATGTTCC | 131 | RP11-259F22 |
| MetaEnhancer_512_- | CACAGAAAGC ATTGCCCCTT | 24 | WDFY1 | AGGCTGGTCT TGAACTCCAA | 60 | TGTAGGAGGA GCAGGTTTGG | 96 | CTGGCAGACAC CTCCACTTA | 132 | RP11-79C2 |

B. Control EP interaction

| MetaEnhancer_600_+ | CTGGTCTTCTC TTCCCCACT | 25 | APOBEC3B | GCCTCAGCCT CTAGAGTAGC | 61 | CCTAGGGTAG CCTCACGTG | 97 | GGGATTACAG GTGCCCAGAA | 133 | RP11-358G23 |
| MetaEnhancer_600_+ | CTGGTCTTCTC TTCCCCACT | 26 | APOBEC3D-1 | ACTCCCAACC TCATGATCCG | 62 | CACCTCTCTG TGCCTCTGAC | 98 | GGGATTACAG GTGCCCAGAA | 134 | RP11-358G23 |

TABLE S4-continued 3C assay primers and BAC clone for induced EP interaction (a) and control EP interaction (b).

| Enhancer ID | eRNA eRNA-primer | SEQ ID NO: | Target gene name | Target promoter-primer1 | SEQ ID NO: | Target promoter-Primer2 | SEQ ID NO: | Control Control primer | SEQ ID NO: | BAC done |
|---|---|---|---|---|---|---|---|---|---|---|
| MetaEnhancer_94_- | CTGCTGGTCTTCTCTTCCCCACAATCAGTCA | 27 | APOBEC3D-2 | TCGAACTCCCAACCTCATGA | 63 | CACCTCTCTGTGCCTCTGAC | 99 | ACAGAGTTCAGGACAGTGGT | 135 | RP11-358G23 |
| MetaEnhancer_1529_+ | CTAGGAGGAGG | 28 | CD2AP | AAGGATTGGGGAGTCTCTCG | 64 | GTATGTGTGGGCATTTGTGC | 100 | TGGTAGGAGCCCAGATTCTG | 136 | RP11-947C14 |
| MetaEnhancer_699_+ | CCATGTTTGCTAGGCTGGTC | 29 | DMXL1-1 | ATCCCTGCGGCCGAAATAT | 65 | CTGCATGCCAACTTAAAACCT | 101 | CCCTGCTGCTTCCCTTTGAA | 137 | RP11-119J15 |
| MetaEnhancer_454_- | CCATGTTTGCTAGGCTGGTC | 30 | DMXL1-2 | TCCACACACTTCCTCTGGAC | 66 | AGAAAGGTGTTTGTGGTGCA | 102 | ATCCACAGAACCATGCTCCA | 138 | RP11-119J15 |
| MetaEnhancer_475_+ | CACTTCTCATTTCTCCAACCACA | 31 | HLA-DMA | GGCCGAAGTACCTAGCATGT | 67 | CAAGCTACTCAGGAGGCTGA | 103 | GACCCAGGAAGAGCTGATGT | 139 | RP11-260B12 |
| MetaEnhancer_157_- | TCCAAACATGCAGCAGTCAC | 32 | HLA-DRA | TCCAAAGGCACCTGAATGAG | 68 | TCTGCTCAGGAATCCTAGGT | 104 | CTGAAGAGTGAcAcacacA | 140 | RP11-379F19 |
| MetaEnhancer_157_- | TCACCACTTCCGGACTTTT | 33 | HLA-DRB5 | ATTCCCCATACAGCACTTCC | 69 | TTGCTTCTCTGTTTTCTTTCCC | 105 | CTGAAGAGTGACACCTCCTCA | 141 | RP11-379F19 |
| MetaEnhancer_820_- | CCAAAAGCACAAGACAGCCT | 34 | IFI35 | GAGAGAGACCACAGCCCTTT | 70 | AAACTCTCCCACGTTCACCC | 106 | CCAGCCCCTTATGCCTCTTA | 142 | RP11-948G15 |
| MetaEnhancer_311_+ | CTGTGGGTCAAATGGGAGGA | 35 | MLLT6 | TATTCCAGGGCCTAGAACGG | 71 | CATCTCCCTCTTGGCTTCCA | 107 | CAGCTTGAAGTGCCTTGTGG | 143 | RP11-607B2 |
| MetaEnhancer_544_- | AGGGACAAGCAAGCATCTCT | 36 | MYCBP2 | GAAGGGGTGGAGGTGAGTAC | 72 | CTCCTTCAGCCACTTCAGGA | 108 | TTTCATGGCTCCAACAACCT | 144 | RP11-775N1 |
| MetaEnhancer_327_+ | AACTTGAGCCCAGACAACCT | 37 | PELI1 | CGATGCGTTTTCTTTATAGCCA | 73 | GCCGGCCAAATATCAGTAG | 109 | CACTTCTGGTTTCTCATTCTCGA | 145 | RP11-46K17 |
| MetaEnhancer_1477_- | GCTTGCCTCTCTTTGCCTTA | 38 | SOCS1-1 | GCGGTCTTATGTGGTATGCC | 74 | AGTCAAGATCCTGGTGGCTT | 110 | CTCTGCCCAGCCTAGGAAC | 146 | RP11-697G17 |
| MetaEnhancer_810_- | CCTTGGTTTCCTGGCCTCTA | 39 | SOCS1-2 | AGTCAAGATCCTGGTGGCTT | 75 | GCGGTCTTATGTGGTATGCC | 111 | CAGGAGGCTCTGGGAAGAAT | 147 | RP11-697G17 |
| MetaEnhancer_1228_+ | TGCATGAGGCAGACTTGTTC | 40 | ZBP1 | CCCAAGTCTCCCTTCTACCA | 76 | GTGTGAAGTCAGGTGCATGG | 112 | AACGGGAGCTTCGACTGTAA | 148 | RP11-1105M4 + RP11-877E5 |
| MetaEnhancer_804_+ | TGTGGTCCATATCCCGTAGA | 41 | ZCCHC2 | CCAGGCTGGCAAATTGAGTT | 77 | CCACTCTTCAGCCTACTCGT | 113 | CAAGTCCTGCCCTGGTTTAC | 149 | RP11-645G19 |
| MetaEnhancer_246_+ | CACGCCCAGCTAATGTTTGT | 42 | ZFAND6 | GCGGAGACTTTAAGGGCTTG | 78 | TTAAACATTTTAGCATCCCAGG | 114 | GAACAAAAGCTCCTGAGGCC | 150 | RP11-916P11 | eRNA KD analysis with siRNA. siRNA duplex for eRNA KD were obtained from Sigma-Aldrich. Their sequences and eRNA region of induced EP pairs and control EP pairs are listed in Table S5 and Table S6, respectively. As a negative control, scrambled siRNA was used. As a mock control, only transfection reagent without siRNA was added to cell sample. 300,000 cells were prepared in 800 μL media in each well of 12 well-plate. Separately, siRNA transfection solution was prepared by adding 1 μL of siRNA (10 uM stock of siRNA) and 5 μL of Mission siRNA transfection reagent (Sigma) to 200 μL OPTI-MEM, followed by incubation for 15-20 min at room temperature. Then, siRNA transfection solution was added to the cell carefully, by dropping it, which was incubated for 5 hours at 37° C. and then changed with fresh media. After 36 hours of incubation, virus solution with the concentration of 50 μL/mL media was added to the cell to activate the inducible immune response gene system. After 12 hours, total RNA was extracted with adding 500 ul of Trizol solution (Invitrogen) to the cell pellet spun down at 1,500 rpm for 3 min and rotating at 4° C. for 5 min.

TABLE S5 siRNAs targeting eRNA of induced EP pairs.

| siRNA name | target gene | Items | SEQ ID NO: | eRNA region | siRNA name | siRNA sequence Position | SEQ ID NO: | Sequence (Sense) 5' to 3' | SEQ ID NO: | Sequence (Antisense) 5' to 3' | SEQ ID NO: |
|---|---|---|---|---|---|---|---|---|---|---|---|
| siRNA# 5A | TNFSF 10-1 | MetaEnhancer_ 116_+ | 151 | TAAACCAGGATCTCTTCAGCCTCCA AGGTAAGGAAATGTGATCTCCAA GCTCCCTCTTGTATGTATTGTGAACGC CACTGTCAGAGAGAAACACCAAAG TTATTCACCTGGAAATGTTGCAGTAT GAAGACCATGTATTTGATGGAGAGG | 116A | GCCACTGTCAG AAGAGAAA | 170 | GCCACUGUCAGA AGAGAAA | 213 | UUUCUCUUCUGA CAGUGGC | 256 |
| siRNA# 5B | | | | | 116B | TCTTCAGCCTCC AAGGTAA | 171 | UCUUCAGCCUCC AAGGUAA | 214 | UUACCUUGGAGG CUGAAGA | 257 |
| siRNA# 5C | | | | | 116C | GGAAATGTGTG ATCTCCAA | 172 | GGAAAUGUGUG AUCUCCAA | 215 | UUGGAGAUCACA CAUUUCC | 258 |
| siRNA# 7A | IRF8 | MetaEnhancer_ 259_+ | 152 | GGCTCAGGCTGAGAGGATATTCTGCC GTTGTAGTTTTGCTCGGGGCCATTCG TTTTAAGAGACTGAGAGTCAGTTC CAGTTTGTCTTGGGGGACTAAGTTCT TATCATGTGTTTCTACTGGTGGCTTA TTAGAACATGCAGGTACAG | 259A | GAGAGGATATT CTGCCGTT | 173 | GAGAGGAUAUU CUGCCGUU | 216 | AACGGCAGAAUAU CCUCUC | 259 |
| siRNA# 7B | | | | | 259B | GGTTTCTACTGG TGGCTTA | 174 | GGUUUCUACUG GUGGCUUA | 217 | UAAGCCACCAGUA GAAACC | 260 |
| siRNA# 8A | MLLT6 | MetaEnhancer_ 311_+ | 153 | CCCAGCCCTCAGTGCCCCACAGCAG CTTGGCTGTCTTCTGGTTTTGTTTCTT CTGCTTCTGCATGATATCTTTGAACAA AAGTCCCAAGTGTACAAACCACCT GAAAGGCGTTCGCAAACCACTGACCT AGATGGAGGAATTGTGAGGAGCAG AGGGCACCCTCTTATAAAATGCCTGT ACTTCGGTGCAGGGTTTGGTGGTGTC GGCCGTTTTGGAGGCCCTTTAAGCTTC CTAACTCCTTGTCACTGGTGGATGGT GGGGTGCCGCAGGAGGGGCATCCCT TTACATAGGGGCTCATTG | 311A | CTCTGCTTCTGC ATGATAT | 175 | CUCUGCUUCUGC AUGAUAU | 218 | AUAUCAUGCAGA AGCAGAG | 261 |
| siRNA# 8B | | | | | 311B | GAGGGCATCCC TTTACATA | 176 | GAGGGCAUCCCU UUACAUA | 219 | UAUGUAAAGGGA UGCCCUC | 262 |
| siRNA# 10 | TLR7-1 | MetaEnhancer_ 502_+ | 154 | GGGGAATGAGAACAAAAGACAAAG GTTAATTATGACACCGGGGCTTTACA ATGCTAAAAATATCCTATATACAAAG GGATATGTAGGCTGTGTTCTTTTTTCCA TGTCATTACAAAGAACAGGCTCAAGG TATCTGCAAATTTCTAATAAAATATT ATTACTTGAAAATG | 502A | GGCTCAAGGTA TCTGCAAA | 177 | GGCUCAAGGUA UCUGCAAA | 220 | UUUGCAGAUACC UUGAGCC | 263 |
| siRNA# 17A | CD38 | MetaEnhancer_ 1694_+ | 155 | GTCCACTTTAGGAGTGTATGTACTT GGACCTAAAAAATATGCTGCCACA AGAACATTTGTTGTAGCATTctgTGCT CATTTATACAGGTCTAGTTAAGTAAA CTCTAGCATACTA | 1694A | AGCATTCTGTGC TCATTTA | 178 | AGCAUUCUGUGC UCAUUUA | 221 | UAAAUGAGCACAG AAUGCU | 264 |
| siRNA# 17B | | | | | 1694B | GAGTGTATGTA CTTGGACA | 179 | GAGUGUAUGUA CUUGGACA | 222 | UGUCCAAGUACA UACACUC | 265 |
| siRNA# 23A | CCR1 | MetaEnhancer_ 258_- | 156 | GCCTTTGAAAGTCTCGCATCTGCTGTT TTTCAGGTCTCCAAGTCCATTCTTTGT GTTTGGACTGGTGAGTGTTTCTCACA CTCTATAATCGCAAAGTAGGAGGTA | 258A | GAGTGTTTCTCA CACTCTA | 180 | GAGUGUUUCUCA CACUCUA | 223 | UAGAGUGUGAGA AACACUC | 266 |
| siRNA# 23B | | | | | 258B | GGAGGTATCTCT TCAAGAA | 181 | GGAGGUAUCUC UUCAAGAA | 224 | UUCUUGAAGAGA UACCUCC | 267 |

TABLE S5-continued siRNAs targeting eRNA of induced EP pairs.

| siRNA name | target gene | Items | eRNA region | SEQ ID NO: | SiRNA name | siRNA sequence Position | SEQ ID NO: | Sequence (Sense) 5' to 3' | SEQ ID NO: | Sequence (Antisense) 5' to 3' | SEQ ID NO: |
|---|---|---|---|---|---|---|---|---|---|---|---|
| siRNA#24A | TLR7-2 | MetaEnhancer_341_- | TCTCTTCAAGAAGACAAGTGTCATTC AAATATTTCTGCATAACAGACCAGAC AAAACTTA AGACTATTTATGCATGCATTGGTCTTT GAGCTGTTCCGCCTGCTGTCTTGTAA ACTCAGAAGCAGTTTTCCTGAGGTGG GTATTACTGACCATCTAGCTCACCATC TGAGACTCATAAGTAGATTTGTGAGT GGTGAGGTGTAGTGAAGACCACTTG TTTGGGATTCAACATACATGCCAGCC AATGAAATGTTAACTCACATCTGCA TATGCCTTCATCTTGTTATGGAACTGG AGGCACCATCATTCATAATGCTTAAA AATAAAACACCTGCA | 157 | 341A | GAGGCACCATC ATTCATAA | 182 | GAGGCACCAUCA UUCAUAA | 225 | UUAUGAAUGAUG GUGCCUC | 268 |
| siRNA#24B | | | | | 341B | CTCACCATCTGA GACTCAT | 183 | CUCACCAUCUGA GACUCAU | 226 | AUGAGUCUCAGA UGGUGAG | 269 |
| siRNA#28A | WDFY1 | MetaEnhancer_512_- | GTTAGGTTACATATCAAGTTAGGTTC ACTGTGTACTGAAAAATCCTTTAGGCC AAAATTAAAATATGTACAACGGAGGC TTTAGTCCAAACTTAATTTAACAGTAC TACAATTAAGTACATCAGTATTGCCATA ATGTATCAGTCAGGGT GCTTGGACCCACAGTACAGATCACCC | 158 | 512A | GGCTTTAGTCCA AACTTAA | 184 | GGCUUUAGUCCA AACUUAA | 227 | UUAAGUUUGGAC UAAAGCC | 270 |
| siRNA#28B | | | | | 512B | GCCATAATTGTA TCAGTCA | 185 | GCCAUAAUUGUA UCAGUCA | 228 | UGACUGAUACAA UUAUGGC | 271 |
| siRNA#28C | | | | | 512C | TAGGTTCACTGT GTACTGA | 186 | UAGGUUCACUGU GUACUGA | 229 | UCAGUACACAGU GAACCUA | 272 |
| siRNA#30 | TNFSF10-2 | MetaEnhancer_734_- | ATCTTGGGCTATCCATCCACTGAGCAAT TGCTGACCTGCATCTCTGTGAGTGG AGCCCCAGGAGACAAGTAAAAGAC CCCAGCCACAAC | 159 | 734A | CACACTGAGCAA TTGCTGA | 187 | CACACUGAGCAA UUGCUGA | 230 | UCAGCAAUUGCUC AGUGUG | 273 |
| siRNA#34A | IFNb1 | MetaEnhancer_1571_+ | TTCTTCTGGCTGCCTGGAAGATGCCT CTGTTATTTTAGTGAAACATTTAGCT CCTCGAAAGTGTAGAGAGACCAAGA GGTAAAGTGTGCCATTGTAGACAGCT GGTGTGTGTGCCAGTAGCAGTGCTT CTGTCTACATCCTGGGATATT | 160 | 1571A | CTGTCTACATCC TGGGATA | 188 | CUGUCUACAUCC UGGGAUA | 231 | UAUCCCAGGAUG UAGACAG | 274 |
| siRNA#34B | | | | | 1571B | TAAAGTGTGCC ATTGTAGA | 189 | UAAAGUGUGCCA UUGUAGA | 232 | UCUACAAUGGCAC ACUUUA | 275 |
| siRNA#35A | IFI16 | MetaEnhancer_1136_+ | TTTCTGCTATCTAGATCTTTGACTACC AACCAGCCAGAGTGTCTGCCTCTT CTTTGGTCTGAGCTTGCCTTGTGCTTA TATTGTTGACCCAAGCGAGT | 161 | 1136A | CTTATATTGTTG ACTACCCAA | 190 | CUUAUAUUGUU GACUACCA | 233 | UUGGGUACAACA AUAUAAG | 276 |
| siRNA#35B | | | | | 1136B | CTATCTAGATCT TGACTA | 191 | CUAUCUAGAUCU UGACUA | 234 | UAGUCAAGAUCU AGAUAG | 277 |
| siRNA#36A | PARP14 | MetaEnhancer_2972_- | CGCGACCGTTCCATTCTGAGTTTCTT CACTTTGCCAGCTTGGGTGTCTCCC GAGGCCGTCGTTCTAGTTATGGCTCA TCCAGCTGACGCTGCAACTTCTCTTGT TCTGTAGCATTTCTTCTTACTTCTTTC TCTACCAGCTGTCAACCGGCT | 162 | 2972A | CAACTTCTCTTG TTCTGTA | 192 | CAACUUCUCUUG UUCUGUA | 235 | UACAGAACAAGAG AAGUUG | 278 |
| siRNA#36B | | | | | 2972B | CTCTTGTTCTGT AGCATTT | 193 | CUCUUGUUCUGU AGCAUUU | 236 | AAAUGCUACAGAA CAAGAG | 279 |
| siRNA#36C | | | | | 2972C | CCGTTCCATTCT GAGTTT | 194 | CCGUUCCAUUCU GAGUUU | 237 | AAACUCAAGAAU GGAACGG | 280 |

TABLE S5-continued siRNAs targeting eRNA of induced EP pairs.

| SiRNA name | target gene | Items | SEQ ID NO: | eRNA region | SiRNA name | siRNA sequence Position | SEQ ID NO: | Sequence (Sense) 5' to 3' | SEQ ID NO: | Sequence (Antisense) 5' to 3' | SEQ ID NO: |
|---|---|---|---|---|---|---|---|---|---|---|---|
| SiRNA# 37A | CD38 | MetaEnhancer_3795_- | 163 | CACATCTCACCCCCAGACCTGCCATT GGCATGCACATCTTAACCACAAACC ACGATTGAAAATGAGAAAGAAAACT CTCCTCTAGCTGGGCGCTTCATAGGA CTAGCCAGTACGACCCATCTCTGAGG GTCTTTGACAGCTCAGTTTTACTGCAT AATCTGTTTTCAAGACCCTTTAAAAG ACCAGAT | 3795A | GAGGGTCTTTG ACAGCTCA | 195 | GAGGGTCUUUG ACAGCUCA | 238 | UGAGCUGUCAAA GACCCUC | 281 |
| SiRNA# 37B | | | | | 3795B | CTGCCATTGGCA TGCACAT | 196 | CUGCCAUUGGCA UGCACAU | 239 | AUGUGCAUGCCA AUGGCAG | 282 |
| siRNA# 37C | | | | | 3795C | GCATGCACATCT TAACCA | 197 | GCAUGCACAUCU UAACCA | 240 | UGGUUAAAGAUG UGCAUGC | 283 |
| SiRNA# 38A | TNFSF 10-3 | MetaEnhancer_2005_+ | 164 | CATAACTACCAGAAGCCATTGGTGC AAGATCTCAATCAGGACATGTCGGTA CAATGCTCTGATTATCTCGCTCGCATC CCTGATTACTTATGGTCCAGATATAA ACTACT | 2005A | CTGATTATCTCG TCTGCAT | 198 | CUGAUUAUCUCG UCUGCAU | 241 | AUGCAGACGAGA UAAUCAG | 284 |
| siRNA# 38B | | | | | 2005B | CTGCATCCCCTGA TTACTTA | 199 | CUGCAUCCCCUGA UUACUUA | 242 | UAAGUAAUCAGG GAUGCAG | 285 |
| SiRNA# 38C | | | | | 2005C | TACTTATGGTCC AGATATA | 200 | UACUUAUGGUCC AGAUAUA | 243 | UAUAUCUGGACC AUAAGUA | 286 |
| SiRNA# 41A | SAMD9 | MetaEnhancer_3039_+ | 165 | GTCCTTAAGGCTGATGTGAATCTCTG CCCTTTCCAATGTGTCATGTGATTGCT CCAAATTAAAACACCTATTATTATTAT TTTG | 3039A | GAATCTCTGCCC TTTCCAA | 201 | GAAUCUCUGCCC UUUCCAA | 244 | UUGGAAAGGGCA GAGAUUC | 287 |
| siRNA# 41B | | | | | 3039B | TCCAATGTGTCA TGTGATT | 202 | UCCAAUGUGUCA UGUGAUU | 245 | AAUCACAUGACAC AUUGGA | 288 |
| SiRNA# 42A | KIAA040 | MetaEnhancer_1115_+ | 166 | CACCTCACTTCTGTTTTCTGTCCATTA ATGCTTCCTGCCCACGTTGTGGGGAG GAGCTCTTGAACCTCTGCGTCCTTCCTG AGGGATTCAAGAGAATATATTTTTGCT CAATTAAAACTCCTAAATCTAATTTGTC TAAAGCTTTCTT | 1115A | CAATTAAAACTCC TAAATCT | 203 | CAAUUAAAACUCC UAAAUCU | 246 | AGAUUUAGGAGU UUAAUUG | 289 |
| siRNA# 42B | | | | | 1115B | CTGAGGGATTC AAGAATAT | 204 | CUGAGGGAUUC AAGAAUAU | 247 | AUAUUCUUGAAU CCCUCAG | 290 |
| SiRNA# 42C | | | | | 1115C | CTGAACCCTCTGC TGCTTCT | 205 | CUGAACCCUCUGC UGCUUCU | 248 | AGAAGCAGCAGAG GUUCAG | 291 |
| SiRNA# 43A | PARP9 | etaEnhancer_2972_- | 167 | ACTTCCTGTCCGCGACCGTTCCATTCT TGAGTTTCTTCACTTTGCCAGCTTGGG TGTCTCTCCCGAGGCCGTGCTTCTAG TTATGGCTCATCCAGCTGACGCTGCA ACTTCTCTTGTTCTGTAGCATTTCTTCT ACTTCTCTTTCTCTACCAGCTGTGTCA ACCGGCTTTG | 2972A | CAACTTCTCTTG TTCTGTA | 206 | CAACUUCUCUUG UUCUGUA | 249 | UACAGAACAAGAG AAGUUG | 292 |
| siRNA# 43B | | | | | 2972B | CCGTTCCATTCT TGAGTTT | 207 | CCGUUCCAUUCU UGAGUUU | 250 | AAACUCAAGAAUG GAACGG | 293 |
| SiRNA# 46A | ZBP1 | MetaEnhancer_1228_+ | 168 | TGATTACCTCACTCTCATGCAGGGCT GAATATTACTGTTTCCCCTGTTAAACA AGGGTGTATTACTTCCGAAATCTGAC AACCCCAAGCACCAAAAGGTTTAAAA ATATCTCGAGATTGTAAAGCCTCCGA CAGAATGCTGAAACAGGATTGCACA GTTGACCAGGAGCTTCTGAGGTTGTG GCGGACCCCTCCATGTTTCTGACTGCC | 1228A | CCGACAGAATG CTGAAACA | 208 | CCGACAGAAUGC UGAAACA | 251 | UGUUUCAGCAUU CUGUCGG | 294 |
| SiRNA# 46A | | | | | 1228B | GGGTGTATTACT TCCGAAA | 209 | GGGUGUAUUACU UCCGAAA | 252 | UUUCGGAAGUAA UACACCC | 295 |
| SiRNA# 46A | | | | | 1228C | CTCATGCAGGG CTGAATAT | 210 | CUCAUGCAGGGC UGAAUAU | 253 | AUAUUCAGCCCUG CAUGAG | 296 |

TABLE S5-continued siRNAs targeting eRNA of induced EP pairs.

| siRNA name | target gene | Items | eRNA region | SEQ ID NO: | siRNA name | siRNA sequence Position | Sequence (Sense) 5' to 3' | SEQ ID NO: | Sequence (Antisense) 5' to 3' | SEQ ID NO: |
|---|---|---|---|---|---|---|---|---|---|---|
| | | | GGACAGTCACAGCCCCCTCTTCCCTAATGCCACCAGATGTTCCCTGGGACACCTGCC | | | | | | | |
| SiRNA# 47 & 48A | MNDA & ACKR1 | MetaEnhancer_1136_+ | TTTCTGCTATCTAGATCTTTGACTACCAACCAGCCAGGAGTGGTCTGCCTCTTCTTTGGTCTGAGCTTGCCTTGTGCTTATATTGTTGTACCCAAGCGAGT | 169 | 1136A | CTTATATTGTTGTACCCAA | 211 | CUUAUAUUGUUGUACCCAA | 254 | UUGGGUACAACAAUAUAAG | 297 |
| SiRNA# 47 & 48B | | | | | 1136B | CTATCTAGATCTTTGACTA | 212 | CUAUCUAGAUCUUUGACUA | 255 | UAGUCAAAGAUCUAGAUAG | 298 |

TABLE S6 siRNAs targeting eRNA of control EP pairs.

| siRNA name | target gene | Items | eRNA region | SEQ ID NO: | siRNA name | siRNA sequence Position | SEQ ID NO: | (Sense) 5' to 3' | SEQ ID NO: | Sequence (Antisense) 5' to 3' | SEQ ID NO: |
|---|---|---|---|---|---|---|---|---|---|---|---|
| siRNA #1A | HLA-DMA | MetaEnhancer_475_+ | ACAGTCTACAAAGAGGCCGTGGAAGCTGT CGGGGAAGGAGAATGTTCAAGTAGCACAG GCAATCAAACATTCCTATTGCTCCAGGTG CCAAAGCAGGAATGAAAACCTGTCCCCTCT GTTGAATACTCTTCTTCTTCACTCCTAAAA CTACACACCTGATGTTAGTCGTCAGCCCTC TTCTTATCACTCTACACCTGCTCTCTGGA GAACTCATCCAGGCCTGTGGCTCCCTGCAC GTCTACACTAGTAACCCTGAATCCACGGT CTCCAGCACTCCCTCCTGCTCCCATCCCCA GGTGGGCAGTCAGGT | 299 | 475A | CACCTGAT GTTAGTC GTCA | 315 | CACCTGA UGUUAGU CGUCA | 353 | UGACGAC UACAUC AGGUG | 391 |
| siRNA #1B | | | | | 475B | CTCTTCTT CTTCACTC CTA | 316 | CUCUUCU UCUUCAC UCCUA | 354 | UAGGAGU GAAGAAG AAGAG | 392 |
| siRNA #2&3 A | HLA-DRA & DRB5 | MetaEnhancer_157_− | GAATTCAAAGGGTCTCTTCTAGAGGATCCT GGGTTATGTCTCCACAGGAACTTTGGTGT TGGCCCCTCTTCCTCAAATGTGAGGATGA CCAATGCCCCCCCATTATCTCCTTTCTTT TTCTTTCTAACTCGAGTTTATAAAGCCT ATATCCCTGTAGTGTATGTAGGTTCTCTGA CAGAAGTTATACTTAGTGCTCTGTCTTTCT TATGGGGAAAAATCCCTGGAACTGAAGCTA AGATCTTTAGTACTTGGAGTCACCCTACAG ATA | 300 | 157A | CTTTCTAA CTCCAATG TTT | 317 | CUUUCUA ACUCCAA UGUUU | 355 | AAACAUU GGAGUUA GAAAG | 393 |
| siRNA #2&3 B | | | | | 157B | GTATGTA GGTTCTCT GACA | 318 | GUAUGUA GGUUCUC UGACA | 356 | UGUCAGA GAACCUAC AUAC | 394 |
| siRNA #2&3 C | | | | | 157C | CCTCAAAT GTGAGGA TGTA | 319 | CCUCAAA UGUGAGG AUGUA | 357 | UACAUCC UCAUAUU UGAGG | 395 |
| siRNA #6A | ZFAND6 | MetaEnhancer_246_+ | ATGGTTTGTTTTCCCCTCTCCTGCTAGAA GCACAAGGGGATTTTCTCTGATAATCATT GTGAGAACCTGTTAGAACTCCTGGAGGTAA AACTCAAAGTATGGCGGCCCCCCCTGAATG AGTCTTCCTGGAATTAACTGTCAAACTTGC CACTCTGAGTCTCCAGCAATTCTTGAATTA CAATTCAGATTTTCCTATCCTGGTACAGGT TCCTGT | 301 | 246A | CTCTGAGT CTCCAGC AATT | 320 | CUCUGAG UCUCCAG CAAUU | 358 | AAUUGCU GGAGACU CAGAG | 396 |
| siRNA #6B | | | | | 246B | GTGAGAA CCTGTTAG AACT | 321 | GUGAGAA CCUGUUA GAACU | 359 | AGUUCUA ACAGGUU CUCAC | 397 |
| siRNA #9A | PELI1 | MetaEnhancer_327_+ | TACCAATGTCTCTGGGCCTTGCTCTACTAG TACAACAGAGGAGAGAAATTCTAGAAGA TTTTCAACTCCCCTCCTGCTCTGTAACTCT GGTTCGCTATGTGCTAAATGCACCTTGAAA TAAACACTTCCTTGTGTGTGTGTGTGTGCG CGGTGGAATCCTCACTTTACAGAAGAGGA | 302 | 327A | CTGTAACT CTGGTTC GCTA | 322 | CUGUAAC UCUGGUU CGCUA | 360 | UAGCGAA CCAGAGU UACAG | 398 |
| siRNA #9B | | | | | 327B | GAGAGAA ATTCTAGA AGAT | 323 | GAGAGAA AUUCUAG AAGAU | 361 | AUCUUCU AGAAUUU CUCUC | 399 |
| siRNA #11& 12A | APOBE C3D-1 & APOBE C3B | MetaEnhancer_600_+ | CACTTGCTTCTCAGGCTGAGGAGGGCGGGG CTGTTGTCAGAGCCCAGAGAATCAAAGCCAG AGGAGCAGGTGGACGTGAGACTGTCCC TCACCCTGCTCCACGGGCAATGTTGAAGT GGGCATCTGGGTGTT | 303 | 600A | TTGTCAG AGCCCAGA AATCA | 324 | UUGUCAG AGCCCAGA AUCA | 362 | UGAUUCU GGGCUCU GACAA | 400 |
| siRNA #11& 12B | | | | | 600B | GCTCCAC GGGCAAT GTTGA | 325 | GCUCCAC GGGCAAU GUUGA | 363 | UCAACAU UGCCCGU GGAGC | 401 |

TABLE S6-continued siRNAs targeting eRNA of control EP pairs.

| siRNA name | target gene | Items | eRNA region | SEQ ID NO: | siRNA name | siRNA sequence Position | SEQ ID NO: | Sequence (Sense) 5' to 3' | SEQ ID NO: | Sequence (Antisense) 5' to 3' | SEQ ID NO: |
|---|---|---|---|---|---|---|---|---|---|---|---|
| siRNA #13A | DMXL1-1 | MetaEnhancer_699_+ | ACCATGACTACCCCTCTTTCCTCGTCACCTG CTAGTCCTCCCATTCACTCCCCTCAGTCAT ATTGGCCTTGCTTCTTCAGACGGGCCAG CCACACTCAGGGCCTTGCACTGACTATTC CTTCTGCCTGGAATGTTCCTCCTCCAAGTA TCCATATGGCTAACTCCCTCAATTCTTTGA GATCTTTAACCACAAGGCGCTTTCCAAAT AAGTCTTCTCTGGCTACCCTTTTTAAAATT TTAACCCCACCCTTCACATTTTATATACT CCCCTTCCTTGCCTTTTTTCAGCTTCTTGTC | 304 | 699A | CTAACTCC CTCAATTC TTT | 326 | CUAACUCC CUCAAUU CUUU | 364 | AAAGAAU UGAGGGA GUUAG | 402 |
| siRNA #13B | | | | | 699B | CTCGTCAC CTGCTAGT CCT | 327 | CUCGUCA CCUGCUA GUCCU | 365 | AGGACUA GCAGGUG ACGAG | 403 |
| siRNA #14A | ZCCHC2 | MetaEnhancer_804_+ | CAATCGCTGCCTGAGTACCTATGTGTTCGT GGCTTGATTTACCTTATCTGTAATTCCTGGA TGTTAAAAGGACACCAAAAATCTGACAC CCTGATTAGCCTACCTTGAAGAACCCAAGC CCAGGATTTCTGCCTTTGCCTAGAAAAAGG ACTGATTCAGAACTTCCTGAGCTACCTAGT ATT | 305 | 804A | GTGTTCGT GGCTTGA TTTA | 328 | GUGUUCG UGGCUUG AUUUA | 366 | UAAAUCA AGCCACGA ACAC | 404 |
| siRNA #14B | | | | | 804B | TTCAGAA CTTCCTGA GCTA | 329 | UUCAGAA CUUCCUG AGCUA | 367 | UAGCUCA GGAAGUU CUGAA | 405 |
| siRNA #14C | | | | | 804C | CTGACAC CCTGATTA GCCT | 330 | CUGACAC CCUGAUUA GCCU | 368 | AGGCUAA UCAGGGU GUCAG | 406 |
| siRNA #16A | CD2AP | MetaEnhancer_1529_+ | CACACAATGAGAGTTGTCCCTAGATTTCACTG GAATGTAAATAAAAGCCTTGATCATTCTCA CTGCTCGACACCAGTTTCACTTTGTTCT TCATGGCTCTGCCAACCCTCTGACAAATCTC AGTCACGGGACTGTGCTCTCCAGCTTTCCT CCAAGAATTTCTCCACTGCCATTGCCTCCT GTTTTTT | 306 | 1529 A | CAGCTTTC CTCCAAG AGAT | 331 | CAGCUUU CCUCCAAG AGAU | 369 | AUCUCUU GGAGGAA AGCUG | 407 |
| siRNA #16B | | | | | 1529 B | GCCACAG TTTCACTT TGTT | 332 | GCCACAG UUUCACU UGUU | 370 | AACAAAG UGAAACU GUGGC | 408 |
| siRNA #16C | | | | | 1529 C | CTCTGCCA ACCCTCTG AAA | 333 | CUCUGCC AACCCUCU GAAA | 371 | UUUCAGA GGGUUGG CAGAG | 409 |
| siRNA #18A | APOBEC3D-2 | MetaEnhancer_94_- | ATCCCTTGACTTGGGCAGAGCTGAGGTA GACATCTGGGTGTCTGGGAAACCCGG GGAAGGTTCCTTTCTGTCCTGTCACTGTCT GTGTGTGCTTATGTGTCTGTGTGTGT GTCTTTGCCACCAGAGGAGTTGGCCTGT TTGCTCATGACCAGCAGCTGTCGAGGAGCCC ACTGTGTACCACATATGCGGCTCCTGAGG | 307 | 94A | CACTGTCT GTGTGTG CTTA | 334 | CACUGUC UGUGUGU GCUUA | 372 | UAAGCAC ACACAGAC AGUG | 410 |
| siRNA #18B | | | | | 94B | CTGTGTCT TTGCCACC AGA | 335 | CUGUGUC UUUGCCA CCAGA | 373 | UCUGGUG GCAAAGA CACAG | 411 |
| siRNA #23A | CCR1 | MetaEnhancer_258_- | GCCTTTGAAAGTCTCCATCTGCTGTTTTC AGGTCTCCAAGTCCATTCTTTGTGTTTGGA CTGGTGAGTGTTTCTCACACTCTATAATCG CAAAGTAGGAGGTATCTTCAAGAAGA CAAGTGTCATTCAAATATTCTGCATAACA AACCAGACAAAACTTA | 308 | 258A | GAGTGTT TCTCACAC TCTA | 336 | GAGUGUU UCUCACAC UCUA | 374 | UAGAGUG UGAGAAA CACUC | 412 |
| siRNA #23B | | | | | 258B | GGAGGTA TCTCTTCA AGAA | 337 | GGAGGUA UCUCUUC AAGAA | 375 | UUCUUGA AGAGAUA CCUCC | 413 |

TABLE S6-continued siRNAs targeting eRNA of control EP pairs.

| siRNA name | target gene | Items | eRNA region | SEQ ID NO: | siRNA name | siRNA sequence Position | SEQ ID NO: | Sequence (Sense) 5' to 3' | SEQ ID NO: | Sequence (Antisense) 5' to 3' | SEQ ID NO: |
|---|---|---|---|---|---|---|---|---|---|---|---|
| siRNA #26A | DMXL1-2 | MetaEnhancer_454_ | CTATCTCTCTCTTCATGGGTCAGTTTCTAT TTCCCCTGTGTTTCTGTTCATTGTCTTCCT GTGGCTAACTTCTGCTTATAGTTTCTGCTC CCTTTTAACTTCGTGTGCACATGACTTGGA CTTGTTATGGTACTATGCTCTGTGCTGAAA CGTAGCCGGTGAGTAAGGCAGCCCTGACTT CTCAGCTCTGCATAGGACCCACAGTAGGGT AGGGAATAAACACACACCACACACACAC ACACACACAGTTGTGATGTGCTATGA | 309 | 454A | CTCTCTCT TTCATGG GTCA | 338 | CUCUCUC UUUCAUG GUCA | 376 | UGACCCA UGAAAGA GAGAG | 414 |
| siRNA #26B | | | | | 454B | CTGTGTTT CTGTTCAT TGT | 339 | CUGUGUU UCUGUUC AUUGU | 377 | ACAAUGA ACAGAAAC ACAG | 415 |
| siRNA #26C | | | | | 454C | CCCACAG TAGGGTA GGGAA | 340 | CCCACAGU AGGGUAG GGAA | 378 | UUCCCUA CCUACU GUGGG | 416 |
| siRNA #29A | MYCBP 2 | MetaEnhancer_544_ | AGGAACTAGCTAACATAGGTTTTGTTATCT GCTTCGAGTGTGCTCTGTGTGCATCCACAC CCAAGTCCCAGCCCCAAGAGTCTGTGTG GAGCTGTGTGATGGGCTGATGGTACCTCTT ACATGAGGCCTTTTGGGAGATACTGAGAA AGCACTGACTAGGAGTTGAGGCTCCACCC CAGATTAGTCATCATCTGTGT | 310 | 544A | GATGGTA CCTCTTAC ATGA | 341 | GAUGGUA CCUCUUA CAUGA | 379 | UCAUGUA AGAGGUA CCAUC | 417 |
| siRNA #29B | | | | | 544B | TGCTCTGT GTGCATC CACA | 342 | UGCUCUG UGUGCAU CCACA | 380 | UGUGGAU GCACACAG AGCA | 418 |
| siRNA #29C | | | | | 544C | GGGAGAT ACTGAGA AAGCA | 343 | GGGAGAU ACUGAGA AAGCA | 381 | UGCUUUC UCAGUAU CUCCC | 419 |
| siRNA #33 | SOCS1-1 | MetaEnhancer_1477_ | TGTAATTATTTGTTTACTGTAGGCCTCCCC TTTGATGAGGAGCCCCCCTGGGAGTGTCAGG CTCTCGTCTCCCCCAGCACCAGCACAA GGC | 311 | 1477A | GTGTCAG GCTCTCTG CTGT | 344 | GUGUCAG GCUCUCU GCUGU | 382 | ACAGCAG AGAGCCU GACAC | 420 |
| siRNA #A39 | SOCS1-2 | MetaEnhancer_810_ | TTAGTTTCAGTTCTTTGATACTTTTTTGAGA GGCCTGAAGGTCCTTTCCTGATATAGAACT CACGTAAACAAATAAAAGCTTCAAGTTTTA AGACAAGAAGGGTCAATTCTTTGTTTATC CAAAAAACTATCTA | 312 | 810A | GGGTCAA TTTCTTTG TTTA | 345 | GGGUCAA UUUCUUU GUUUA | 383 | UAAACAA AGAAAUU GACCC | 421 |
| siRNA #39B | | | | | 810B | GTCCTTTC CTGATATA GAA | 346 | GUCCUUU CCUGAUA UAGAA | 384 | UUCUAUA UCAGGAA AGGAC | 422 |
| siRNA #39C | | | | | 810C | CAATTTCT TTGTTTAT CCA | 347 | CAAUUUC UUUGUUU AUCCA | 385 | UGGAUAA ACAAAGA AAUUG | 423 |
| siRNA #40A | IFI35 | MetaEnhancer_820_ | CCTACACTGAAAGCCCATGGGGTTGAAGC AGGATTGGTTCACGCTAGAACTTCTGAGA GTCAGTTGTGTATCTTGATAAACAGCAACAG AGCTTAGTCATGAGTTTCCCTGTAACTGGCT GCTCAGAGAGTTTGCTCCCCACCTCTCGGG GAGAACTTACCTGGGAAGAGGCCAATGTTT CTATCTAAGCCTGTCCCGTCCTCTGAGTTT CCAACCCTTCTAATTTCACGTTGGAGTGCC TC | 313 | 820A | CAGTGTG TATCTTGA TAAA | 348 | CAGUGUG UAUCUUG AUAAA | 386 | UUUAUCA AGAUACA CACUG | 424 |
| siRNA #40B | | | | | 820B | GAGTCAG TGTGTATC TTGA | 349 | GAGUCAG UGUGUAU CUUGA | 387 | UCAAGAU ACACACUG ACUC | 425 |

TABLE S6-continued siRNAs targeting eRNA of control EP pairs.

| siRNA name | target gene | Items | eRNA region | SEQ ID NO: | siRNA name | siRNA sequence Position | SEQ ID NO: | Sequence (Sense) 5' to 3' | SEQ ID NO: | Sequence (Antisense) 5' to 3' | SEQ ID NO: |
|---|---|---|---|---|---|---|---|---|---|---|---|
| siRNA #46A | ZBP1 | MetaEnhancer_1228_+ | TGATTACCTCACTCTCATGCAGGGCTGAAT ATTACTGTTTCCCCTGTTAAACAAGGTGT ATTACTTCCGAAATCTGACAACCCCAAGCA CCAAAAGGTTTAAAAATATCTCGAGATTGT AAGCCTCCGACAGAATGCTGAAACAGGA TTGCACAGTTGACCAGGAGCTTCTGAGGTT GTGGCCGACCCTCCATGTTTCTGACTGCCG GACAGTCACAGCCCCCTCTTCCCTAATGCC ACCAGATGTCCCTGGGACACCTGCC | 314 | 1228 A | CCGACAG AATGCTG AAACA | 350 | CCGACAGA AUGCUGA AACA | 388 | UGUUUCA GCAUUCU GUCGG | 426 |
| siRNA #46A | | | | | 1228 B | GGGTGTA TTACTTCC GAAA | 351 | GGGUGUA UUACUUC CGAAA | 389 | UUUCGGA AGUAAUA CACCC | 427 |
| siRNA #46A | | | | | 1228 C | CTCATGCA GGGCTGA ATAT | 352 | CUCAUGC AGGGCUG AAUAU | 390 | AUAUUCA GCCCUGC AUGAG | 428 |

TABLE S7 eRNA and target gene expression fold changes after eRNA KD with siRNA.

| siRNA name | target gene | Enhancer ID | Distance | eRNA expression fold | mRNA expression fold |
|---|---|---|---|---|---|
| #1A siRNA | HLA-DMA | MetaEnhancer_475_+ | 75000 | 0 | 1.423721 |
| #1B siRNA | | | 75000 | 0.540862333 | 0.87843 |
| #2A siRNA | HLA-DRA | MetaEnhancer_157_− | 26000 | 2.163449332 | 1.016281 |
| #2B siRNA | | | 26000 | 0.615600653 | 0.668948 |
| #2C siRNA | | | 26000 | 1.689660424 | 0.366013 |
| #3A siRNA | HLA-DRB5 | MetaEnhancer_157_− | 44000 | 2.163449332 | 0.799221 |
| #3B siRNA | | | 44000 | 0.615600653 | 0.628507 |
| #3C siRNA | | | 44000 | 1.689660424 | 0.268563 |
| #5AsiRNA | TNFSF10-1 | MetaEnhancer_116_+ | 69000 | 0.60149862 | 0.69573 |
| #5BsiRNA | | | 69000 | 0.684600064 | 0.874542 |
| #5CsiRNA | | | 69000 | 0.77916458 | 1.228246 |
| #6A siRNA | ZFAND6 | MetaEnhancer_246_+ | 34000 | 2.518677954 | 0.963707 |
| #6B siRNA | | | 34000 | 0.827405623 | 0.331405 |
| #7AsiRNA | IRF8 | MetaEnhancer_259_+ | 73000 | 0.707106781 | 0.649169 |
| #7BsiRNA | | | 73000 | 1.194687532 | 0.521233 |
| #8AsiRNA | MLLT6 | MetaEnhancer_311_+ | 50000 | 2.795810671 | 0.831238 |
| #8BsiRNA | | | 50000 | 7.193364285 | 2.434007 |
| #9A siRNA | PELI1 | MetaEnhancer_327_+ | 82000 | 1.713096791 | 2.750969 |
| #9B siRNA | | | 82000 | 0.983915733 | 1.018613 |
| #10 siRNA | TLR7-1 | MetaEnhancer_502_+ | 20000 | 0.631417726 | 2.93494473 |
| #11A siRNA | APOBEC3D-1 | MetaEnhancer_600_+ | 65000 | 1.580082624 | 1.701334 |
| #11B siRNA | | | 65000 | 0.763129604 | 1.990779 |
| #12A siRNA | APOBEC3B | MetaEnhancer_600_+ | 26000 | 1.580082624 | 1.239708 |
| #12B siRNA | | | 26000 | 0.381564802 | 0.552227 |
| #13A siRNA | DMXL1-1 | MetaEnhancer_699_+ | 37000 | 0.625320044 | 1.815038 |
| #13B siRNA | | | 37000 | 1.006722921 | 1.624505 |
| #14AsiRNA | ZCCHC2 | MetaEnhancer_804_+ | 15000 | 1.447336117 | 5.27791 |
| #14BsiRNA | | | 15000 | 6.573826285 | 6.276528 |
| #14CsiRNA | | | 15000 | 0 | 4.469045 |
| #16A siRNA | CD2AP | MetaEnhancer_1529_+ | 62000 | 2.417082417 | 1.781797 |
| #16B siRNA | | | 62000 | 0.990777721 | 1.749165 |
| #16C siRNA | | | 62000 | 0.692538733 | 1.280464 |
| #17A siRNA | CD38-1 | MetaEnhancer_1694_+ | 5500 | 0.409896999 | 1.04005993 |
| #17B siRNA | | | 5500 | 3.863745316 | 0.369249 |
| #18A siRNA | APOBEC3D-2 | MetaEnhancer_94_− | 65000 | 0.287114879 | 1.59479 |
| #18B siRNA | | | 65000 | 2.356588726 | 3.2566 |
| #23A siRNA | CCR1 | MetaEnhancer_258_− | 91000 | 2.328929014 | 0.604271 |
| #23B siRNA | | | 91000 | 3.49833068 | 0.759576 |
| #24A siRNA | TLR7-2 | MetaEnhancer_341_− | 22000 | 6.320330495 | 8.186991 |
| #24B siRNA | | | 22000 | 0.761368436 | 1.48795751 |
| #26A siRNA | DMXL1-2 | MetaEnhancer_454_− | 38000 | 0.835087919 | 1.35347352 |
| #26B siRNA | | | 38000 | 3.792283097 | 1.543993 |
| #26C siRNA | | | 38000 | 0 | 4.958831 |
| #28A siRNA | WDFY1 | MetaEnhancer_512_− | 2600 | 0.174742204 | 0.104627 |
| #28B siRNA | | | 2600 | 1.522736872 | 2.075319 |
| #28C siRNA | | | 2600 | 0.540862333 | 0.169184 |
| #29A siRNA | MYCBP2 | MetaEnhancer_544_− | 87000 | 3.023039857 | 0.664328 |
| #29B siRNA | | | 87000 | 4.845458993 | 1.119846 |
| #29C siRNA | | | 87000 | 0.422395587 | 0.084786 |
| #30 siRNA | TNFSF10-2 | MetaEnhancer_734_− | 67000 | 0.835087919 | 0.73373618 |
| #34A siRNA | IFNb1 | MetaEnhancer_1571_+ | 18000 | 0 | 0.502316 |
| #34B siRNA | | | 18000 | 0.410845157 | 0.575678 |
| #35A siRNA | IFI16 | MetaEnhancer_1136_+ | 2300 | 0.23648036 | 0.439317 |
| #35B siRNA | | | 2300 | 0.34268249 | 1.254112 |
| #36A siRNA | PARP14 | MetaEnhancer_2972_− | 18000 | 0.434280777 | 0.993115 |
| #36B siRNA | | | 18000 | 0.720315074 | 1.887792 |
| #36C siRNA | | | 18000 | 0.699001117 | 0.667435 |
| #37A siRNA | CD38-2 | MetaEnhancer_3795_− | 22000 | 1.032923445 | 1.135504 |
| #37B siRNA | | | 22000 | 0.779182582 | 0.562529 |
| #37C siRNA | | | 22000 | 0.240376317 | 0.92445 |
| #38AsiRNA | TNFSF10-3 | MetaEnhancer_2005_+ | 27000 | 0.801069878 | 0.279955 |
| #38BsiRNA | | | 27000 | 0.92873141 | 1.219762 |
| #38CsiRNA | | | 27000 | 0.930879716 | 0.391369 |
| #39A siRNA | SOCS1-2 | MetaEnhancer_810_− | 48400 | 1.587364376 | 2.244872 |
| #39B siRNA | | | 48400 | 1.498272459 | 3.160092 |
| #39C siRNA | | | 48400 | 1.674000548 | 1.286365 |
| #40A siRNA | IFI35 | MetaEnhancer_820_− | 77000 | 0.550952558 | 0.237062 |
| #40B siRNA | | | 77000 | 0.217637641 | 0.390483 |
| #41A siRNA | SAMD9 | MetaEnhancer_3039_+ | 62000 | 0.848664754 | 0.304244 |
| #41B siRNA | | | 62000 | 0.168007786 | 0.281909 |
| #42A siRNA | KIAA0040 | MetaEnhancer_1115_+ | 94000 | 0.187712939 | 0.554426 |
| #42B siRNA | | | 94000 | 0.295917448 | 0.255678 |
| #42C siRNA | | | 94000 | 0.251146313 | 0.425059 |
| #43A siRNA | PARP9 | etaEnhancer_2972_− | 96000 | 0.297982601 | 0.29937 |
| #43B siRNA | | | 96000 | 0.751059963 | 0.40239 |

TABLE S7-continued eRNA and target gene expression fold changes after eRNA KD with siRNA.

| siRNA name | target gene | Enhancer ID | Distance | eRNA expression fold | mRNA expression fold |
|---|---|---|---|---|---|
| #46A siRNA | ZBP1 | MetaEnhancer_1228_+ | 120000 | 0.227930622 | 0.903335 |
| #46B siRNA | | | 120000 | 5.051341805 | 2.065751 |
| #46C siRNA | | | 120000 | 0.082469244 | 0.3423 |
| #47A siRNA | MNDA | MetaEnhancer_1136_+ | 156000 | 0.23981603 | 0.430276 |
| #47B siRNA | | | 156000 | 0.273573425 | 0.733736 |
| #48A siRNA | ACKR1 | MetaEnhancer_1136_+ | 196000 | 0.23981603 | 0.673617 |
| #48B siRNA | | | 196000 | 0.273573425 | 0.842842 |

RT-qPCR. was performed to check the transcription level after siRNA KD for eRNA and promoter RNA. Total RNA extract with Trizol (Invitrogen) was treated with DNaseI (Roche) for 30 min at 37° C. and further extracted with acidic phenol: chloroform and precipitated with salt, glycogen, and pure ethanol. The RNA was reverse-transcribed using ImProm-II™ (Promega) with 100 uM of oligo-dTs or random decamers. The resulting cDNA was incubated with 10 μg of RNaseH and RNase cocktail for 30 min at 37° C. and purified using the PCR purification kit (MACHEREY-NAGEL). 5~10 ng of purified cDNA was quantified by using a FastStart Universal SYBR Green Mater Mix (Roche) on qPCR machine (Realplex2, Eppendorf in Germany). The inventor used GAPDH as the internal control. The primers of GAPDH for RT-qPCR are forward 5'-TGCACCAC-CAACTGCTTAGC-3' (SEQ ID NO: 647) and reverse 5'-GGCATGGACTGTGGTCATGAG-3' (SEQ ID NO: 648). To calculate the relative expression fold change (sample/control), he used the scrambled siRNA transfection as the negative control. The qPCR primers were designed against each siRNA-targeting region of eRNA and promoter and the sequences of primers were listed in Table S8 and Table S9.

TABLE S8 eRNA primers

| target gene | enhancer ID | sequence | SEQ ID NO: | eRNA-Forward primer ID | Forward primer sequence | SEQ ID NO: | eRNA-Reverse primer ID | Reverse primer sequence | SEQ ID NO: |
|---|---|---|---|---|---|---|---|---|---|
| HLA-DMA | MetaEnhancer_475_+ | ACAGTCTACAAAGAGGCCGTGGAAGCTGTCGGGGAAGGAGAATGTTCAAGTAGCACAGGCAATCAAACACTTCCTATTGCTCCAGGTGCCAAAGCAGGAATGAAAACCTGTCCCCTCTGTTGAATACTCTTCTTCTTCACTCCTAAAACTACACACCTGATGTTAGTCGTCAGCCCTCTTCTTATCACTCTACACCTGCTGCTCTGGAGAACTCATCCAGGCCTGTGGCTCCCTGCACGTCTACACTAGTAACCTCTGAATCCACGGTCTCCAGCACTCCCTCCTGCTCCCATCCCCAGGTGGCAGTCAGGT | 429 | eRNA#1A-F | CTTCTTCACTCCTAAAACTACACACC | 460 | eRNA#1A-R | AGAGTGATAAGAAGAGGGCTGA | 521 |
| | | | | eRNA#1B-F | AATGAAAACCTGTCCCCTCTG | 461 | eRNA#1B-R | AGGTGTGTAGTTTTAGGAGTGAAGAA | 522 |
| HLA-DRA5 & DRB5 | MetaEnhancer_157_- | GAATTCAAAGGGTCTCTTCTAGAGGATCCTGGGTTATGTCCTCCACAGGAACTTTGGTGTTGGCCCCTCTTCCTCAAATGTGAGGATGTACCAATGGCCTCCCCATTATCTCCTTTCTTTTTCTTTCTAACTCCAATGTTTATAAAGCCTATATCCCTGTAGTGTATGTAGGTTCTCTGACAGAAGTTATACTTAGTGCTCTGTCTTTCTTATGGGGAAAAATCCCTGGAACTGAAGCTAAGATCTTTAGTACTTGGAGTCACCCTACAGATA | 430 | eRNA#2-3A-F | CTCCCCATTATCTCCTTTCTTTT | 462 | eRNA#2-3A-R | AGGGATATAGGCTTTATAAACATTGG | 523 |
| | | | | eRNA#2-3B-F | GTGTATGTAGGTTCTCTGACAGAAGT | 463 | eRNA#2-3B-R | TTTTTCCCCATAAGAAAGACAGA | 524 |
| | | | | eRNA#2-3C-F | TCCTCCACAGGAACTTTGGT | 464 | eRNA#2-3C-R | GGCCATTGGTACATCCTCAC | 525 |

TABLE S8-continued eRNA primers

| target gene | enhancer ID | sequence | eRNA-Forward primer ID | Forward primer sequence | SEQ ID NO: | eRNA-Reverse primer ID | Reverse primer sequence | SEQ ID NO: |
|---|---|---|---|---|---|---|---|---|
| TNFSF10-1 | MetaEnhancer_116_+ | TAAACCAGGATCTTCTTCAGCCTCCAAGGTAAGGAAATGTGTGATCTCCAAGCTCCCTCTTGTATGTATTGTGAACGCCACTGTCAGAAGAGAAACACCAAAGTTATTCACTGGAAATGTTGCAGTATGAAGACCATGTATTTGATGGAGAGG | 431 | eRNA#5A-F | TTGTATGTATTGTGAACGCCACT | 465 | eRNA#5A-R | CATTTCCAGGTGAATAACTTTGG | 526 |
| | | | | eRNA#5BC-F | AGGATCTTCTTCAGCCTCCA | 466 | eRNA#5BC-R | AATACATACAAGAGGGAGCTTGG | 527 |
| ZFAND6 | MetaEnhancer_246_+ | ATGGTTTGTTTTCCCCTCTCCCTGCTAGAAGCACAAGGGGATTTTTCTCTGATAATCATTGTGAGAACCTGTTAGAACTCCTGGAGGTAAAACTCAAAGTATGGCGGCCCCCCTGAATGAGTCTTCCTGGAATTAACTGTCAAACTTGCCACTCTGAGTCTCCAGCAATTCTTGAATTACAATTCAGATTTTCCTATCCTGGTACAGGTTCCTGT | 432 | eRNA#6A-F | TCTTCCTGGAATTAACTGTCAAA | 467 | eRNA#6A-R | TGTAATTCAAGAATTGCTGGAGAC | 528 |
| | | | | eRNA#6B-F | GGGATTTTTCTCTGATAATCATTGT | 468 | eRNA#6B-R | TTGAGTTTTACCTCCAGGAGTTCT | 529 |
| IRF8 | MetaEnhancer_259_+ | GGCTCAGGCTGAGAGGATATTCTGCCGTTGTAGTTTTGTCGGGGCCATTCGTTTTAAGAAGACTGGAGAGTCAGTTCCAGTTTGTCTTGGGGACTAAGTTCTTATCATGTGGTTTCTACTGGTGGCTTATTGAGAACACATGCAGGTACAG | 433 | eRNA#7A-F | TGAGAGGATATTCTGCCGTTG | 469 | eRNA#7A-R | GAACTGACTCTCCAGTCTTCTTAAA | 530 |
| | | | | eRNA#7B-F | TGGGGGACTAAGTTCTTATCATGT | 470 | eRNA#7B-R | CCTGCATGTGTTCTCAATAAGC | 531 |
| MLLT6 | MetaEnhancer_311_+ | CCCAGCCCTCAGTGGCCCCACAGCAGCTTGGCTGTTCTTGGTTTTGTTTCTCTCTGCTTCTGCATGATATCTTTGAACAAAAGTCCCAAGTGTACAAAAAGTCCCGAAAGGCGTTCGCAAACCACTGACCTAGATGGAGGGAATTGTGAGGAGCAGAGGGCACCCTCTTATAAAATGCCTGTACTTCGGTGCAGGGTTTGGTGGTGTCGGCGGTTTGGAGGCCCTTTAAGCTTCCTAACTCCTTGTCACTGGTGGATGGTGGGTGCCGGCAGGAGGGCATCCCTTTACATAGGGGCTCATTG | 434 | eRNA#8A-F | TGGCTGTTCTTGGTTTTGTTT | 471 | eRNA#8A-R | CGGGACTTTTTGTACACTTGG | 532 |
| | | | | eRNA#8B-F | ACTCCTTGTCACTGGTGGATG | 472 | eRNA#8B-R | GCCCCTATGTAAAGGGATGC | 533 |
| PELI1 | MetaEnhancer_327_+ | TACCAATGTCTCTGGCCTTGCTCTACTAGTACAACAGAGGAGAGAGAATTCTAGAAGATTTTCAACTCCCCTCCTGCTCTGTAACTCTGGTTCGCTATGTGCTAAATGCACCTTGAAATAAACACTTCCTTTGTGTGTGTGTGTTGCGCGGTGGAATCCTCACTTTACAGAAGAGGA | 435 | eRNA#9A-F | TTTTCAACTCCCCTCCTGCT | 473 | eRNA#9A-R | TTTCAAGGTGCATTTAGCACA | 534 |
| | | | | eRNA#9B-F | TCTCTGGGCCTTGCTCTACT | 474 | eRNA#9B-R | GCAGGAGGGGAGTTGAAAAT | 535 |
| TLR7-1 | MetaEnhancer_502_+ | GGGGAATGAGAAACAAAAGACAAGGTTAATTATGACACCGGGGCTTTACAATGCTAAAAATATCCTATATACAAAGGGAT | 436 | eRNA#10-F | AGGCTGTGTTCTTTTTCCATGT | 475 | eRNA#10-R | AGAAATTTGCAGATACCTTGAGC | 536 |

TABLE S8-continued

| | | | eRNA | | | | |
|---|---|---|---|---|---|---|---|
| target gene | enhancer ID | sequence | eRNA-Forward primer ID | Forward primer sequence | SEQ ID NO: | eRNA-Reverse primer ID | Reverse primer sequence | SEQ ID NO: |

| target gene | enhancer ID | sequence | eRNA-Forward primer ID | Forward primer sequence | SEQ ID NO: | eRNA-Reverse primer ID | Reverse primer sequence | SEQ ID NO: |
|---|---|---|---|---|---|---|---|---|
| | | ATGTAGGCTGTGTTCT TTTTCCATGTCATTAC AAAGAACAGGCTCAAG GTATCTGCAAATTTCT AATAAAAATATTATTA CTTGAAAAATG | | | | | | |
| APOB EC3D-1 & APOB EC3B | MetaEnhancer_ 600_+ | CACTTGCTTCTAGGCT GAGGAGGGCGGGGCTG TTGTCAGAGCCCAGAA TCAAAGCCAGAGGAGC AGGTGGACGCTGAGAC TGTCCCCTCACCCTGC TCCACGGGCAATGTTG AAGTGGGCATCTGGGT GTGT | 437 | eRNA#1 1-12A-F eRNA#1 1-12B-F | CACTTGCTTCTAGG CTGAGGA AGGTGGACGCTGA GACTGT | 476 477 | eRNA#1 1-12A-R eRNA#1 1-12B-R | TCCTCTGGCTTTGA TTCTGG CCAGATGCCCACTT CAACAT | 537 538 |
| DMXL 1-1 | MetaEnhancer _699_* | ACCATGACTCACCCTC TTTCCTCGTCACCTGC TAGTCCTCCCATTCAC TCCCCTTCAGTCATAT TGGCCTTGCTTCTCTT CAGACGGGCCAGCCAC ACTCAGGGCCTTTGCA CTGACTATTCCTTCTG CCTGGAATGTTCCTCC TCCAAGTATCCATATG GCTAACTCCCTCAATT CTTTGAGATCTTTAAC CACAAGGCGCTTTCCC AAATAAGTCTTCTCTG GCTACCCTTTTAAAA TTTTAACCCCCACCCT TCACATTTTATATACT CCCCTTCCTTGCCTTT TTTCAGCTTCTTGTC | 438 | eRNA#1 3A-F eRNA#1 3B-F | CTGGAATGTTCCTC CTCCAA ACCCTCTTTCCTCG TCACCT | 478 479 | eRNA#1 3A-R eRNA#1 3B-R | AAGCGCCTTGTGG TTAAAGA GCAAGGCCAATAT GACTGAA | 539 540 |
| ZCCHC 2 | MetaEnhancer_ 804_+ | CAATCGCTGCCTGAGT ACCTATGTGTTCGTGG CTTGATTTACCTTATC TGTAATTCCTGGATGT TAAAAGGACACCAAAA ATCTCTGACACCCTG ATTAGCCTACCTTGAA GAACCCAAGCCCAGGA TTTTCTGCCTTTGCCT AGAAAAAGGACTGATT CAGAACTTCCTGAGCT ACCTAGTATT | 439 | eRNA#1 4A-F eRNA#1 4B-F eRNA#1 4C-F | CCTATGTGTTCGTG GCTTGA AAGAACCCAAGCC CAGGAT AAGGACACCAAAA ATCTCTGACA | 480 481 482 | eRNA#1 4A-R eRNA#1 4 B-R eRNA#1 4C-R | TTTGGTGTCCTTTT AACATCCA GCTCAGGAAGTTC TGAATCAGTC ATCCTGGGCTTGG GTTCTT | 541 542 543 |
| CD38 | MetaEnhancer_ 1694_ | GTCCACTTTTAGGAGT GTATGTACTTGGACAC CTAAAAAATATGCTG CCACAAGAACATTTGT TGTAGCATTCTGTGCT CATTTATACAGGTCTA GTTAAGTAAACTCTAG CATACTA | 440 | eRNA#1 7A-F eRNA#1 7B-F | GTAGCATTCTGTGC TCATTTATAC CCACTTTTAGGAGT GTATGTACTTGG | 483 484 | eRNA#1 7A-R eRNA#1 7B-R | TAAATGAGCACAG AATGC CAAATGTTCTTGTG GCAGCA | 544 545 |
| APOB EC3D-2 | MetaEnhancer_ 94_- | ATCCTCTGACTTGGGG CAGAGCTGAGGTAGAC ATCTGGGTGTGTCTGG GAAACCCCGGGGAAGG TTCCTTTCTGTCCTGT CACTGTCTGTGTGTGC TTATGTGTCTGTGTGT GTCTGTGTCTTTGCCA CCAGAAGGAGTTGGGC CTGTTTGCTCATGAGC ACTGTCGAGGAGGCCC ACTGTGTCCACATATG CGGCTCCTGAGG | 441 | eRNA#1 8A-F eRNA#1 8B-F | ATCTGGGTGTGTC TGGGAAA ATGAGCAGCTGTC GAGGAG | 485 486 | eRNA#1 8A-R eRNA#1 8B-R | GCACACACAGACA GTGACAGG ACACAGACAGTGC CTCAGGA | 546 547 |

TABLE S8-continued eRNA primers

| target gene | enhancer ID | sequence | eRNA-SEQ ID NO: | Forward primer ID | Forward primer sequence | SEQ ID NO: | eRNA-Reverse primer ID | Reverse primer sequence | SEQ ID NO: |
|---|---|---|---|---|---|---|---|---|---|
| CCR1 | MetaEnhancer_258_- | GCCTTTGAAAGTCTCGCATCTGCTGTTTTCAGGTCTCCAAGTCCATTCTTTGTGTTTGGACTGGTGAGTGTTTCTCACACTCTATAATCGCAAAGTAGGGAGGTATCTCTTCAAGAAGACAAGTGTCATTCAAATATTTCTGCATAACAAACCAGTACAAAACTTA | 442 | eRNA#23A-F | TCCATTCTTTGTGTTTGGACTG | 487 | eRNA#23A-R | TGCGATTATAGAGTGTGAGAAACA | 548 |
|  |  |  |  | eRNA#23B-F | CGCAAAGTAGGGAGGTATCTCTT | 488 | eRNA#23B-R | TGCAGAAATATTTGAATGACACTTG | 549 |
| TLR7-2 | MetaEnhancer_341_- | AGACTATTTATGCATGCATTGGTCTTTGAGCTGTTCCGCCTGCTGTCTTGTAAACTCAGAAGCAGTTTTCCTGAGGTGGGTATTACTGACCATCTAGCTCACCATCTGAGACTCATAAGTAGATTTGTGAGTGGTGAGGTGTAGTGAAGACCACTTGTTTGGGATTAACATACATGGCCAGCCAATGAAAATGTTAACTCACATCTGCATATGCCTTCATCTTGTTATGAACTGGAGGCACCATCATTCATAATGCTTAAAAATAAAACACCTGCA | 443 | eRNA#24A-F | TATGGAACTGGAGGCACCAT | 489 | eRNA#24A-R | TGCAGGTGTTTTATTTTTAAGCA | 550 |
|  |  |  |  | eRNA#24B-F | TGACCATCTAGCTCACCATCTG | 490 | eRNA#24B-R | TCCCAAACAAGTGTCTTCA | 551 |
| DMXL1-2 | MetaEnhancer_454_- | CTATCTCTCTCTTTCATGGGTCAGTTTCTATTTCCCTCTGTGTTTCTGTTCATTGTCTTCCTGGTGGCTAACTTCTGCTTATAGTTTCTGCTCCCTTTTAACTTCTGTGTGCACATGACTTGGACTTGTTATGGTACTATGCTCTGTGCTGGAAACGTAGCGGTGAGTAAGGCAGCCCTGACTTCTCAGCTCTGCATAGGACCCACAGTAGGGTAGGGAATAAACACACACACACACACACACACACACAGTTGTGATGTGCTATGA | 444 | eRNA#26AB-F | TCTCTCTTTCATGGGTCAGTTTC | 491 | eRNA#26AB-R | GCAGAAGTTAGCCACCAGGA | 552 |
|  |  |  |  | eRNA#26C-F | CAGCCCTGACTTCTCAGCTC | 492 | eRNA#26C-R | CAACTGTGTGTGTGTGTGTG | 553 |
| WDFY1 | MetaEnhancer_512_- | GTTAGGTTACATATCAAGTTAGGTTCACTGTGTACTGAAAAACCTTTAGGCCAAAATTAAAATATGTACAACGGAGGCTTTAGTCCAAACTTAATTTAACAGTACTACAATTAAGTATCAGTATTGCCATAATTGTATCAGTCAGGGT | 445 | eRNA#28A-F | GGCCAAAATTAAAATATGTACAACG | 493 | eRNA#28A-R | ACTGTTAAATTAAGTTTGGACTAAAGC | 554 |
|  |  |  |  | eRNA#28B-F | CAACGGAGGCTTTAGTCCAA | 494 | eRNA#28B-R | GACTGATACAATTATGGCAATACTGA | 555 |
|  |  |  |  | eRNA#28C-F | GGTTACATATCAAGTTAGGTTCACTG | 495 | eRNA#28C-R | TTTTGGCCTAAAGGTTTTTA | 556 |
| MYCBP2 | MetaEnhancer_544_- | AGGAACTAGCTAACATAGGTTTTGTTATCTGCTTCGAGTGTGCTCTGTGTGCATCCACACCCAAGTCCCAGGCCCCAAGAGTCTGTGTGGAGCTGTGTGATGGCTGATGGTACCTCTTACATGAGGCCTTTTGGGAGATACTGAGAAAGCACTGGACTA | 446 | eRNA#29A-F | CTGTGTGGAGCTGTGTGATG | 496 | eRNA#29A-R | CTCCCAAAAGGCCTCATGTA | 557 |
|  |  |  |  | eRNA#29B-F | CTGCTTCGAGTGTGCTCTGT | 497 | eRNA#29B-R | TCACACAGCTCCACACAGACT | 558 |
|  |  |  |  | eRNA#29C-F | GGCCTTTTGGGAGATACTGA | 498 | eRNA#29C-R | GGTTGGAGCCTCAACTCCTA | 559 |

TABLE S8-continued eRNA primers

| target gene | enhancer ID | sequence | eRNA-Forward primer ID | Forward primer sequence | SEQ ID NO: | eRNA-Reverse primer ID | Reverse primer sequence | SEQ ID NO: |
|---|---|---|---|---|---|---|---|---|
| | | GGAGTTGAGGCTCCAA CCCCAGATTAGCATCA TCTGTGTGT | | | | | | |
| TNFSF10-2 | MetaEnhancer_734_- | GCTTGGACCCACAGTA CAGATCACCCATCTTG GCCTATCACACTGAG CAATTGCTGACCTGCA TCTCTGTGGAGTGGAG CCCCCAGGAGACAAGT AAAAGACCCCCAGCCA CAAC | 447 | eRNA#30-F | CCATCTTGGGCCTA TCACAC | 499 | eRNA#30-R | CTCCACAGAGATG CAGGTCA | 560 |
| IFNb1 | MetaEnhancer_1571_ | TTCTTCTGGCTGCCTG GAAGATGCCTCTGTTA TTTTAGTGAAAACATT TAGCTCCTCGAAAGGT AGAGAGAACCAAGAGG TAAAGTGTGCCATTGT AGACAGCTGGTGTGTG TGCCAGGTAGCAGTGC TTCTGTCTACATCCTG GGATATT | 448 | eRNA#34A-F<br>eRNA#34B-F | TTTAGCTCCTCGAA AGGTAGAGA<br>GCCTGGAAGATGC CTCTGTT | 500<br>501 | eRNA#34A-R<br>eRNAB#48-R | TTTAGCTCCTCGAA AGGTAGAGA<br>CTACCTGGCACAC ACACCAG | 561<br>562 |
| IFI16 | MetaEnhancer_1136_ | TTTCTGCTATCTAGAT CTTTGACTACCAACCA GCCAGGAGTGGTCTGC CTCTTCTTTGGTCTGA GCTTGCCTTGTGCTTA TATTGTTGTACCCAAG CGAGT | 449 | eRNA#35-F | CTGCTATCTAGATC TTTG | 502 | eRNA#35-R | CTCGCTTGGGTAC AACAAT | 563 |
| PARP14 | MetaEnhancer_2972_- | CGCGACCGTTCCATTC TTGAGTTTCTTCACTT TGCCAGCTTGGGTGTC TCTCCCGAGGCCGTCG TTCTAGTTATGGCTCA TCCAGCTGACGCTGC AACTTCTCTTGTTCTG TAGCATTTCTTCTACT TCTCTTTCTCTACCAG CTGTGTCAACCGGCT | 450 | eRNA#36AB-F<br>eRNA#36C-F | CGACCGTTCCATTC TTGAGT<br>CGACCGTTCCATTC TTGAGT | 503<br>504 | eRNA#36AB-R<br>eRNA#36C-R | AGAGAAGTTGCAG CGTCAGC<br>AGAGAAGTTGCAG CGTCAGC | 564<br>565 |
| CD38 | MetaEnhancer_3795_- | CACATCTCACCCCCAG ACCTGCCATTGGCATG CACATCTTTAACCACA AACCACGATTGAAAAT GAGAAAGAAAACTCTC CTCTAGCTGGGCGC TTCATAGGACTAGCCA GGTACGACCATCTCTG AGGGTCTTTGACAGCT CAGTTTTACTGCATAA TCTGTTTTCAAGACCC TTTAAAAGACCAGAT | 451 | eRNA#37A-F<br>eRNA#37BC-F | TGGGCGCTTCATA GGACT<br>ACATCTCACCCCCA GACCT | 505<br>506 | eRNA#37A-R<br>eRNA#37BC-R | TCTGGTCTTTTAAA GGGTCTTGA<br>CTATGAAGCGCCC AGCTAGA | 566<br>567 |
| TNFSF10-3 | MetaEnhancer_2005_ | CATAACTACCAGAAGC CATTGGTGGCAAGATC TCAATCAGGACATGTC GGTACAATGCTCTGAT TATCTCGTCTGCATCC CTGATTACTTATGGTC CAGATATAAACTACT | 452 | eRNA#38AB-F<br>eRNA#38C-F | TGGTGGCAAGATC TCAATCA<br>CGGTACAATGCTCT GATTATCTCG | 507<br>508 | eRNA#38AB-R<br>eRNA#38C-R | TCAGGGATGCAGA CGAGATA<br>GGACCATAAGTAA TCAGGGATGC | 568<br>569 |
| SOCS1 | MetaEnhancer_810_- | TTAGTTTCAGTT CTTTGATACTTT TTTGAGAGGCCT GAAGGTCCTTTC CTGATATAGAAC TCACGTAAACAA ATAAAAGCTTCA AGTTTTAAGACA AGAAGGGTCAAT | 453 | eRNA#39AC-F<br>eRNA#39B-F | TCACGTAAACAAA TAAAAGCTTCA<br>TTTTTGAGAGGCCT GAAGGT | 509<br>510 | eRNA#39AC-R<br>eRNA#39B-R | CAAAGAAATTGAC CCTTCTTGTC<br>TGAAGCTTTTATTT GTTTACGTGAG | 570<br>571 |

TABLE S8-continued

| | | | eRNA | | | eRNA | | |
| | | | SEQ | Forward | | Reverse | | |
| target | | | ID | primer | Forward primer | SEQ ID | primer | Reverse primer | SEQ ID |
| gene | enhancer ID | sequence | NO: | ID | sequence | NO: | ID | sequence | NO: |
|---|---|---|---|---|---|---|---|---|---|
| | | TTCTTTGTTTAT CCAAAAAACTAT CTA | | | | | | | |
| IFI35 | MetaEnhancer_ 820_- | CCTACACTGAAAG CCCATGGGGTTGA AGCAGGATTTGGT TCACGCTAGAACT TCTGAGAGTCAGT GTGTATCTTGATA AACAGCAACAGAG CTTAGTCATGAGT TCCCTGTAACTGG CTGCTCAGAGAGT TTGCTCCCCACCT CCTGGGGAGAACT TACCTGGGAAGAG GCCAATGTTTCTA TCTAAGCCTGTCC CGTCCTCTGAGTT TCCAACCTTCTAA TTTCACGTTGGG AGTGCCTC | 454 | eRNA#4 0-F | ATGGGGTTGAAGC AGGATTT | 511 | eRNA#4 0-R | CAGCCAGTTACAG GGAACTCA | 572 |
| SAMD 9 | MetaEnhancer_ 3039_ | GTCCTTAAGGCTG ATGTGAATCTCTG CCCTTTCCAATGT GTCATGTGATTGC TCCAAATTAAAAC ACCTATTATTATT ATTTTG | 455 | eRNA#4 1-F | AAGGCTGATGTGA ATCTCTGC | 512 | eRNA#4 1-R | TGGAGCAATCACA TGACACA | 573 |
| KIAA0 40 | MetaEnhancer_ 1115_ | CACCTCACTTCTG TTTTCTGTCCATT AATGCTTCCTGCC CACGTTGTGGGGA GGAGCTCTCTGAA CCTCTGCTGCTTC TGAGGGATTCAAG AATATATTT | 456 | eRNA#4 2A-F eRNA#4 2BC-F | TCTGCTGCTTCTGA GGGATT CCACGTTGTGGGG AGGAG | 513 514 | eRNA#4 2A-R eRNA#4 2BC-R | GATTTAGGAGTTT AATTGAGCAAAAA GAATCCCTCAGAA GCAGCAG | 574 575 |
| PARP9 | MetaEnhancer_ 2972_- | ACTTCCTGTCCGC GACCGTTCCATTC TTGAGTTTCTTCA CTTTGCCAGCTTG GGTGTCTCTCCCG AGGCCGTCGTTCT AGTTATGGCTCAT CCAGCTGACGCTG CAACTTCTCTTGT TCTGTAGCATTTC TTCTACTTCTCTT TCTCTACCAGCTG TGTCAACCGGCT TTG | 457 | eRNA#4 3A-F eRNA#4 3B-F | GGCCGTCGTTCTA GTTATGG CGACCGTTCCATTC TTGAGT | 515 516 | eRNA#4 3A-R eRNA#4 3B-R | CCGGTTGACACAG CTGGTAG TCAGCTGGATGAG CCATAACT | 576 577 |
| ZBP1 | MetaEnhancer_ 1228_ | TGATTACCTCAC TCTCATGCAGGG CTGAATATTACT GTTTCCCTGTT AAACAAGGGTGT ATTACTTCCGAA ATCTGACAACCC CAAGCACCAAAA GGTTTAAAAATA TCTCGAGATTGT AAAGCCTCCGAC AGAATGCTGAAA CAGGATTGCACA GTTGACCAGGAG CTTCTGAGGTTG TGGCGGACCCTC CATGTTTCTGAC | 458 | eRNA#4 6A-F eRNA#4 68C-F | ACCAAAAGGTTTA AAAATATCTCG CACTCTCATGCAG GGCTGA | 517 518 | eRNA#4 6A-R eRNA#4 6BC-R | ACCTCAGAAGCTC CTGGTCA GTGCTTGGGGTTG TCAGATT | 578 579 |

TABLE S8-continued eRNA primers

| target gene | enhancer ID | sequence | eRNA-SEQ ID NO: | Forward primer ID | Forward primer sequence | SEQ ID NO: | eRNA-Reverse primer ID | Reverse primer sequence | SEQ ID NO: |
|---|---|---|---|---|---|---|---|---|---|
| | | TGCCGGACAGTCACAGCCCCTCTTCCCTAATGCCACCAGATGTTCCCTGGGACACCTGCC | | | | | | | |
| MNDA & ACKR1 | MetaEnhancer_1136_ | TTTCTGCTATCTAGATCTTGACTACCAACCAGCCAGGAGTGGTCTGCCTCTTCTTTGGTCTGAGCTTGCCTTGTGCTTATATTGTTGTACCCAAGCGAGT | 459 | eRNA#47-48A-F | CAGGAGTGGTCTGCaCTTC | 519 | eRNA#47-48A-R | ACTCGCTTGGGTACAACAAT | 580 |
| | | | | eRNA#47-48B-F | TGCTATCTAGATCTTGACTACCAACC | 520 | eRNA#47-48B-R | GAAGAGGCAGACCACTCCTG | 581 |

TABLE S9 mRNA primers

| Gene name | Forward primer | SEQ ID NO: | Reverse primer | SEQ ID NO: |
|---|---|---|---|---|
| HLA-DMA | GATCTAAGGCCACCCTCTCG | 582 | GCAGCTCCTTGGTTCTGTTC | 613 |
| HLA-DRA | TCCCGAGCTCTACTGACTCC | 583 | TGATAGCCCATGATTCCTGA | 614 |
| HLA-DRB5 | CCAGCATGGTGTGTCTGAAG | 584 | AGCCAGTGGGGAGCTCAG | 615 |
| TNFSF10 | AAGGAAGGGCTTCAGTGACC | 585 | GACTGCAGGAGCACTGTGAA | 616 |
| ZFAND6 | CCAATCCAGTGGCTCTCCT | 586 | CCTCCGTCCGCTGTTTATTA | 617 |
| IRF8 | TCGACACCAGCCAGTTCTTC | 587 | CTCTTCCCAGCCTCTTCTGC | 618 |
| MLLT6 | AGCTCATGGGAGTATGAAGGA | 588 | AGTAGACCAGCGGGTTCTCG | 619 |
| PELI1 | CCCTCCTTGCGAGTGTATGT | 589 | CCGCTGCTGCTAGTGGAG | 620 |
| TLR7 | TCCCATCAGAGGCTCATGGA | 590 | ATGATTGTCTGTGGCCAGGG | 621 |
| APOBEC3D | AACTTGGCTCACTGCAACCT | 591 | GAGTTCGAGACCAGCCTGAC | 622 |
| APOBEC3B | TGCTGGGACACCTTTGTGTA | 592 | CCATCCTTCAGTTTCCCTGA | 623 |
| DMXL1 | GTGTCCGTTGCAGGACTAGG | 593 | CCACGGAGAAGCAGTGGT | 624 |
| ZCCHC2 | CCTGAGGGAACACTTGGAGA | 594 | AACTTGCACGGCTCTACCTC | 625 |
| CD2AP | GCGCTGAAGAGACTGGTAGG | 595 | GCTCCTCCTCCTCCTCCTC | 626 |
| CD38 | GGGAGGTCAGTTTCAGAAC | 596 | CGAGGATCAGGACCAGGATA | 627 |
| CCR1 | CATCTCCAACCAAGGACCCC | 597 | CACACAGTGGGCACATTTTGT | 628 |
| SEMA4D | AACACTCACCGTGAAGGTCTG | 598 | CGTCTGGAGTCTGTCCCTTC | 629 |
| WDFY1 | GGCCGAAATCCACTCCAG | 599 | CTCCTTGGGGATGAGCAG | 630 |
| MYC8P2 | GAAGGAGGTCGCTGTCTTTG | 600 | ACACACAGCCCTTTTCCAAC | 631 |
| SOCS1 | CTGGAGCACTACGTGGCG | 601 | AGGGGAAGGAGCTCAGGTAG | 632 |
| IFNB1 | TCTCCTAGCCTGTGCCTCTG | 602 | GCCATCAGTCACTTAAACAGCA | 633 |
| IFI16 | GAATAGGAGCAAGCCAGCAC | 603 | AAGTTCCCAGAAACGGAACC | 634 |

TABLE S9-continued mRNA primers

| Gene name | Forward primer | SEQ ID NO: | Reverse primer | SEQ ID NO: |
|---|---|---|---|---|
| PARP14 | TACTTCCAGAGCCCGAAGAG | 604 | CGGGTAGAAGAACACCAGGA | 635 |
| CD38 | GGGAGGTGCAGTTTCAGAAC | 605 | CGAGGATCAGGACCAGGATA | 636 |
| IFI35 | AGGGATTTCACGGAAATGAA | 606 | AAGGGCTGTGGTCTCTCTCA | 637 |
| SAMD9 | CCGTTAAAACCAGAATGAGGA | 607 | TGTGGGGAAAACCATCTCTT | 638 |
| KIAA0040 | TTCAGGAAGTTGTGCCTGTG | 608 | TGTGTTCCCTGCCTTCCTAC | 639 |
| PARP9 | CTGCCCTTTCACTGAACTCC | 609 | CGAAGGAAGCTGGAGAGCTA | 640 |
| ZBP1 | GCATCTATTTCCGGGCTGTA | 610 | CTGCAAGGAGTCGGAGAGAC | 641 |
| MNDA | TGGCTCTAACAAGTGCCATT | 611 | CACTGTCCGTAAAGCTTTGGA | 642 |
| ACKR1 | CTGTCCCATTGTCCCCTAGA | 612 | CTGTCGAGGCTGCATAATGA | 643 |

Apoptosis assay. To evaluate the cell viability, the inventor performed Western-Blot with cleaved caspase-3 antibody (Cell Signaling technology, #9661) and Annexin-V apoptosis detection flow cytometry assay as described (Goodwin et al., 2017). Virus was infected at 36 hours after siRNA transfection as described in previous method section (targeting TNFSF10 eRNAs and IFNB1 eRNA, L2), and cells (300,000 per well) were harvested at 24 hours, 72 hours, and 96 hours after virus infection with cold PBS wash. For the negative control experiment, 5 uM of TIC10 (SML1068, Sigma-Aldrich) was treated for 48 hrs to activate the apoptosis pathway by inducing the level of TNFSF10 expression.

Western blot. In order to extract protein from each well, 40 ul of RIPA buffer with freshly made proteinase inhibitor cocktail (Roche) was added to cell pellet. 12% SDS gel was run for 1 hour with constant voltage (120V), followed by transfer to a membrane (Immun-Blot PVDF membrane sandwiches, BioRad) with constant 0.1 A for 45 min. The size of cleaved caspase-3 is 17-19 kDa. β-Actin (45 kDa) was used as an internal standard.

Flow cytometry. Cell death was measured using the PE Annexin-V Apoptosis Detection Kit I (BD Pharmingen) according to the manufacturer's instruction. Cells were collected and stained with annexin-V and 7-AAD and analyzed by flow cytometry (SH800, Sony) and FlowJo software.

Data accession. Time-course GRO-seq and ChIP-seq data have been uploaded to the Array Express (world-wide-web at ebi.ac.uk/arrayexpress/) with the accession numbers E-MTAB-6047 and E-MTAB-6050, respectively.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

F. REFERENCES

The following references, to the extent that they provide exemplary procedural or other details supplementary to those set forth herein, are specifically incorporated herein by reference.

Andersson, R., Gebhard, C., Miguel-Escalada, I., Hoof, I., Bornholdt, J., Boyd, M., Chen, Y., Zhao, X., Schmidl, C., Suzuki, T., et al. (2014). An atlas of active enhancers across human cell types and tissues. Nature 507, 455-461.

Banerjee, A. R., Kim, Y. J., and Kim, T. H. (2014). A novel virus-inducible enhancer of the interferon-beta gene with tightly linked promoter and enhancer activities. Nucleic Acids Res 42, 12537-12554.

Bradner, J. E., Hnisz, D., and Young, R. A. (2017). Transcriptional Addiction in Cancer. Cell 168, 629-643.

Cao, Q., Anyansi, C., Hu, X., Xu, L., Xiong, L., Tang, W., Mok, M. T. S., Cheng, C., Fan, X., Gerstein, M., et al. (2017). Reconstruction of enhancer-target networks in 935 samples of human primary cells, tissues and cell lines. Nat Genet 49, 1428-1436.

Consortium, E. P., Birney, E., Stamatoyannopoulos, J. A., Dutta, A., Guigó, R., Gingeras, T. R., Margulies, E. H., Weng, Z., Snyder, M., Dermitzakis, E. T., et al. (2007). Identification and analysis of functional elements in 1% of the human genome by the ENCODE pilot project. Nature 447, 799-816.

Core, L. J., Waterfall, J. J., and Lis, J. T. (2008). Nascent RNA sequencing reveals widespread pausing and divergent initiation at human promoters. Science 322, 1845-1848.

Decque, A., Joffre, O., Magalhaes, J. G., Cossec, J. C., Blecher-Gonen, R., Lapaquette, P., Silvin, A., Manel, N., Joubert, P. E., Seeler, J. S., et al. (2016). Sumoylation coordinates the repression of inflammatory and anti-viral gene-expression programs during innate sensing. Nat Immunol 17, 140-149.

Engreitz, J. M., Haines, J. E., Perez, E. M., Munson, G., Chen, J., Kane, M., McDonel, P. E., Guttman, M., and Lander, E. S. (2016). Local regulation of gene expression by lncRNA promoters, transcription and splicing. Nature 539, 452-455.

Ernst, J., and Kellis, M. (2010). Discovery and characterization of chromatin states for systematic annotation of the human genome. Nat Biotechnol 28, 817-825.

Goodwin, J., Neugent, M. L., Lee, S. Y., Choe, J. H., Choi, H., Jenkins, D. M. R., Ruthenborg, R. J., Robinson, M. W., Jeong, J. Y., Wake, M., et al. (2017). The distinct metabolic phenotype of lung squamous cell carcinoma defines selective vulnerability to glycolytic inhibition. Nat Commun 8, 15503.

Hah, N., Murakami, S., Nagari, A., Danko, C. G., and Kraus, W. L. (2013). Enhancer transcripts mark active estrogen receptor binding sites. Genome Res 23, 1210-1223.

Heintzman, N. D., Hon, G. C., Hawkins, R. D., Kheradpour, P., Stark, A., Harp, L. F., Ye, Z., Lee, L. K., Stuart, R. K., Ching, C. W., et al. (2009). Histone modifications at human enhancers reflect global cell-type-specific gene expression. Nature 459, 108-112.

Heintzman, N. D., Stuart, R. K., Hon, G., Fu, Y., Ching, C. W., Hawkins, R. D., Barrera, L. O., Van Calcar, S., Qu, C., Ching, K. A., et al. (2007). Distinct and predictive chromatin signatures of transcriptional promoters and enhancers in the human genome. Nat Genet 39, 311-318.

Heinz, S., Benner, C., Spann, N., Bertolino, E., Lin, Y. C., Laslo, P., Cheng, J. X., Murre, C., Singh, H., and Glass, C. K. (2010). Simple combinations of lineage-determining transcription factors prime cis-regulatory elements required for macrophage and B cell identities. Mol Cell 38, 576-589.

Heinz, S., Romanoski, C. E., Benner, C., and Glass, C. K. (2015). The selection and function of cell type-specific enhancers. Nat Rev Mol Cell Biol 16, 144-154.

Hnisz, D., Shrinivas, K., Young, R. A., Chakraborty, A. K., and Sharp, P. A. (2017). A Phase Separation Model for Transcriptional Control. Cell 169, 13-23.

Hogner, K., Wolff, T., Pleschka, S., Plog, S., Gruber, A. D., Kalinke, U., Walmrath, H. D., Bodner, J., Gattenlohner, S., Lewe-Schlosser, P., et al. (2013). Macrophage-expressed IFN-beta contributes to apoptotic alveolar epithelial cell injury in severe influenza virus pneumonia. PLoS pathogens 9, e1003188.

Huang da, W., Sherman, B. T., and Lempicki, R. A. (2009a). Bioinformatics enrichment tools: paths toward the comprehensive functional analysis of large gene lists. Nucleic Acids Res 37, 1-13.

Huang da, W., Sherman, B. T., and Lempicki, R. A. (2009b). Systematic and integrative analysis of large gene lists using DAVID bioinformatics resources. Nat Protoc 4, 44-57.

Jacob, N. T., Lockner, J. W., Kravchenko, V. V., and Janda, K. D. (2014). Pharmacophore reassignment for induction of the immunosurveillance cytokine TRAIL. Angewandte Chemie 53, 6628-6631.

Jamieson, A. R., Giger, M. L., Drukker, K., Li, H., Yuan, Y., and Bhooshan, N. (2010). Exploring nonlinear feature space dimension reduction and data representation in breast Cadx with Laplacian eigenmaps and t-SNE. Medical physics 37,339-351.

Jin, F., Li, Y., Dixon, J. R., Selvaraj, S., Ye, Z., Lee, A. Y., Yen, C. A., Schmitt, A. D., Espinoza, C. A., and Ren, B. (2013). A high-resolution map of the three-dimensional chromatin interactome in human cells. Nature 503, 290-294.

Joo, J. Y., Schaukowitch, K., Farbiak, L., Kilaru, G., and Kim, T. K. (2016). Stimulus-specific combinatorial functionality of neuronal c-fos enhancers. Nat Neurosci 19, 75-83.

Kaikkonen, M. U., Spann, N. J., Heinz, S., Romanoski, C. E., Allison, K. A., Stender, J. D., Chun, H. B., Tough, D. F., Prinjha, R. K., Benner, C., et al. (2013). Remodeling of the enhancer landscape during macrophage activation is coupled to enhancer transcription. Mol Cell 51, 310-325.

Kim, T. K., Hemberg, M., Gray, J. M., Costa, A. M., Bear, D. M., Wu, J., Harmin, D. A., Laptewicz, M., Barbara-Haley, K., Kuersten, S., et al. (2010). Widespread transcription at neuronal activity-regulated enhancers. Nature 465, 182-187.

Kim, Y. J., Cecchini, K. R., and Kim, T. H. (2011). Conserved, developmentally regulated mechanism couples chromosomal looping and heterochromatin barrier activity at the homeobox gene A locus. Proc Natl Acad Sci USA 108, 7391-7396.

Kim, Y. J., Greer, C. B., Cecchini, K. R., Harris, L. N., Tuck, D. P., and Kim, T. H. (2013). HDAC inhibitors induce transcriptional repression of high copy number genes in breast cancer through elongation blockade. Oncogene 32, 2828-2835.

Kulakovskiy, I. V., Vorontsov, I. E., Yevshin, I. S., Soboleva, A. V., Kasianov, A. S., Ashoor, H., Ba-Alawi, W., Bajic, V. B., Medvedeva, Y. A., Kolpakov, F. A., et al. (2016). HOCOMOCO: expansion and enhancement of the collection of transcription factor binding sites models. Nucleic Acids Res 44, D116-125.

Lai, W. K. M., and Pugh, B. F. (2017). Understanding nucleosome dynamics and their links to gene expression and DNA replication. Nat Rev Mol Cell Biol.

Lawrence, M., Huber, W., Pages, H., Aboyoun, P., Carlson, M., Gentleman, R., Morgan, M. T., and Carey, V. J. (2013). Software for computing and annotating genomic ranges. PLoS Comput Biol 9, e1003118.

Li, W., Notani, D., Ma, Q., Tanasa, B., Nunez, E., Chen, A. Y., Merkurjev, D., Zhang, J., Ohgi, K., Song, X., et al. (2013). Functional roles of enhancer RNAs for oestrogen-dependent transcriptional activation. Nature 498, 516-520.

Li, W., Notani, D., and Rosenfeld, M. G. (2016). Enhancers as non-coding RNA transcription units: recent insights and future perspectives. Nat Rev Genet 17, 207-223.

Love, M. I., Huber, W., and Anders, S. (2014). Moderated estimation of fold change and dispersion for RNA-seq data with DESeq2. Genome Biol 15, 550.

Melo, C. A., Drost, J., Wijchers, P. J., van de Werken, H., de Wit, E., Oude Vrielink, J. A., Elkon, R., Melo, S. A., Leveille, N., Kalluri, R., et al. (2013). eRNAs are required for p53-dependent enhancer activity and gene transcription. Mol Cell 49, 524-535.

Mousavi, K., Zare, H., Dell'orso, S., Grontved, L., Gutierrez-Cruz, G., Derfoul, A., Hager, G. L., and Sartorelli, V. (2013). eRNAs promote transcription by establishing chromatin accessibility at defined genomic loci. Mol Cell 51, 606-617.

Rada-Iglesias, A., Bajpai, R., Swigut, T., Brugmann, S. A., Flynn, R. A., and Wysocka, J. (2011). A unique chromatin signature uncovers early developmental enhancers in humans. Nature 470, 279-283.

Rahman, S., Zorca, C. E., Traboulsi, T., Noutahi, E., Krause, M. R., Mader, S., and Zenklusen, D. (2017). Single-cell profiling reveals that eRNA accumulation at enhancer-promoter loops is not required to sustain transcription. Nucleic Acids Res 45, 3017-3030.

Ren, B., Chee, K. J., Kim, T. H., and Maniatis, T. (1999). PRDI-BF1/Blimp-1 repression is mediated by corepressors of the Groucho family of proteins. Genes Dev 13, 125-137.

Roadmap Epigenomics, C., Kundaje, A., Meuleman, W., Ernst, J., Bilenky, M., Yen, A., Heravi-Moussavi, A., Kheradpour, P., Zhang, Z., Wang, J., et al. (2015). Integrative analysis of 111 reference human epigenomes. Nature 518, 317-330.

Romanoski, C. E., Link, V. M., Heinz, S., and Glass, C. K. (2015). Exploiting genomics and natural genetic variation to decode macrophage enhancers. Trends Immunol 36, 507-518.

Sanyal, A., Lajoie, B. R., Jain, G., and Dekker, J. (2012). The long-range interaction landscape of gene promoters. Nature 489, 109-113.

Schaukowitch, K., Joo, J. Y., Liu, X., Watts, J. K., Martinez, C., and Kim, T. K. (2014). Enhancer RNA facilitates NELF release from immediate early genes. Mol Cell 56, 29-42.

Thurman, R. E., Rynes, E., Humbert, R., Vierstra, J., Maurano, M. T., Haugen, E., Sheffield, N.C., Stergachis, A. B., Wang, H., Vernot, B., et al. (2012). The accessible chromatin landscape of the human genome. Nature 489, 75-82.

Wang, D., Garcia-Bassets, I., Benner, C., Li, W., Su, X., Zhou, Y., Qiu, J., Liu, W., Kaikkonen, M. U., Ohgi, K. A., et al. (2011). Reprogramming transcription by distinct classes of enhancers functionally defined by eRNA. Nature 474, 390-394.

Whalen, S., Truty, R. M., and Pollard, K. S. (2016). Enhancer-promoter interactions are encoded by complex genomic signatures on looping chromatin. Nat Genet 48, 488-496.

What is claimed is:

1. A method of inhibiting a TNFSF10 gene expression in a human cell comprising contacting the human cell with a single-stranded antisense compound comprising a sequence selected from SEQ ID NOs: 170, 171, 172, 213, 214, 215, 187, 230, 198, 199, 200, 241, 242, or 243, thereby inhibiting expression of the TNFSF10 gene in the human cell.

2. The method of claim 1, wherein the eRNA transcription is initiated from an RNA polymerase II (PolII) binding site and is capable of elongating bidirectionally.

3. The method of claim 1, wherein the eRNA transcription is initiated from an RNA polymerase II (PolII) binding site and is capable of elongating unidirectionally.

4. The method of claim 2, wherein the eRNA is capable of enhancing transcription of the TNFSF10 gene.

5. The method of claim 1, wherein the transcriptional start site of the TNFSF10 gene is located on a chromosome at least about 1 kilobase (kb) from the genomic enhancer sequence or region.

6. The method of claim 1, wherein the human cell is an epithelium cell, a hematopoietic cell, a monocyte, a macrophage, a fibroblast cell, a neuron, a breast cell, or a cancer cell.

7. The method of claim 6, wherein the human cell contacted with the antisense compound is in a subject.

8. The method of claim 3, wherein the eRNA is capable of enhancing transcription of the TNFSF10 gene.

* * * * *

UNITED STATES PATENT AND TRADEMARK OFFICE
CERTIFICATE OF CORRECTION

| | | |
|---|---|---|
| PATENT NO. | : 11,866,708 B2 | Page 1 of 1 |
| APPLICATION NO. | : 17/076696 | |
| DATED | : January 9, 2024 | |
| INVENTOR(S) | : Kim | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 327 days.

Signed and Sealed this
First Day of July, 2025

Coke Morgan Stewart
*Acting Director of the United States Patent and Trademark Office*